US012751818B2

(12) United States Patent
Chau et al.

(10) Patent No.: US 12,751,818 B2
(45) Date of Patent: Oct. 6, 2026

(54) SYSTEMS AND METHODS FOR HEART VALVE LEAFLET REPAIR

(71) Applicant: Edwards Lifesciences Corporation, Irvine, CA (US)

(72) Inventors: Mark Chau, Laguna Hills, CA (US); Sam Shafigh, Irvine, CA (US); Travis Zenyo Oba, Yorba Linda, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 806 days.

(21) Appl. No.: 17/993,563

(22) Filed: Nov. 23, 2022

(65) Prior Publication Data

US 2023/0142064 A1 May 11, 2023

Related U.S. Application Data

(63) Continuation of application No. PCT/US2021/039587, filed on Jun. 29, 2021.

(Continued)

(51) Int. Cl.
*A61F 2/24* (2006.01)

(52) U.S. Cl.
CPC .......... *A61F 2/2418* (2013.01); *A61F 2/2436* (2013.01); *A61F 2220/0016* (2013.01)

(58) Field of Classification Search
CPC ........ A61F 2/24; A61F 2/2418; A61F 2/2436; A61F 2/2466; A61F 2220/0016;

(Continued)

(56) References Cited

U.S. PATENT DOCUMENTS

| | | | |
|---|---|---|---|
| 6,152,144 A | 11/2000 | Lesh et al. | |
| 6,626,930 B1 | 9/2003 | Allen et al. | |

(Continued)

FOREIGN PATENT DOCUMENTS

| | | | |
|---|---|---|---|
| CN | 215019732 U | 12/2021 | |
| CN | 115105265 A * | 9/2022 | .......... A61F 2/2463 |

(Continued)

OTHER PUBLICATIONS

Dwivedi P., et al. "Biometric Polymer Adhesives", ACS Publications, Jun. 5, 2022, pp. A-U, 22 Pages, Retrieved on [Jun. 9, 2022] Retrieved from URL: https://doi.org./10.1021/acsapm .1c01285.

(Continued)

*Primary Examiner* — Seema Mathew
(74) *Attorney, Agent, or Firm* — Thomas C. Richardson

(57) ABSTRACT

An implant includes an interface and a wing that is coupled to the interface. A catheter is transluminally advanceable to a heart chamber upstream of a heart valve of a subject and houses the implant. A delivery tool comprises a shaft and a driver. Via engagement with the interface, the shaft is configured to (i) deploy the implant out of the catheter such that, within the chamber, the wing extends away from the interface; and (ii) position the implant in a position in which the interface is at a site in the heart and the wing extends over a first leaflet of the valve toward an opposing leaflet of the valve. The driver is configured to secure the implant in the position by driving an anchor through the interface and into tissue at the site. Other embodiments are also described.

26 Claims, 65 Drawing Sheets

Related U.S. Application Data

(60) Provisional application No. 63/124,704, filed on Dec. 11, 2020, provisional application No. 63/046,638, filed on Jun. 30, 2020.

(58) Field of Classification Search
CPC .... A61F 2/2445; A61F 2/2409; A61F 2/2412; A61F 2/2427; A61F 2/243; A61F 2210/0014; A61F 2220/0008; A61F 2/2457; A61F 2/246; A61F 2/2454; A61F 2/2442
See application file for complete search history.

(56) References Cited

U.S. PATENT DOCUMENTS 7,025,791 B2 4/2006 Levine et al.
7,527,646 B2 5/2009 Rahdert et al.
7,618,449 B2 11/2009 Tremulis et al.
8,308,759 B2 11/2012 Olsen et al.
8,366,767 B2 2/2013 Zhang
8,398,708 B2 3/2013 Meiri et al.
8,403,983 B2 3/2013 Quadri et al.
8,579,964 B2 11/2013 Lane et al.
8,778,017 B2 7/2014 Eliasen et al.
8,820,851 B2 9/2014 Mercat et al.
8,926,690 B2 1/2015 Kovalsky
8,956,404 B2 2/2015 Bortlein et al.
9,211,124 B2 12/2015 Campbell et al.
11,759,321 B2 * 9/2023 Khairkhahan ........ A61F 2/2466 623/2.42
12,109,116 B2 * 10/2024 Khairkhahan ....... A61B 17/068
12,150,856 B2 * 11/2024 Khairkhahan ..... A61B 17/0401
12,285,336 B2 * 4/2025 Khairkhahan ........ A61F 2/2445
12,295,845 B2 * 5/2025 Khairkhahan .......... A61F 2/246
12,350,153 B2 * 7/2025 Khairkhahan ........ A61F 2/2442
12,458,341 B2 * 11/2025 Khairkhahan ..... A61B 17/0401
12,478,474 B2 * 11/2025 Khairkhahan .......... A61F 2/246
12,599,482 B2 * 4/2026 Khairkhahan ........ A61F 2/2445
2002/0148643 A1 10/2002 Contreras et al.
2003/0093148 A1 5/2003 Bolling et al.
2003/0130731 A1 7/2003 Vidlund et al.
2003/0167062 A1 9/2003 Gambale et al.
2004/0049211 A1 3/2004 Tremulis et al.
2004/0127982 A1 7/2004 Machold et al.
2005/0075654 A1 4/2005 Kelleher
2005/0119671 A1 6/2005 Reydel et al.
2005/0159810 A1 7/2005 Filsoufi
2005/0177180 A1 8/2005 Kaganov et al.
2005/0251177 A1 11/2005 Saadat et al.
2005/0267478 A1 12/2005 Corradi et al.
2006/0030885 A1 2/2006 Hyde
2006/0069429 A1 3/2006 Spence et al.
2006/0173524 A1 8/2006 Salahieh et al.
2006/0241745 A1 10/2006 Solem
2006/0264980 A1 11/2006 Khairkhahan et al.
2007/0049942 A1 3/2007 Hindrichs et al.
2007/0083230 A1 4/2007 Javois
2007/0093890 A1 4/2007 Eliasen et al.
2007/0112425 A1 5/2007 Schaller et al.
2007/0219612 A1 9/2007 Andreas et al.
2007/0244554 A1 10/2007 Rafiee et al.
2007/0244555 A1 10/2007 Rafiee et al.
2007/0244556 A1 10/2007 Rafiee et al.
2007/0282375 A1 12/2007 Hindrichs et al.
2007/0282429 A1 12/2007 Hauser et al.
2008/0033460 A1 2/2008 Ziniti et al.
2008/0228223 A1 9/2008 Alkhatib
2008/0288061 A1 11/2008 Maurer et al.
2009/0043381 A1 2/2009 Macoviak et al.
2009/0048668 A1 2/2009 Wilson et al.
2009/0171456 A1 7/2009 Kveen et al.
2010/0010538 A1 1/2010 Juravic et al.
2010/0324585 A1 12/2010 Miles et al.
2011/0094801 A1 4/2011 Buchanan et al.
2011/0106247 A1 5/2011 Miller et al.
2011/0137397 A1 6/2011 Chau et al.
2011/0184510 A1 7/2011 Maisano et al.
2011/0208290 A1 8/2011 Straubinger et al.
2011/0282361 A1 11/2011 Miller et al.
2012/0022633 A1 1/2012 Olson et al.
2012/0053642 A1 3/2012 Lozier et al.
2012/0078350 A1 3/2012 Wang et al.
2012/0158023 A1 6/2012 Mitelberg et al.
2012/0197388 A1 8/2012 Khairkhahan et al.
2012/0203336 A1 8/2012 Annest
2012/0245604 A1 9/2012 Tegzes
2012/0253386 A1 10/2012 Rowe et al.
2013/0006343 A1 1/2013 Kassab
2013/0023985 A1 1/2013 Khairkhahan et al.
2013/0068531 A1 3/2013 Joulin et al.
2013/0165965 A1 6/2013 Carlson et al.
2013/0231701 A1 9/2013 Voss et al.
2014/0046347 A1 2/2014 Cully et al.
2014/0067048 A1 * 3/2014 Chau ..................... A61F 2/2454 623/2.1
2014/0067052 A1 3/2014 Chau et al.
2014/0067054 A1 * 3/2014 Chau ..................... A61F 2/2442 623/2.36
2014/0131033 A1 5/2014 Galvan-Sanchez et al.
2014/0148828 A1 5/2014 Ewers et al.
2014/0179993 A1 6/2014 Alexander et al.
2014/0277426 A1 9/2014 Dakin et al.
2014/0311805 A1 10/2014 Mageren et al.
2015/0119981 A1 4/2015 Khairkhahan et al.
2015/0230919 A1 8/2015 Chau et al.
2015/0250482 A1 9/2015 Slaughter et al.
2015/0297212 A1 10/2015 Reich et al.
2015/0342612 A1 12/2015 Wu et al.
2015/0366556 A1 12/2015 Khairkhahan et al.
2016/0015512 A1 1/2016 Zhang et al.
2016/0022273 A1 1/2016 Kassab
2016/0030034 A1 2/2016 Graul et al.
2016/0256149 A1 9/2016 Sampson et al.
2016/0256274 A1 9/2016 Hayoz et al.
2016/0287383 A1 10/2016 Rowe
2016/0302917 A1 10/2016 Schewel
2016/0345962 A1 12/2016 Marczyk et al.
2016/0346084 A1 12/2016 Taylor et al.
2017/0002654 A1 1/2017 Buchanan et al.
2017/0086975 A1 3/2017 Gilmore et al.
2017/0095332 A1 4/2017 Bruchman
2017/0100119 A1 4/2017 Baird et al.
2017/0112618 A1 * 4/2017 Li ......................... A61F 2/2445
2017/0189186 A1 7/2017 Mohl
2017/0245993 A1 8/2017 Gross et al.
2017/0258590 A1 * 9/2017 Khairkhahan ........ A61F 2/2463
2017/0265995 A1 9/2017 Khairkhahan et al.
2018/0078361 A1 3/2018 Naor et al.
2018/0133008 A1 5/2018 Kizuka et al.
2018/0140420 A1 5/2018 Hayoz et al.
2018/0221014 A1 8/2018 Darabian
2018/0325663 A1 11/2018 Taylor et al.
2018/0353182 A1 12/2018 Wei
2019/0029817 A1 * 1/2019 Seguin .................. A61F 2/2442
2019/0060072 A1 2/2019 Zeng
2019/0076249 A1 3/2019 Khairkhahan et al.
2019/0091445 A1 3/2019 House
2019/0117113 A1 4/2019 Curran
2019/0167197 A1 6/2019 Abunassar et al.
2019/0175344 A1 6/2019 Khairkhahan
2019/0192296 A1 6/2019 Schwartz et al.
2019/0201191 A1 * 7/2019 McLean ................ A61F 2/0063
2019/0290431 A1 * 9/2019 Genovese ............. A61F 2/2463
2019/0290432 A1 9/2019 Duffy et al.
2019/0350705 A1 11/2019 Schewel et al.
2020/0138569 A1 5/2020 Basude et al.
2020/0178956 A1 6/2020 Mitelberg et al.
2020/0237357 A1 7/2020 Cao et al.
2020/0268512 A1 8/2020 Mohl
2021/0015615 A1 1/2021 Groothuis et al.
2021/0228354 A1 7/2021 Rafiee et al.
2021/0338418 A1 11/2021 Feld
2021/0353413 A1 * 11/2021 Zhang ................... A61F 2/2436
2021/0361238 A1 11/2021 Bak-Boychuk et al.

(56) References Cited

U.S. PATENT DOCUMENTS

| | | | | |
|---|---|---|---|---|
| 2021/0378818 | A1 | 12/2021 | Manash et al. | |
| 2022/0133327 | A1 | 5/2022 | Zhang et al. | |
| 2022/0183839 | A1* | 6/2022 | Khairkhahan | A61F 2/2445 |
| 2022/0233311 | A1* | 7/2022 | Khairkhahan | A61F 2/2445 |
| 2022/0257196 | A1 | 8/2022 | Massmann | |
| 2022/0296248 | A1 | 9/2022 | Abunassar et al. | |
| 2022/0313438 | A1 | 10/2022 | Chappel-Ram | |
| 2022/0409372 | A1* | 12/2022 | Khairkhahan | A61F 2/2454 |
| 2023/0014540 | A1 | 1/2023 | Metchik et al. | |
| 2023/0040410 | A1* | 2/2023 | Khairkhahan | A61F 2/2445 |
| 2023/0132907 | A1* | 5/2023 | McLean | A61F 2/2445 623/2.36 |
| 2023/0149170 | A1 | 5/2023 | Giese et al. | |
| 2023/0218291 | A1 | 7/2023 | Zarbatany et al. | |
| 2023/0270549 | A1 | 8/2023 | Guidotti et al. | |
| 2023/0404757 | A1* | 12/2023 | Khairkhahan | A61F 2/2466 |
| 2024/0033083 | A1* | 2/2024 | Khairkhahan | A61F 2/2445 |
| 2024/0099736 | A1 | 3/2024 | Elsheikh et al. | |
| 2024/0148505 | A1 | 5/2024 | Datta et al. | |
| 2024/0335287 | A1* | 10/2024 | Chau | A61F 2/2463 |
| 2024/0335288 | A1* | 10/2024 | Ruban | A61F 2/2463 |
| 2025/0099241 | A1* | 3/2025 | Zimmerman | A61F 2/2466 |
| 2025/0161049 | A1* | 5/2025 | Peleg | A61F 2/2463 |

FOREIGN PATENT DOCUMENTS

| | | | | |
|---|---|---|---|---|
| CN | 118382407 | A * | 7/2024 | |
| DE | 102009036818 | A1 | 2/2011 | |
| WO | 2007098212 | A2 | 8/2007 | |
| WO | 2014162343 | A1 | 10/2014 | |
| WO | WO-2014207575 | A2 * | 12/2014 | A61F 2/2463 |
| WO | WO-2016004798 | A1 * | 1/2016 | A61F 2/246 |
| WO | WO-2016087145 | A1 | 6/2016 | |
| WO | WO-2016202708 | A1 | 12/2016 | |
| WO | WO-2018169878 | A1 | 9/2018 | |
| WO | 2019116322 | A1 | 6/2019 | |
| WO | WO-2022006087 | A2 * | 1/2022 | A61B 17/068 |
| WO | 2022157592 | A1 | 7/2022 | |
| WO | 2022250983 | A1 | 12/2022 | |
| WO | 2023003755 | A1 | 1/2023 | |
| WO | 2023004098 | A1 | 1/2023 | |
| WO | 2023288003 | A1 | 1/2023 | |
| WO | WO-2023114289 | A1 * | 6/2023 | A61F 2/2466 |
| WO | WO-2025085321 | A1 | 4/2025 | |

OTHER PUBLICATIONS

Lee H., et al., “A Reversible Wet/Dry Adhesive Inspired by Mussels and Geckos,” Nature Publishing Group, Nature, New York, United States, Jul. 19, 2007, vol. 448, pp. 338-341,6 Pages, Aug. 2007.

Lee H., et al. “Single-Molecule Mechanics of Mussel Adhesion,” Proceedings of the National Academy of Sciences of the United States of America, Washington, District of Columbia, United States, Aug. 29, 2006, vol. 13, No. 35, p. 12999-13003, DOI: 10.1073/pnas.0605552103.

North M.A., et al. “High Strength Underwater Bonding with Polymer Mimics of Mussel Adhesive Proteins,” ACS Publications, Feb. 8, 2017, vol. 9, pp. 7866-7872, Retrieved on [Oct. 12, 2018] Retrieved from URL: https://doi.org/10.1021/acsami.7b00270.

* cited by examiner

FIG. 3
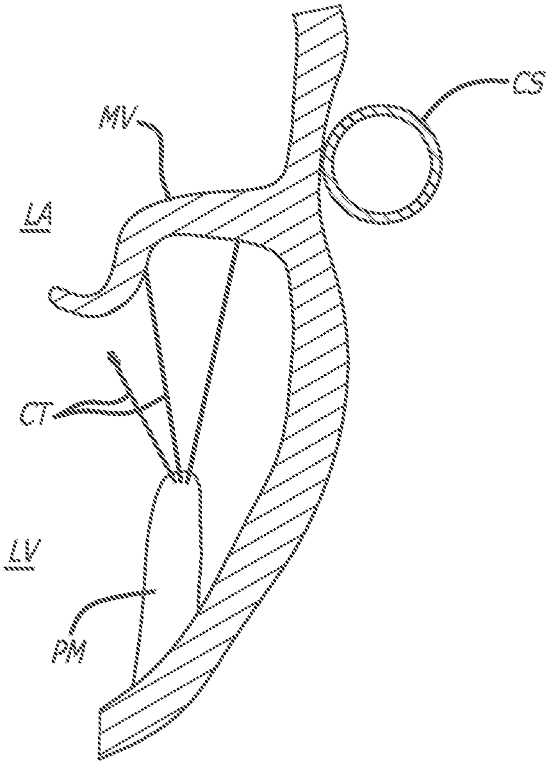
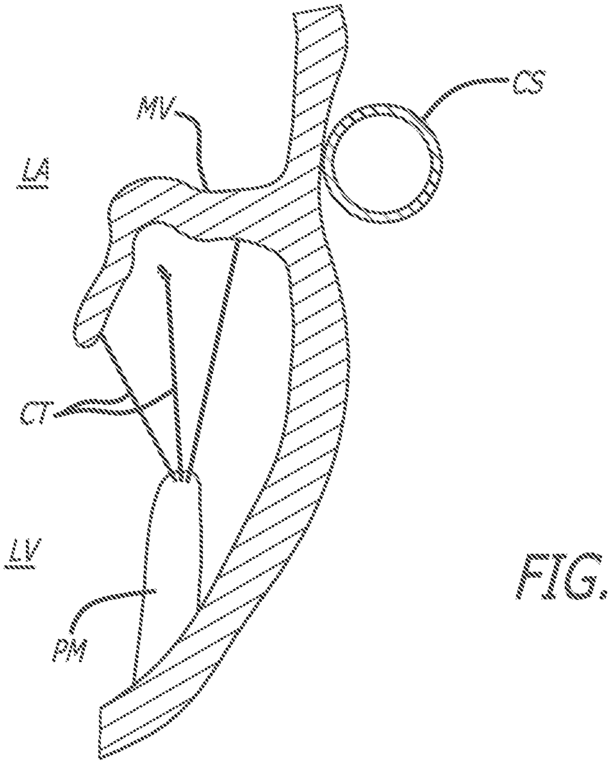
FIG. 4

FIG. 14
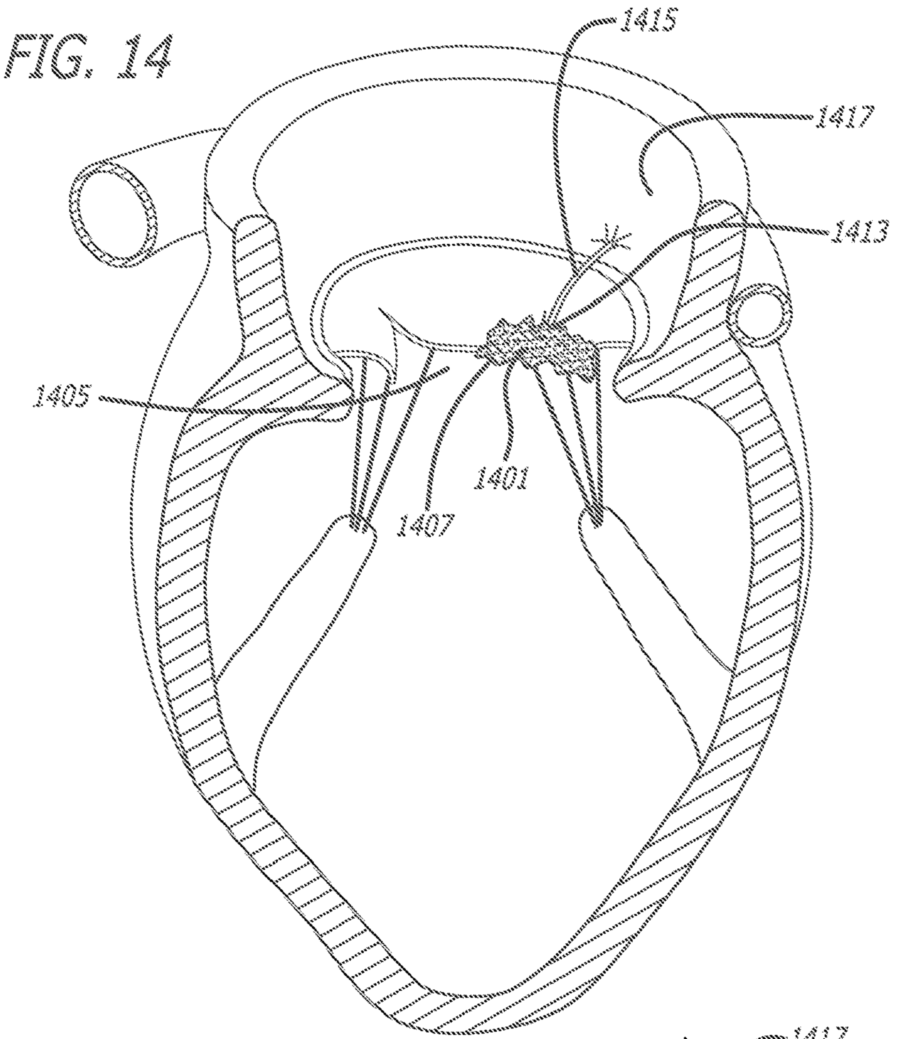
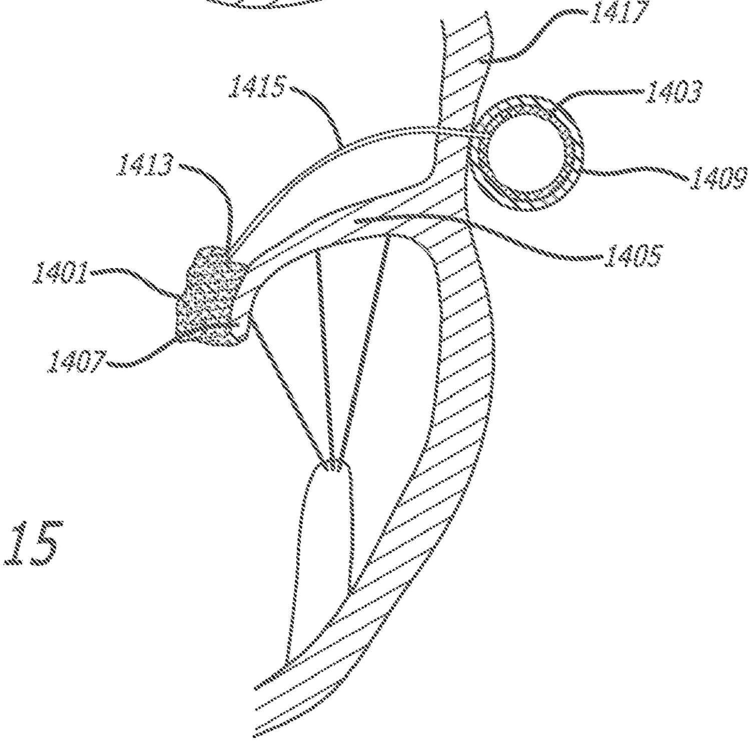
FIG. 15

FIG. 20A
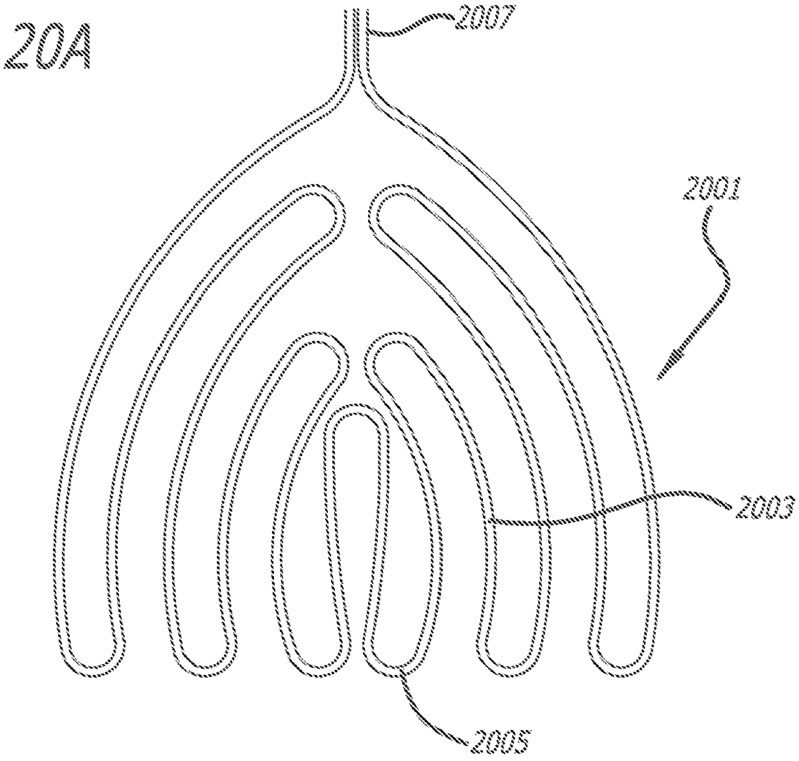
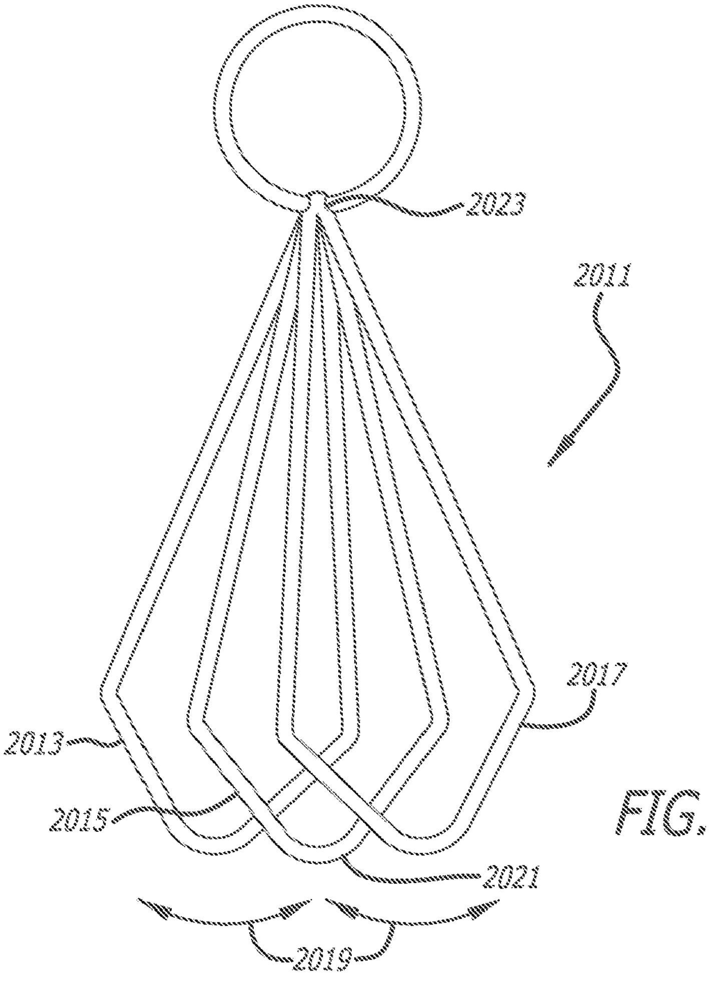
FIG. 20B

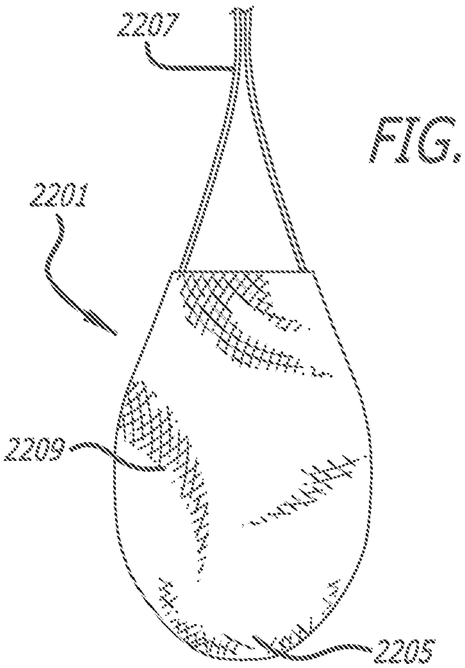
FIG. 22A
FIG. 22B
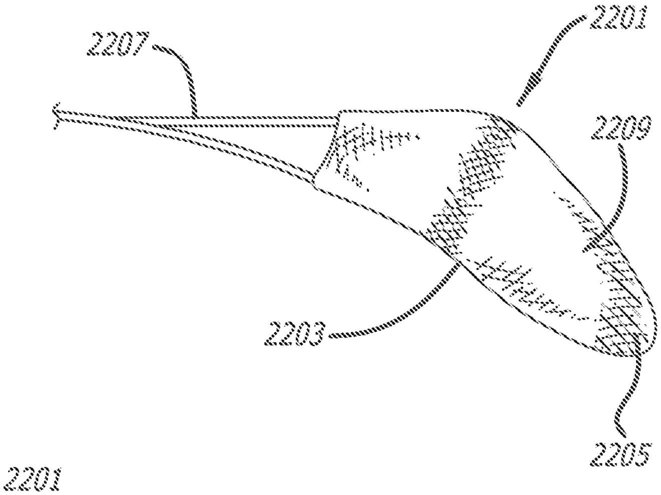
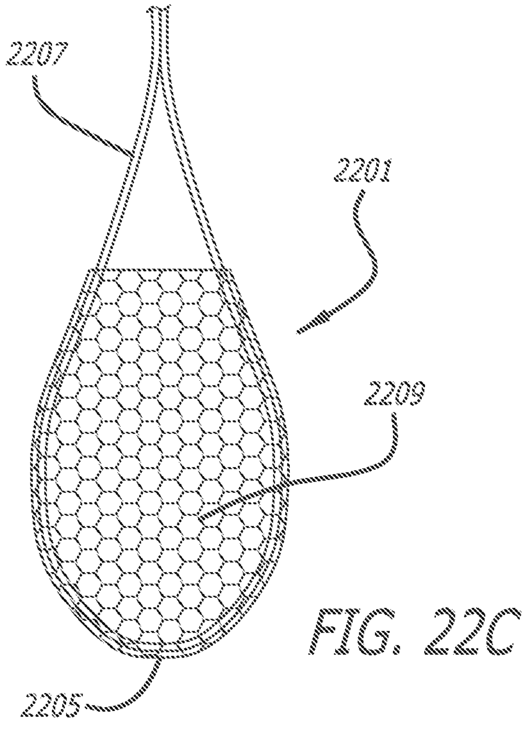
FIG. 22C

FIG. 23D
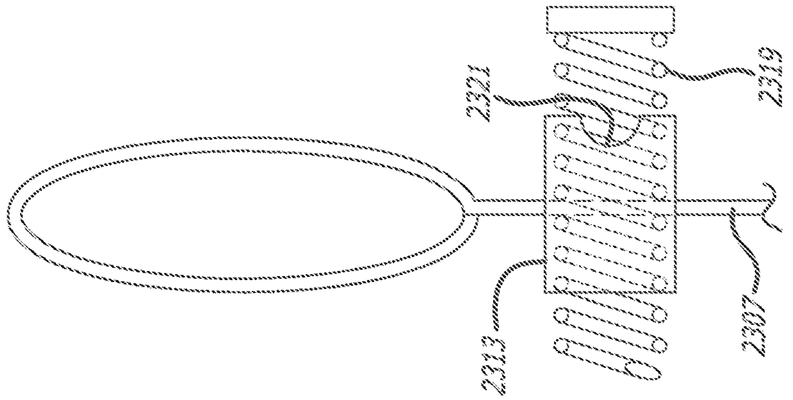
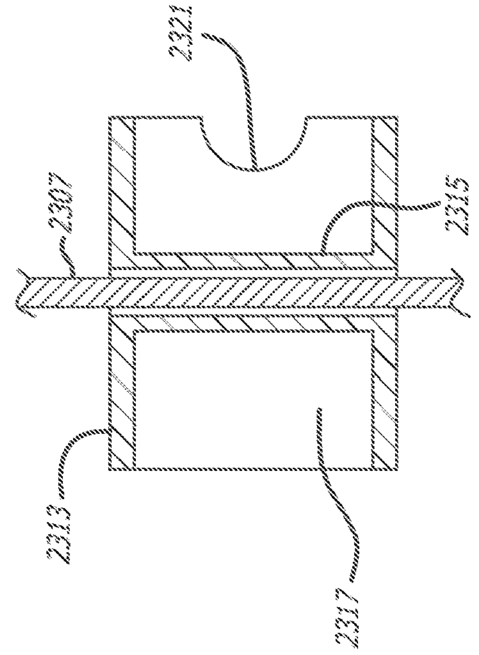
FIG. 23C
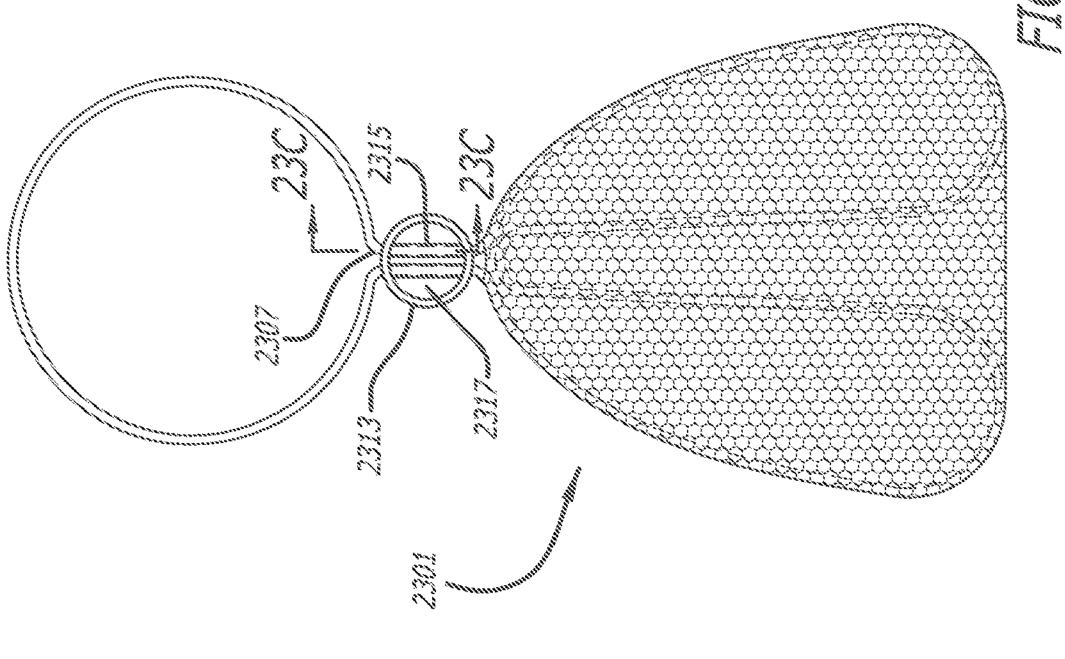
FIG. 23B

FIG. 24C
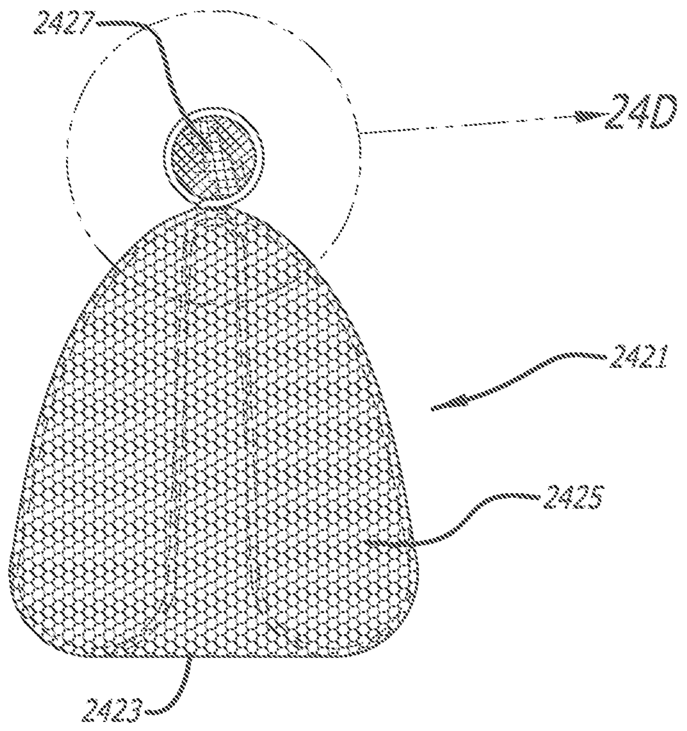
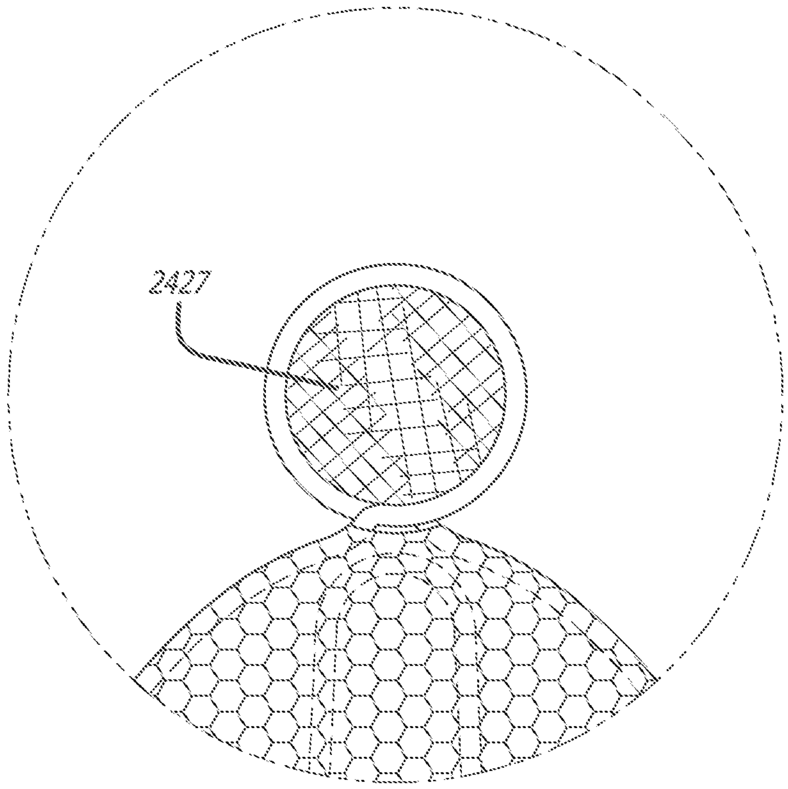
FIG. 24D

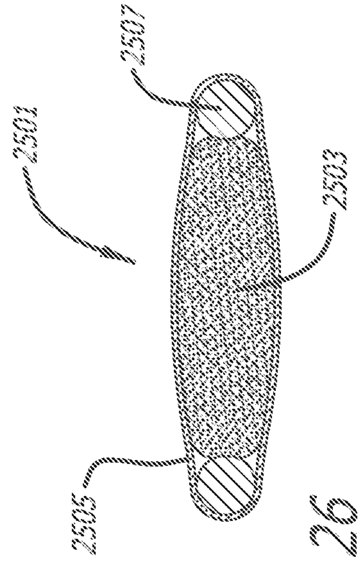
FIG. 26
FIG. 25
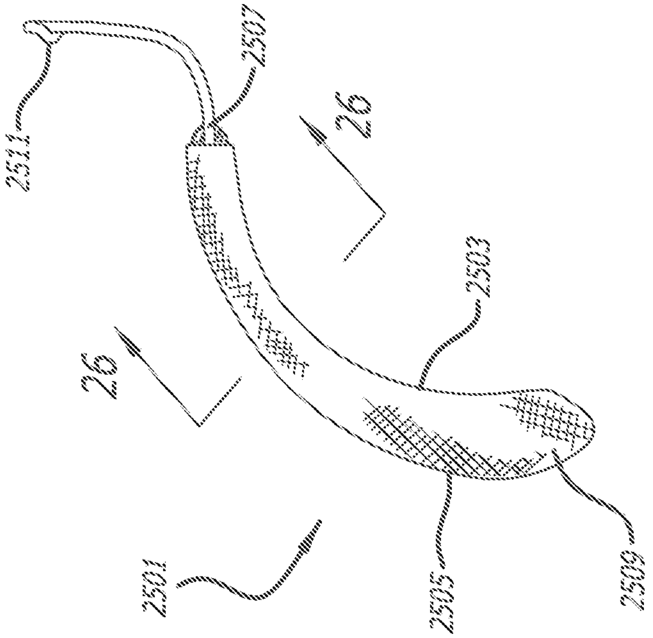

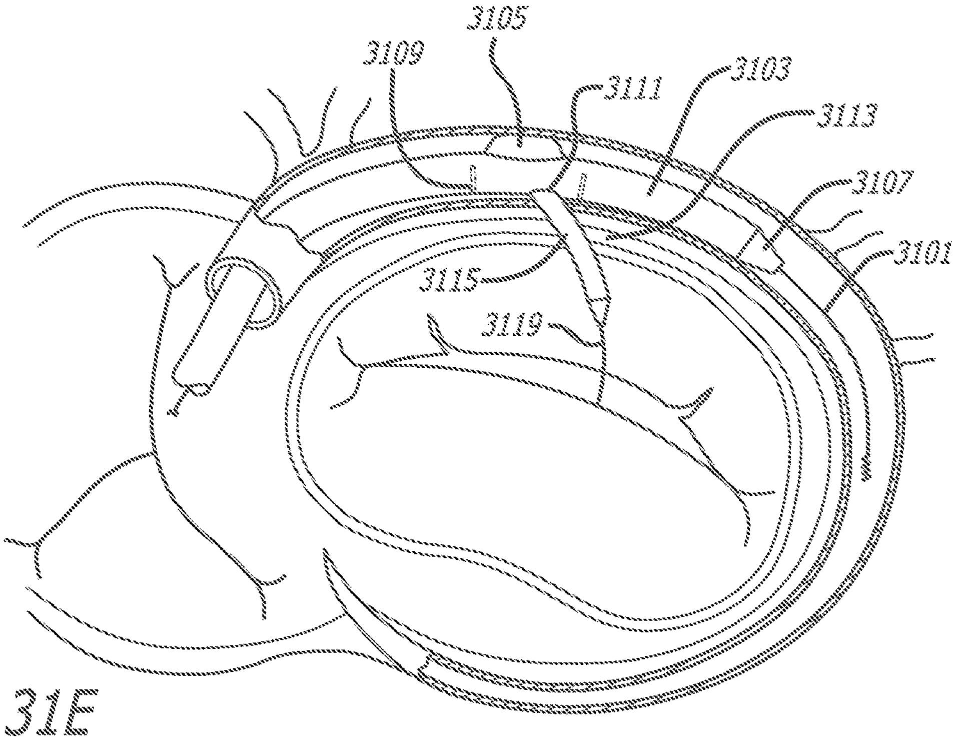
FIG. 31E
FIG. 31F
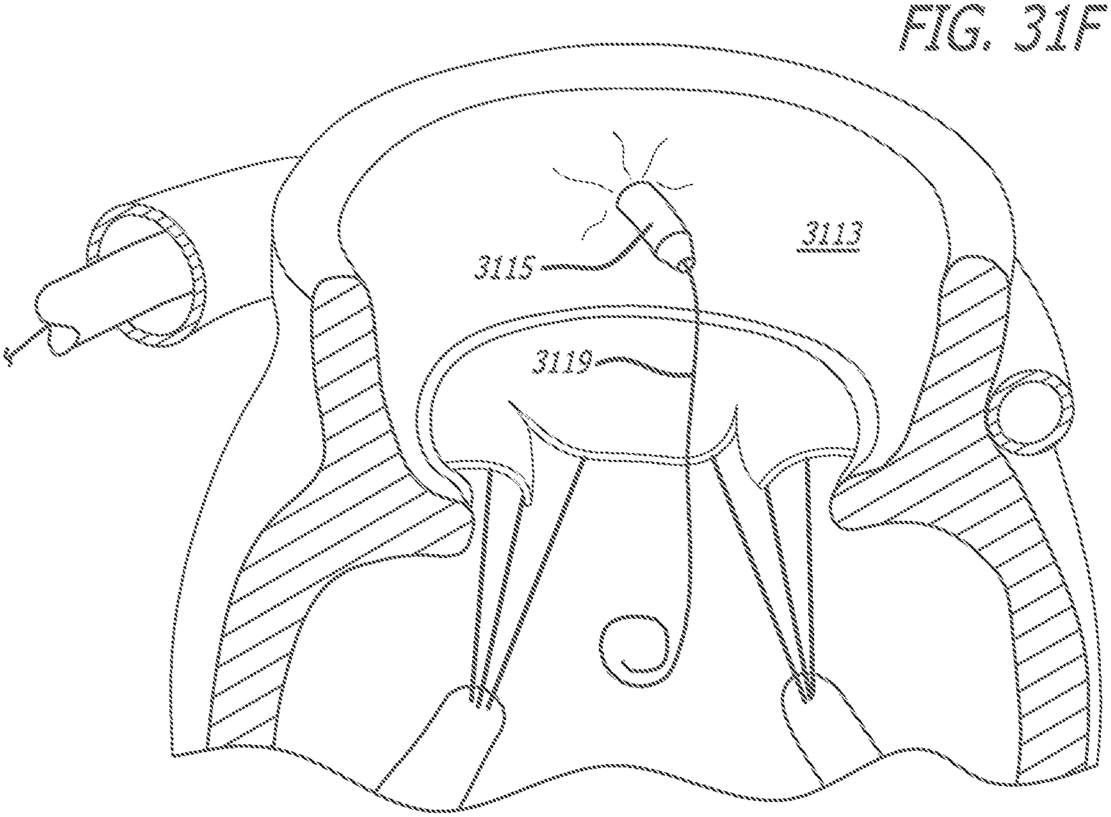

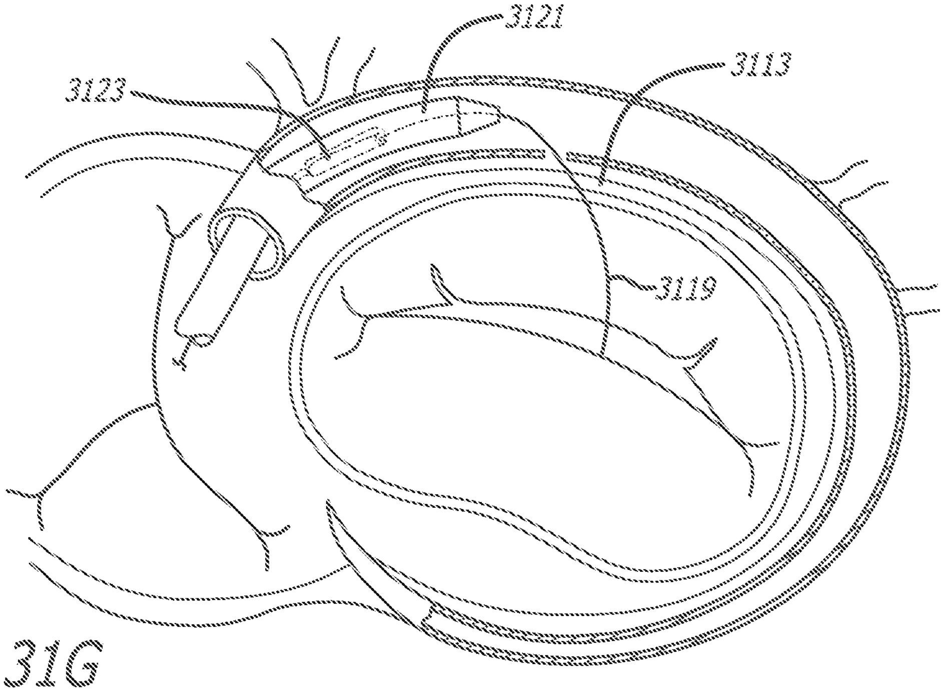
FIG. 31G
FIG. 31H
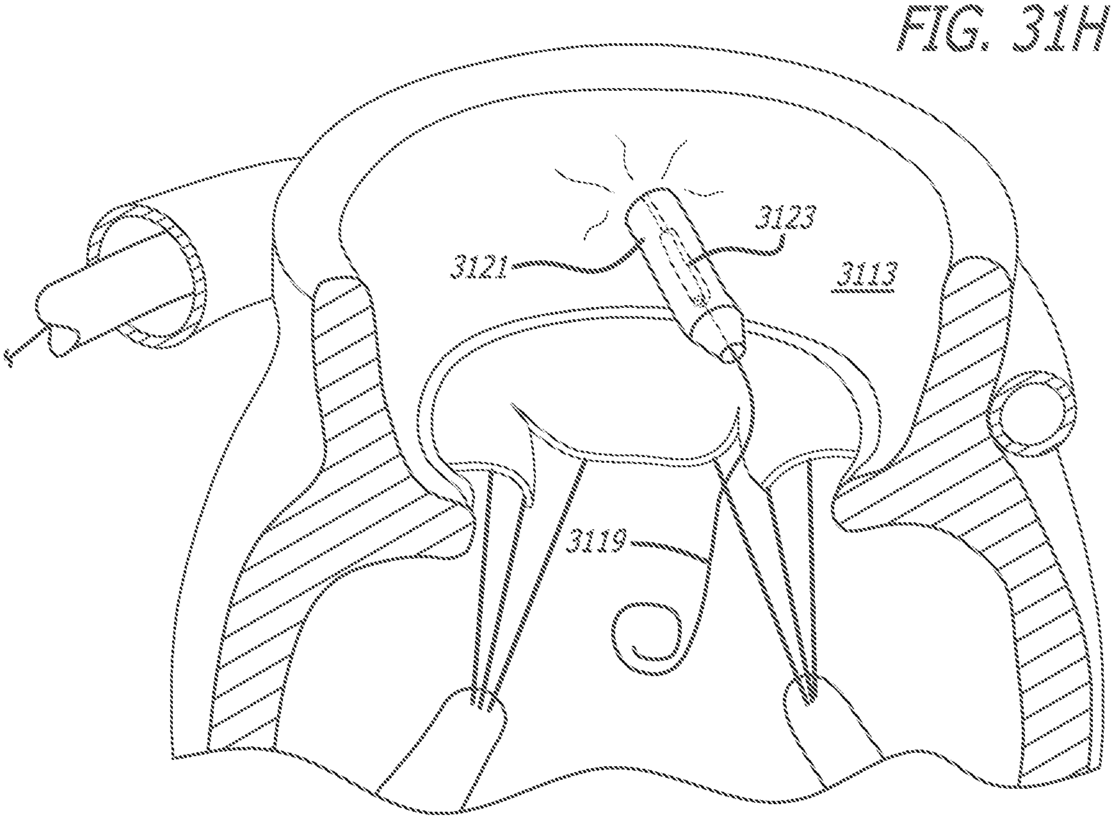

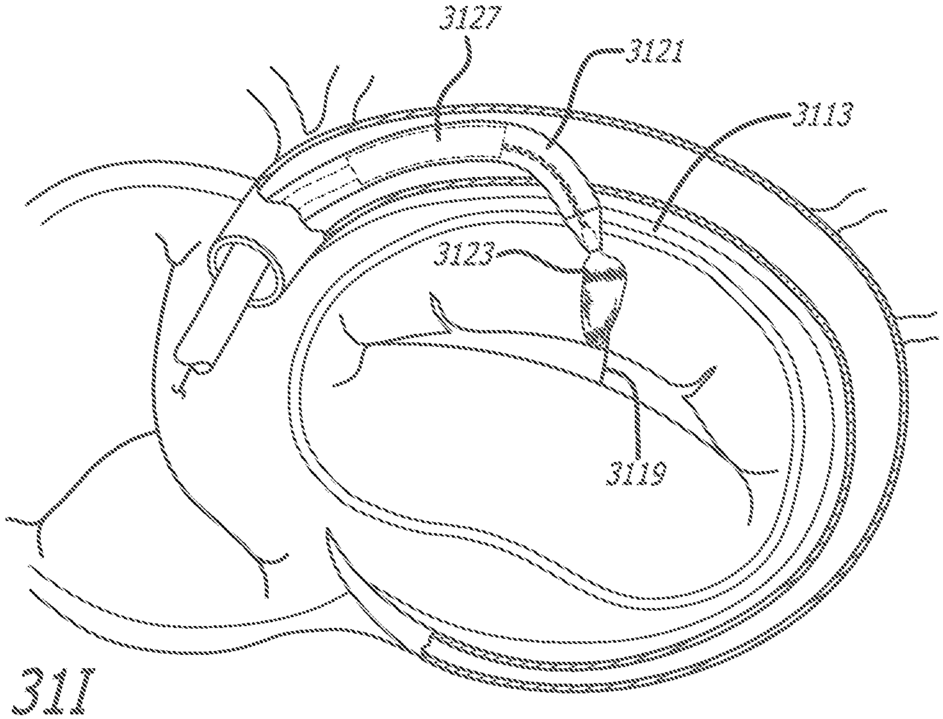
FIG. 31I
FIG. 31J
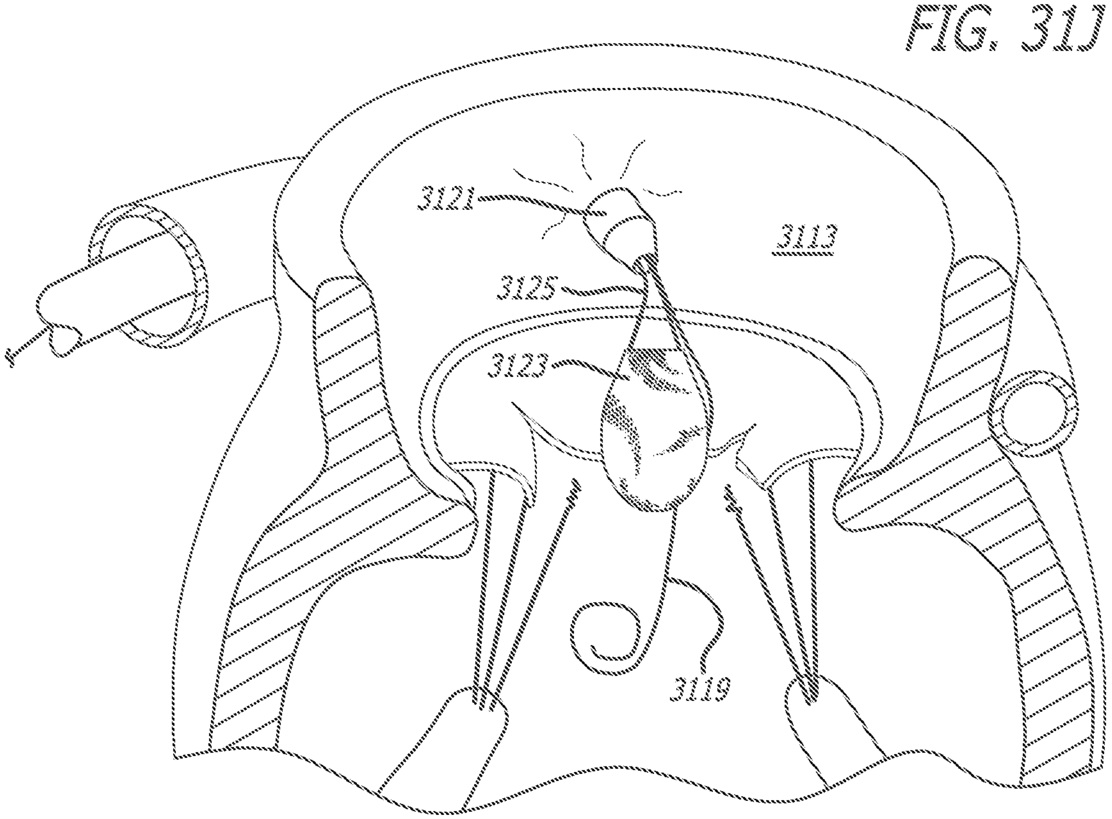

FIG. 42
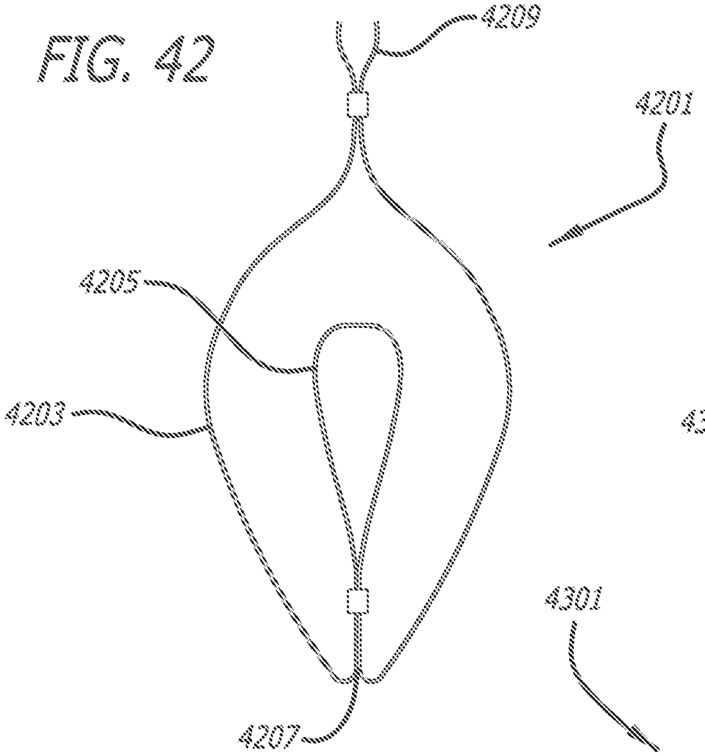
FIG. 43
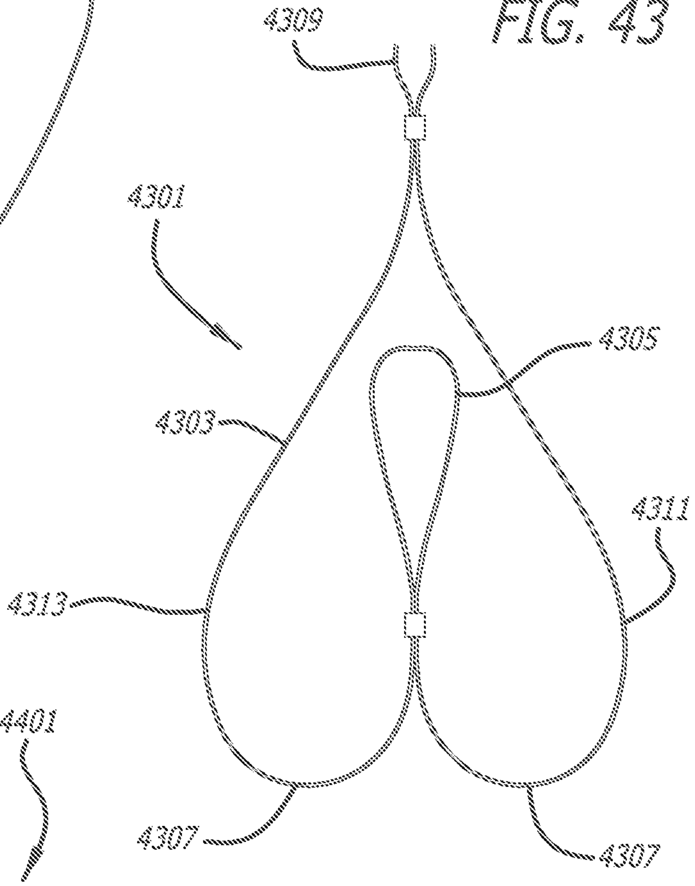
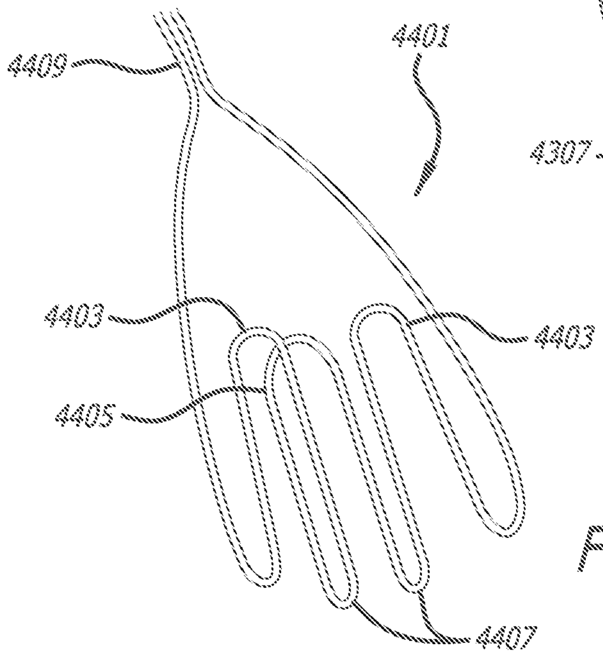
FIG. 44

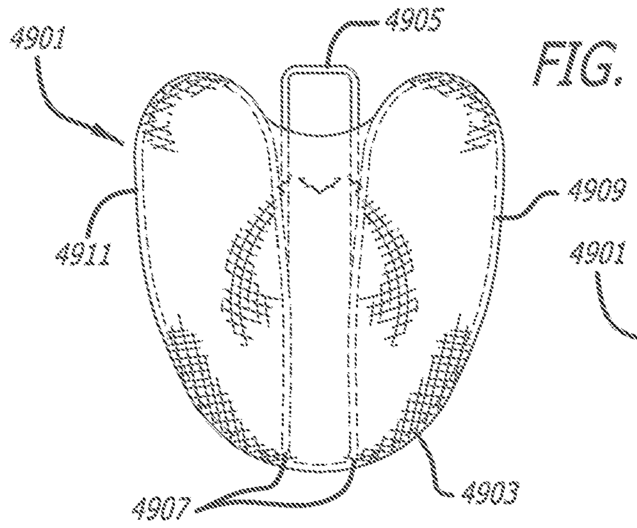
FIG. 49
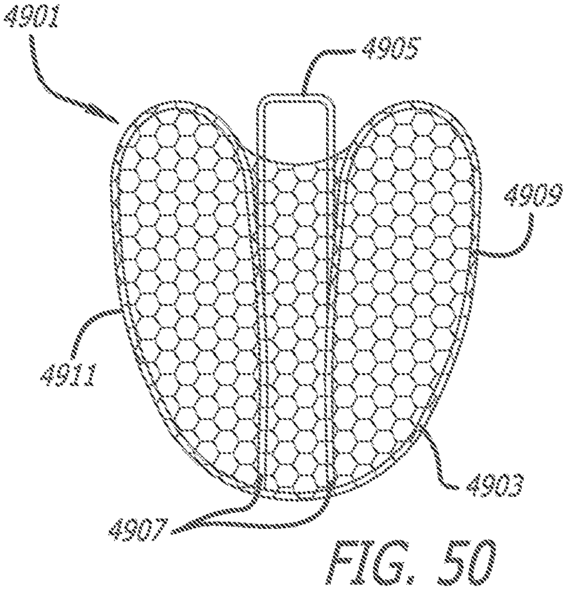
FIG. 50
FIG. 51
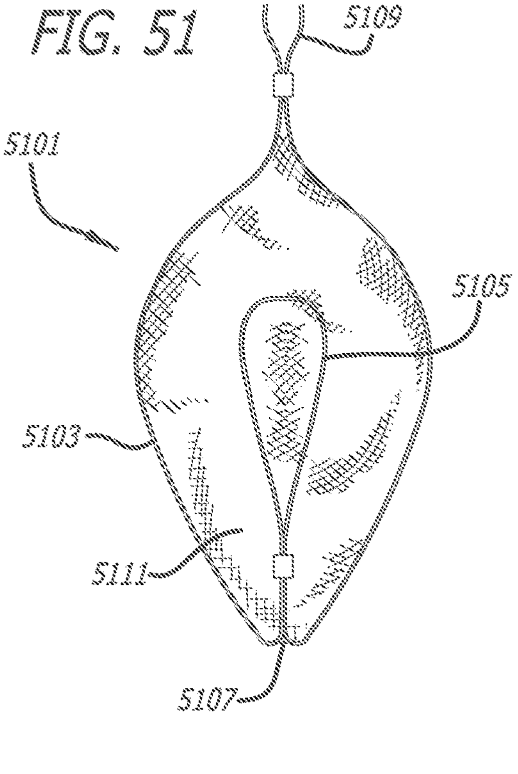
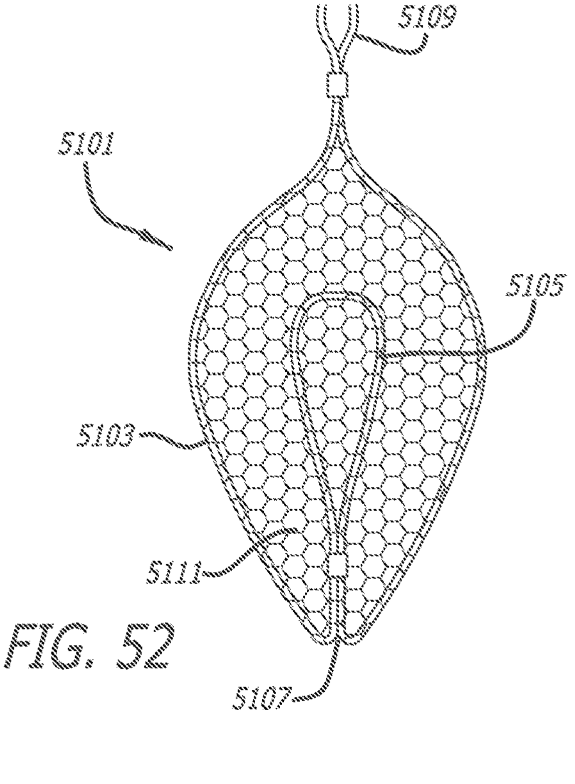
FIG. 52

SYSTEMS AND METHODS FOR HEART VALVE LEAFLET REPAIR

CROSS-REFERENCES TO RELATED APPLICATIONS

The present application is a Continuation of International Patent Application PCT/US2021/039587 to Chau et al., filed Jun. 29, 2021, which published as WO 2022/006087, and which claims priority to:

U.S. Provisional Patent Application 63/046,638 to Chau et al., filed Jun. 30, 2020; and U.S. Provisional Patent Application 63/124,704 to Chau et al., filed Dec. 11, 2020.

Each of the above-referenced applications is incorporated herein by reference in their entirety for all purposes.

BACKGROUND

The native heart valves (i.e., the aortic, pulmonary, tricuspid, and mitral valves) serve critical functions in assuring the forward flow of an adequate supply of blood through the cardiovascular system. These heart valves can be rendered less effective by congenital malformations, inflammatory processes, infectious conditions, or disease. Such damage to the valves can result in serious cardiovascular compromise or death. Treatment for such disorders can be done with the surgical repair or replacement of the valve during open heart surgery or with transcatheter transvascular techniques for introducing and implanting prosthetic devices in a manner that is much less invasive than open heart surgery.

A healthy heart has a generally conical shape that tapers to a lower apex. The heart has four chambers: the left atrium, right atrium, left ventricle, and right ventricle. The left and right sides of the heart are separated by a wall generally referred to as the septum. The native mitral valve of the human heart connects the left atrium to the left ventricle. The mitral valve includes an annulus portion, which is an annular portion of the native valve tissue surrounding the mitral valve orifice, and a pair leaflets (as referred to as cusps) that extend downward from the annulus into the left ventricle. The mitral valve annulus can form a “D” shaped, oval, or otherwise out-of-round cross-sectional shape having major and minor axes. The anterior leaflet can be larger than the posterior leaflet, forming a generally “C” shaped boundary between the abutting free edges of the leaflets when they are closed together.

When operating properly, the anterior leaflet and the posterior leaflet function together as a one-way valve to allow blood to flow only from the left atrium to the left ventricle. The left atrium receives oxygenated blood from the pulmonary veins. When the muscles of the left atrium contract and the left ventricle dilates, the oxygenated blood that is collected in the left atrium flows into the left ventricle. When the muscles of the left atrium relax and the muscles of the left ventricle contract, the increased blood pressure in the left ventricle urges the two leaflets together, thereby closing the one-way mitral valve so that blood cannot flow back to the left atrium and is instead expelled out of the left ventricle through the aortic valve. To prevent the two leaflets from prolapsing or flailing under pressure and folding back through the mitral annulus toward the left atrium, a plurality of fibrous cords called chordae tendineae tether the leaflets to papillary muscles in the left ventricle.

Valve regurgitation occurs when the native valve fails to close properly and blood flows into the left atrium from the left ventricle during the systole phase of heart contraction. Valve regurgitation (especially mitral valve regurgitation) is the most common form of valvular heart disease. Mitral regurgitation has different causes, including leaflet prolapse or flail, restricted leaflet motion (e.g., due to leaflet rigidity/leaflet calcification), and/or dysfunctional papillary muscles stretching.

Some techniques for treating leaflet valve regurgitation due to flail and prolapse include stitching or otherwise coupling portions of the native valve leaflets directly to one another, but there is a continuing need for improved devices and methods for treating leaflet flail, prolapse, and restricted leaflet motion.

SUMMARY OF THE INVENTION

Many examples herein are directed to towards systems, apparatuses, devices, methods, etc. that can mitigate leaflet flail, prolapse, abnormal leaflet motion, and/or other problems. For example, various embodiments of systems, devices, etc. provide contact pressure on the flailed, prolapsed, or restricted region of the leaflet. Some embodiments of systems, devices, etc. herein are anchored within nearby vasculature. Some embodiments of systems, devices, etc. herein are anchored directly to the annulus and/or a leaflet. Some embodiments of systems, devices, etc. are compressed onto the leaflet to be repaired.

In some applications, a system (e.g., a leaflet repair system, an arrestor system, a prolapse repair system, a flail repair system, a repair system, etc.) is for use within a heart valve. The system can include a device (e.g., a repair device, a leaflet repair device, an arrestor, etc.) comprising a contact face contoured to and capable of providing contact pressure onto an influent face of a heart valve leaflet (e.g., onto an atrial side of an atrioventricular valve). The system includes an anchor capable of anchoring within vasculature. And the system includes a connector or an anchor receiver that connects the device and the anchor.

In some applications, the device is an implant that comprises a flexible wing and an interface, and the system comprises a delivery tool that is engageable with the interface, and that can be used to position and anchor the interface to tissue of the heart (e.g., to an annulus of the valve being treated) such that the wing extends over a first leaflet of the valve (e.g., over a prolapsing or flailing portion of the leaflet), toward an opposing leaflet of the valve. For some such applications, the wing is curved, and the positioning and anchoring is such that the wing curves downstream between the leaflets, e.g., such that a tip (e.g., a free end) of the wing is disposed within the ventricle downstream of the valve being treated.

In some applications, the contact face of the device has a length and a width to cover a prolapse or a flail of the heart valve leaflet.

In some applications, the contact face of the device is capable of providing contact pressure onto a prolapse or a flail of the heart valve leaflet.

In some applications, the system further includes a coaptation portion that is extended from the contact face, the coaptation portion is capable extending the length of the device into coaptation area of the valve.

In some applications, the coaptation portion is capable of helping promote coaptation between the leaflets of the valve.

In some applications, the device is a wire form.

In some applications, the wire form is nitinol, cobalt-chrome (CoCr), stainless steel, titanium, polyglycolic acid (PGA), polylactic acid (PLA), poly-D-lactide (PDLA), polyurethane (PU), poly-4-hydroxybutyrate (P4HB), polycaprolactone (PCL), polyether ether ketone (PEEK), cyclic olefin copolymers (COCs), polyethylene vinyl acetate (EVA), polytetrafluorethylene (PTFE), perfluoroether (PFA), or fluorinated ethylene propylene (FEP).

In some applications, the wire form is compactible to fit within a delivery catheter.

In some applications, the wire form is self-expanding.

In some applications, the system further includes a sheet that is attached upon the wire form, the sheet forming the contact face.

In some applications, the sheet has a length and a width to cover a prolapse or a flail of the heart valve leaflet.

In some applications, the sheet is capable of providing contact pressure onto a prolapse or a flail of the heart valve leaflet.

In some applications, the sheet is permeable, semipermeable, or impermeable.

In some applications, the sheet is a mesh.

In some applications, the sheet is poly(lactic-co-glycolic) acid (PLGA), polyvinylchloride (PVC), polyethylene (PE), polypropylene (PP), polytetrafluoroethylene (PTFE), polyurethane (PU), polyethylene terephthalate (PET), polyethersulfone (PES), polyglycolic acid (PGA), polylactic acid (PLA), poly-D-lactide (PDLA), poly-4-hydroxybutyrate (P4HB), or polycaprolactone (PCL).

In some applications, the system further includes a latch or a hook capable of latching or hooking within a heart valve leaflet commissure or cleft.

In some applications, the system includes a static portion and a dynamic portion. The dynamic portion is capable of being repositioned or resized.

In some applications, the anchor is a wire stent.

In some applications, the anchor is a pin fastener.

In some applications, the anchor is a wire fastener that clasps a wire.

In some applications, the connector or anchor receiver comprises one or more of a rivet, suture, staple, wire, pin, shaft, sheet, mesh, housing, tubular member, cross-bar, etc.

In some applications, the system further includes a clamp that is capable of clamping the device (e.g., repair device, leaflet repair device, arrestor, etc.) to the leaflet.

In some applications, a tether extends from the device and is capable of extending to a pinning location on the effluent side of the valve (e.g., on the ventricular side of an atrioventricular valve).

In some applications, the device incorporates an internal gap in coaptation area of the device. The internal gap is free of wire form.

In some applications, the device incorporates a coaptation element, spacer, gap filler, etc.

In some applications, the coaptation element/spacer/filler comprises foam, hydrogel, or silicone.

In some applications, the coaptation element/spacer/filler comprises a scissor mechanism or a coil.

In some applications, the device incorporates an expandable stent.

In some applications, the device is configured to be implanted within a mitral valve, a tricuspid valve, an aortic valve, or a pulmonic valve.

In some applications, the anchor is configured to be implanted within vasculature nearby the valve, and wherein the connector traverses a chamber wall.

In some applications, the device is configured to be implanted within the mitral valve, the anchor is configured to be implanted within the coronary sinus, and the connector traverses the left atrium wall.

In some applications, the system further includes a delivery catheter. The device, the connector, and the anchor are each compactable within the delivery catheter.

In some applications, the delivery catheter is configured to be delivered via a transfemoral, subclavian, transapical, transseptal, or transaortic approach.

The methods herein, e.g., delivery of the systems/devices herein, can be performed on a living animal or on a simulation, such as on a cadaver, cadaver heart, simulator (e.g., with the body parts, heart, tissue, etc. being simulated), etc.

In some applications, a compressive device is for use within a heart valve. The compressive device includes an influent portion, an effluent portion, and a coaptation portion. The influent portion is capable of situating upon the influent face of a heart valve leaflet. The effluent portion is capable of situating upon the effluent face of a heart leaflet. In some applications, the coaptation portion connect the influent portion and the effluent portion. The influent portion and the effluent portion are capable of compressing together such that the stent can stabilize upon a heart valve leaflet when implanted. The stent is contoured to the shape of heart valve leaflet.

In some applications, the influent portion is capable of providing contact pressure onto a heart valve leaflet prolapse or flail.

In some applications, the compressive device is a wire form.

In some applications, the wire form is nitinol, cobalt-chrome (CoCr), stainless steel, titanium, polyglycolic acid (PGA), polylactic acid (PLA), poly-D-lactide (PDLA), polyurethane (PU), poly-4-hydroxybutyrate (P4HB), polycaprolactone (PCL), polyether ether ketone (PEEK), cyclic olefin copolymers (COCs), polyethylene vinyl acetate (EVA), polytetrafluorethylene (PTFE), perfluoroether (PFA), or fluorinated ethylene propylene (FEP).

In some applications, the wire form is compactible to fit within a delivery catheter.

In some applications, the wire form is self-expanding.

In some applications, the compressive device further includes a sheet that is attached upon the influent portion of wire form.

In some applications, the sheet has a length and a width to cover a prolapse or a flail of the heart valve leaflet.

In some applications, the sheet is capable of providing contact pressure onto a prolapse or a flail of the heart valve leaflet.

In some applications, the sheet is permeable, semipermeable, or impermeable.

In some applications, the sheet is a mesh.

In some applications, the sheet is poly(lactic-co-glycolic) acid (PLGA), polyvinylchloride (PVC), polyethylene (PE), polypropylene (PP), polytetrafluoroethylene (PTFE), polyurethane (PU), polyethylene terephthalate (PET), polyethersulfone (PES), polyglycolic acid (PGA), polylactic acid (PLA), poly-D-lactide (PDLA), poly-4-hydroxybutyrate (P4HB), or polycaprolactone (PCL).

In some applications, the compressive device further includes an extended coaptation portion that is capable of extending beyond a leaflet edge. The extended coaptation portion incorporates an impermeable sheet.

In some applications, the extended coaptation portion incorporates a thickened material. The impermeable sheet covers the thickened material, and the thickened material is capable of filling a gap within the aperture of a heart valve when it is closed.

In some applications, the extended coaptation portion includes a bent angle.

In some applications, the compressive device further includes an anchor capable of anchoring within vasculature and a connector or an anchor receiver that connect the compressive device and the anchor.

In some applications, the anchor is a wire stent.

In some applications, the anchor is a pin fastener.

In some applications, the anchor is a wire fastener that clasps a wire.

In some applications, the connector or anchor receiver comprises one or more of a rivet, suture, staple, wire, pin, shaft, sheet, mesh, housing, tubular member, cross-bar, etc.

In some applications, the compressive device is configured to be implanted within a mitral valve, a tricuspid valve, an aortic valve, or a pulmonic valve.

In some applications, the anchor is configured to be implanted within vasculature nearby the valve, and wherein the connector is traverse to a chamber wall.

In some applications, the compressive device is configured to be implanted within the mitral valve, the anchor is configured to be implanted within the coronary sinus, and the connector is traverse the left atrium wall.

In some applications, the compressive device further comprises a delivery catheter and the compressive device is compacted within the delivery catheter.

In some applications, the delivery catheter is configured to be delivered via a transfemoral, subclavian, transapical, transseptal, or transaortic approach.

The methods herein, e.g., delivery of the systems/devices herein, can be performed on a living animal or on a simulation, such as on a cadaver, cadaver heart, simulator (e.g., with the body parts, heart, tissue, etc. being simulated), etc.

In some applications, a bar device is for use within a heart mitral valve. The bar device includes an arched bar. The bar device includes a hook or latch on each of the two distal ends of the arched bar that are capable of hooking or latching into the commissures of a mitral valve. The bar device includes an anchor capable of anchoring within vasculature. And the bar device includes a connector that connects the arched bar and the anchor.

In some applications, the anchor is a wire stent.

In some applications, the anchor is a pin fastener.

In some applications, the anchor is a wire fastener that clasps a wire.

In some applications, the connector comprises one or more of a rivet, suture, staple, wire, pin, shaft, sheet, mesh, housing, tubular member, cross-bar, etc.

In some applications, a sheet is extended from the arched bar.

In some applications, a gap filler/spacer/coaptation element is extended from the arched bar.

In some applications, the arched bar is a telescoping bar comprising an inner bar and an outer. The inner bar is capable of sliding within the outer bar such that the length of the telescoping bar is adjustable.

In some applications, a method is provided to deliver a system (e.g., a leaflet repair system, an arrestor system, a prolapse repair system, a flail repair system, a repair system, etc.) to a native valve (e.g., mitral valve, tricuspid valve, etc.) via transcatheter delivery. In some applications, the method includes guiding a puncture catheter or other puncture device (e.g., via a first guide wire, etc.) to vasculature of the heart (e.g., coronary sinus, coronary artery, etc.) adjacent a chamber of the heart (e.g., an atrium, a ventricle, etc.). The method includes puncturing the vasculature (e.g., coronary sinus, etc.) luminal wall and the chamber wall (e.g., atrium wall, etc.). The method includes guiding a delivery catheter (e.g., via a second guide wire, etc.) into the chamber (e.g., atrium, etc.) via the puncture in the vasculature (e.g., coronary sinus, etc.) luminal wall and the chamber wall (e.g., atrium wall, etc.).

In some applications, the method includes releasing a device (e.g., a repair device, a leaflet repair device, an arrestor, etc.) from the delivery catheter within the chamber (e.g., within the atrium, etc.). The method includes situating, using the delivery catheter, the device onto a portion of the leaflet (e.g., a posterior leaflet, etc.) of the native valve (e.g., mitral valve, tricuspid valve, etc.) that is experiencing prolapse or flail.

In some applications, the method includes releasing a connector or an interface and an anchor from the delivery system such that the anchor is within the vasculature (e.g., coronary sinus, etc.) and the connector or interface connects the device to the anchor traversing the vasculature (e.g., coronary sinus, etc.) luminal wall and the chamber wall (e.g., atrium wall, etc.).

In some applications, the delivery catheter reaches the vasculature (e.g., coronary sinus, etc.) via a transfemoral, a subclavian, a transapical, a transseptal, or a transaortic approach.

The above method(s) can be performed on a living animal or on a simulation, such as on a cadaver, cadaver heart, simulator (e.g., with the body parts, heart, tissue, etc. being simulated), etc.

In some applications, a method is to deliver a compressive device (e.g., stent, clasp, form, etc.) to a native valve (e.g., mitral valve, etc.) via transcatheter delivery. In some applications, the method includes guiding a puncture catheter or other puncture device (e.g., via a first guide wire, etc.) to vasculature of the heart (e.g., coronary sinus, coronary artery, etc.) adjacent a chamber of the heart (e.g., an atrium, a ventricle, etc.). In some applications, the method incudes puncturing the vasculature luminal wall (e.g., coronary sinus luminal wall, coronary artery luminal wall, etc.) and the chamber wall (e.g., atrium wall, ventricular wall, etc.).

In some applications, the method includes guiding a delivery catheter (e.g., via a second guide wire, etc.) into the chamber (e.g., atrium, ventricle, left atrium, left ventricle, etc.) via the puncture in the vasculature luminal wall and the chamber wall.

In some applications, the method includes releasing a compressive device from the delivery catheter within the chamber (e.g., within the atrium or ventricle).

In some applications, the method includes using the delivery catheter (e.g., an actuator associated therewith) to compress the compressive device onto a portion of a posterior leaflet or other leaflet of the native valve (e.g., mitral valve, etc.) that is experiencing prolapse or flail.

In some applications, the method further includes releasing a connector or an interface and an anchor from the delivery system such that the anchor is within the vasculature (e.g., coronary sinus, etc.) and the connector or interface connects the compressive device to the anchor traversing the vasculature (e.g., coronary sinus, etc.) luminal wall and the chamber wall (e.g., atrium wall, etc.).

In some applications, the delivery catheter reaches the vasculature (e.g., coronary sinus, etc.) via a transfemoral, a subclavian, a transapical, a transseptal, or a transaortic approach.

In some applications, a gap filler/coaptation element/spacer system is configured for use within a heart valve. The gap filler/coaptation element/spacer system includes a gap filler, coaptation element, or spacer capable of expanding within gaps of a heart valve aperture when the valve is closed to fill any gaps in the valve and prevent or inhibit valvular regurgitation. The gap filler/coaptation element/spacer system includes an anchor capable of anchoring within vasculature. The gap filler/coaptation element/spacer system includes a connector or anchor receiver that connects the gap filler/coaptation element/spacer and the anchor.

In some applications, the gap filler/coaptation element/spacer comprises poly(lactic-co-glycolic) acid (PLGA), polyvinylchloride (PVC), polyethylene (PE), polypropylene (PP), polytetrafluoroethylene (PTFE), polyurethane (PU), polyethylene terephthalate (PET), polyethersulfone (PES), polyglycolic acid (PGA), polylactic acid (PLA), poly-D-lactide (PDLA), poly-4-hydroxybutyrate (P4HB), or polycaprolactone (PCL).

In some applications, the anchor is a wire stent.

In some applications, the anchor is a pin fastener.

In some applications, the anchor is a wire fastener that clasps a wire.

In some applications, the connector or anchor receiver comprises one or more of a rivet, suture, staple, wire, pin, shaft, sheet, mesh, housing, tubular member, cross-bar, etc.

In some applications, the gap filler/coaptation element/spacer is configured to be implanted within a mitral valve, a tricuspid valve, an aortic valve, or a pulmonic valve.

In some applications, the anchor is configured to be implanted within vasculature nearby the valve, and wherein the connector traverses a chamber wall.

In some applications, the device (e.g., repair device, leaflet repair device, arrestor, etc.) is configured to be implanted within the mitral valve, the anchor is configured to be implanted within the coronary sinus, and the connector traverses the left atrium wall.

In some applications, the gap filler/coaptation element/spacer system further includes a delivery catheter. The gap filler/coaptation element/spacer, the connector, and the anchor are each compactable and/or otherwise configured to fit within the delivery catheter.

In some applications, the delivery catheter is configured to be delivered via a transfemoral, subclavian, transapical, transseptal, or transaortic approach.

The above method(s) can be performed on a living animal or on a simulation, such as on a cadaver, cadaver heart, simulator (e.g., with the body parts, heart, tissue, etc. being simulated), etc.

In some applications, a system (e.g., a leaflet repair system, an arrestor system, a prolapse repair system, a flail repair system, a repair system, etc.) is for use within a heart valve for providing contact pressure onto a leaflet. The system includes a device (e.g., a repair device, a leaflet repair device, an arrestor, etc.) having a contact face capable of providing contact pressure onto an influent face of a heart valve leaflet. The system includes an anchor attached to the device capable of anchoring within tissue of the leaflet, the annulus, or chamber wall.

In some applications, the contact face can be contoured to help provide appropriate contact pressure.

In some applications, the contact face of the device has a length and a width to cover a prolapse or a flail of the heart valve leaflet.

In some applications, the contact face of the device is capable of providing contact pressure onto a prolapse or a flail of the heart valve leaflet.

In some applications, the system includes a coaptation portion that is extended from the contact face. The coaptation portion is capable of extending the length of the device into coaptation area of the valve.

In some applications, the coaptation portion is capable of helping promote coaptation between the leaflets of the valve.

In some applications, the device is a wire form.

In some applications, the wire form is nitinol, cobalt-chrome (CoCr), stainless steel, titanium, polyglycolic acid (PGA), polylactic acid (PLA), poly-D-lactide (PDLA), polyurethane (PU), poly-4-hydroxybutyrate (P4HB), polycaprolactone (PCL), polyether ether ketone (PEEK), cyclic olefin copolymers (COCs), polyethylene vinyl acetate (EVA), polytetrafluorethylene (PTFE), perfluoroether (PFA), or fluorinated ethylene propylene (FEP).

In some applications, the wire form is compactible to fit within a delivery catheter.

In some applications, the wire form is self-expanding.

In some applications, the system includes undulating wire or intersecting wire to provide contact pressure onto a prolapse or a flail of the heart valve leaflet.

In some applications, the system includes a sheet that is attached upon the wire form. The sheet forms the contact face.

In some applications, the sheet has a length and a width to cover a prolapse or a flail of the heart valve leaflet.

In some applications, the sheet is capable of providing contact pressure onto a prolapse or a flail of the heart valve leaflet.

In some applications, the device contains an impermeable coaptation portion and a permeable non-coaptation portion.

In some applications, the impermeable coaptation portion is thickened.

In some applications, the impermeable coaptation portion is capable of being thickened at the site of implantation.

In some applications, the sheet is poly(lactic-co-glycolic) acid (PLGA), polyvinylchloride (PVC), polyethylene (PE), polypropylene (PP), polytetrafluoroethylene (PTFE), polyurethane (PU), polyethylene terephthalate (PET), polyethersulfone (PES), polyglycolic acid (PGA), polylactic acid (PLA), poly-D-lactide (PDLA), poly-4-hydroxybutyrate (P4HB), or polycaprolactone (PCL).

In some applications, the system includes a counterforce support opposite the coaptation area.

In some applications, the counterforce support is configured to engage a heart chamber wall.

In some applications, the anchor is a helical anchor, W-shaped anchor, a T-shaped anchor, or 1-turn spiral.

In some applications, the anchor is one or more helical anchors within a tubular compartment housing. The tubular compartment housing is connected the device.

In some applications, the one or more helical anchors is a single helical anchor coiled within itself that is compressed within the tubular compartment housing.

In some applications, the one or more helical anchors is two more helical anchors layered on top of one another in tandem and compressed within the tubular compartment housing.

In some applications, the one or more helical anchors is two more helical anchors comprising an inner helix (or inner helical anchor portion) and an outer helix (or outer helical anchor portion) and compressed within the tubular compartment housing.

In some applications, the two or more helical anchors are configured to embed within the tissue at two angles askew from each other.

In some applications, the system includes a fulcrum connected to the tubular compartment housing such that the plane of the device contact face is adjustable.

In some applications, the system includes a sliding mechanism incorporated on edges of the tubular compartment housing such that the plane of the device contact face is adjustable.

In some applications, the system includes a swing hinge or a soft hinge connected to the device.

In some applications, the device incorporates an internal gap in coaptation area of the device. The internal gap is free of wire form.

In some applications, the device incorporates a gap filler, coaptation element, or spacer.

In some applications, the gap filler/coaptation element/spacer comprises material selected from: foam, hydrogel, or silicone.

In some applications, the gap filler/coaptation element/spacer comprises a scissor mechanism or a coil.

In some applications, the device incorporates an expandable stent.

In some applications, the device is configured to be implanted within the mitral valve.

In some applications, the system includes a delivery catheter, wherein the device and the anchor are each compactable within the delivery catheter.

In some applications, the delivery catheter is configured to be delivered via a transfemoral, subclavian, transapical, transseptal, or transaortic approach.

In some applications, the device and the anchor are configured to be delivered via a transcatheter procedure through a coronary sinus to a mitral valve.

In some applications, a netting system is for used within a heart valve. The netting system includes a netting device having a netting with a contact face capable providing contact pressure onto an influent face of a heart valve leaflet. The lateral edges of the netting device are capable of situating within a heart valve crevice. The netting system includes an anchor attached to the netting and capable of anchoring within tissue of the leaflet, the annulus, or chamber wall.

In some applications, the netting is poly(lactic-co-glycolic) acid (PLGA), polyvinylchloride (PVC), polyethylene (PE), polypropylene (PP), polytetrafluoroethylene (PTFE), polyurethane (PU), polyethylene terephthalate (PET), polyethersulfone (PES), polyglycolic acid (PGA), polylactic acid (PLA), poly-D-lactide (PDLA), poly hydroxybutyrate (P4HB), or polycaprolactone (PCL).

In some applications, the anchor is a helical anchor configured to be housed within a tubular compartment connected to the netting device.

In some applications, the netting system includes a tether that extends from a coaptation portion of the netting device.

In some applications, the netting system includes a wire form outlining the netting.

In some applications, the netting device is configured to be implanted within a mitral valve, a tricuspid valve, an aortic valve, or a pulmonic valve.

In some applications, the netting system includes a delivery catheter. The netting device and the anchor are each compactable within the delivery catheter.

In some applications, a method of repairing a native heart valve of a heart comprises advancing a delivery catheter transvascularly to the native heart valve, advancing an anchor (which can be the same as or similar to any anchors or securing features described herein) from the delivery catheter into tissue of the heart, thereby anchoring a leaflet repair implant/device (which can be the same as or similar to any implants/devices described herein) to the tissue, and releasing the leaflet repair implant/device from the delivery catheter, such that the leaflet repair implant/device extends along a portion of a leaflet of the native heart valve.

In some applications, advancing the anchor from the delivery catheter into tissue of the heart thereby anchoring the leaflet repair implant/device to the tissue is done prior to releasing the leaflet repair implant from the delivery catheter, such that the leaflet repair implant extends along a portion of the leaflet of the native heart valve.

In some applications, advancing the anchor from the delivery catheter into tissue of the heart thereby anchoring the leaflet repair implant to the tissue is done subsequently to releasing the leaflet repair implant from the delivery catheter, such that the leaflet repair implant extends along a portion of the leaflet of the native heart valve.

In some applications, advancing a delivery catheter transvascularly to the native heart valve is done via a transfemoral, a subclavian, a transapical, a transseptal, or a transaortic approach.

In some applications, advancing a delivery catheter transvascularly to the native heart valve is done via a transseptal approach across an atrial septum, and wherein the native heart valve is a mitral valve.

In some applications, the anchor is a helical anchor and advancing the anchor from the delivery catheter into tissue of the heart thereby anchoring the leaflet repair implant/device to the tissue includes rotating the helical anchor into the tissue. Other types of anchors are also possible.

In some applications, the tissue is part of an annulus of the native heart valve, and wherein rotating the helical anchor into the tissue includes rotating the helical anchor into the annulus of the native heart valve.

In some applications, releasing the leaflet repair implant/device from the delivery catheter, such that the leaflet repair implant/device extends along the portion of the leaflet of the native heart valve, includes releasing the leaflet repair implant/device from the delivery catheter, such that the leaflet repair implant/device extends along and applies a contact pressure to at least one of a prolapse portion of the leaflet and a flail portion of the leaflet.

In some applications, releasing the leaflet repair implant/device from the delivery catheter includes transitioning the leaflet repair implant/device from a compressed delivery configuration inside the delivery catheter to an expanded configuration outside of the delivery catheter.

In some applications, the leaflet repair implant/device is a contact pressure implant configured to apply a contact pressure to a native leaflet. The implant/device can be the same as or similar to any of the implants/devices described anywhere herein that apply a contract pressure to a leaflet of a native valve.

In some applications, the leaflet repair implant/device is a compressive implant/device and releasing the leaflet repair implant from the delivery catheter includes attaching the compressive implant/device to the leaflet such that a portion of the leaflet experiencing prolapse, flail, or rigidity is compressed between an influent side (e.g., a side attached to or in contact with an influent side of the leaflet) and an effluent side (e.g., a side attached to or in contact with an effluent side of the leaflet) of the compressive device. The compressive implant/device can be the same as or similar to any of the implants/devices described anywhere herein that apply a compressive force to or compress a leaflet of a native valve.

In some applications, the leaflet repair implant/device is a bar implant/device, and wherein releasing the leaflet repair implant from the delivery catheter includes securing ends of the bar device into commissures of the native heart valve.

The bar implant/device can be the same as or similar to any of the implants/devices described anywhere herein that comprise a bar, elongate extension, arch, arched bar, etc.

In some applications, the leaflet repair implant/device is a netting implant/device releasing the leaflet repair implant/device from the delivery catheter includes releasing the netting implant/device from the delivery catheter. The netting implant/device can be the same as or similar to any of the implants/devices described anywhere herein that include a netting.

There is further provided, in accordance with some applications, a system and/or an apparatus for use with a valve of a heart of a subject (e.g., a native valve, mitral valve, tricuspid valve, other valve, etc.), the heart having a chamber upstream of the valve, and the system/apparatus including an implant, an anchor, a catheter, and a delivery tool. The implant can include an interface, and/or a flexible wing. The wing can be coupled to the interface. The wing can have a contact face and an opposing face opposite the contact face. The catheter is typically, transluminally advanceable to the chamber, and configured to house the implant.

The delivery tool can comprise a shaft, engaged with the interface. The shaft can be configured, via engagement with the interface, to deploy the implant out of the catheter such that, within the chamber, the wing extends away from the interface. Alternatively or additionally, the shaft can be configured to position the implant in a position in which the interface is at a site in the heart, the wing extends over a first leaflet of the heart toward at least one opposing leaflet (e.g., an opposing leaflet portion) of the heart, and the contact face faces the first leaflet.

The delivery tool can comprise a driver, engaged with the anchor, and configured to secure the implant in the position by using the anchor to anchor the interface to tissue of the heart.

In some applications, the implant does not include a downstream anchor.

In some applications, the implant includes exactly one anchor.

In some applications, the contact face is concave.

In some applications, the catheter is configured to house the implant while the wing is constrained within the catheter.

In some applications, the driver is configured to secure the implant in the position by using the anchor to anchor the interface at the site.

In some applications, the site is on an annulus of the valve, the delivery tool is configured to position the implant in the position in which the interface is at the site on the annulus, and the driver is configured to secure the implant in the position by using the anchor to anchor the interface to tissue of the annulus.

In some applications, the site is on a wall of the chamber, the delivery tool is configured to position the implant in the position in which the interface is at the site on wall of the chamber, and the driver is configured to secure the implant in the position by using the anchor to anchor the interface to tissue of the wall of the chamber.

In some applications, the chamber is an upstream chamber, the heart has a downstream chamber downstream of the valve, the delivery tool is configured to press the interface against the first leaflet such that the first leaflet becomes sandwiched between the delivery tool and a wall of the downstream chamber, and the driver is configured to anchor the interface by driving the anchor through the first leaflet and into the wall of the downstream chamber.

In some applications, the driver is configured to secure the implant in the position by driving the anchor through the first leaflet and into the tissue of the heart.

In some applications, the shaft is configured, via the engagement with the interface, to deploy the wing entirely out of the catheter, and the driver is configured to secure the implant in the position subsequently to the shaft deploying the wing entirely out of the catheter.

In some applications, the shaft is configured, via the engagement with the interface, to deploy the implant entirely out of the catheter, and the driver is configured to secure the implant in the position subsequently to the shaft deploying the implant entirely out of the catheter.

In some applications, the driver extends through the shaft.

In some applications, the shaft is configured, via the engagement with the interface, to deploy the implant out of the catheter while the driver is disposed within the shaft.

In some applications, the shaft is configured, via the engagement with the interface, to deploy the implant out of the catheter while the anchor is disposed within the shaft.

In some applications, the implant is configured to be housed within the catheter with the wing distal to the interface.

In some applications, the shaft is configured to deploy the implant out of the catheter such that the wing becomes exposed from the catheter prior to the interface.

In some applications, the implant includes an anchor receiver at the interface (e.g., the interface can comprise an anchor receiver), and the driver is configured to anchor the interface to the tissue by using the anchor to anchor the anchor receiver to the tissue.

In some applications, the interface defines a space therein, and the anchor receiver is disposed in the space.

In some applications, the implant includes a housing that defines at least part of the interface and at least part of the anchor receiver.

In some applications, the housing includes a lateral wall that circumscribes an aperture, and the lateral wall defines the interface.

In some applications, the housing defines an obstruction that protrudes at least partway across the aperture, and the driver is configured to anchor the interface to the tissue by driving the anchor through the housing until the anchor presses the obstruction toward the tissue.

In some applications, the lateral wall and the shaft define respective engagement elements, the shaft being engaged with the interface via engagement between the engagement elements of the shaft and the engagement elements of the lateral wall.

In some applications, the driver is configured to anchor the anchor receiver to the tissue by anchoring the anchor to the anchor receiver and to the tissue.

In some applications, the driver is configured to anchor the anchor to the anchor receiver by driving the anchor through the anchor receiver.

In some applications, the anchor includes a tissue-engaging element and a head, the anchor receiver defines an aperture therethrough, and includes an obstruction that protrudes medially into the aperture in a manner that facilitates passage of the tissue-engaging element through the aperture but inhibits obstructs passage of the head through the aperture, and the driver is configured to anchor the anchor to the anchor receiver by driving the tissue-engaging element through the anchor receiver until the head of the anchor becomes obstructed by the obstruction.

In some applications, the obstruction includes a cross-bar that traverses the aperture.

In some applications, the obstruction includes a collar.

In some applications, the obstruction includes a sheet that is penetrable by the tissue-engaging element.

In some applications, the tissue-engaging element is a helical tissue-engaging element, and the driver is configured to drive the tissue-engaging element through the anchor receiver by screwing the tissue-engaging element through the anchor receiver.

In some applications, the position is a first position, the site is a first site, and via the engagement with the interface, the shaft is configured to, after placing the implant in the first position, reposition the implant into a second position in which the interface is at a second site in the heart, the wing extends over the first leaflet toward the opposing leaflet, and the contact face faces the first leaflet, the second position being different from the first position, and the second site being different from the first site.

In some applications, the shaft is configured to reposition the implant into the second position while the wing remains entirely outside of the catheter.

In some applications, the shaft is configured to reposition the implant into the second position while the implant remains entirely outside of the catheter.

In some applications, the wing includes a frame and a sheet spread over the frame.

In some applications, the frame includes at least one frame material selected from the group consisting of: of nitinol, cobalt-chrome, stainless steel, titanium, polyglycolic acid, polylactic acid, poly-D-lactide, polyurethane, poly-4-hydroxybutyrate, polycaprolactone, polyether ether ketone, a cyclic olefin copolymer, polyethylene vinyl acetate, poly-tetrafluorethylene, a perfluoroether, and fluorinated ethylene propylene.

In some applications, the frame is compactible to fit within the catheter.

In some applications, the frame is self-expanding.

In some applications, the frame is attached to the interface.

In some applications, the sheet includes at least one sheet material selected from the group consisting of: poly(lactic-co-glycolic) acid, polyvinylchloride, polyethylene, polypropylene, polytetrafluoroethylene, polyurethane, polyethylene terephthalate, polyethersulfone, polyglycolic acid, polylactic acid, poly-D-lactide, poly-4-hydroxybutyrate, and polycaprolactone.

In some applications, the wing has a root that is coupled to the interface, a tip at an opposite end of the wing from the root, and two lateral sides extending from the root to the tip.

In some applications, the chamber is an upstream chamber, the heart has a downstream chamber downstream of the valve, and an angular disposition of the wing with respect to the interface is such that positioning, by the shaft, of the implant in the position disposes the tip within the downstream chamber.

In some applications, the first leaflet has a lip, and an angular disposition of the wing with respect to the interface is such that positioning, by the shaft, of the implant in the position disposes the tip downstream of the lip of the first leaflet.

In some applications, the frame defines two loops extending from the root alongside each other.

In some applications, the two loops extend alongside each other from the root to the tip.

In some applications, the frame connects the two loops to each other only at the interface.

In some applications, the sheet is spread over the frame such that the sheet extends over and between the two loops.

In some applications, each of the loops circumscribes a space that is substantially absent of frame components.

In some applications, each of the loops is substantially teardrop-shaped. In some applications, each of the loops is substantially oval, ovoid, or triangular.

In some applications, the wing is curved in the direction of the valve leaflet. In some applications, the wing curves from the interface in one direction and then curves in the opposite direction moving toward the end.

In some applications, the frame defines an elongate space between the two loops, extending from the root toward the tip, and the sheet is spread over the frame such that the sheet extends across the two loops and the space.

In some applications, the elongate space runs along a plane of reflectional symmetry of the wing.

In some applications, the elongate space extends from the root to the tip, such that the frame does not bridge the two loops at the tip.

In some applications, the sheet has a plurality of holes therethrough.

In some applications, the holes are polygonal and are tessellated.

In some applications, the holes are hexagonal.

In some applications, a curvature of the wing is such that, in a cross-section of the implant through the interface and the wing, the contact face is concave.

In some applications, in the cross-section of the implant, the curvature of the wing increases with distance from the interface.

In some applications, the cross-section is in a plane of reflectional symmetry of the implant.

In some applications, the implant further includes a counterforce support, extending from the interface and away from the wing.

In some applications, the counterforce support is shaped such that, in the position, the counterforce support lies against a wall of the chamber.

In some applications, the catheter has a distal opening, and is configured to house the implant with the wing disposed distally from the interface, and the interface disposed distally from the counterforce support.

In some applications, the counterforce support includes a wire loop.

In some applications, the shaft is configured to be engaged with the interface within the catheter such that the shaft extends, within the catheter, proximally away from the interface and past the counterforce support.

In some applications, the anchor is a first anchor, and the system/apparatus further includes a second anchor that is configured to anchor the interface to the tissue.

In some applications, the driver is configured to secure the implant in the position by using the second anchor to anchor the interface to the tissue.

In some applications, the driver is a first driver, and the delivery tool further includes a second driver, engaged with the second anchor, and configured to secure the implant in the position by using the second anchor to anchor the interface to the tissue.

In some applications, the anchor includes a helical tissue-engaging element, and the driver is configured to secure the implant in the position by screwing the tissue-engaging element into the tissue.

In some applications, the tissue-engaging element is a first tissue-engaging element, and the anchor further includes a second helical tissue-engaging element, the first tissue-engaging element and the second tissue-engaging element arranged as a double helix.

In some applications, the anchor has a proximal end and a distal end, and each of the first tissue-engaging element and the second tissue-engaging element has a sharpened distal tip at the distal end of the anchor, and is shaped as a conic helix that widens toward the distal end of the anchor.

In some applications, the first tissue-engaging element is defined by a first wire, and the second tissue-engaging element is defined by a second wire.

In some applications, along a longitudinal axis of the anchor, the anchor has: a tissue-engaging region in which: a first wire defines the first tissue-engaging element, a second wire defines the second tissue-engaging element, and the first wire and the second wire each has a tissue-engaging pitch that is such that, within the double helix, turns of the first wire are axially spaced apart from turns of the second wire.

In some applications, the anchor also has a head region in which the first wire and the second wire each has a head pitch that is such that, within the double helix, turns of the first wire abut turns of the second helix. The head region can also be arranged along the longitudinal axis of the anchor.

In some applications, the tissue-engaging pitch of the first wire is at least 4 times greater than a thickness of the first wire.

In some applications, the anchor includes a wire that has a sharpened distal tip. In some applications, the wire has: a first helical portion that has a first pitch, and that defines a head of the anchor, and a second helical portion that has a second pitch that is greater than the first pitch, that defines the tissue-engaging element, and that terminates at the sharpened distal tip. In some applications, the first pitch configures the first helical portion to resist being screwed into the tissue.

In some applications, the contact face is shaped to define leaflet-thickening elements, configured to induce thickening of the first leaflet where the wing extends over the first leaflet.

In some applications, the leaflet-thickening elements include protrusions.

In some applications, the leaflet-thickening elements include recesses.

There is further provided, in accordance with some applications, a method for use with a valve of a heart of a subject (e.g., a native valve, mitral valve, tricuspid valve, other valve, etc.), the heart having a chamber upstream of the valve, and the method including, within a catheter, advancing to the chamber (1) an implant that includes an interface and a flexible wing coupled to the interface, the wing having a contact face, and an opposing face opposite the contact face, and (2) a shaft engaged with the interface.

In some applications, the method further comprises, using the shaft to deploy the implant out of the catheter such that, within the chamber, the wing extends away from the interface.

In some applications, the method further comprises subsequently, using the shaft, positioning the implant in a position in which the interface is at a site in the heart, the wing extends over a first leaflet of the valve toward at least one opposing leaflet (e.g., an opposing leaflet portion) of the valve, and the contact face faces the first leaflet.

In some applications, the method further comprises subsequently securing the implant in the position by anchoring the interface to tissue of the heart.

In some applications, advancing the implant to the chamber includes advancing the implant to the chamber while the wing is constrained within the catheter.

In some applications, the wing has a root that is coupled to the interface, and a tip at an opposite end of the wing from the root, the chamber is an upstream chamber, the heart has a downstream chamber downstream of the valve, and positioning the implant in the position includes positioning the implant such that the tip is disposed within the downstream chamber.

In some applications, the wing has a root that is coupled to the interface, and a tip at an opposite end of the wing from the root. In some applications, the first leaflet of the valve has a lip, and positioning the implant in the position includes positioning the implant such that the tip is disposed downstream of the lip of the first leaflet.

In some applications, the contact face is concave, and positioning the implant in the position includes positioning the implant such that the concave contact face contacts the first leaflet.

In some applications, positioning the implant in the position includes positioning the implant such that the opposing face contacts the opposing leaflet.

In some applications, the valve is a mitral valve of the heart, the chamber is a left atrium of the heart, and advancing the implant to the chamber includes advancing the implant to the left atrium.

In some applications, the valve is a tricuspid valve of the heart, the chamber is a right atrium of the heart, and advancing the implant to the chamber includes advancing the implant to the right atrium.

In some applications, the valve is an aortic valve of the heart, the chamber is a left ventricle of the heart, and advancing the implant to the chamber includes advancing the implant to the left ventricle.

In some applications, the valve is a pulmonary valve of the heart, the chamber is a right ventricle of the heart, and advancing the implant to the chamber includes advancing the implant to the right ventricle.

In some applications, the site is on an annulus of the valve, and anchoring the interface to the tissue of the heart includes anchoring the interface to tissue of the annulus.

In some applications, the site is on a wall of the chamber, and anchoring the interface to the tissue of the heart includes anchoring the interface to tissue of the wall of the chamber.

In some applications, anchoring the interface to the tissue of the heart includes pinning the first leaflet to the tissue of the heart.

In some applications, the chamber is an upstream chamber, the heart has a downstream chamber downstream of the valve, positioning the implant in the position includes pressing the interface against the first leaflet such that the first leaflet becomes sandwiched between the delivery tool and a wall of the downstream chamber, and securing the implant in the position includes driving an anchor through the first leaflet and into the wall of the downstream chamber.

In some applications, anchoring the interface to the tissue includes using a driver to drive an anchor into the tissue.

In some applications, the anchor includes a tissue-engaging element, and using the driver to drive the anchor into the tissue includes using the driver to screw the tissue-engaging element into the tissue.

In some applications, the implant includes an anchor receiver at the interface, and the method further includes using the driver to anchor the anchor to the anchor receiver.

In some applications, anchoring the interface to the tissue includes using the driver to drive the anchor through the anchor receiver and into the tissue.

In some applications, the anchor includes a tissue-engaging element and a head, the anchor receiver defines an aperture therethrough, and includes an obstruction that protrudes medially into the aperture, and using the driver to drive the anchor through the anchor receiver and into the tissue includes using the driver to drive the tissue-engaging element beyond the obstruction until the head of the anchor becomes obstructed by the obstruction.

In some applications, the obstruction includes a cross-bar that traverses the aperture, and using the driver to drive the tissue-engaging element beyond the obstruction until the head of the anchor becomes obstructed by the obstruction includes using the driver to drive the tissue-engaging element beyond the cross-bar until the head of the anchor becomes obstructed by the cross-bar.

In some applications, the obstruction includes a collar, and using the driver to drive the tissue-engaging element beyond the obstruction until the head of the anchor becomes obstructed by the obstruction includes using the driver to drive the tissue-engaging element beyond the collar until the head of the anchor becomes obstructed by the collar.

In some applications, the obstruction includes a flexible sheet, and using the driver to drive the tissue-engaging element beyond the obstruction until the head of the anchor becomes obstructed by the obstruction includes using the driver to pierce the sheet with the tissue-engaging element, and to drive the tissue-engaging element through the sheet until the head of the anchor becomes obstructed by the sheet.

In some applications, the implant includes a housing that includes a lateral wall that circumscribes an aperture, the lateral wall defining at least part of the interface, and positioning the implant in the position includes positioning the implant in the position using the shaft while the shaft is engaged with the lateral wall.

In some applications, the implant defines an obstruction that protrudes at least partway across the aperture, and anchoring the interface to the tissue includes anchoring the housing to the tissue by using the driver to drive the anchor through the housing until the anchor presses the obstruction toward the tissue.

In some applications, the implant further includes a counterforce support, and deploying the implant out of the catheter includes deploying the implant out of the catheter such that the counterforce support extends from the interface and away from the wing.

In some applications, the position is a position in which the counterforce support lies against a wall of the chamber, and positioning the implant in the position includes positioning the implant in the position in which the counterforce support lies against the wall of the chamber.

In some applications, deploying the implant out of the catheter includes deploying, out of the catheter, the wing, followed by the interface, followed by the counterforce support.

In some applications, deploying the implant out of the catheter includes deploying the wing out of the catheter while the shaft extends, within the catheter, proximally away from the interface and past the counterforce support.

In some applications, positioning the implant in the position includes positioning the implant in the position subsequently to deploying the wing entirely out of the catheter.

In some applications, positioning the implant in the position includes positioning the implant in the position subsequently to deploying the implant entirely out of the catheter.

In some applications, the position is a first position, the site is a first site, and the method further includes, after placing the implant in the first position, repositioning the implant into a second position in which the interface is at a second site in the heart, the wing extends over the first leaflet toward the opposing leaflet, and the contact face faces the first leaflet, the second position being different from the first position, and the second site being different from the first site.

In some applications, the first site is a first site on an annulus of the valve and the second site is a second site on the annulus of the valve.

In some applications, repositioning the implant into the second position includes, using the shaft, sliding the interface along the annulus.

In some applications, repositioning the implant into the second position includes, using the shaft, lifting the interface away from the annulus at the first site, and replacing the interface against the annulus at the second site.

In some applications, repositioning the implant into the second position includes repositioning the implant into the second position prior to anchoring the interface to the tissue.

In some applications, the method further includes, subsequently to anchoring the interface to the tissue, de-anchoring the interface from the tissue, repositioning the implant into the second position includes repositioning the implant into the second position subsequently to de-anchoring the interface from the tissue, and the method further includes, subsequently to repositioning the implant into the second position, re-anchoring the interface to the tissue.

In some applications, the method further includes receiving information indicative of regurgitation through the valve while the implant is positioned at the first position, and repositioning the implant into the second position includes repositioning the implant into the second position responsively to receiving the information.

In some applications, the information is echocardiographic information, and repositioning the implant into the second position includes repositioning the implant into the second position responsively to receiving the echocardiographic information.

In some applications, repositioning the implant into the second position includes repositioning the implant into the second position while the wing remains entirely outside of the catheter.

In some applications, repositioning the implant into the second position includes repositioning the implant into the second position while the implant remains entirely outside of the catheter.

In some applications, the deploying the implant out of the catheter includes deploying the implant out of the catheter while the driver is disposed within the shaft.

In some applications, the deploying the implant out of the catheter includes deploying the implant out of the catheter while the anchor is disposed within the shaft.

The above method(s) can be performed on a living animal or on a simulation, such as on a cadaver, cadaver heart, simulator (e.g., with the body parts, heart, tissue, etc. being simulated), etc.

The present invention will be more fully understood from the following detailed description of applications thereof, taken together with the drawings, in which:

BRIEF DESCRIPTION OF THE DRAWINGS

FIGS. 3 and 4 are schematic illustrations of a heart valve leaflet flail and a heart valve leaflet prolapse, respectively, as a reference for various embodiments;

FIGS. 14 and 15 are schematic illustrations of an example gap filler, coaptation element, or spacer device implanted on a native valve;

FIGS. 20A-B, 21A-B, 22A-C, 23A-D, 24A-D, and 25-30 are schematic illustrations of example devices in accordance with some applications;

FIGS. 31A-31L are schematic illustrations of an example method to deliver a device to a native valve via a transcatheter procedure;

FIGS. 36-59 are schematic illustrations of example compressive devices;

DETAILED DESCRIPTION

Figure 1:
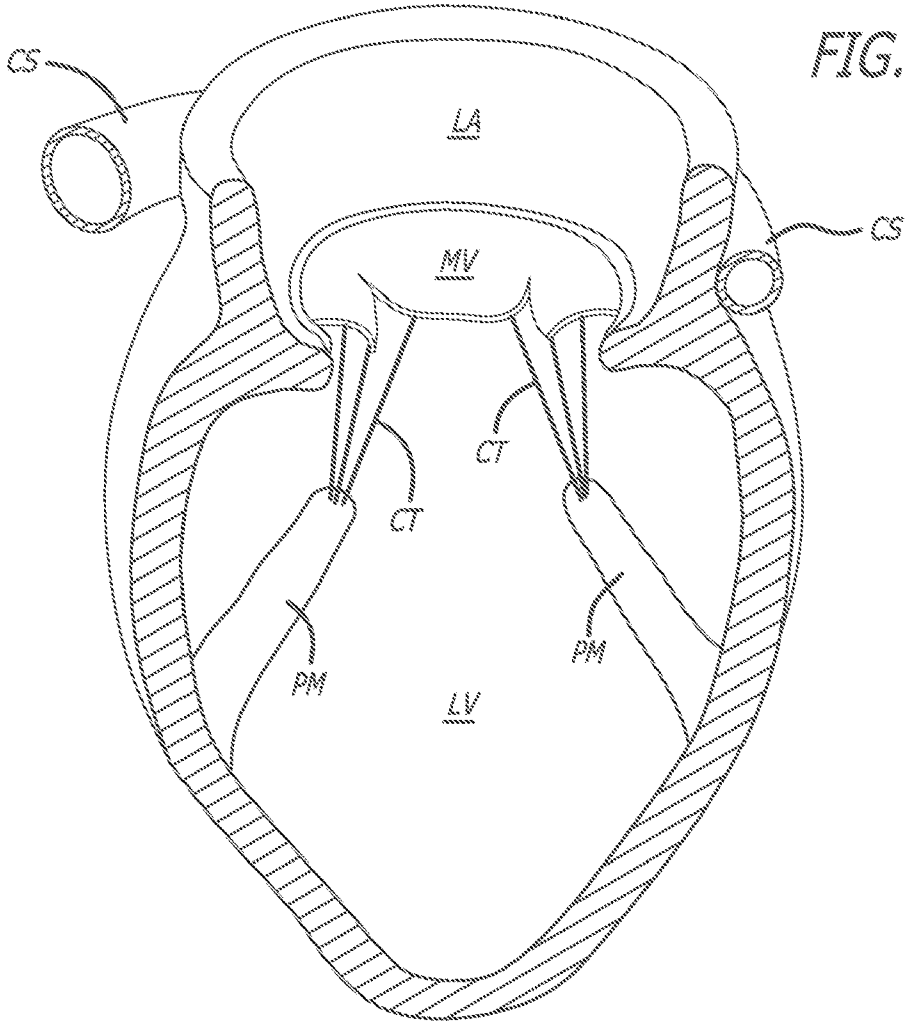
FIG. 1 is a schematic illustration of the left chambers of a heart as a reference for various embodiments.

Systems, apparatuses, devices, methods, etc. for mitigating heart valve regurgitation are described herein. In some applications, systems, apparatuses, devices, methods, etc. include implants/devices that situate within the valvular annulus and anchor within the annulus and/or nearby vasculature. The systems, apparatuses, devices, methods, etc. can be configured to provide contact pressure onto and/or support to the leaflet region experiencing flail, prolapse, rigidity, etc. In some applications, systems, apparatuses, devices, methods, etc. capable of compressing onto a leaflet and providing contact pressure onto and/or support to the leaflet region experiencing flail, prolapse, rigidity, etc. are described, e.g., compressive devices, clasps, splints, forms, etc. In some applications, systems, apparatuses, devices, etc. are described that further anchor to into the leaflet annulus or a nearby vasculature, the systems, apparatuses, devices, etc. providing contact pressure onto and/or support to the leaflet region experiencing flail, prolapse, rigidity, etc. Various examples of methods of delivering to and implanting systems, apparatuses, devices, etc. at the site of flail, prolapse, rigidity, etc. are described. An example of where these can be helpful is when used at the posterior leaflet of a mitral valve experiencing flail, prolapse, rigidity, and/or another issue.

The described systems, apparatuses, devices, methods, etc. should not be construed as limiting in any way. Instead, the present disclosure is directed toward all novel and nonobvious features and aspects of the various disclosed implementations and applications, alone and in various combinations and sub-combinations with one another. The disclosed systems, apparatuses, devices, methods, etc. are not limited to any specific aspect, feature, or combination thereof, nor do the disclosed systems, apparatuses, devices, methods, etc. require that any one or more specific advantages be present or problems be solved. Further, the techniques, methods, operations, steps, etc. described or suggested herein can be performed on a living animal (e.g., human, other mammal, etc.) or on a non-living simulation, such as on a cadaver, cadaver heart, simulator (e.g., with the body parts, tissue, etc. being simulated), anthropomorphic phantom, etc.

Various implementations of systems, devices, examples of prosthetic implants, etc. are disclosed herein, and any combination of the described features, components, and options can be made unless specifically excluded. For example, various descriptions of anchors, can be used with any appropriate prosthetic device, and/or delivered and implanted by any appropriate method, even if a specific combination is not explicitly described. Likewise, the different constructions and features of devices and systems can be mixed and matched, such as by combining any implant device type/feature, attachment type/feature, site of repair, etc., even if not explicitly disclosed. In short, individual components of the disclosed systems can be combined unless mutually exclusive or physically impossible.

Although the operations of some of the disclosed methods are described in a particular, sequential order for convenient presentation, it should be understood that this manner of description encompasses rearrangement, unless a particular ordering is required by specific language set forth below. For example, operations described sequentially can in some cases be rearranged or performed concurrently. Moreover, for the sake of simplicity, the attached figures may not show the various ways in which the disclosed systems, apparatuses, devices, methods, etc. can be used in conjunction with other systems, apparatuses, devices, methods, etc.

Figure 2:
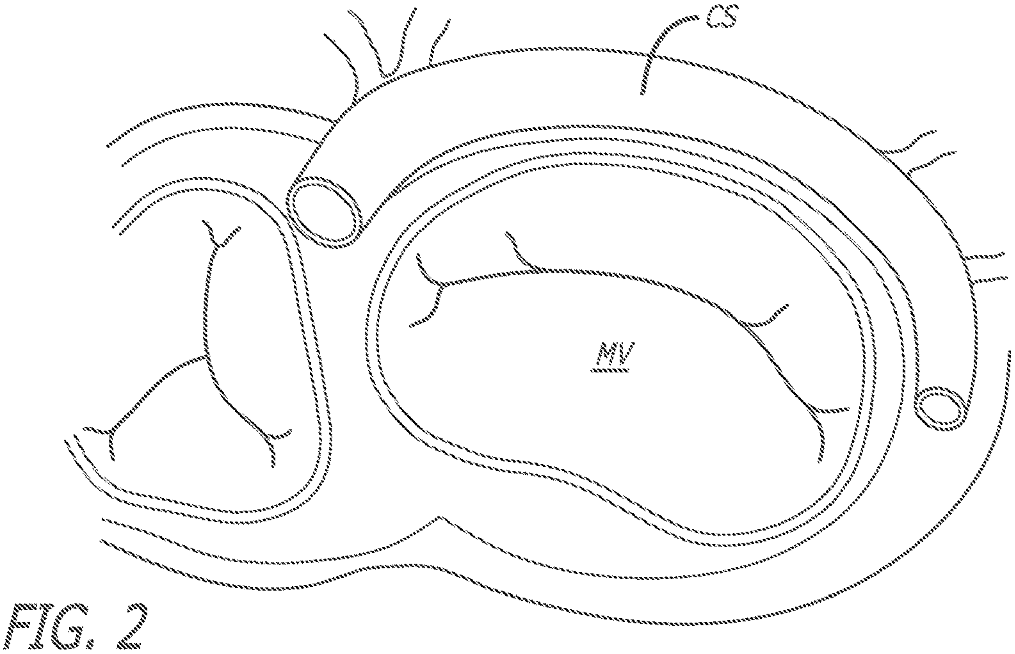
FIG. 2 is a schematic illustration of a mitral valve as a reference for various embodiments.

FIG. 1 is a coronal-plane view within the left chambers sectioning through the coaptation area of the mitral valve and FIG. 2 is a traverse-plane view within the left atrium superior to the mitral valve. The left ventricle (LV) is separated from the left atrium (LA) mitral valve (MV). Each of the four valves of the heart has flexible leaflets extending inward across the respective orifices that come together or "coapt" in the bloodstream to form the one-way, fluid-occluding surfaces. Accordingly, referring back to the left chambers, oxygenated blood is brought to the left atrium from the pulmonary vein (not shown) and then transferred across the mitral valve into the left ventricle. The left ventricle pumps the oxygenated passing through the aortic valve, into the aorta, and throughout the body.

Also shown in FIG. 1 are the papillary muscles (PM), which are attached to the left ventricle wall and connected to the mitral valve (MV) leaflets via the chordae tendineae (CT). These muscles and cords assist in the function of the mitral valve (MV) to open the leaflets to form an aperture, to coapt the leaflets to close the aperture, and to maintain leaflet shape and position.

FIG. 1 also shows the coronary sinus (CS), which is a vasculature that surrounds the left ventricle. Throughout the disclosure, the coronary sinus is used as an example as a nearby vasculature site for docking anchors for various implementations described.

FIG. 3 provides an example of leaflet flail and FIG. 4 provides an example of leaflet prolapse. Leaflet flail occurs when the coapting portion of the leaflet flips backwards against blood flow. Likewise, leaflet prolapse occurs when a portion of the leaflet protrudes backward. Flail and prolapse can occur due to various conditions, including (but not limited to) papillary muscle (PM) and/or chordae tendineae (CT) dysfunction. In the examples provided in FIG. 3 and FIG. 4, breaks in the chordae tendineae (CT) result in leaflet flail and prolapse, respectively. Leaflet flail and prolapse can also occur due to the chordae tendineae (CT) stretching out. Leaflet flail, prolapse, rigidity, and/or other leaflet issues can result in a failure of coaptation, resulting in regurgitant blood flow.

Throughout the document, description and drawings often refer to the left chambers, and specifically to the mitral valve (MV) and coronary sinus (CS), as examples for the various implementations described. It is to be noted, however, that the various implementations and applications described can be utilized on other valves (e.g., tricuspid valve, pulmonary valve, aortic valve, etc.) and other vasculature (e.g., coronary artery, etc.) mutatis mutandis, as can be appreciated by those skilled in the art.

Several implementations and applications herein are directed towards systems, apparatuses, devices, etc. (e.g., leaflet repair systems, arrestor systems, prolapse repair systems, flail repair systems, repair systems, etc.) that arrest or otherwise treat valve leaflet issues, such as flail, prolapse, rigidity, etc. In some applications, a system, apparatus, device, etc. herein is capable of being situated at the influent side of a valve such that it can apply contact pressure or support onto a region of flail, prolapse, rigidity, etc. The contact pressure or support provided by various implementations can help flatten out and/or reshape the flail, prolapse, rigidity, and/or abnormality, which helps to extend the coapting edge of a leaflet back towards the coaptation area when in a closed position. Proper coaptation that results in a fully closed valve prevents valve regurgitation. In some applications, the system, apparatus, device, etc. is configured to support, arrest, and/or depress a leaflet to prevent the leaflet from flailing or flipping towards the influent side of the valve. Likewise, in some applications, the system, apparatus, device, etc. is configured to support, arrest, and/or depress a leaflet to prevent the leaflet from prolapsing or from protruding or bulging towards the influent side of the valve.

In some applications, a system, apparatus, device, etc. herein (e.g., leaflet repair system, arrestor system, prolapse repair system, flail repair system, repair system, etc.) includes (but is not limited to) one face that is to directly contact the face of a leaflet experiencing leaflet issues, e.g., flail, prolapse, rigidity, etc. Typically, the influent face of a leaflet is the face that experiences flail, prolapse, rigidity, and/or other issues. In some applications, the contact face of the device is contoured to the influent face of a leaflet, which can be a hyperbolic paraboloid-like contour. In some applications, the contact face of the system/device provides contact pressure on a leaflet flail, prolapse, rigidity, and/or abnormality. In some applications, the contact face has a width and a length such that it can cover the region of the leaflet experiencing flail, prolapse, rigidity, and/or abnormality. In some applications, the length of the system/device extends into the coaptation area of the leaflet. In some applications, the coaptation portion of the system/device helps promote coaptation of the leaflets when closed.

In some applications, the system, apparatus, device, etc. herein includes an anchor to stabilize the system/device at the site of implantation. In some applications, a system/device includes a portion that is in connection with the anchor. In some applications, the anchor connection point (e.g., anchor receiver, etc.) is near or in contact with the valve annulus or a ventricle or atrium wall. In some applications, an anchor connection point includes a hinge capable of adjusting the plane of the contact face of the system/device relative to the anchoring point. In some applications, a swing hinge is utilized. In some applications, a hinge is made of soft compliable material (e.g., cloth or mesh) such that the plane of the system/device contact face is adjustable relative to the anchoring point. In some applications, a fulcrum is incorporated at the anchoring point such that the plane of the contact face is adjustable relative to the anchoring point. In some applications, sliding mechanisms are incorporated at the edges of the anchoring point such that the plane of the contact face is adjustable relative to the anchoring point.

In some applications, the anchor connection point or anchor receiver is configured as an interface. The interface can connect with a catheter or shaft for delivering and positioning the system/device.

In some applications, an anchor is situated near or in contact with the valve annulus, leaflet area, or atrium/ventricle wall. In some applications, an anchor is a helical anchor, screw, or other feature capable of screwing/rotating within or embedding within the valve annulus, leaflet, or atrium/ventricle wall.

In some applications, a helical anchor is housed within a tubular compartment, the tubular compartment connected to or a part of the device to be anchored. In some applications, the tubular compartment includes one, two, or more helixes or helical anchor portions therein to anchor the device. In some applications, the helix(es) or helical anchor portion(s) are pushed through the tubular compartment to screw or rotate within the tissue at the anchoring site. In some applications, the helix(es) or helical anchor portion(s) are compressible (e.g., like a spring) within the tubular compartment such that the tubular compartment maintains a low profile; the helix(es) or helical anchor portion(s) are decompressed as the helix(es) or helical anchor portion(s) are screwed or rotated within the tissue at the anchoring site. In some applications having a single helix or helical anchor portion within the housing, the helix or helical anchor portion is coiled within itself to maintain a very low profile. In some applications having two or more helix(es) or helical anchor portion(s) within the housing, the helix(es) or helical anchor portion(s) are layered on top of one another in tandem. In some applications having two or more helix(es) or helical anchor portion(s) within the housing, one helix or helical anchor portion is radially within the other helix or helical anchor portion such that there is at least one an inner helix or inner helical anchor portion and at least one outer helix or outer helical anchor portion. In some applications having two or more helix(es) or helical anchor portion(s) within the housing, the helix(es) or helical anchor portion(s) are configured to embed within the tissue at the anchoring site at two angles askew from each other.

In some applications, an anchor is situated near or in contact with the ventricle or atrium wall on the opposite side of the wall from the anchor connection point (e.g., within nearby vasculature). In some applications, a connector is utilized to connect the anchor, the connector traversing through the ventricle or atrium wall. Any appropriate connector can be utilized, such as (for example) a screw, rivet, suture, staple, wire, pin, or shaft. In some applications, a connector wire is utilized such that the wire tension between the device and the anchor is taut.

In some applications, an anchor is situated within vasculature that is on the opposite side of a chamber (i.e., ventricle or atrium) wall. For example, various implant or device implementations herein are configured to mitigate leaflet issues, such as flail, prolapse, and/or rigidity, of the mitral valve and thus are situated within the left atrium. In these various implementations, a device can be connected with an anchor situated within the coronary sinus utilizing a connector traversing through the atrial wall. Any appropriate anchor can be utilized. In some applications, an anchor is wire stent or wire form capable of expanding within vasculature. In some applications, an anchor is a pin fastener (e.g., R-pin, etc.) or wire fastener capable of pinning a device via a connector to the ventricle or atrium wall. In some applications, a pin or wire fastener is utilized on the opposite side of a ventricle or atrium wall and the connector traverses the wall. In some applications, a pin fastener is utilized within vasculature that is on the opposite of a ventricle or atrium wall. In some applications, a wire fastener is capable of pinching a connector wire to hold the wire in place and create tension between the wire fastener anchor and the device.

In some applications, a system and/or device is anchored utilizing a T-shaped anchor capable of fitting within and clinging to a crevice within the heart valve (e.g., cleft or commissure). In some applications, a T-shaped anchor has two arms (i.e., the cross portion of the T-shape) and connecting portion (i.e., the vertical portion of the T-shape). In some applications, the connecting portion is connected to a device to hold the device at the site of deployment. In some applications, the two arms are capable of contracting and expanding; in a contracted state the two arms are parallel (or near parallel) with the connecting portion and in the expanded state the two arms are orthogonal (or near orthogonal) with the connecting portion. In some applications, when the anchored is deployed, the two arms enter into the crevice in a contracted state and are expanded within a crevice within the heart valve and under the leaflet such that it is secured within the crevice.

In some applications, a system, implant, and/or device herein is additionally directly anchored or fastened to the leaflet experiencing issues, e.g., flail, prolapse, rigidity, and/or other issues. In some applications, an anchor is a pin fastener (e.g., R-pin, R-key, etc.) or wire fastener capable of pinning a device via a connector to the leaflet. In some applications, a pin or wire fastener is utilized on the effluent side of a leaflet (e.g., a ventricular side of an atrioventricular valve leaflet) and the connector traverses through the leaflet. In some applications, an anchored system/device has a length that extends from the anchor to the coapting edge of a leaflet, where a clamp is utilized to anchor the system/device to the leaflet edge by pinching or compressing the device edge and leaflet edge together.

In some applications, a system and/or device herein incorporates a tether or artificial chord for further stabilization at the site of implantation. In some applications, a tether or chord extends from the coaptation portion of a device to a pinning location on the effluent side of the valve, where the tether is pinned down. The pinning location can be any sturdy feature, such as (for example) ventricle wall, atrium wall, papillary muscle, and/or nearby vasculature.

In some applications, a system and/or device herein (e.g., leaflet repair system/device, arrestor system/device, prolapse repair system/device, flail repair system/device, repair system/device, etc.) comprises wire form frame and/or a wire form device (e.g., a device comprising a wire form frame). Any appropriate material to produce a wire form can be utilized, including (but not limited to) nitinol, cobalt-chrome (CoCr), stainless steel, titanium, polyglycolic acid (PGA), polylactic acid (PLA), poly-D-lactide (PDLA), polyurethane (PU), poly-4-hydroxybutyrate (P4HB), polycaprolactone (PCL), polyether ether ketone (PEEK), cyclic olefin copolymers (COCs), poly ethylene vinyl acetate (EVA), polytetrafluorethylene (PTFE), perfluoroether (PFA), fluorinated ethylene propylene (FEP), additives thereof, and derivatives thereof. In some applications, a wire form device or wire form frame is contractible, which is useful to fit within a catheter in a more compact or collapsed configuration for less invasive catheter delivery methodologies. In some applications, nitinol is utilized for its self-expanding properties, which can be useful to implant the device in less invasive catheter delivery methodologies.

Various shapes of wire form devices or wire form frames can be utilized in various different implementations and applications. In some applications, a wire form frame/device is shaped to have portions of the wire form provide contact pressure or support on the leaflet issue, e.g., on the flail, prolapse, and/or rigidity of a leaflet. In some applications, a wire form frame/device has length and width to surround an area of flail or prolapse and utilizes a sheet extending across the area to provide contact pressure on the flail, prolapse, rigidity, etc. In some applications, a wire form frame or wire form device has length and width to surround an area of flail or prolapse and utilizes wire that undulates or intersects across the area to provide contact pressure on the flail, prolapse, rigidity, etc. In some applications, a wire form frame or wire frame device is free of wire at an internal portion of the coaptation area devoid of wire such that any future procedures that may be needed at some later time can still be performed on the native leaflet coaptation area (e.g., edge to edge repair, such as suturing or clamping leaflet edges together). In some applications, a wire form frame or wire form device includes a support or counterforce support extending from the portion of the wire form device opposite of the coaptation area, which can help the wire form device provide contact pressure on the flail, prolapse, rigidity, etc. In some applications, the support or counterforce support is configured to contact a heart chamber wall (e.g., atrium or ventricle wall). In some applications, a wire form device includes an indentation or hook formed via the wire, which can help secure the device within the site of implantation by fitting within or hooking onto the commissures, clefts or other similar valve areas.

In some applications, a system and/or device herein (e.g., leaflet repair system/device, arrestor system/device, prolapse repair system/device, flail repair system/device, repair system/device, etc.) incorporates a sheet attached on a wire form capable of forming a contact face. In some applications, a sheet provides a surface capable of providing contact pressure or support onto a leaflet experiencing issues, such as flail, prolapse, and/or rigidity. A sheet can be impermeable, semipermeable, or permeable to fluids (e.g., blood or plasma). In some applications, the sheet is a mesh. In some applications, a mesh is formed utilizing interleaving strings that overlap and intersect. A mesh or permeable sheet can beneficially provide contact pressure/support without restricting the flow of blood or plasma, which can be important in various applications. For instance, an impermeable sheet may trap blood or plasma between the device and leaflet, which in turn might create undesired pressures with the valve and/or create pressures that dislodges the device or alters its position. In some applications, the sheet is partially an impermeable material and partially a permeable mesh. For instance, in some applications, a cooptation portion of a system/device herein utilizes an impermeable material while a non-coaptation portion of the device utilizes a permeable mesh. In some applications, the impermeable coaptation portion helps promote proper closure of a native valve when coapting. In some applications, a mesh is formed utilizing a mesh sheet. Any appropriate material can be utilized for a sheet and/or mesh, including (but not limited to) poly(lactic-co-glycolic) acid (PLGA), polyvinylchloride (PVC), polyethylene (PE), polypropylene (PP), polytetrafluoroethylene (PTFE), polyurethane (PU), polyethylene terephthalate (PET), polyethersulfone (PES), polyglycolic acid (PGA), polylactic acid (PLA), poly-D-lactide (PDLA), poly-4-hydroxybutyrate (P4HB), and polycaprolactone (PCL). Any appropriate means to attach a sheet and/or mesh onto a wire form can be utilized, including (but not limited to) stitching, staples, and glue. Optionally, in some applications, the sheet is a form-fitted cover that stretches across the wire form or wire form frame.

In some applications, a wire form device or a system/device having a wire form frame has a static portion and a dynamic portion. In some applications, the static portion is capable of situating within the valve and can include indents and or hooks to secure the device within the site of implantation by fitting with or hooking onto the commissures or other similar leaflet areas. In some applications, the dynamic portion includes a sheet to help provide contact pressure on and/or support to a leaflet, e.g., to address flail, prolapse, rigidity, etc. In some applications, the dynamic portion is capable of being repositioned and/or resized during the implantation process such that it can be adequately cover the leaflet region experiencing the flail, prolapse, rigidity, and/or other issue.

In some applications, the systems/devices are configured to help promote coaptation of the leaflets when closed. In some applications, a gap filler, coaptation element, or spacer is incorporated with the system/device. In some applications, the gap filler, coaptation element, or spacer extends from or within the coaptation portion, which can help fill gaps within the valve aperture. In some applications, the system/device includes an extended portion with an impermeable sheet that extends from the leaflet lip into the aperture, which can help form coaptation with the other leaflet(s). In some applications, the system/device includes an extended portion that is thickened, which acts as gap filler or spacer to help fill gaps within the valve aperture. Having a gap filler, coaptation element, or spacer is expected to beneficially help the systems/devices better treat functional mitral regurgitation by filling a gap in the valve.

In some applications, the systems/devices herein comprise an expandable gap filler, expandable coaptation element, or expandable spacer. The gap filler/coaptation element/spacer can be expandable in a variety of ways, e.g., via inflation, injection, filling, balloon-expansion, self-expansion (e.g., using a shape memory material), mechanical expansion, etc. Mechanisms of expanding the expandable gap filler/coaptation element/spacer herein can include any of the expansion mechanisms described herein, including (but not limited to) filling with a material (e.g., foam, hydrogel, or silicone), inflation, self-expansion, balloon-expansion, mechanical expansion, expanding via a stent (e.g., self-expanding, balloon, mechanical), expanding via a scissor mechanism or scissor like mechanism (e.g., with articulating joints), expanding via twisting a coil, and/or any combinations of these.

In some applications, systems/devices herein comprise a gap filler/coaptation element/spacer that is filled or is fillable with a material at the site of implantation, which can be done as the device is implanted or in a subsequent procedure (e.g., right after or after some time as passed, such as days, weeks, or months). Accordingly, in these applications, a material is delivered via a catheter to the device at the site of implantation and then the device is filled, injected, inflated, etc. with the material, and thus increase the size of the gap filler/coaptation element/spacer in vivo. Various materials can be utilized, such as (for example) a foam, hydrogel, or silicone. In some applications, a system/device with a gap filler/coaptation element/spacer includes a stent that encases the gap-filling portion of the device. Accordingly, a stent can be expanded at the site of implantation, which can be self-expanding (e.g., nitinol), expanded mechanically, or expanded via a balloon. The systems/devices can have a guide or guide wire that helps advance the catheter to the correct location on the gap filler/coaptation element/spacer to inject the material into the gap filler/coaptation element/spacer.

In some applications, a system/device with a gap filler, coaptation element, or spacer is expanded at the site of implantation utilizing mechanical expansion. For example, an expansion mechanism configured as a scissor or scissor-like mechanism (or mechanism with pivoting struts) within the gap filler/coaptation element/spacer portion could be used to cause the mechanical expansion, which can be done as the device is implanted or in a subsequent procedure. Accordingly, in these applications, the scissor or scissor-like mechanism (or mechanism with pivoting struts) can be expanded via hydraulic, pneumatic, mechanical, or magnetic means, and thus increase the size of the gap filler/coaptation element/spacer. In some applications, a catheter is delivered to the implant/device and provides a hydraulic, pneumatic, mechanical, or magnetic force to expand the expansion mechanism. In some applications, a magnetic force is applied externally of the body to expand the expansion mechanism. In some applications, a series of struts can be connected at a joint and articulate or move from a radially expanded configuration to a radially compressed configuration by the various struts articulating or moving at the joints, e.g., in a scissor-like movement.

In some applications, systems/devices with gap filler/coaptation element/spacer are mechanically expanded at the site of implantation utilizing a coil within the gap filler/coaptation element/spacer portion, which can be done as the device is implanted or in a subsequent procedure. Accordingly, in some applications, the circumference of the coil can be increased by twisting the coil, and thus increase the gap filler/coaptation element/spacer size. Various mean can be used to relieve tension as the coil is twisted, such as (for example) the coil contain a number of slits or furrows on the inner portion of the coil.

In some applications, systems/devices herein incorporate or comprise an impermeable cooptation portion and a permeable and/or open non-coaptation portion. In some applications, the impermeable coaptation portion extends into the coaptation area of the leaflet. In some applications, the impermeable coaptation portion is elongated to reach the effluent side of one or two of the opposing leaflets to help the leaflets coapt. In some applications, the impermeable coaptation portion contains or can be injected with a filler material that thickens the coaptation portion, which can help fill gaps within the valve aperture. In some applications, the impermeable coaptation portion is expanded at the site of implantation. Mechanisms of expanding the impermeable coaptation portion can include any of the expansion mechanisms described herein, including (but not limited to) filling with a material (e.g., foam, hydrogel, or silicone), inflation, self-expansion, balloon-expansion, mechanical expansion, expanding via a stent (e.g., self-expanding, balloon, mechanical), expanding via a scissor mechanism or scissor like mechanism (e.g., with articulating joints), expanding via twisting a coil, and/or any combinations of these.

Various implementations and applications of devices herein are to be used on any leaflet experiencing flail or prolapse. Accordingly, in some applications, a device is capable of being utilized on a leaflet of a mitral, a tricuspid, an aortic, and/or a pulmonic valve. Likewise, various implementations and applications of devices can be utilized on any area of the leaflet experiencing flail or prolapse. In some applications, a device is capable of being utilized on or near a leaflet commissure and/or any area between a leaflet's commissures.

To reach the site of implantation, any appropriate surgical, minimally invasive, or percutaneous technique may be utilized, including (but not limited to) a transcatheter delivery system, which can utilize a transfemoral, subclavian, transapical, transseptal, or transaortic approach. In some applications, a delivery catheter is utilized to incorporate a device, then delivered to the site of deployment via a guidewire and utilized to anchor the device at the site of implantation.

Some applications are directed to methods of delivering a device to the site of deployment. The various techniques, methods, operations, steps, etc. described or suggested anywhere herein (including in documents incorporated by reference herein) can be performed on a living animal (e.g., human, mammal, other animal, etc.) or on a non-living simulation, such as on a cadaver, cadaver heart, simulator (e.g., with the body parts, tissue, etc. being simulated), etc. Accordingly, methods of delivery include both methods of treatment (e.g., treatment of human subjects) and methods of training and/or practice (e.g., utilizing an anthropomorphic phantom that mimics human vasculature to perform method).

Figure 5:
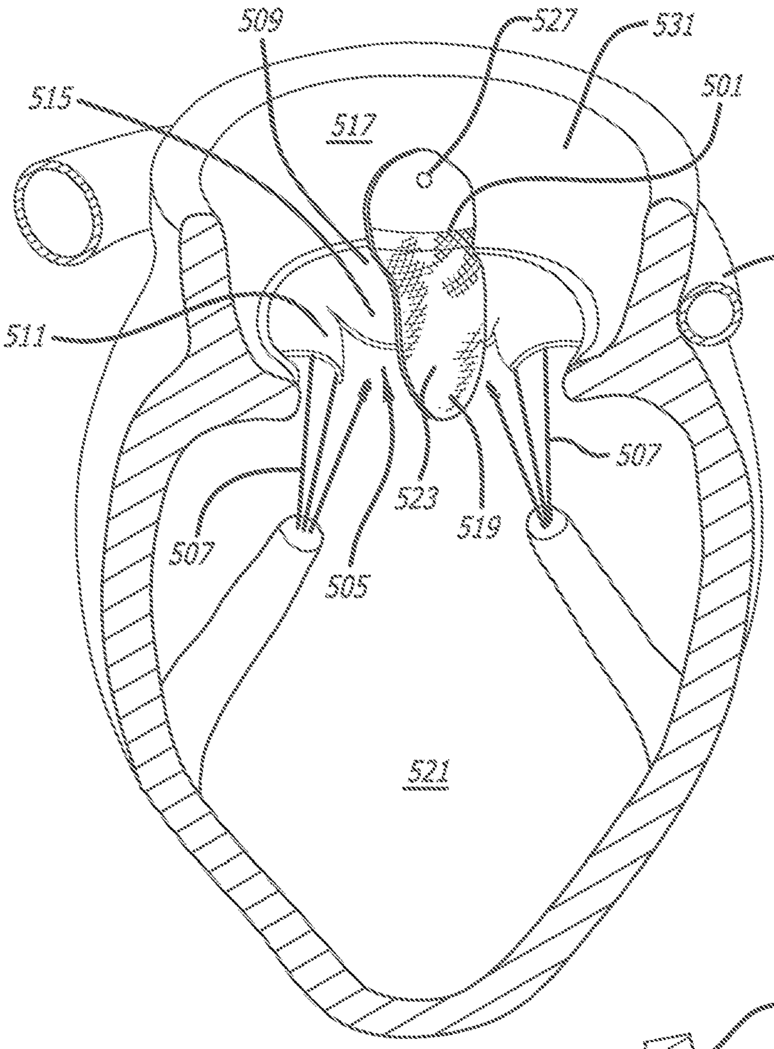
FIGS. 5-9, 10A-C, and 11-13 are schematic illustrations of various example devices implanted on native valves.
Figure 6:
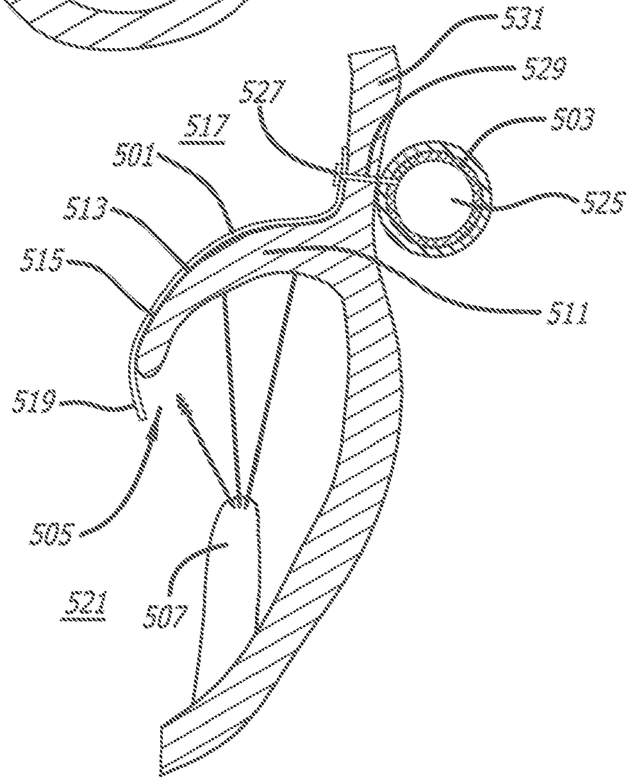

FIGS. 5 and 6 provide an example depicting an implant or device 501 with a stent anchor 503 at a site of implantation. As shown here, the device is on the mitral valve 505 for illustration. In this example, one or more chordae tendineae 507 of the valve are broken resulting in leaflet flail and/or prolapse in the P2 area 509 of the posterior leaflet 511 of the valve 505. The contact face 513 of the device 501 is situated on the influent face 515 (or atrial side) of the posterior leaflet 511 within the left atrium 517 at the site of a leaflet issues, e.g., flail, prolapse and/or rigidity. The contact face 513 can provide contact pressure onto the leaflet (e.g., a portion of the leaflet having flail, prolapse and/or rigidity) to help flatten out the leaflet (e.g., protrusion, bulge, etc. thereof) and mitigate regurgitant blood flow.

In some applications, the device 501 includes a coaptation portion 519 that extends beyond the edge of the posterior leaflet 511 and into the left ventricle 521. The coaptation portion 519 can coapt with the anterior leaflet to help promote coaptation when the valve is closed. The device 501 has a cover or sheet 523 that can help provide contact pressure on the leaflet to address an issue (e.g., such as flail, prolapse, and/or rigidity) and to help coaptation of the leaflets. The coaptation portion can be configured as a wing or wing portion or be part of a wing or wing portion.

In some applications, the anchor 503 is a stent (e.g., a wire stent, stent with alternating struts, laser-cut stent, braided stent, balloon-expandable stent, self-expanding stent, etc.) expanded within the coronary sinus 525 adjacent to the left atrium 517. The anchor 503 is connected to the connection point 527 (e.g., anchor receiver, etc.) of the device 501 via a connector 529 that traverses through the atrium wall 531. Accordingly, the anchor 503 stabilizes the device 501 at the mitral valve 505. In some applications, a different type of anchor (e.g., helical anchor, t-shaped anchor, clamp anchor, sutured anchor, etc.) can alternatively or additionally be used, e.g., an anchor could be used to anchor the device/system directly to the valve annulus or other nearby tissue.

In some applications, the anchor connection point or anchor receiver is configured as an interface. The interface can connect with a catheter or shaft for delivering and positioning the system/device.

Figure 9:
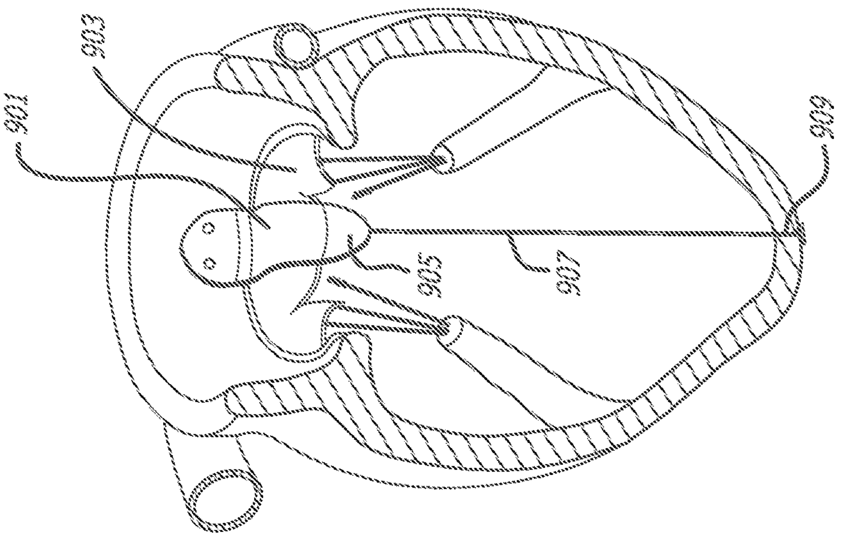
Figure 8:
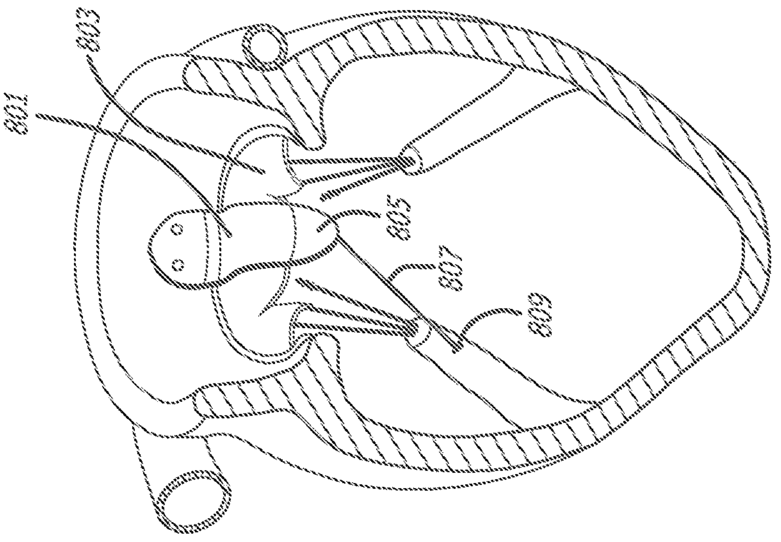
Figure 7:
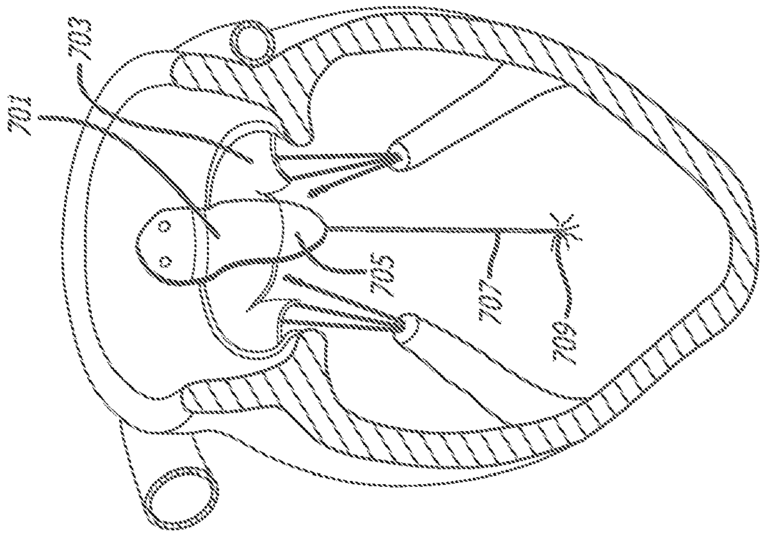

FIGS. 7, 8 and 9 show examples of implants or devices (e.g., repair devices, leaflet repair devices, prolapse/flail repair devices, contact pressure devices, support devices, etc.) comprising a tether to further stabilize the device at a site of implantation. As shown here, the device is implantable at a native valve. The implant/devices can be anchored in the coronary sinus, at the annulus, onto the leaflet, and/or any other way described herein. The implant/devices can be configured to apply a contact pressure or added support to the leaflet (e.g., a portion of the leaflet, etc.).

In FIG. 7, an implant/device 701 is shown situated and implanted on a native valve 703, depicted as a mitral valve for illustration. Extending from the coaptation portion 705 of the device 701 is a tether 707 that extends to and connects (e.g., anchors, clamps, attaches, adheres, links, etc.) to an area of ventricle wall 709.

In FIG. 8, an implant/device 801 is situated and implanted on the native valve 803. Extending from the coaptation portion 805 of the device 801 is a tether 807 that extends to and connects (e.g., anchors, clamps, attaches, adheres, links, etc.) to a papillary muscle 809.

In FIG. 9, an implant/device 901 is situated and implanted on the native valve 903. Extending from the coaptation portion 905 of the device 901 is a tether 907 that extends to and connects (e.g., anchors, clamps, attaches, adheres, links, etc.) to the apex 909 of the ventricle.

Figure 10C:
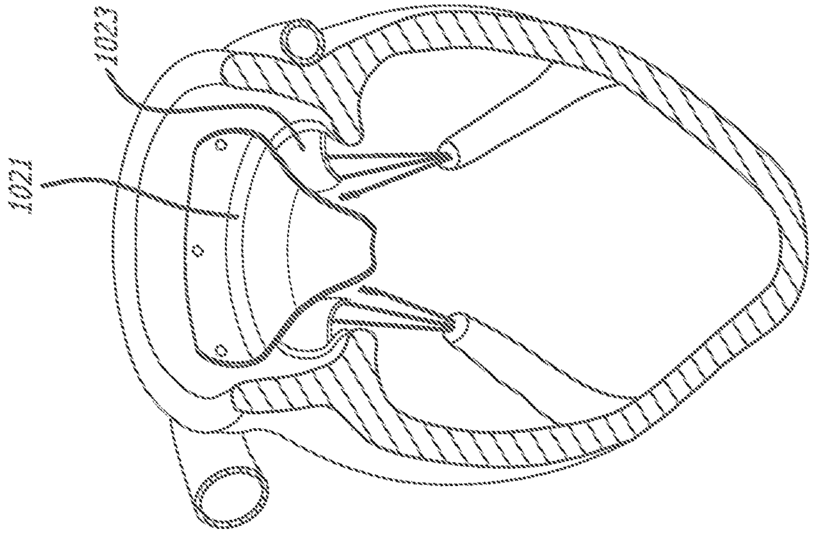
Figure 10B:
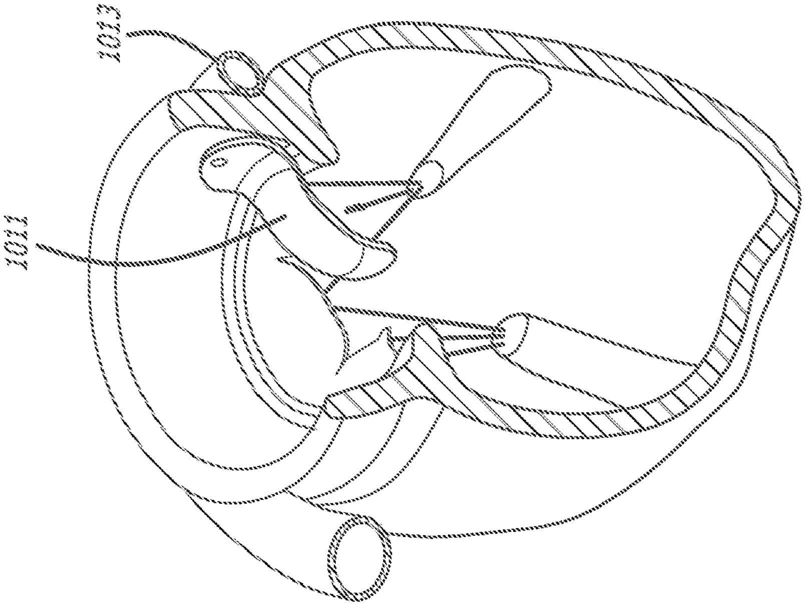
Figure 10A:
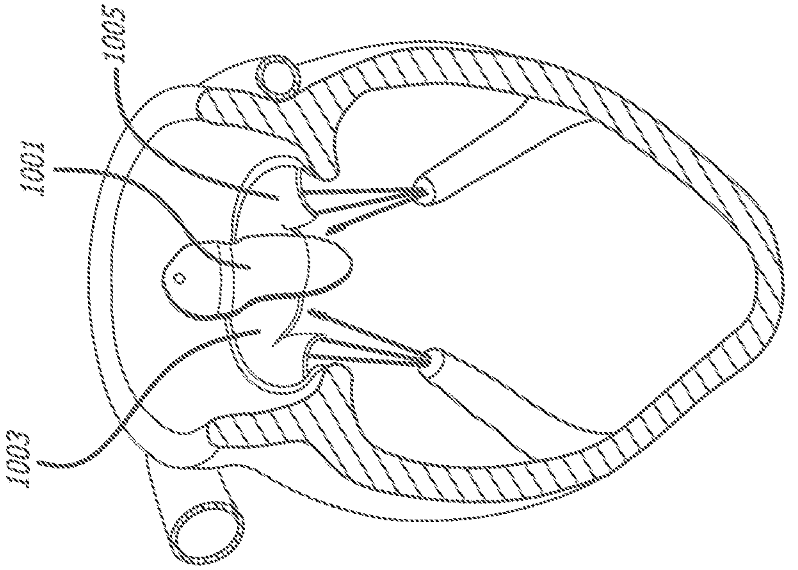

FIGS. 10A, 10B, and 10C show examples of implants or devices (e.g., repair devices, leaflet repair devices, prolapse/flail repair devices, contact pressure devices, support devices, etc.) situated in various different sites of implantation along the posterior leaflet of the mitral valve. The implant/devices can be configured to apply a contact pressure or added support to the leaflet (e.g., a portion of the leaflet, etc.).

In FIG. 10A, an implant/device 1001 is situated and implanted on top of the cleft between P2 1003 and P3 1005 of the posterior leaflet. The device can be anchored in a variety of ways. In some applications, the device 1001 is anchored within the coronary sinus. In some applications, the device 1001 is anchored to the annulus.

In FIG. 10B, an implant/device 1011 is situated and implanted on top of the commissure between the posterior leaflet 1013 and the anterior leaflet (not shown). The device can be anchored in a variety of ways. In some applications, the device 1011 is anchored within the coronary sinus. In some applications, the device 1011 is anchored to the annulus.

In FIG. 10C, an implant/device 1021 is configured to span across much of the posterior leaflet 1023, including covering parts of P1, all of P2, and parts of P3. The device can be anchored in a variety of ways. In some applications, the device 1021 is anchored within the coronary sinus. In some applications, the device 1021 is anchored to the annulus.

Although examples of implantation sites are depicted along the posterior leaflet of the mitral valve, it should be understood that various implementations and applications can be utilized on other leaflets or within other valves.

Figure 11:
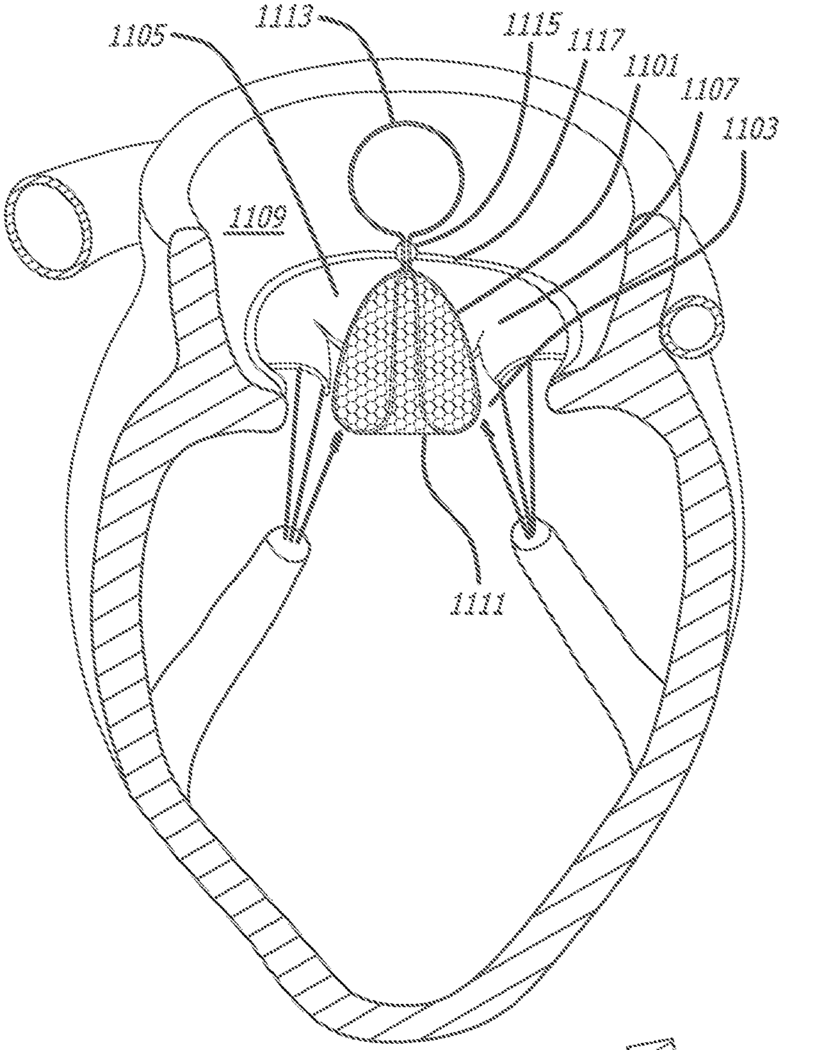
Figure 12:
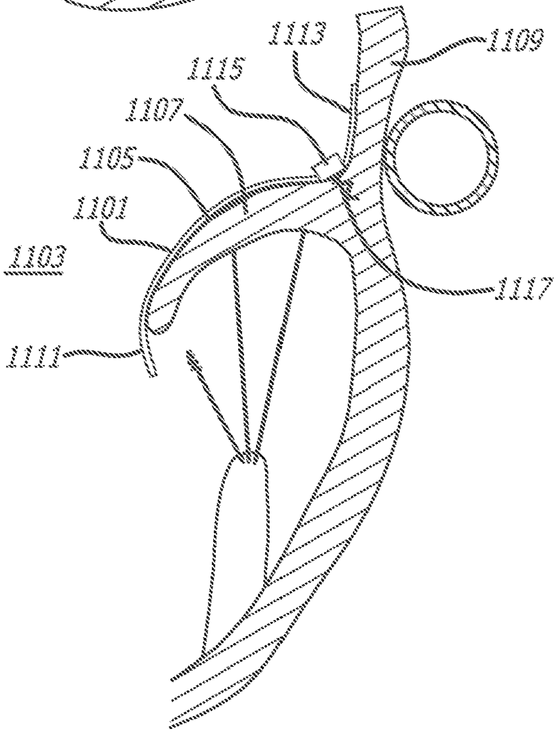

FIGS. 11 and 12 show an example implant or device 1101 (e.g., a repair device, a leaflet repair device, a prolapse/flail repair device, contact pressure device, support device, etc.) with an anchor. The implant/device can be anchored in a variety of ways. In some applications, the implant/device 1101 is anchorable within the coronary sinus. In some applications, the implant/device is anchorable to a valve annulus at a site of implantation, e.g., as shown in FIG. 12. The implant/devices can be configured to apply a contact pressure or added support to the leaflet (e.g., a portion of the leaflet, etc.).

As shown in FIGS. 11 and 12, the device is implantable at a native valve 1103 (e.g., a mitral valve, tricuspid valve, etc.). The contact face of the device 1101 is situated on the influent face 1105 (or atrial side) of a native leaflet 1107 (shown as a posterior leaflet) within the atrium 1109 at the site of flail, prolapse, rigidity, and/or other leaflet abnormality. The contact face can provide contact pressure and/or support onto the flail, prolapse, rigidity, etc. to help flatten out and/or reshape the bulge, protrusion, flail, etc. and mitigate regurgitant blood flow. The device 1101 includes a coaptation portion 1111. The coaptation portion 1111 can be configured to cover some or all of the native leaflet. In some applications, the coaptation portion 1111 is configured to extend beyond a lower edge of the native leaflet 1107. The coaptation portion can be configured as a wing or wing portion or be part of a wing or wing portion.

In some applications, the device 1101 has a covering that spans the contact face and can help provide contact pressure and/or support on the flail, prolapse, rigidity, leaflet abnormality, etc. and can help coaptation. In some applications, the covering is mesh sheet. In some applications, the covering is one or more of a fabric sheet, polymer sheet, pericardium sheet, etc. The contact face and/or covering can be configured to allow blood and plasma to flow therethrough such that pressure from blood does not disrupt, deflect, or dislodge the device. A mesh covering can be particularly useful to allow blood and plasma to flow therethrough without disrupting device function.

In some applications, the device 1101 includes an optional support 1113 (e.g., a counterforce support, atrial support, etc.). The support 1113 can be configured to press or abut against a wall of the heart (e.g., the wall of atrium 1109) to help orient and/or maintain the position of the device, which can help the device provide contact pressure and/or support on a native leaflet (e.g., to mitigate or eliminate flail, prolapse, rigidity issues, and/or other leaflet abnormalities). The support 1113 can also be configured to help prevent the contact face and/or a cover thereon from flailing or otherwise moving back into or toward the atrium in an undesired way. For some applications, and as shown, support 1113 comprises (e.g., consists essentially of) a wire loop.

In some applications, the device 1101 further includes an anchor 1115 that anchors the device 1101 to the valve annulus 1117. The anchor can be the same as or similar to any other anchors or anchoring mechanisms described herein. In some applications, the anchor 1115 is a helical anchor (e.g., as shown in FIG. 12) that can be screwed or rotated into tissue. A helical anchor rotated into annulus tissue can be particularly good at anchoring and holding the device at the native valve, as the annulus tissue is strong and helical designs allows for plenty of contact surface and engagement with the tissue.

Figure 13:
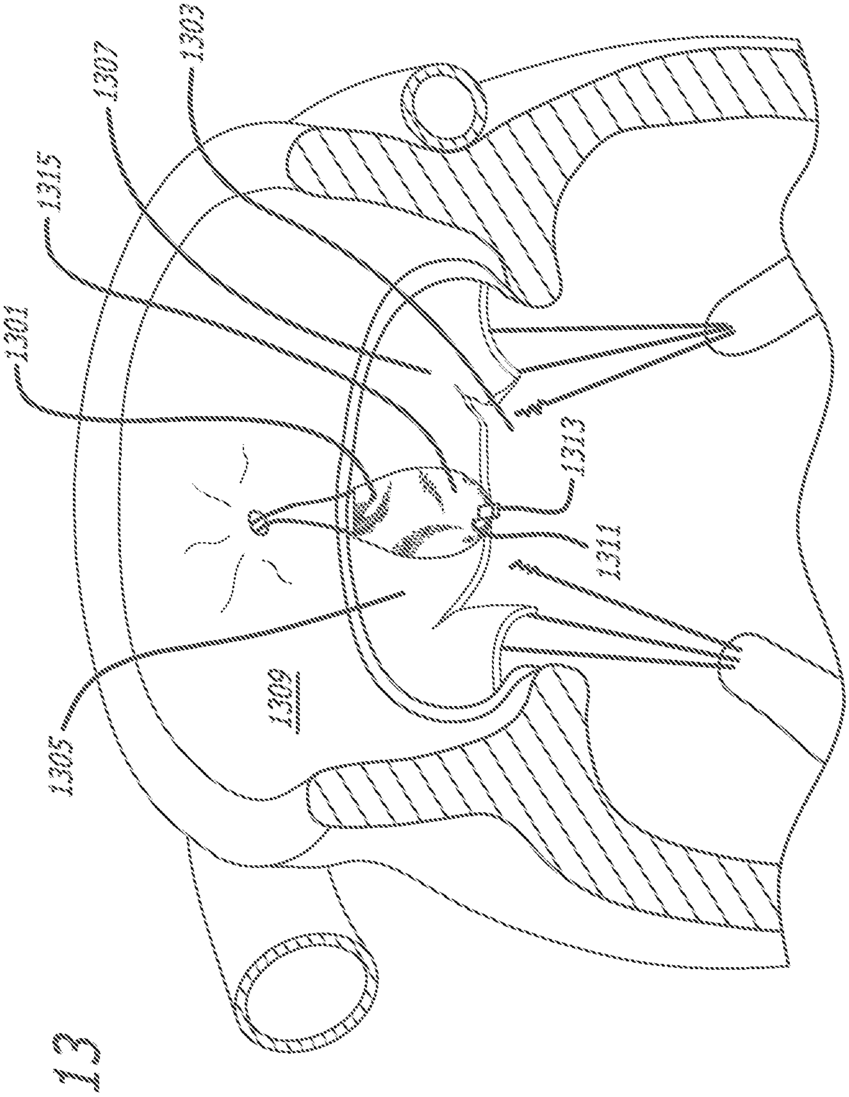

FIG. 13 shows an example implant or device 1301 (e.g., repair device, leaflet repair device, prosthetic device, contact pressure device, support device, etc.) comprising a stent anchor (not shown) at a site of implantation that is further clamped onto a leaflet of a native valve 1303. In some applications, as shown here, the device is implantable at the mitral valve. The contact face of the device 1301 is situated on the influent face 1305 (or atrial side) of the native leaflet 1307 (e.g., a posterior leaflet, etc.) within the atrium 1309 at the site of flail, prolapse, rigidity issue, and/or other leaflet abnormality. The contact face can provide contact pressure and/or support onto the flail, prolapse, etc. to help flatten out and/or reshape the leaflet (e.g., a protrusion, bulge, etc.) and mitigate or eliminate regurgitant blood flow. The device 1301 includes a coaptation portion 1311. The coaptation portion can be configured to extends to the edge of the leaflet 1307. A clamp 1313 can be attached at the edge of the leaflet to help secure the coaptation portion 1311 and/or the contact face to the leaflet 1307 edge. The clamp 1313 secures the device 1301 to the posterior leaflet 1307, which allows the device 1301 to move with the posterior leaflet 1307 as it opens and closes.

In some applications, the device 1301 has a covering 1315. The covering 1315 can be the same as or similar to other coverings described herein. In some applications, the covering spans the contact face and can help provide contact pressure on the flail, prolapse, rigidity, etc. and can help coaptation.

FIGS. 14 and 15 show an example system or implant/device with a gap filler/coaptation element/spacer 1401 and an anchor. The anchor can be the same as or similar to other anchors described herein. In some applications, the system/device comprises a stent anchor 1403 at a site of implantation and/or within a blood vessel of the heart (e.g., coronary sinus, etc.). As shown here, the gap filler/coaptation element/spacer is implantable at a native valve 1405, e.g., a mitral valve, a tricuspid valve, etc. In some applications, the gap filler/coaptation element/spacer 1401 is a bulky substance capable of filing in gaps that may occur at the leaflet coaptation area 1407 when the native valve 1405 is closed. In some applications, the anchor 1403 is a stent expanded within a blood vessel, such as the coronary sinus 1409 adjacent to the left atrium 1411. In some applications, the anchor 1403 is connected to the connection point 1413 of the gap filler/coaptation element/spacer 1401 via a connector 1415 that traverses through the atrium wall 1417. Accordingly, the anchor 1403 stabilizes the gap filler/coaptation element/spacer 1401 at the native valve 1405.

Figure 16A:
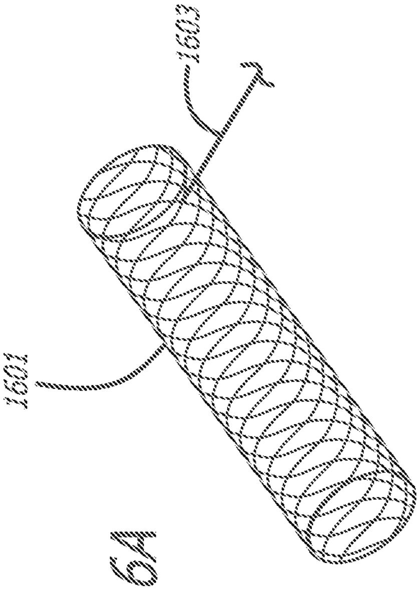
FIGS. 16A-D are schematic illustrations of example anchors for use within vasculature.
Figure 16B:
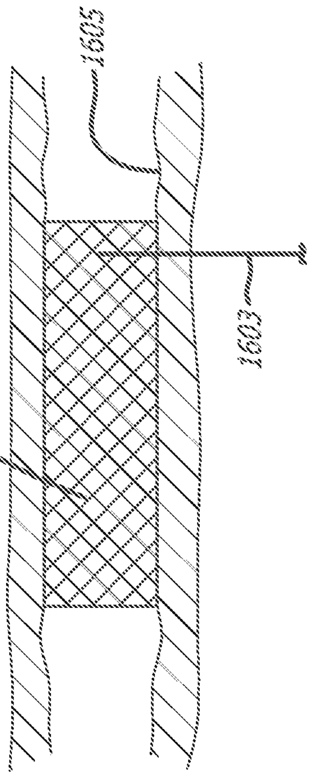

FIGS. 16A and 16B an example of an expandable stent anchor 1601 with a connector 1603. The anchor 1601 can be expanded within vasculature (e.g., coronary sinus, circumflex artery, etc.) to the walls 1605 of the vasculature. The connector 1603 (e.g., tether, suture, line, wire, etc.) can extend from the anchor 1601 and traverse through the vasculature wall 1605 connecting or coupling an implanted device to the anchor such that the implanted device is secured, e.g., via tensile forces.

Figure 16C:
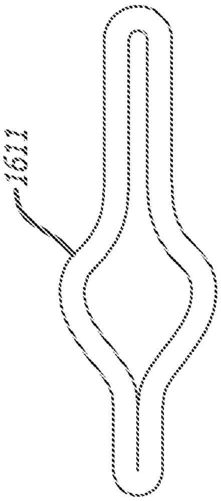
Figure 16D:
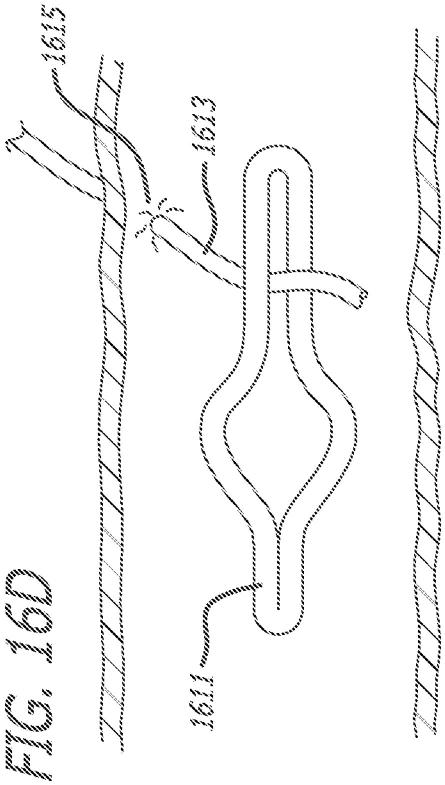

FIGS. 16C and 16D show an example anchor 1611 with a connector 1613 (e.g., tether, suture, line, wire, etc.). The anchor 1611 can be situated proximate to the walls 1615 of the vasculature. The connector 1613 can extend from the anchor 1611 and traverse through the vasculature wall 1615 connecting or coupling the anchor to implanted device to secure the implanted device, e.g., by creating a tensile force between the anchor 1611 and the implanted device that secures the anchor 1611 and device in place.

Figure 17A:
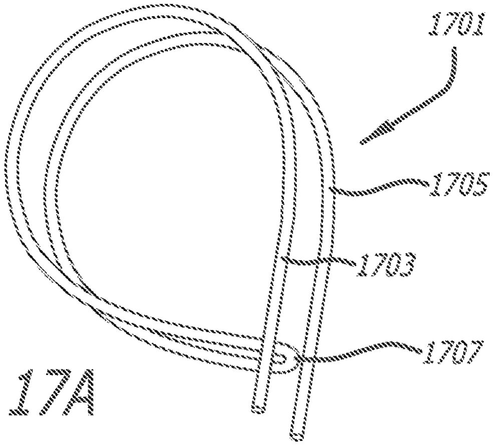
FIGS. 17A-E are schematic illustrations of example anchors for use within a heart valve.
Figure 17B:
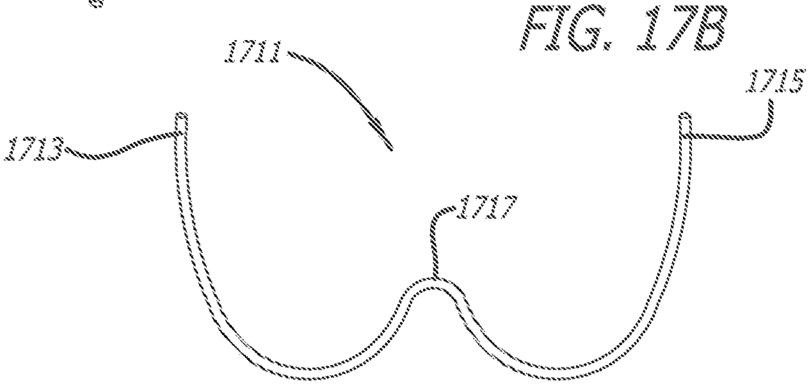
Figure 17C:
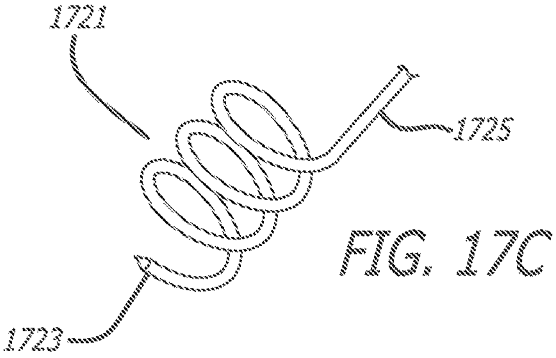

FIGS. 17A, 17B, and 17C each illustrate an example of an anchor capable of being secured (e.g., embedded, lodged, screwed, etc.) into native tissue. FIG. 17A illustrates an example of a curved or looped anchor 1701 with an upper portion 1703 and lower portion 1705 and a central loop 1707. The upper and lower portions 1703 and 1705 can embed with the tissue and the central loop 1707 can interlink with a device to secure it to the tissue at the site of implantation.

FIG. 17B illustrates an example of an anchor 1711 with two distal ends 1713 and 1715 and an inner ridge 1717. The two distal ends 1713 and 1715 can embed with the tissue and the inner ridge 1717 can interlink with a device to secure it to the tissue at the site of implantation.

FIG. 17C illustrates an example of a helical anchor 1721 capable of screwing or rotating into tissue at the lower end 1723 and attaching to a device at its upper end 1725 to secure the device to the tissue at the site of implantation.

Figure 17D:
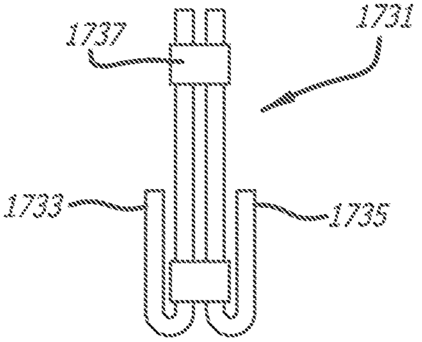
Figure 17E:
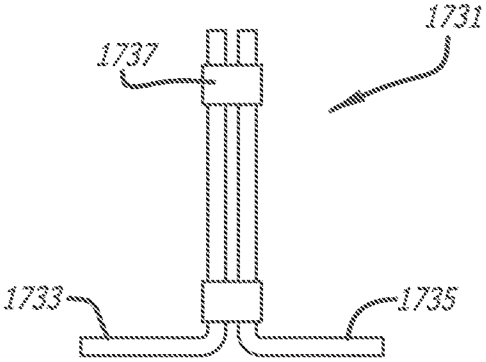

FIGS. 17D and 17E illustrate an example of a T-anchor 1731 capable of anchoring within a crevice within the heart valve (e.g., in a cleft and/or commissure). The T-anchor 1731 includes two arms 1733 and 1735 and a connecting portion 1737. As the T-anchor 1731 is being deployed into a crevice, the two arms 1733 and 1735 can remain in a contracted position (see FIG. 17D). To secure the anchor 1731, the two arms 1733 and 1735 can expand outward within a crevice and under the leaflet such that it can secured within the crevice (see FIG. 17E). The connecting portion 1737 connects the anchor to an implant or device.

Figure 18A:
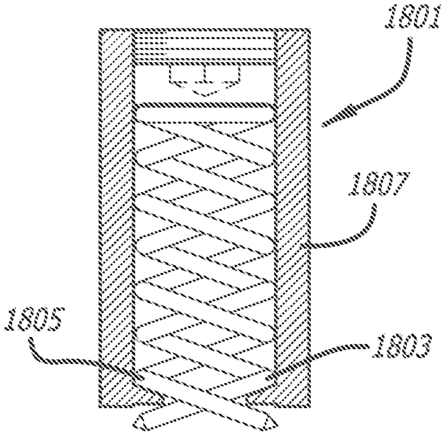
FIGS. 18A-H are schematic illustrations of example helical anchors.
Figure 18B:
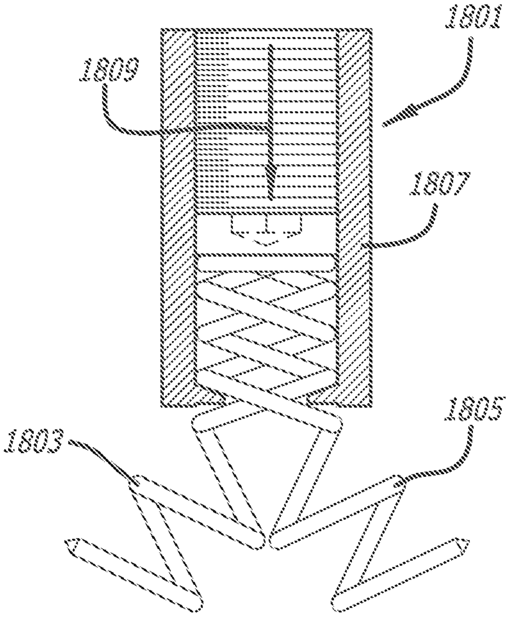

FIGS. 18A and 18B illustrate cross-sectional views of an example of a dual helix anchor in its housing. In some applications, the housing is the anchor head. The anchor 1801 includes two helixes or helical anchor portions 1803 and 1805 that, in a first configuration, are stacked, nested, or arranged within a tubular compartment or housing 1807. The two helixes/anchor portions 1803 and 1805 can be configured to transition to a second configuration in which the helixes/anchor portions extend from the housing 1807 askew or at different angles from each other (see FIG. 18B). The two helixes or helical anchor portions 1803 and 1805 can be configured to extend out of the housing 1807 in different directions or at different angles as the helixes/anchor portions are pushed or rotated out 1809 of the tubular compartment/housing 1807. The helixes or helical anchor portions 1803 and 1805 can beneficially be extended from the housing different amounts or lengths depending on the anatomy of the patient and/or other factors. For example, in some circumstances, the user may want to extend the helixes/anchor portions more (or so a greater length extends from the housing) to increase depth of penetration and strength of retention, and in other circumstances, the user may want to extend the helixes/anchor portions less (or so a shorter length extends from the housing) to avoid damaging a blood vessel of the heart, etc.

Figure 18C:
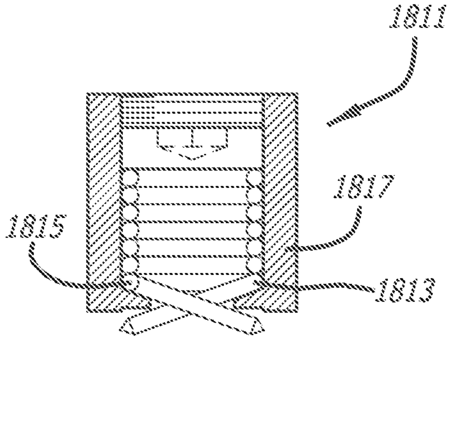
Figure 18D:
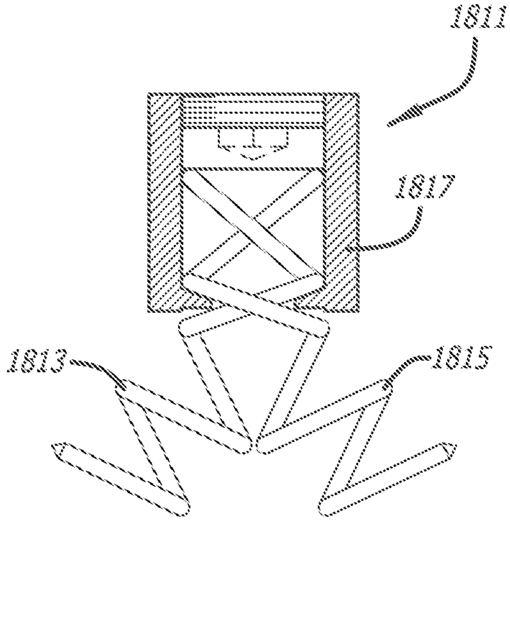

FIGS. 18C and 18D illustrate cross-sectional views of an example of a low-profile dual helix anchor that is compressed or compressible within its housing. The anchor 1811 includes two spring-like compressible helixes or helical anchor portions 1813 and 1815 that, in a first configuration, are stacked, nested, or arranged within a tubular compartment or housing 1817. In the first configuration, the two helixes/anchor portions 1813 and 1815 are compressed (e.g., axially compressed to a smaller height) within the tubular compartment/housing 1817. The helixes/anchor portions 1813 and 1815 are configured to decompress or axially extend as they extend or are pushed or rotated out from the compartment/housing. The two helixes/anchor portions 1813 and 1815 can be configured to transition to a second configuration in which the helixes/anchor portions extend from the housing 1817 askew or at different angles from each other (see FIG. 18D). The two helixes/anchor portions 1813 and 1815 can be configured to extend out of the housing 1817 in different directions or at different angles as the helixes/anchor portions are pushed or rotated out of the tubular compartment/housing 1817. The anchors or anchor portions 1813 and 1815 can beneficially be extended from the housing different amounts or lengths depending on the anatomy of the patient and/or other factors, e.g., as discussed above with respect to anchor 1801.

Figure 18E:
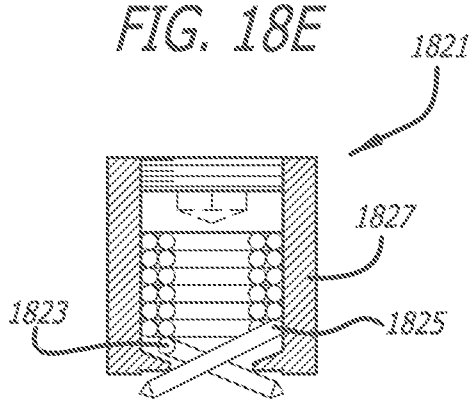
Figure 18F:
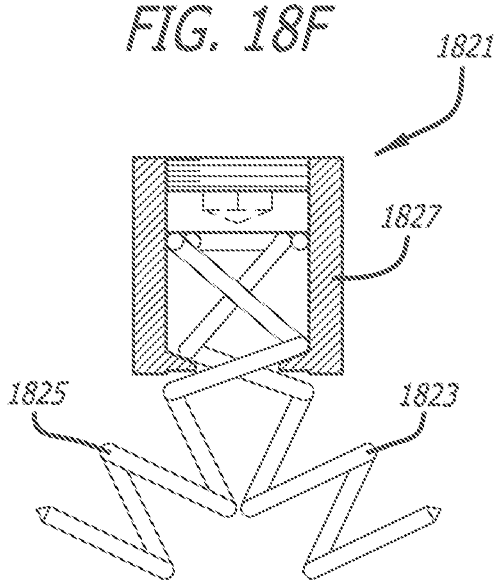

FIGS. 18E and 18F provide cross-sectional views of an example of a low-profile dual helix anchor that is compressed or compressible within its housing. The anchor 1821 includes an inner 1823 spring-like compressible helix or helical anchor portion and an outer 1825 spring-like compressible helix or helical anchor portion, that in a first configuration, are stacked, nested, or arranged together within a tubular compartment or housing 1827 with the inner helix/anchor portion 1823 radially inside the outer helix/anchor portion 1825 (e.g., the inner helix/anchor portion 1823 can have a smaller diameter than the outer helix/anchor portion 1825). In the first configuration, the inner and outer helixes/anchor portions 1823 and 1825 are compressed (e.g., axially compressed to a smaller height) within the tubular compartment/housing 1827. The helixes/anchor portions 1823 and 1825 are configured to decompress or axially extend as they extend or are pushed or rotated out from the compartment/housing. The inner and outer helixes/anchor portions 1823 and 1825 can be configured to transition to a second configuration in which the helixes/anchor portions extend from the housing 1827 askew or at different angles from each other (see FIG. 18F). The inner and outer helixes/anchor portions 1823 and 1825 can be configured to extend out of the housing 1827 in different directions or at different angles as the helixes/anchor portions are pushed or rotated out of the tubular compartment/housing 1827. The anchors or anchor portions 1823 and 1825 can beneficially be extended from the housing different amounts or lengths depending on the anatomy of the patient and/or other factors, e.g., as discussed above with respect to anchors 1801 and 1811.

Figure 18G:
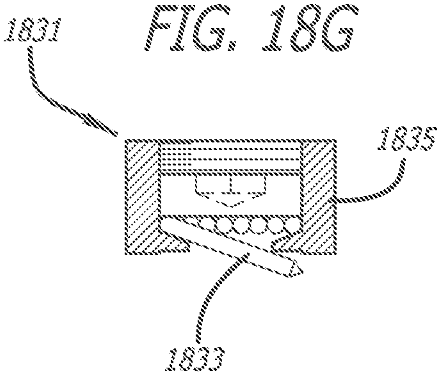
Figure 18H:
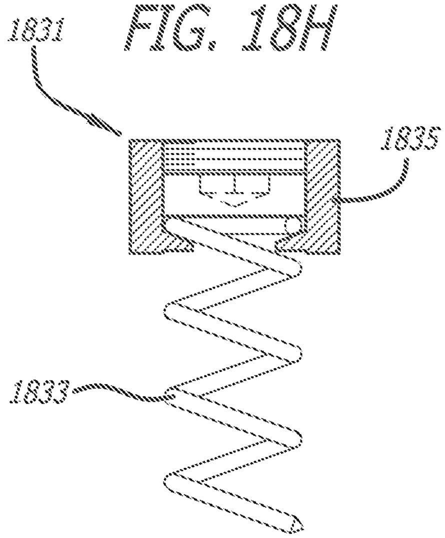

FIGS. 18G and 18H provide cross-sectional views of an example of a low-profile single helix anchor that is compressed and coiled within its housing. The anchor 1831 includes a single spring-like compressible helical anchor or anchor portion 1833 that, in a first configuration, is coiled within a tubular compartment/housing 1835. In the first configuration, the helical anchor/anchor portion 1833 is compressed within the tubular compartment/housing 1835. The anchor/anchor portion 1833 is configured to decompress or axially extend as it extends or is pushed/rotated out from the compartment/housing. The anchor/anchor portion 1833 can thereby transition to a second configuration in which the anchor/anchor portion extends from the housing 1837. In some applications, the anchor/anchor portion 1833 is arranged in the housing such that each turn or loop of the coil has the same or a similar diameter, such that each turn/loop of the coil is stacked on top of an adjacent turn/loop of the coil until the end, e.g., in the form of a helix. In some applications, and as shown, the anchor/anchor portion 1833 is arranged or configured such that, in the housing, the helical anchor/anchor portion is in a single plane (e.g., with a large outer turn/loop of the coil and each subsequent turn/loop of the coil having a slightly smaller diameter radially inside an adjacent larger diameter turn/loop), e.g., in the form of a planar spiral.

Figure 19A:
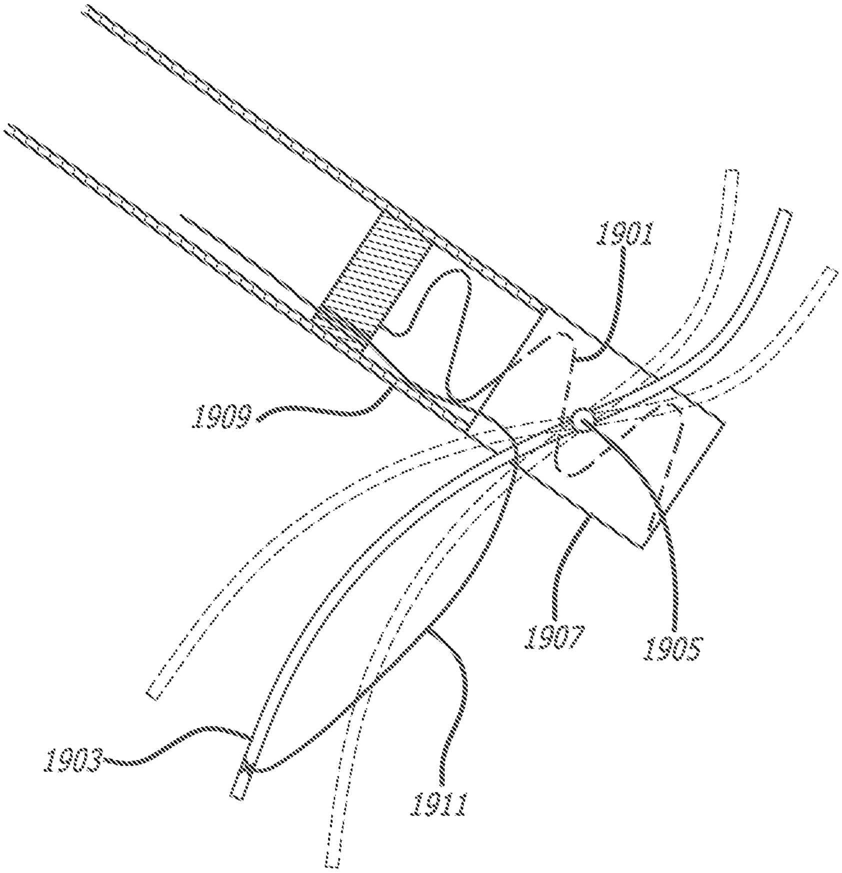
FIGS. 19A-C are schematic illustrations of an example system having a device with an adjustable contact-face angle.

FIG. 19A illustrates a cross-sectional view an example of a system with an anchor 1901 and implant/device 1903 with an adjustable contact-face angle. There are multiple potential mechanisms that could be used to adjust the contact-face angle of the implant/device as it is being anchored into tissue. In some applications, the implant/device 1903 incorporates a fulcrum 1905 that is connected to the anchor housing 1907. A deployment tool 1909 is utilized to anchor the anchor into tissue. In some applications, the deployment tool 1909 includes a cable 1911 that extends to the front of the device 1903. The cable 1911 in conjunction with the fulcrum 1905 can adjust the contact-face angle of the implant/device 1903 to match the angle of the native tissue. Once matched, the deployment tool 1909 can anchor the anchor 1901 into the native tissue. The anchor 1901 is shown as a helical anchor, but other anchor configurations are also possible.

Figure 19B:
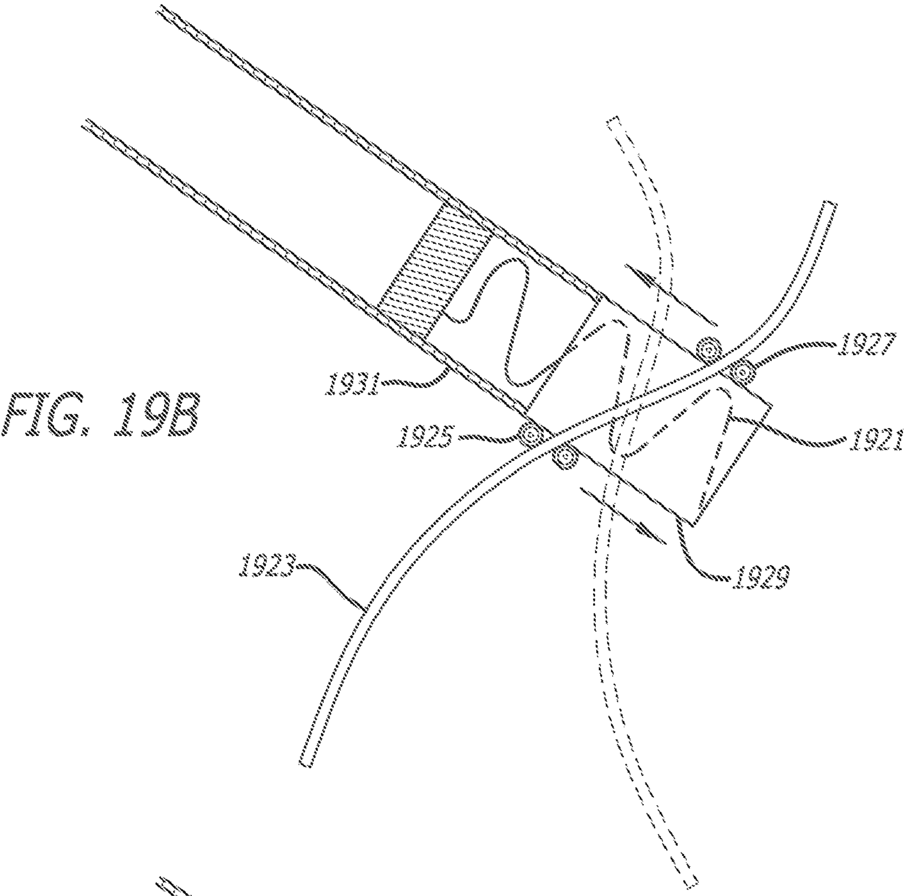
Figure 19C:
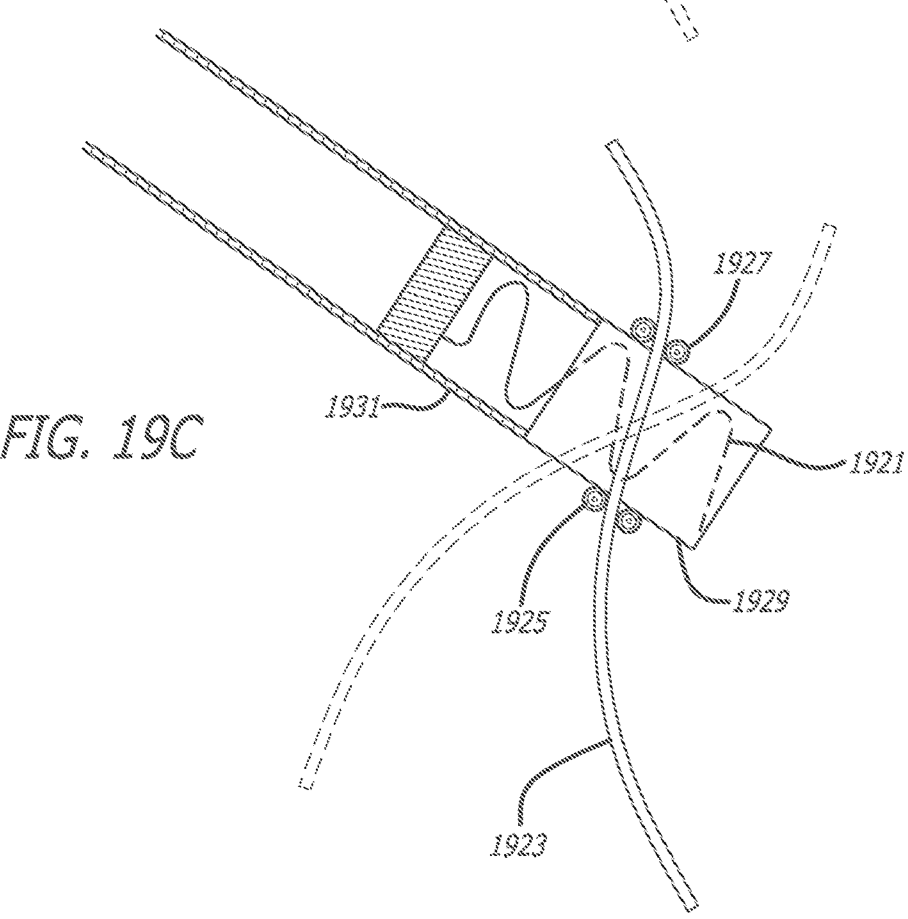

FIGS. 19B and 19C illustrate a cross-sectional view of an example of an anchor 1921 and an implant/device 1923 with an adjustable contact-face angle. This example portrays one mechanism to adjust the contact-face angle of the device as it is being anchored into tissue. The implant/device 1923 incorporates two sliding mechanisms 1925 and 1927 on respective sides (e.g., opposite sides) of the anchor housing 1929. A deployment tool 1931 is utilized to anchor the helical anchor into tissue. The sliding mechanisms 1925 and 1927 can adjust the contact-face angle of the implant/device 1923 to match the angle of the native tissue. Once matched, the deployment tool 1931 can anchor the helical anchor 1921 into the native tissue. The anchor 1921 is shown as a helical anchor, but other anchor configurations are also possible.

FIG. 20A illustrates an example depicting an implant/device 2001 (e.g., repair device, leaflet repair device, prosthetic device, contact pressure device, support device, etc.) comprises a wire form for providing contact pressure and/or support to a leaflet. The implant/device 2001 includes a contact face formed by undulating wire 2003 capable of providing contact pressure on and/or support to a leaflet (e.g., to address flail, prolapse, rigidity, and/or other leaflet abnormalities). The implant/device 2001 includes a coaptation portion 2005 that can extend into the coaptation area of a leaflet and help promote coaptation between leaflets. The implant/device 2001 includes a connector 2007 that can connect with an anchor. In some applications, the implant/device 2001 can optionally include a permeable, semipermeable, or impermeable cover or sheet (not shown) that can help provide contact pressure on and/or support to a leaflet flail, prolapse, rigidity, and/or leaflet abnormality. Optionally, the cover or sheet can be a mesh sheet or mesh covering (not shown).

FIG. 20B illustrates an example implant or device 2011 (e.g., repair device, leaflet repair device, prosthetic device, contact pressure device, support device, etc.) comprising a wire form for providing contact pressure and/or support to a leaflet. The implant/device 2001 includes a contact face formed by three sectional wireforms 2013, 2015, and 2017 that intersect or overlap one another and are capable of providing contact pressure on and/or support to a leaflet flail, prolapse, rigidity, and/or leaflet abnormality. The three sectional wireforms 2013, 2015, and 2017 can expand or contract 2019 laterally (e.g., fanning outwards to various degrees) to adapt to the specifics of the native leaflet flail, prolapse, rigidity, and/or leaflet abnormality. The implant/device 2011 includes a coaptation portion 2021 that can extend into the coaptation area of a leaflet and help promote coaptation between leaflets. The implant/device 2001 includes a connector or connection point 2023 that can connect with an anchor. In some applications, the implant/device 2001 can optionally include a permeable, semipermeable, or impermeable cover or sheet (not shown) that can help provide contact pressure on and/or support to a leaflet flail, prolapse, rigidity, and/or leaflet abnormality. Optionally, the cover/sheet can be a mesh sheet or cover (not shown). The connector or connection point can comprise an anchor receiver and/or an interface.

Figure 21A:
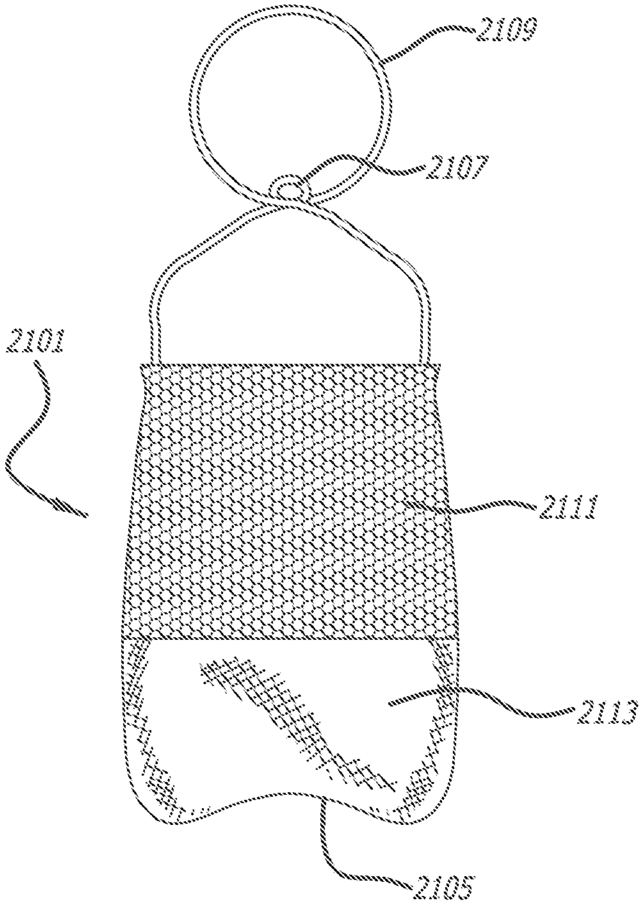
Figure 21B:
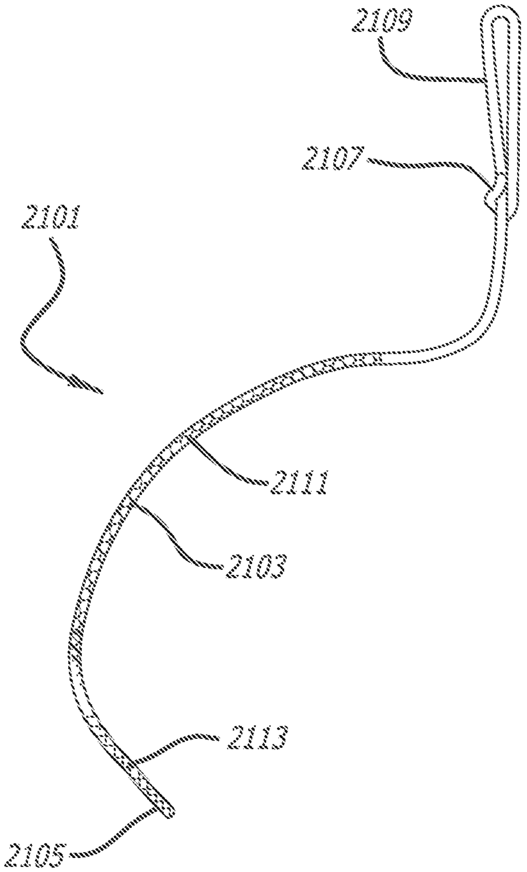

FIGS. 21A and 21B illustrates an example implant or device 2101 (e.g., repair device, leaflet repair device, prosthetic device, contact pressure device, support device, etc.) comprising a wire form for providing contact pressure and/or support to a leaflet. The implant/device 2101 includes a contact face 2103 capable of providing contact pressure on and/or support to a leaflet flail, prolapse, rigidity, and/or abnormality. The implant/device 2001 includes a coaptation portion 2105 that can extend into the coaptation area of a leaflet and help promote coaptation between leaflets. The device 2001 includes an anchor connection point 2107 that can connect with an anchor. The anchor connection point can comprise an anchor receiver. In some applications, the anchor connection point or anchor receiver comprises or is configured as an interface. The interface can connect with a catheter or shaft for delivering and positioning the system/device and can be the same as or similar to other interfaces herein. The portion extending below the anchor connection point can be considered a wing or wing portion that comprises the contact face 2103 and coaptation portion 2105. The implant or device 2101 can be configured to be anchored in any of the ways described herein to any of the locations described herein, e.g., to the annulus, in a coronary vessel, etc.

In some applications, the coaptation portion 2105 can include an optional clip, fastener, or other anchor mechanism to be attached or clamped onto a leaflet edge, which may allow the device 2101 to move with the leaflet as it opens and closes.

In some applications, the device includes an optional counterforce support 2109 that can press against an atrium wall to help the device provide contact pressure on a leaflet flail, prolapse, rigidity, and/or abnormality.

In some applications, the device 2001 (e.g., the wing portion of the device) includes a permeable non-coaptation portion 2111, which can made of mesh or otherwise include openings, to provide contact pressure on a leaflet flail, prolapse, rigidity, and/or abnormality and includes an impermeable coaptation portion 2113 that can help promote coaptation. It is noted that various examples can include an elongated impermeable coaptation portion 2113 capable of reaching the effluent side (or ventricular side) of one or two opposing native leaflets to help valve closure. In various examples, the impermeable coaptation portion 2113 is thickened such that it can fill gaps within the valve aperture, e.g., serving as a gap filler/coaptation element/spacer. In some applications, coaptation portion 2113 can be filled and/or expanded at the site of implantation.

In some applications, as shown in FIG. 21A, the device 2001 (e.g., the wing portion of the device) includes an open or uncovered area between the permeable non-coaptation portion 2111 and the anchor connection point 2107. In some applications, this open or uncovered area allows blood to freely flow therethrough and will not have any tissue ingrowth, which can help prevent the blood from moving the device in an undesired way. In some applications, the permeable non-coaptation portion 2111 can be omitted leaving this entire area (e.g., the area between the impermeable coaptation portion 2113 and the anchor connection point 2107) open with blood able to flow therethrough. The frame and coaptation portion 2113 provide the contract pressure, while the open or uncovered area allows blood flow and avoids undue pressure on the device, and avoids tissue ingrowth in the uncovered region. The frame of the device can be of a variety of sizes and shapes (including any of the other frame shapes, sizes, configurations described herein or depicted in the figures with respect to any example, and can include one or multiple anchor connection points and/or interfaces), e.g., tear drop, oval, ovoid, triangular, etc. The open or uncovered area, permeable non-coaptation portion 2111 (if included), and impermeable coaptation portion 2113 can be of various sizes and shapes beyond those depicted in FIG. 21A For example, the device can include an impermeable coaptation portion 2113 that covers between 20%-80% of the area inside the frame, while having an open portion that accounts for between 10%-80% of the area inside the frame, and/or optionally having a permeable non-coaptation portion that accounts for between 10%-80% of the area inside the frame. In some applications, the device 2001 includes an impermeable coaptation portion 2113 that covers between 40%-70% of the area inside the frame and an open/uncovered portion in 30%-60% of the area inside the frame. In some applications, the impermeable coaptation portion 2113 may be omitted, while a permeable portion 2111 (which could then be used in the coaptation region) and an open/uncovered portion are used, and can be arranged or designed similarly to the above.

FIGS. 22A and 22B illustrate an example implant or device 2201 (e.g., repair device, leaflet repair device, prosthetic device, contact pressure device, support device, etc.) comprising a wireform. The device 2201 includes a contact face 2203 capable of providing contact pressure on and/or support to a leaflet flail, prolapse, rigidity, and/or abnormality. The device 2201 includes a coaptation portion 2205 that can extend into the coaptation area of a leaflet and help promote coaptation between leaflets. The coaptation portion 2205 can be clamped onto a leaflet edge, which will allow the device 2201 to move with the leaflet as it opens and closes. The device 2201 includes an anchor connection point 2207 (which can comprise an anchor receiver) capable of connecting to anchor. In some applications, the device 2201 includes a permeable, semipermeable, or impermeable cover or sheet 2209 that can help provide contact pressure on and/or support to a leaflet flail, prolapse, rigidity, and/or abnormality. Optionally, the cover or sheet can be a mesh sheet or mesh cover (such as shown in FIG. 22C).

Figure 23A:
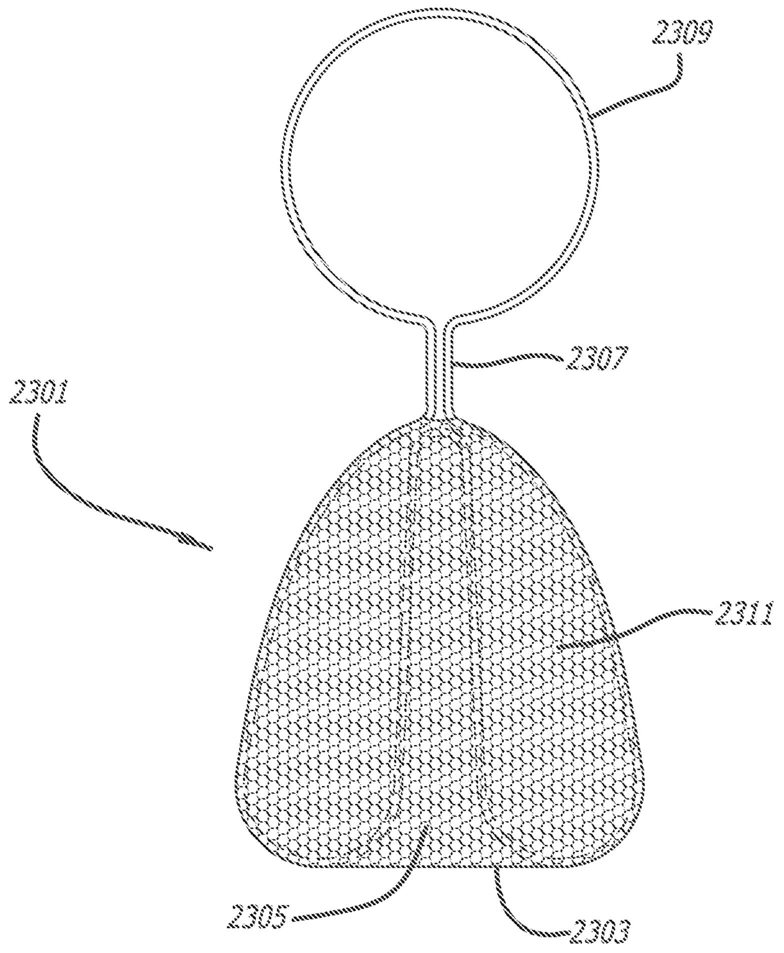

FIG. 23A illustrates an example implant or device 2301 comprising a wire form for providing contact pressure and/or support to a leaflet. The device 2301 includes a contact face capable of providing contact pressure and/or support on a leaflet flail, prolapse, rigidity, and/or abnormality. The device 2301 includes a coaptation portion 2303 that can extend into the coaptation area of a leaflet and help promote coaptation between leaflets. The coaptation portion 2303 includes an internal portion devoid of wire form 2305 such that various procedures can be performed on the native leaflet coaptation area. The device 2301 includes an anchor connection point 2307 (which can comprise an anchor receiver) that can connect with an anchor, e.g., any of the various anchors described herein. In some applications, the device includes an optional counterforce support 2309 that can press against an atrium wall to help the device provide contact pressure on a leaflet flail, prolapse, rigidity, and/or abnormality. In some applications, the device 2301 includes a permeable mesh 2311 that can help provide contact pressure and/or support on a leaflet issue, e.g., flail, prolapse, rigidity, etc. In some applications, the anchor connection point or anchor receiver comprises or is configured as an interface. The interface can connect with a catheter or shaft for delivering and positioning the system/device. The portion extending below the anchor connection portion or interface can be considered a wing or wing portion that comprises the coaptation portion, etc.

Illustrated in FIG. 23B is an example implant or device 2301 comprising a wire form for providing contact pressure and/or support to a leaflet. The example depicted in FIG. 23B is the same as the example of FIG. 23A with an added anchor receiver at the interface or anchor connection point, which can be configured as a housing or tubular compartment 2313, for housing and/or connecting a helical anchor to the implant/device. For some applications, the anchor receiver or housing or tubular compartment 2313 is connected with the implant/device 2301 at the interface or anchor connection point 2307. FIG. 23C is an enlarged cross-sectional view of the housing/tubular compartment 2313 and the wire form of the anchor connection point 2307 intersecting therethrough. The anchor connection point wire form 2307 passes through guide tubes 2315 (e.g., defined by housing 2313), securing the housing/tubular compartment 2313 to the device 2301. The housing/tubular compartment 2313 includes an aperture 2317 for which a helical anchor 2319 can pass through, as shown in FIG. 23D. Guide tubes 2315 and/or wire form 2307 may serve as cross-bars that traverse aperture 2317. The helical anchor 2319 anchors the housing/tubular compartment 2313 and thus the implant/device 2301 to a secure portion of tissue (e.g., the annulus) at the site of deployment. In some applications, this is achieved by helical anchor 2319 (i.e., a helical tissue-engaging element of the anchor) being screwed around and over a cross-bar that traverses aperture 2317 (e.g., guide tube 2315, wire form, and/or another cross-bar element defined by housing 2313), and into the tissue until a head of the anchor abuts the cross-bar. The housing/tubular compartment 2313 is depicted with a rounded groove 2321 that can precisely engage with a tool (e.g., cloaked screwdriver, anchor driver, etc.) with a complementary round protrusion.

Methods of delivering implant/device 2301 and other implants/devices herein (e.g., implant/device 2421, etc.) can include advancing a delivery catheter transvascularly (e.g., via a transfemoral, a subclavian, a transapical, a transseptal, or a transaortic approach) to the native heart valve, advancing the anchor (which can be the same as or similar to any anchors or securing features described herein) from the delivery catheter into tissue of the heart, thereby anchoring the implant/device to the tissue, and releasing the implant/device from the delivery catheter, such that the implant/device extends along a portion of a leaflet of the native heart valve. Advancing the anchor from the delivery catheter into tissue of the heart and releasing the leaflet repair implant from the delivery catheter can be done in either order.

Where the anchor is a helical anchor, advancing the anchor can include rotating the helical anchor into the tissue (e.g., into the annulus or a wall of the heart).

The implant/device can transition from a compressed delivery configuration inside the delivery catheter (for a smaller delivery profile) to an expanded configuration outside of the delivery catheter to better cover the leaflet or problem portion of the leaflet.

This method can be performed on a living animal or on a simulation, such as on a cadaver, cadaver heart, simulator (e.g., with the body parts, heart, tissue, etc. being simulated), etc.

Figure 24A:
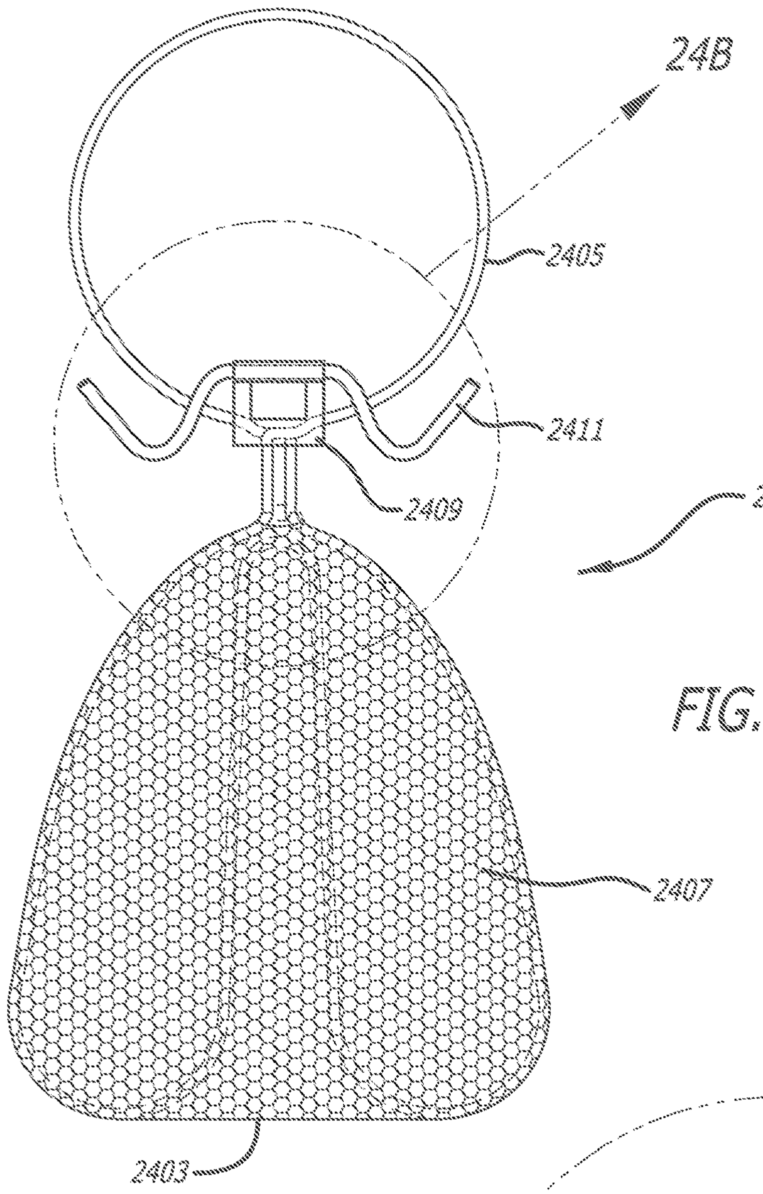
Figure 24B:
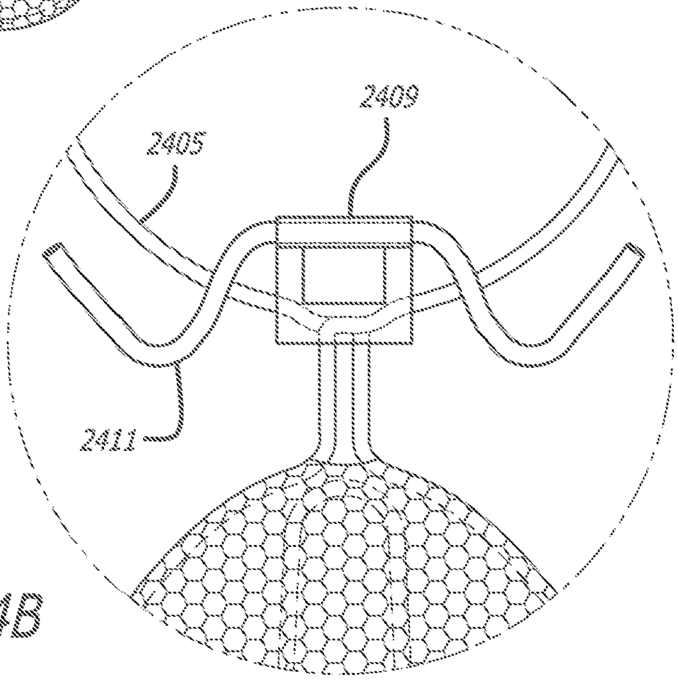

FIG. 24A illustrates an example implant or device 2401 comprising a wire form with swing hinge to adjust the contact-face angle. The device 2401 includes a contact face capable of providing contact pressure on and/or support to a leaflet, e.g., to address leaflet flail, prolapse, rigidity, and/or abnormality. The device 2401 includes a coaptation portion 2403, an optional counterforce support 2405, and a permeable mesh 2407. The device 2401 further includes a swing hinge 2409 that connects the device 2401 with a W-shaped anchor 2411. The swing hinge 2409 can adjust the angle of the W-shaped anchor 2411 with reference to the contact-face angle of the device 2401 to match the angle of the native tissue. A detailed close-up image of the hinge is provided in FIG. 24B.

FIG. 24C illustrates an example implant or device 2421 comprising a wire form with a soft compliable hinge to adjust the contact-face angle. The device 2421 includes a contact face capable of providing contact pressure on and/or support to a leaflet, e.g., to address leaflet flail, prolapse, rigidity, and/or other issues. The device 2421 includes a coaptation portion 2423 and a permeable mesh 2425. The device 2421 further includes an interface or hinge 2427 made of soft pliable material (e.g., PTFE) that allows a helical anchor to anchor the device 2421 to tissue. The pliability of the soft hinge 2427 adjusts allows the contact-face angle of the device 2421 to match the angle of the native tissue regardless of the deployment angle of the helical anchor. A detailed close-up image of the hinge is provided in FIG. 24D. The portion extending below the interface or hinge can be considered a wing or wing portion.

FIGS. 25 and 26 illustrates an example implant or device 2501 comprising a wire form with a gap filler, coaptation element, or spacer 2503. FIG. 26 is a cross-sectional view of the device 2501 provided in FIG. 25. The device 2501 includes a sheet 2505 surrounding the wire form 2507 and a coaptation element, spacer, or filler 2503. The device also includes a contact face 2503 capable of providing contact pressure on and/or support to a leaflet, e.g., to address leaflet flail, prolapse, rigidity, and/or other issues. The device 2501 includes a coaptation portion 2509 that can extend into the coaptation area of a leaflet and help promote coaptation between leaflets. The gap filler/coaptation element/spacer 2503 expands the thickness within the coaptation portion 2509 such that the coaptation portion 2509 can fill a gap within the coaptation area of a valve to help it close and/or prevent or inhibit valvular regurgitation. The device 2501 includes an anchor connection point 2511 that can connect with an anchor via a connector or an anchor receiver. A permeable, semipermeable, impermeable, or mesh sheet can be utilized. The coaptation element or spacer 2503 can comprise a material (e.g., shape memory material, foam, etc.) or a mechanism to expand the device, e.g., via balloon expansion, self-expansion, mechanical expansion, etc. For instance, the coaptation element or spacer 2503 can comprise a foam, a hydrogel, or a silicone material. Optionally, the coaptation element or spacer 2503 can comprise a scissor mechanism or an expandable coil. Furthermore, the device can include an expandable stent within or on top of the sheet 2505. The anchor connection point can comprise an interface, which can be the same as or similar to other interfaces herein.

Figure 27:
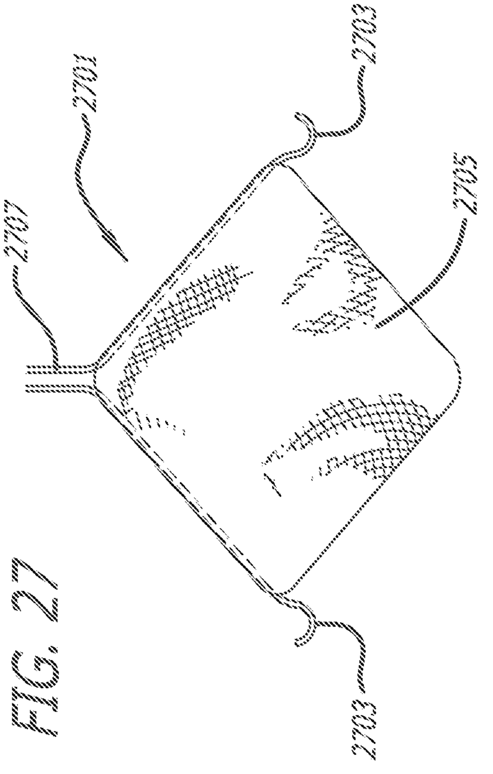

FIG. 27 illustrates an example implant or device 2701 comprising a wire form with small anchors configured as hooks 2703 capable of hooking into a crevice with a valve (e.g., cleft or commissure). The device 2701 includes a sheet 2705 that extends between the hooks 2703 that is capable of applying contact pressure on a leaflet flail, prolapse, rigidity, and/or abnormality. The sheet can be permeable, semipermeable, impermeable, or a mesh. The device 2701 includes an anchor connector 2707 capable of connecting to an additional anchor, but can optionally utilize an anchor connection point as described for FIG. 20. The anchor connector or anchor connection point can comprise an interface, which can be the same as or similar to other interfaces herein.

Figure 28:
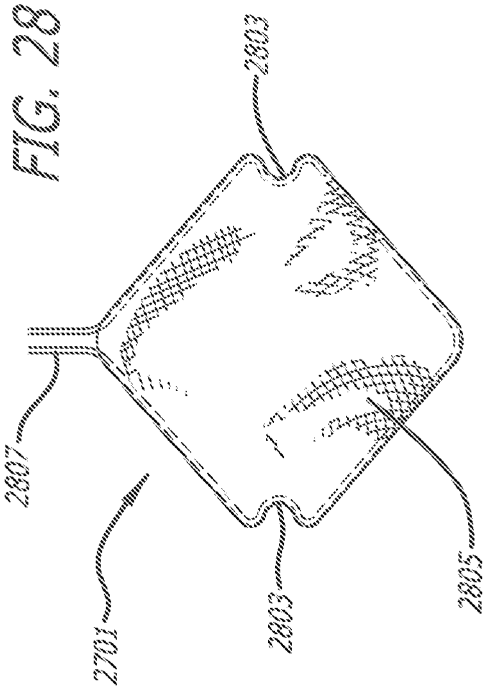

FIG. 28 illustrates an example implant or device 2801 comprising a wire form with indentations 2803 capable of securing within a crevice with a valve (e.g., cleft or commissure). The device 2801 includes a sheet 2805 that extends between the indentations 2803 that is capable of applying contact pressure on a leaflet flail, prolapse, rigidity, and/or abnormality. The sheet can be permeable, semipermeable, impermeable, or a mesh. The device 2801 includes an anchor connector 2807 capable of connecting to an anchor, but can optionally utilize an anchor connection point as described for FIG. 20. The anchor connector or anchor connection point can comprise an interface, which can be the same as or similar to other interfaces herein.

Figure 29:
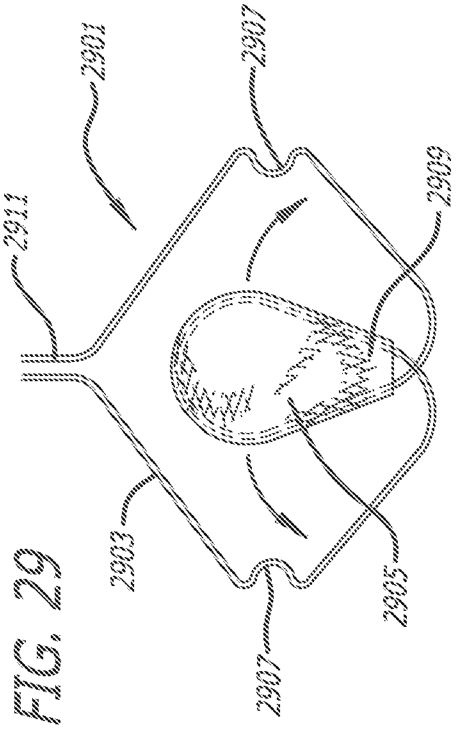

FIG. 29 illustrates an example implant or device 2901 comprising a wire form with a static portion 2903 and a dynamic portion 2905. The static portion 2903 is utilized to situate and secure the device 2901 and include indentations 2907 capable of securing within a crevice with a valve (e.g., cleft or commissure). The dynamic portion 2905 is capable of being adjusted such that it can be situated onto a leaflet flail, prolapse, rigidity, and/or abnormality. The dynamic portion 2905 incorporates a sheet 2909 that is capable of applying contact pressure on a leaflet flail, prolapse, rigidity, and/or abnormality. The sheet can be permeable, semipermeable, impermeable, or a mesh. The device 2901 includes an anchor connector 2911 capable of connecting to anchor, but can optionally utilize an anchor connection point as described for FIG. 20. The anchor connector or anchor connection point can comprise an interface, which can be the same as or similar to other interfaces herein.

Figure 30:
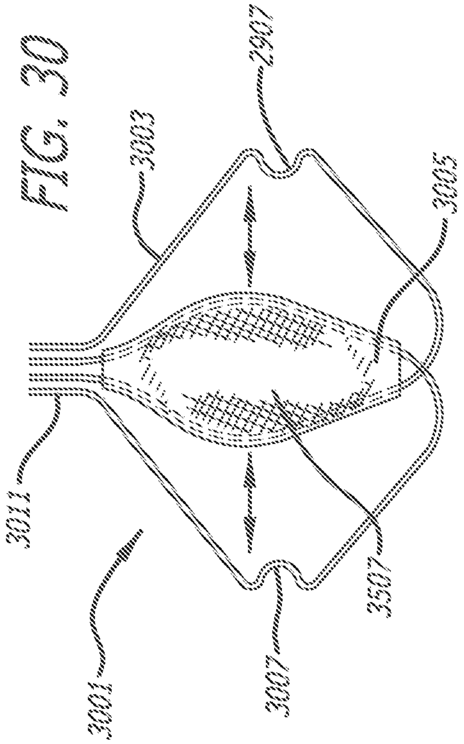

FIG. 30 illustrates an example implant or device 3001 comprising a wire form with a static portion 3003 and a dynamic portion 3005. The static portion 3003 is utilized to situate and secure the device 3001 and include indentations 3007 capable of securing within a crevice with a valve (e.g., cleft or commissure). The dynamic portion 3005 is capable of being adjusted such that widened or elongated, situating onto a leaflet flail, prolapse, rigidity, and/or abnormality. The dynamic portion 3005 incorporates a sheet 3009 that is capable of applying contact pressure on and/or support to a leaflet flail, prolapse, rigidity, and/or abnormality. The sheet can be permeable, semipermeable, impermeable, or a mesh. The device 3001 includes an anchor connector 3011 capable of connecting to anchor, but can optionally utilize an anchor connection point as described for FIG. 20. The anchor connector or anchor connection point can comprise an interface, which can be the same as or similar to other interfaces herein.

FIGS. 31A-31L are schematic views of example steps that can be used in delivering an implant or prosthetic device to a mitral valve and secure the implant with an anchor located in the coronary sinus, utilizing a connector to that traverse through a wall of the coronary sinus and left atrium. To help understand the delivery process, several figures provide a traverse-plane view within the left atrium superior to the mitral valve and several other figures provide a coronal-plane view within the left chambers sectioning through the coaptation area of the mitral valve. While described with respect to the coronary sinus and mitral valve, the system, devices, methods, steps, etc. can be equally applied to other vasculature of the heart and other valves mutatis mutandis.

Figure 31A:
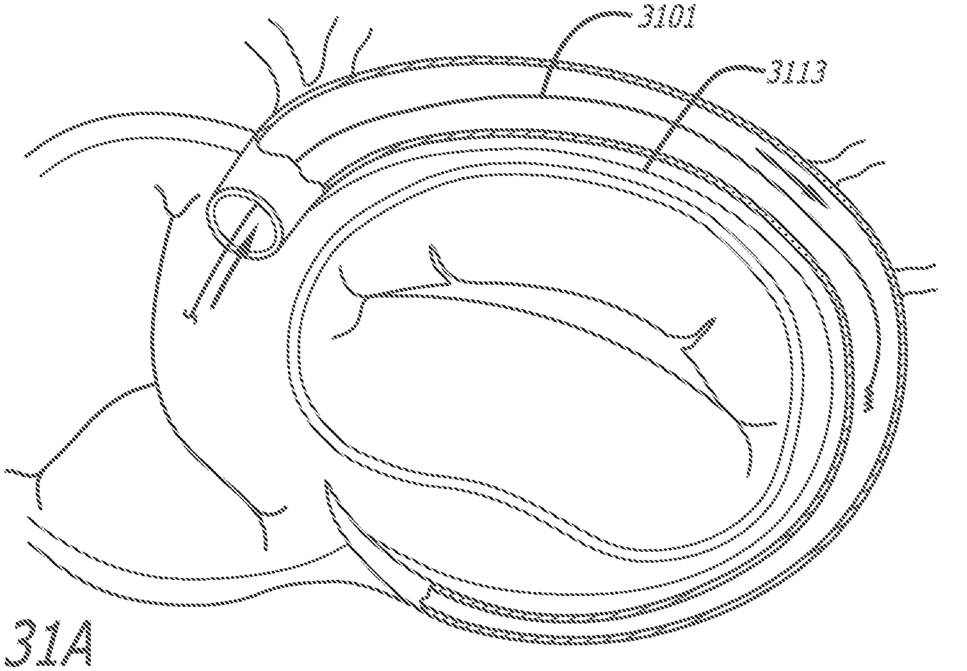
Figure 31B:
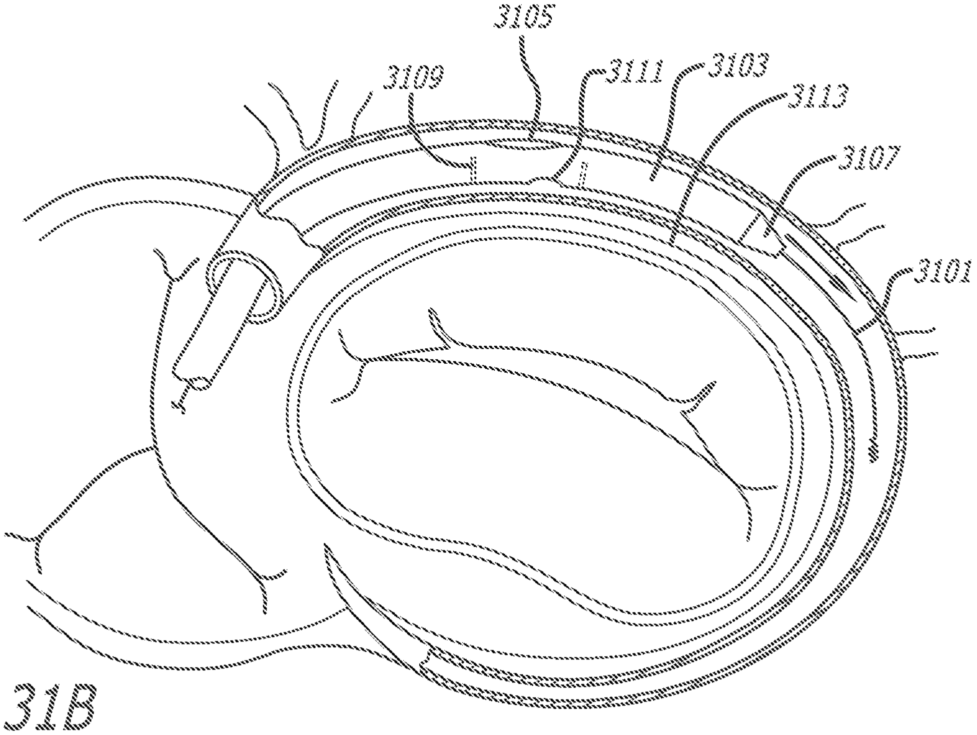

FIG. 31A shows a guidewire 3101 being advanced from the right atrium into the coronary sinus through its ostium or opening. A puncture catheter 3103 is then advanced over the guidewire 3101, as seen in FIG. 31B. The puncture catheter 3103 is introduced into the body through a proximal end of an introducer sheath (not shown). An introducer sheath provides access to the particular vascular pathway (e.g., jugular or subclavian vein) and may have a hemostatic valve therein. While holding the introducer sheath at a fixed location, the puncture catheter 3103 is directed to a site of the coronary sinus/left atrium wall to traverse.

At least a distal end of the puncture catheter 3103 preferably has a slight curvature built therein, with a radially inner and a radially outer side, so as to conform to the curved coronary sinus. An expandable anchoring member 3105 is exposed along a radially outer side of the catheter 3103 adjacent a distal segment 3107 that may be thinner than or tapered narrower from the proximal extent of the catheter. Radiopaque markers 3109 on the catheter 3103 help determine the precise advancement distance for desired placement of the anchoring member 3105 within the coronary sinus.

Figure 31C:
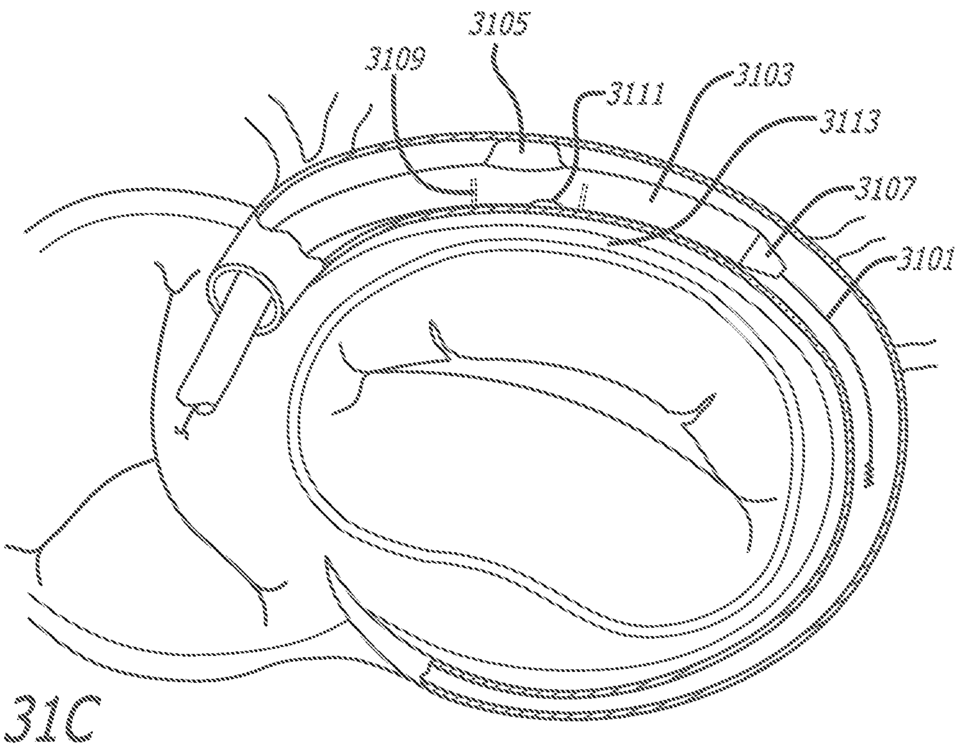

FIG. 31C shows radially outward deployment of the expandable anchoring member 3105, which in the illustrated example as a bulbous balloon but could also be a braided mesh. One advantage of a mesh is that it avoids excessive blockage of blood flow through the coronary sinus during the procedure. Other possible anchoring structures include (but are not limited to) nitinol wire form stent like structures. Expansion of the anchoring member 3105 presses the radially inner curve of the catheter against the luminal wall of the coronary sinus. The expandable anchoring member 3105 is located adjacent the distal segment 3107 of the puncture catheter 3103, and expands opposite a needle port 3111 formed in the radially inner side wall of the catheter. The needle port 3111 abuts the luminal wall and faces toward a tissue wall 3113 between the coronary sinus and the left atrium. The catheter 3103 is advanced so that the needle port 3111 is properly located at the appropriate site to traverse the tissue wall 3113, which can be guided by visualizing the radiopaque markers 3109. For instance, the needle port 3111 can be located approximately above the P2 segment of the posterior leaflet of the mitral valve as shown. The anchoring member 3105 may be centered diametrically across the catheter 3103 from the needle port 3111, or as shown may be slightly offset in a proximal direction from the needle port 3111 to improve leverage.

Figure 31D:
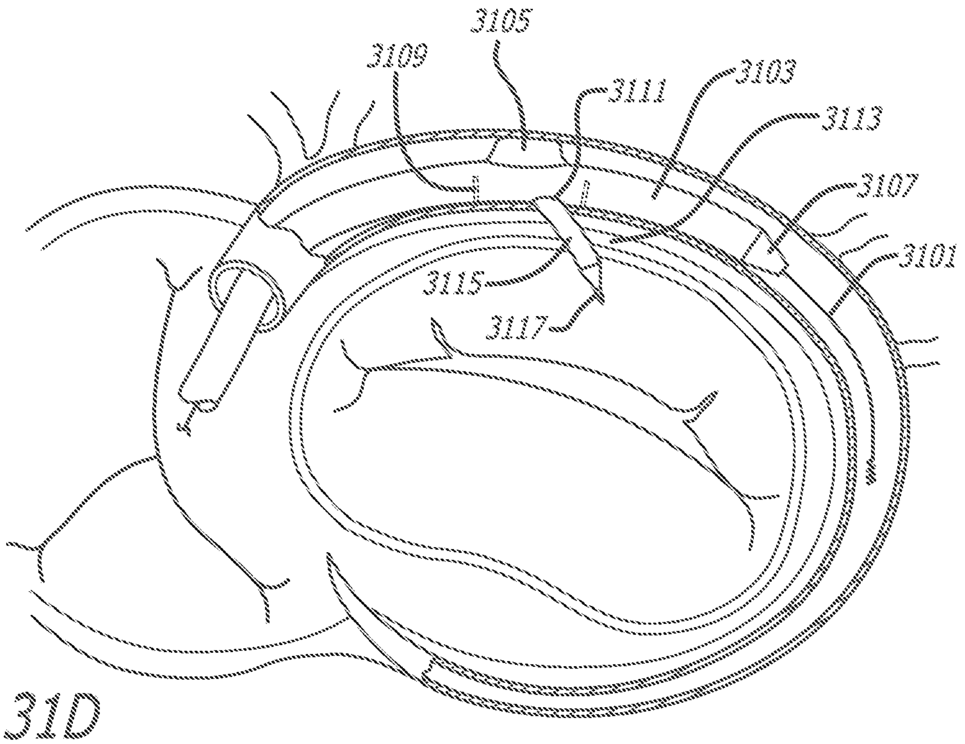

The curvature at the distal end of the puncture catheter 3103 aligns proximal to the anatomy within the coronary sinus and orients the needle port 3111 inward, while the anchoring member 3105 holds the catheter 3103 in place relative to the coronary sinus. Subsequently, as seen in FIG. 31D, a puncture sheath 3115 having a puncture needle 3117 with a sharp tip advances along the catheter 3103 such that it exits the needle port 3111 at an angle from the longitudinal direction of the catheter and punctures through the wall 3113 into the left atrium. The anchoring member 3105 provides rigidity to the system and holds the needle port 3111 against the wall 3113. The puncture needle 3117 is retracted from within the puncture sheath 3115 and is removed completely from the catheter 3103.

FIGS. 31E and 31F then show advancement of a second guidewire 3119 through the puncture sheath 3115 lumen, crossing through the left atrium the mitral valve aperture and into the left ventricle. FIG. 31F further illustrates removal of the puncture sheath 3115 from the left atrium and into the puncture catheter 3103, which leaves just the guidewire 3119 extending through the coronary sinus and into the left chambers. During these steps, the anchoring member 3105 remains expanded against the opposite luminal wall of the coronary sinus for stability, but is subsequently removed along with the puncture catheter 3103 to allow a delivery catheter 3121 to enter into the left chambers.

FIGS. 31G and 31H show a delivery catheter 3121 advanced along the guidewire 3119 and through the tissue wall 3113 into the left atrium. Within the delivery catheter 3121 is a compressed device 3123 that is to be implanted within the left chambers and onto a flail, flail, prolapse, rigidity, and/or other abnormality of the P2 segment of the posterior leaflet.

Figure 31K:
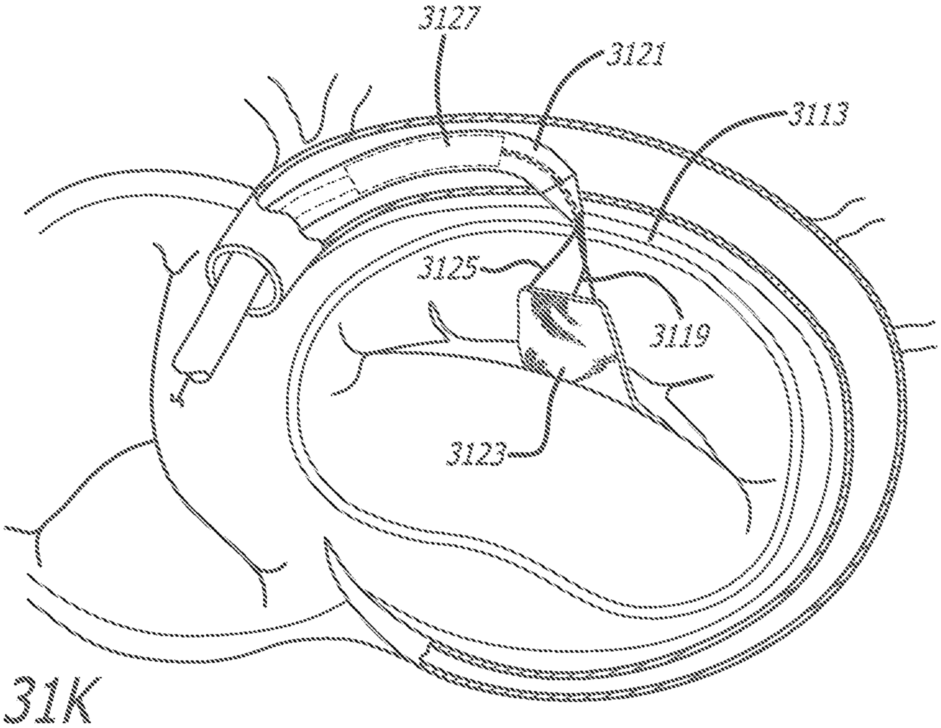

FIG. 31I then shows advancement of the device 3123 into the left chambers and the simultaneous retraction of the delivery catheter 3121 back through the atrium tissue wall 3113. As the device 3123 advances, it expands into form. FIG. 31J shows a fully expanded device 3123 at the site of implantation, which is the P2 segment of the posterior leaflet. FIGS. 31J and 31K show a connector 3125 of the device 3123 is released as the delivery catheter 3121 retracts back through the tissue wall 3113 into the coronary sinus such that the connector traverses the tissue wall 3113. The connector 3125 connects the expanded and released device 3123 with a condensed wire stent anchor 3127 still within the delivery catheter 3121.

Figure 31L:
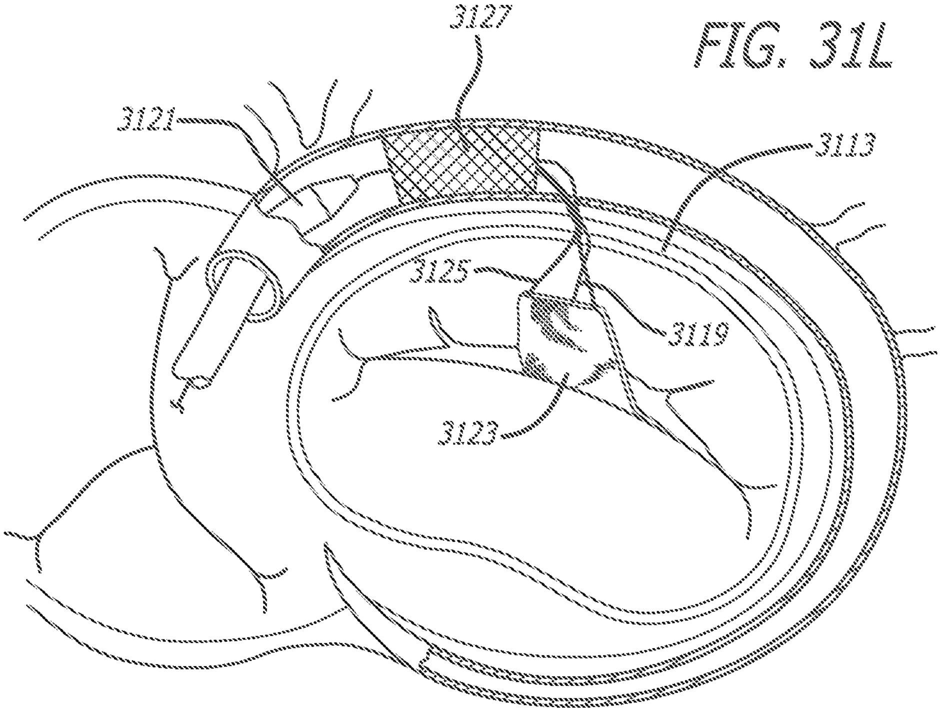

FIGS. 31K and 31L shows further retraction of the delivery catheter 3121, which results in the advancement and release of the wire stent anchor 3127 that expands and anchors within the coronary sinus. Subsequently, the entire delivery catheter 3121 is removed along the guidewire 3119 from the body, which is then removed from the body. The delivery process results in the device 3123 implanted onto the P2 segment of the mitral valve's posterior leaflet that is anchored utilizing a wire stent anchor 3127 expanded within the coronary sinus.

Some examples herein are directed towards compressive devices (e.g., compressive stents, compressive clamps, compressive splints, compressive forms, etc.) for mitigating heart valve leaflet flail, prolapse, rigidity, and/or other abnormalities. In some applications, a compressive device is capable of clamping onto a leaflet, holding onto its place on the leaflet while providing compressive and contact pressure onto a region of flail, prolapse, rigidity, and/or abnormality. The compressive and contact pressure provided by various stent implementations helps flatten out and/or reshape the flail, prolapse, rigidity, and/or abnormality, which helps extend the coapting edge of a leaflet back towards the coaptation area when in a closed position. Proper coaptation that results in a fully closed valve prevents valve regurgitation.

In some applications, a compressive device has an effluent portion and an influent portion that compress together via compression forces. When attached onto the leaflet, the effluent portion sits on the effluent face of the leaflet and the influent portion sits on the influent face of the leaflet, the two portions interconnected. Accordingly, in some applications, the influent portion of a stent provides contact pressure on and/or support to a leaflet, e.g., to address flail, prolapse, rigidity, and/or another abnormality. In some applications, the effluent portion and influent portion compress together to create a force to hold to maintain its position on the leaflet. In some applications, a torsion spring is utilized to provide compressive forces. In some applications, a compressive device is contoured to the shape of leaflet. In some applications, a compressive device is texturized on its surface with a roughened surface, indentations, notches, protrusions, and/or barbs to provide further grip to hold the stent in place. In some applications, a compressive device incorporates a wavy ridged wire to provide further grip (like a bobby pin grip).

In some applications, a compressive device comprises a wire form stent. Any appropriate material to produce a wire form can be utilized, including (but not limited to) using nitinol, cobalt-chrome (CoCr), stainless steel, titanium, polyglycolic acid (PGA), polylactic acid (PLA), poly-D-lactide (PDLA), polyurethane (PU), poly-4-hydroxybutyrate (P4HB), polycaprolactone (PCL), polyether ether ketone (PEEK), cyclic olefin copolymers (COCs), poly ethylene vinyl acetate (EVA), polytetrafluorethylene (PTFE), perfluoroether (PFA), fluorinated ethylene propylene (FEP), additives thereof, and derivatives thereof. In some applications, a compressive device is contractible, which can be useful to fit within a catheter device for less invasive catheter delivery methodologies. In some applications, nitinol is utilized for its self-expanding properties, which may be useful to implant the compressive device via less invasive catheter delivery methodologies.

Various shapes of wire form compressive devices can be utilized in various different implementations. In some applications, a compressive wire form stent is shaped to have portions of the wire form to provide contact pressure on and/or support to the flail, prolapse, rigidity, and/or abnormality. In some applications, a compressive wire form stent has length and width to surround an area of flail or prolapse and utilizes a sheet extending across the area to provide contact pressure on and/or support to the flail, prolapse, rigidity, and/or abnormality.

In some applications, a compressive implant or compressive device incorporates a sheet on a wire form. In some applications, a sheet or cover is provided on the influent portion of a compressive device and provides a surface capable of providing contact pressure onto and/or support to a leaflet experiencing flail, prolapse, rigidity, and/or another issue. A sheet or cover can be impermeable, semipermeable, or permeable to fluids (e.g., blood or plasma). In some applications, the sheet or cover is a mesh. In some applications, a mesh is formed utilizing a mesh sheet. In some applications, a mesh is formed utilizing interleaving strings that overlap and intersect. A mesh or permeable sheet can provide contact pressure without restricting the flow of blood or plasma, which can be important in various applications. For instance, an impermeable sheet or cover may trap blood within the compressive device, which in turn may create undesired pressures within the valve or possibly result in pressures that dislodge the implant/device or alter its position. A sheet, covering, and/or mesh herein can comprise any one or more of the following: poly(lactic-co-glycolic) acid (PLGA), polyvinylchloride (PVC), polyethylene (PE), polypropylene (PP), polytetrafluoroethylene (PTFE), polyurethane (PU), polyethylene terephthalate (PET), polyethersulfone (PES), polyglycolic acid (PGA), polylactic acid (PLA), poly-D-lactide (PDLA), poly-4-hydroxybutyrate (P4HB), and polycaprolactone (PCL).

Various implementations of compressive devices help promote coaptation of the leaflets when closed. In some applications, a gap filler/coaptation element/spacer is incorporated with the compressive device, which can help fill gaps within the valve aperture. In some applications, a compressive device includes an extended portion with an impermeable sheet that extends from the leaflet lip into the aperture, which can help form coaptation with the other leaflet(s). In some applications, a compressive device includes an extended portion that extends to the effluent face of another valve leaflet to contact the other leaflet when the valve closes such that it assists the opposite leaflet to come together with the stented leaflet and coapt. In some applications, an extended portion that extends to the effluent face of another valve leaflet has a bent angle towards the other leaflet (e.g., to reach another leaflet in a tricuspid, aortic, or pulmonary valve).

In some applications, a compressive device includes an anchor to stabilize the stent at the site of implantation. In some applications, the influent portion of a compressive device includes a portion that is in connection with the anchor. In some applications, the anchor connection point is near or in contact with the valve annulus or a ventricle or atrium wall. In some applications, an anchor is situated near or in contact with the valve annulus. In some applications, an anchor is situated near or in contact with the ventricle or atrium wall on the opposite side of the wall from the anchor connection point. In some applications, a connector is utilized to connect the anchor, the connector traversing through the ventricle or atrium wall. Any appropriate connector can be utilized, such as (for example) a screw, rivet, suture, staple, wire, pin, shaft, ribbon, sheet, etc.

In some applications, an anchor is situated within vasculature that is on the opposite side of a ventricle or atrium wall. For example, various compressive device implementations mitigate flail, prolapse, rigidity, and/or other abnormalities of the mitral valve and thus are situated within the left atrium. In these various implementations, a compressive device can be connected with an anchor situated within the coronary sinus utilizing a connector traversing through the atrial wall. Any appropriate anchor can be utilized. In some applications, an anchor is wire stent capable of expanding within vasculature. In some applications, an anchor is a pin, pin clamp (e.g., R-clamp, R-pin, R-key) or wire capable of pinning a compressive device via a connector to the ventricle or atrium wall. In some applications, a pin or wire fastener is utilized on the opposite side of a ventricle or atrium wall and the connector traverses the wall. In some applications, a pin or wire fastener is utilized within vasculature that is on the opposite of a ventricle or atrium wall. In some applications, a wire fastener is capable of pinching a connector wire to hold the wire in place and create tension between the wire fastener or wire anchor and the compressive device. In some applications, an anchor comprises a screw, helix, or helical anchor that is anchored within the valve annulus or an atrium or a ventricle wall.

In some applications, a compressive device is designed to include space and/or features permitting further medical intervention at a later time. In some applications, a wire form stent includes space within the coaptation area configured as a space between the wires of the wire form such that, if needed sometime in the future, a percutaneous edge to edge mitral valve repair device can still be implanted without the implant/device interfering.

Various implementations of compressive devices are to be used on any leaflet experiencing flail or prolapse. Accordingly, in some applications, a compressive device is capable of being utilized on a leaflet of a mitral, a tricuspid, an aortic, and/or a pulmonic valve. Likewise, various implementations of compressive devices can be utilized on any area of the leaflet experiencing flail or prolapse. In some applications, a compressive device is capable of being utilized on or near a leaflet commissure and/or any area between a leaflet's commissures.

To reach the site of implantation, any appropriate surgical technique can be utilized, including (but not limited to) a transcatheter delivery system, which can utilize a transfemoral, subclavian, transapical, transseptal, or transaortic approach. In some applications, a delivery catheter is utilized to incorporate a compressive device, then delivered to the site of deployment via a guidewire and utilized to attach the stent to a leaflet.

Some applications are directed to methods of delivering a compressive device to the site of deployment. The various methods described or suggested anywhere herein (including in documents incorporated by reference herein) can be performed on a living animal (e.g., human, mammal, other animal, etc.) or on a non-living simulation, such as on a cadaver, cadaver heart, simulator (e.g., with the body parts, tissue, etc. being simulated), etc. Accordingly, methods of delivery include both methods of treatment (e.g., treatment of human subjects) and methods of training and/or practice (e.g., utilizing an anthropomorphic phantom that mimics human vasculature to perform method).

Figure 32:
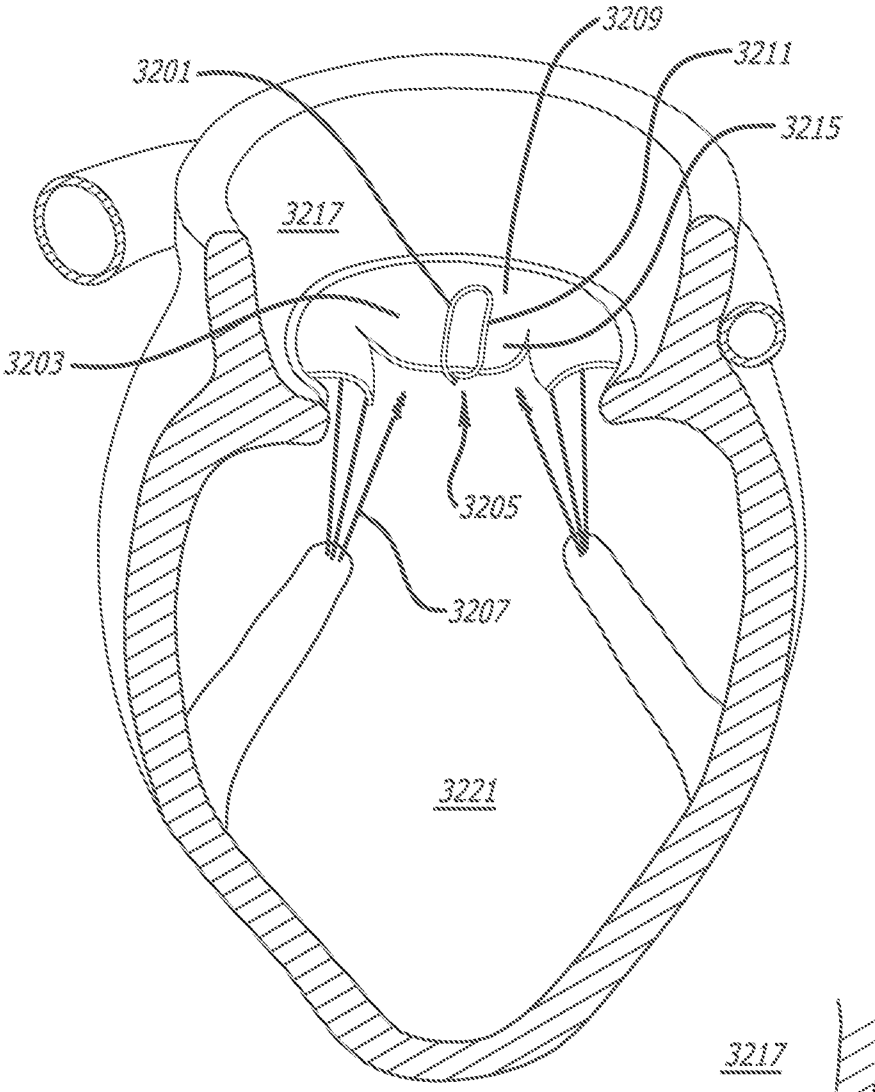
FIGS. 32-35 are schematic illustrations of example compressive devices implanted on a native valve.
Figure 33:
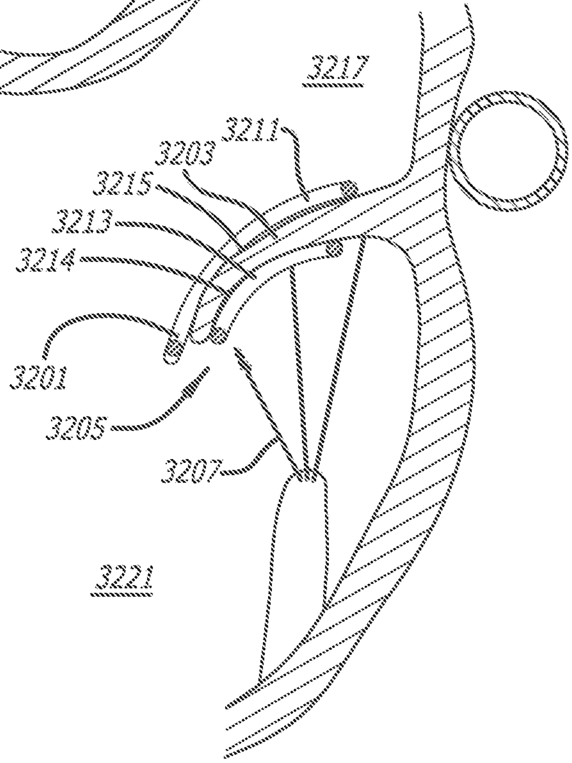

FIGS. 32 and 33 illustrate an example implant or device 3201 (e.g., a compressive device, repair device, repair implant, etc.) implanted and/or compressed onto a leaflet 3203 at a site of implantation. As shown here, the implant/device is on the native valve 3205 (e.g., mitral valve, tricuspid valve, etc.). In this example, the valve chordae tendineae is broken 3207 resulting in leaflet flail and/or prolapse in the P2 area 3209 of the posterior leaflet 3203 of the valve 3205. The implant/device 3201 has an influent portion 3211 and an effluent portion 3213. The influent portion 3211 is situated on and in contact with the influent face 3215 of the posterior leaflet 3203 within the atrium 3217 at the site of flail and/or prolapse. The effluent portion 3213 is situated on and in contact with the effluent face 3219 of the posterior leaflet 3203 within the ventricle 3221 at the site of flail and/or prolapse. The implant/device acts as a compressive device wherein the influent portion 3211 and the effluent portion 3213 are configured to utilize compressive forces on the flail, prolapse, and/or other abnormality to help flatten out and/or reshape the leaflet (e.g., a protrusion, bulge, etc.) and mitigate regurgitant blood flow. The implant/device 3201 includes a coaptation portion 3223 that extends beyond the edge of the posterior leaflet 3203 and connects the influent portion 3211 and the effluent portion 3213.

Figure 34:
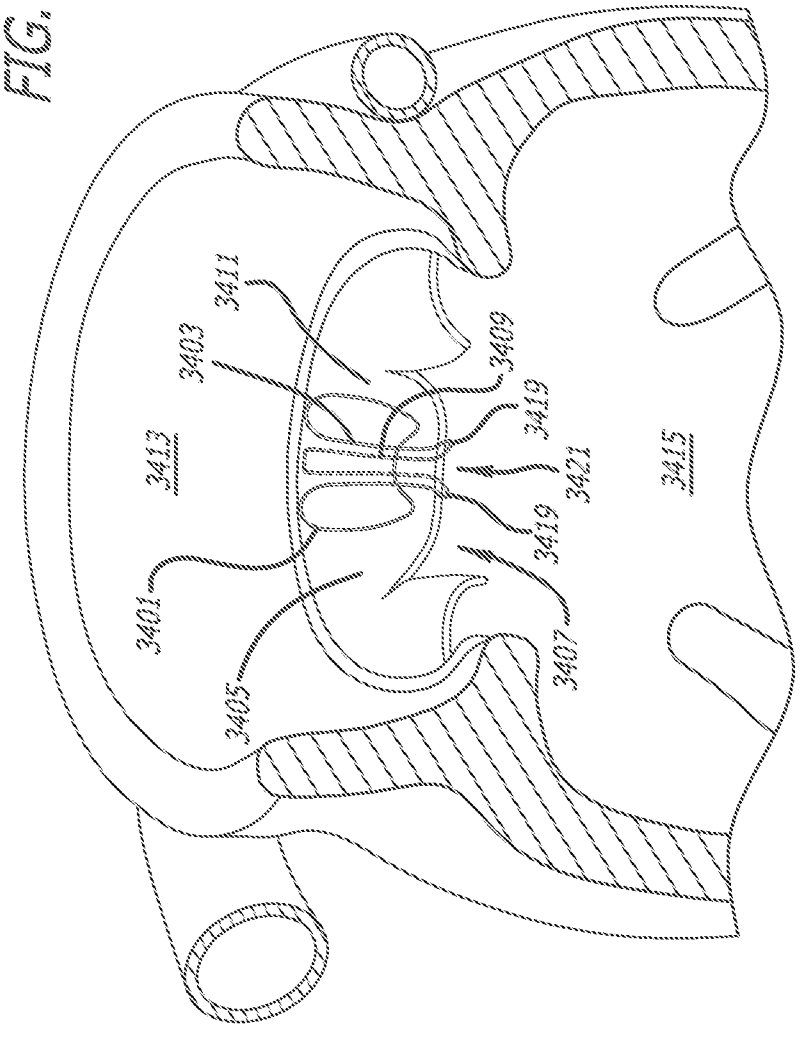

FIG. 34 illustrates an example implant or device 3401 (e.g., a compressive device, repair device, repair implant, etc.) with an expanded influent portion 3403 having multiple loops implanted or compressed onto a leaflet 3405 at a site of implantation. As shown here, the implant/device is on the native valve 3407 (e.g., a mitral valve, tricuspid valve, etc.). The implant/device also includes an effluent portion 3409, indicated by dashed lines. The influent portion 3403 is situated on and in contact with the influent face 3411 of the posterior leaflet 3405 within the atrium 3413 at the site of flail, prolapse, rigidity, and/or abnormality. The effluent portion 3409 is situated on and in contact with the effluent face and of the posterior leaflet 3405 within the ventricle 3415 at the site of flail, prolapse, rigidity, and/or abnormality. The implant/device acts as a compressive device wherein influent portion 3403 and the effluent portion 3409 are configured to utilize compressive forces on the flail, prolapse, rigidity, and/or abnormality to help flatten out and/or reshape the leaflet (e.g., a protrusion, bulge, flail, etc.) and/or mitigate regurgitant blood flow. In addition, the expanded influent portion 3403 with multiple loops increases contact compared to the influent portion of device 3201 and thus can provide additional contact pressure and/or support at the sites of leaflet flail, prolapse, rigidity, and/or abnormality. Accordingly, various device shapes or stent shapes can increase contact pressure on a leaflet flail, prolapse, rigidity, and/or abnormality by increasing the amount of contact between the stent and leaflet. The device 3401 includes two coaptation portions 3419 that extend beyond the edge of the posterior leaflet 3405 and connect the influent portion 3403 and the effluent portion 3409. The two coaptation portions are spaced apart providing an area 3421 for further medical intervention at a later time (e.g., later edge to edge repair, such as implanting a device that holds leaflets together) on the valve leaflets.

Figure 35:
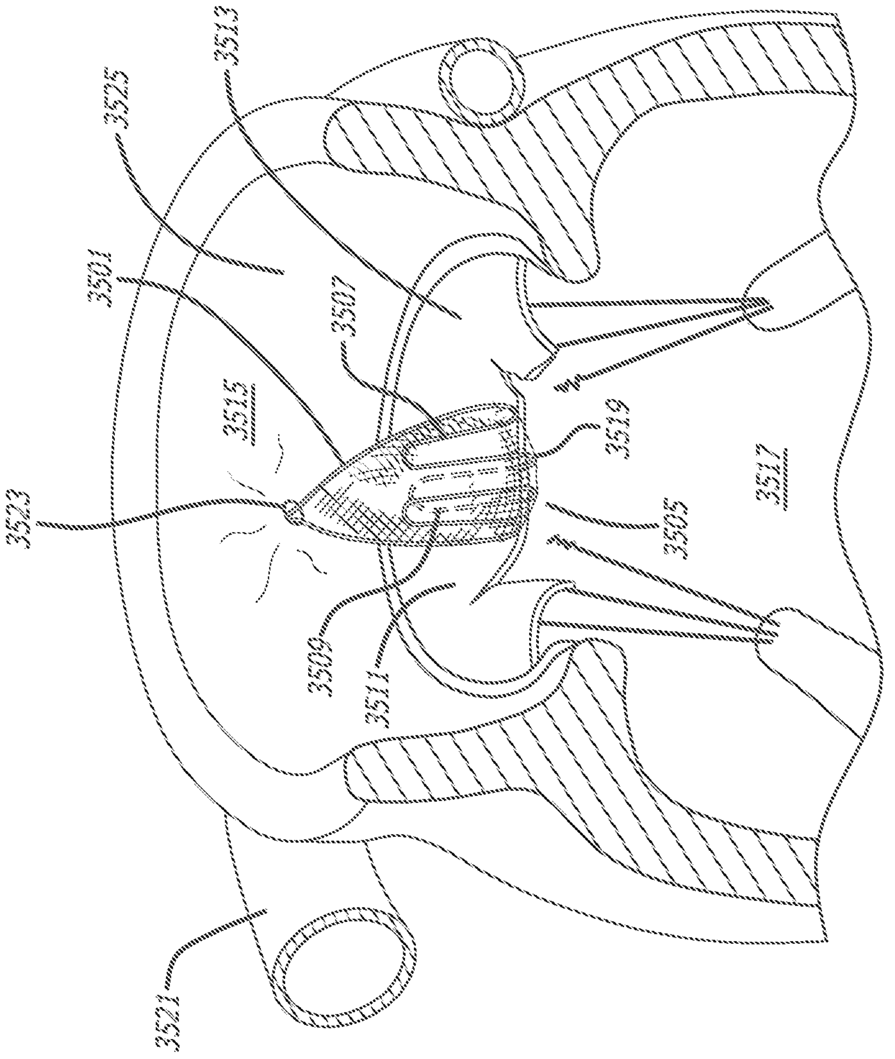

FIG. 35 illustrates an example implant or device 3501 (e.g., compressive device, repair device, etc.) comprising a wire stent anchor (not shown) at a site of implantation. As shown here, the implant/device is on the native valve 3505 (e.g., mitral valve, tricuspid valve, etc.). The implant/device 3501 has an influent portion 3507 and an effluent portion 3509, indicated by dashed lines. The influent portion 3507 is situated on and in contact with the influent face 3511 of the posterior leaflet 3513 within the atrium 3515 at the site of flail, prolapse, rigidity, and/or abnormality. The effluent portion 3509 is situated on and in contact with the effluent face and of the posterior leaflet 3513 within the ventricle 3517 at the site of flail, prolapse, rigidity, and/or abnormality. The implant/device acts as a compressive device wherein the influent portion 3507 and the effluent portion 3509 are configured to utilize compressive forces on the flail, prolapse, rigidity, and/or abnormality to help flatten out and/or reshape the leaflet (e.g., a protrusion, bulge, flail, etc.) and mitigate regurgitant blood flow. The implant/device 3501 can include a coaptation portion 3519 that extends beyond the edge of the posterior leaflet 3513 and connects the influent portion 3507 and the effluent portion 3509.

In some applications, the anchor is a wire form expanded within the coronary sinus 3521 adjacent to the left atrium 3515 (or within another blood vessel at or near another chamber of the heart). The anchor 3503 is connected to the compressive device 3501 via a connector 3523 that traverses through the atrium wall 3525. Accordingly, the anchor helps stabilize the implant/device 3501 at the native valve 3505.

FIGS. 36 to 44 illustrate examples of implants or devices configured as compressive devices (e.g., compressive wire forms and/or stents). In these examples, for the sake of simplicity, a first portion of the compressive device is denoted an influent portion and a second portion is denoted an effluent portion. It is to be understood, however, that an effluent portion can be the influent portion, and that an influent portion can be the effluent portion, as the side of the leaflet in which these portions contact is interchangeable.

Figure 36:
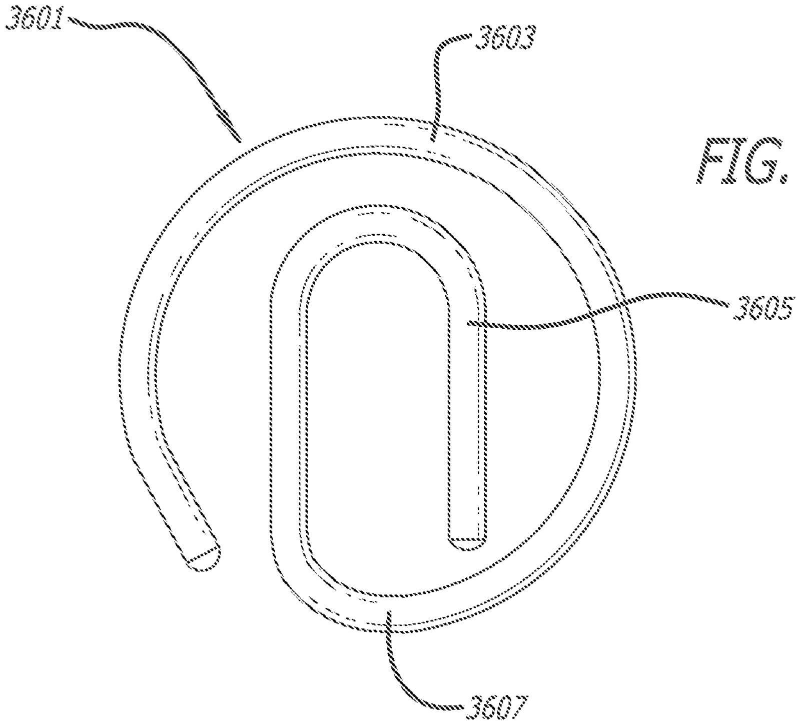

FIG. 36 illustrates an example implant or device configured as a compressive device or compressive wire form stent 3601. The device or wire form stent includes an influent portion 3603 and an effluent portion 3605 connected via a coaptation portion 3607.

Figure 37:
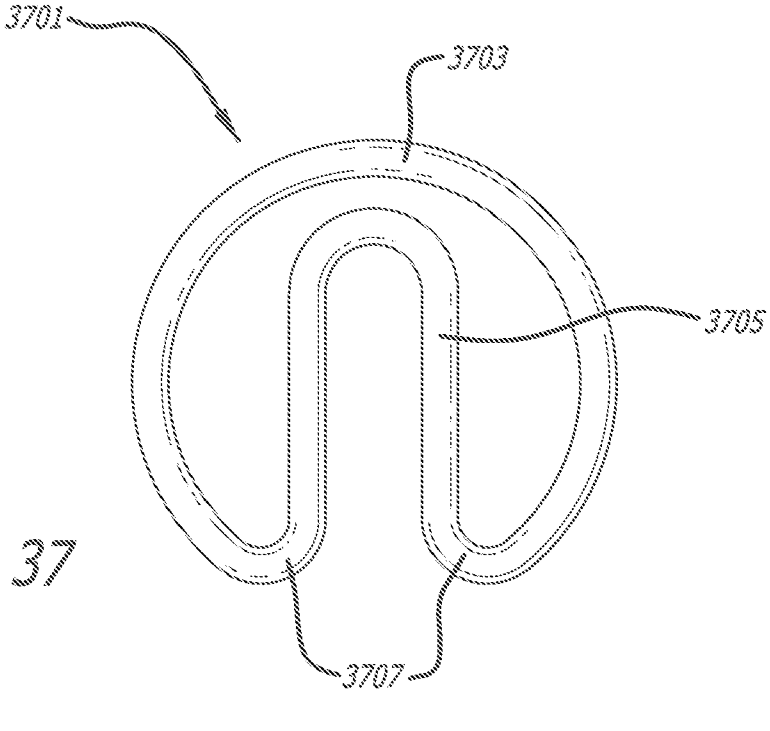

FIG. 37 illustrates an implant or device configured as a compressive device or compressive wire form stent 3701 in a singular wire that has no wire ends. The wire form stent includes an influent portion 3703 and an effluent portion 3705 connected via a coaptation portion 3707.

Figure 38:
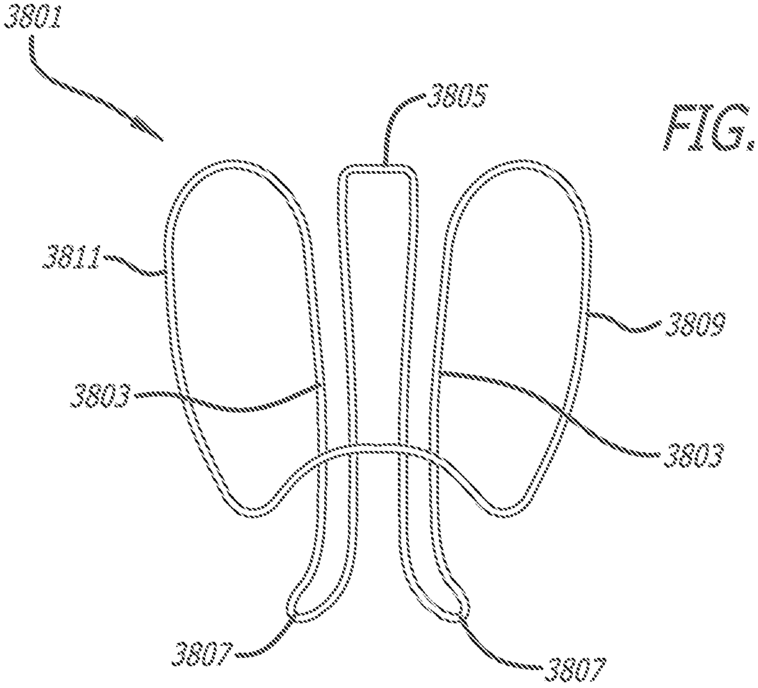

FIG. 38 illustrates an implant or device configured as a compressive device or compressive wire form stent 3801 with additional curvature to increase wire contact with a leaflet prolapse and/or flail. The device or wire form stent includes an influent portion 3803 and an effluent portion 3805 connected via coaptation portions 3807. The influent portion 3803 includes two loops 3809, 3811 as additional curvature that increases the contact points of the influent portion 3803 with the influent face of a leaflet. The coaptation portions 3807 are spaced apart to allow further subsequent medical intervention (e.g., later edge to edge repair) on the valve leaflets.

Figure 39:
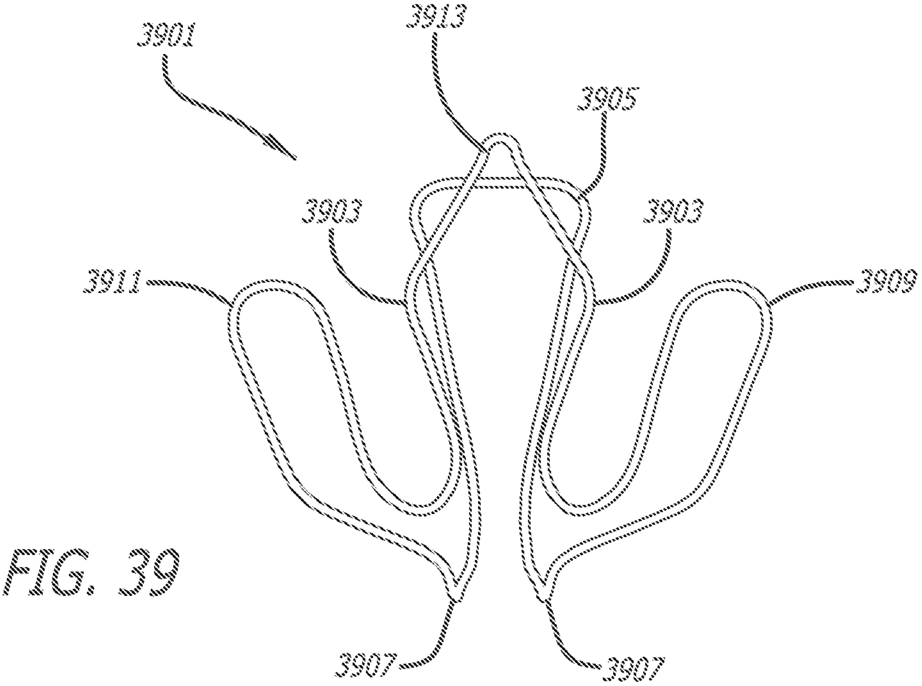

FIG. 39 illustrates an implant or device configured as a compressive device or compressive wire form stent 3901 with additional curvature to increase wire contact with a leaflet prolapse and/or flail. The device or wire form stent includes an influent portion 3903 and an effluent portion 3905 connected via a coaptation portions 3907. The influent portion 3903 includes outer wing-like loops 3909, 3911 and a large inner loop 3913 as additional curvature that increases the contact points of the influent portion 3903 with the influent face of a leaflet. The coaptation portions 3907 are spaced apart to leave a space to allow further medical intervention at some later time (e.g., later edge to edge repair) on the valve leaflets without interference from the implant/device.

Figure 41:
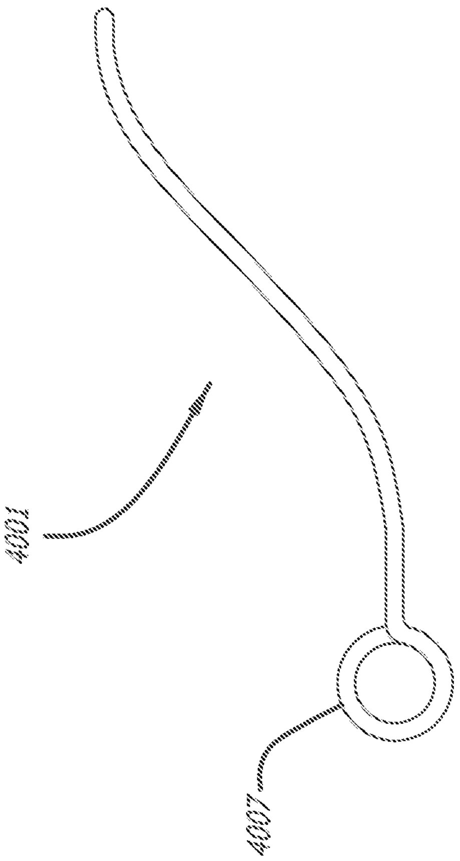
Figure 40:
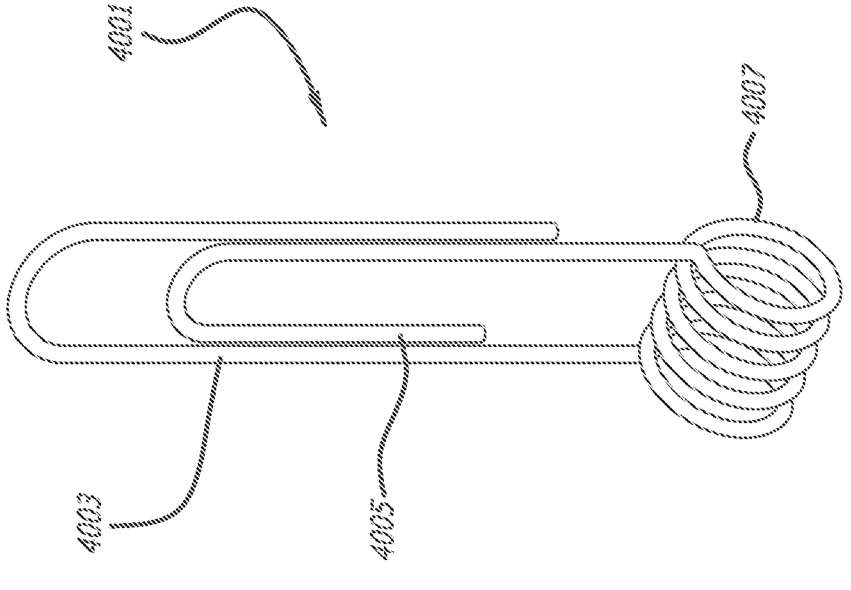

FIGS. 40 and 41 illustrate an implant or device configured as a compressive device or compressive wire form stent 4001 with a torsion spring. The device or wire form stent includes an influent portion 4003 and an effluent portion 4005 connected via a coaptation portion. The coaptation portion includes a torsion spring 4007 to increase the compression forces provided between the influent portion 4003 and the effluent portion 4005. The torsion spring 4007 can be situated within an open area on the effluent side of the valve (e.g., within the left ventricle area if used on the mitral valve).

FIG. 42 illustrates an implant or device configured as a compressive device or compressive wire form stent 4201 with a connector to connect with an anchor. The wire form stent includes an influent portion 4203 and an effluent portion 4205 connected via a coaptation portion 4207. A connector 4209 is extended from the influent portion 4203 and connects with an anchor (not shown). In some applications, the connector 4209 is capable of traversing through heart or vasculature tissue. The connector can also be an anchor connection point and/or anchor receiver similar to those described elsewhere herein. For example, in some applications, the compressive device or stent 4201 can comprise an anchor receiver at an anchor connection point configured such that the device 4201 is anchored to the annulus.

FIG. 43 illustrates an implant or device configured as a compressive device or compressive wire form stent 4301 with a connector and additional curvature to increase wire contact with a leaflet prolapse and/or flail. The device or wire form stent includes an influent portion 4303 and an effluent portion 4305 connected via a coaptation portion 4307. A connector 4309 is extended from the influent portion 4303 and connects with an anchor (not shown). In some applications, the connector is capable of traversing through heart or vasculature tissue. The influent portion 4303 includes two loops 4311, 4313 as additional curvature that increases the contact points of the influent portion 4303 with the influent face of a leaflet. The coaptation portions 4307 are spaced apart to allow further medical intervention at a later time (e.g., subsequent edge to edge repair) on the valve leaflets. The connector can also be an anchor connection point and/or anchor receiver similar to those described elsewhere herein. For example, in some applications, the compressive device or stent can comprise an anchor receiver at an anchor connection point configured such that the device is anchored to the annulus.

FIG. 44 illustrates an implant or device configured as a compressive device or compressive wire form stent 4401 with a connector and additional curvature to increase wire contact with a leaflet prolapse and/or flail. The device or wire form stent includes an influent portion 4403 and an effluent portion 4405 connected via coaptation portions 4407. A connector 4409 is extended from the influent portion 4403 and connects with an anchor (not shown). In some applications, the connector is capable of traversing through heart or vasculature tissue. The influent portion 4403 includes a back-and-forth pattern as additional curvature that increases the contact points of the influent portion 4403 with the influent face of a leaflet. The connector can also be an anchor connection point and/or anchor receiver similar to those described elsewhere herein. For example, in some applications, the compressive device or stent can comprise an anchor receiver at an anchor connection point configured such that the device is anchored to the annulus.

Figure 45:
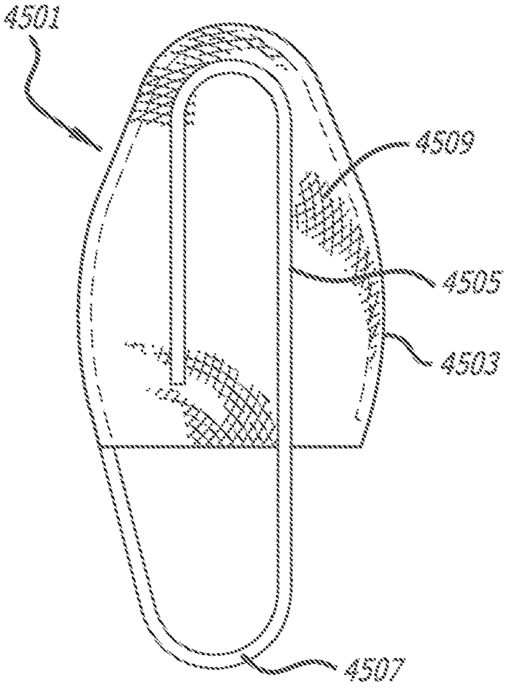
Figure 46:
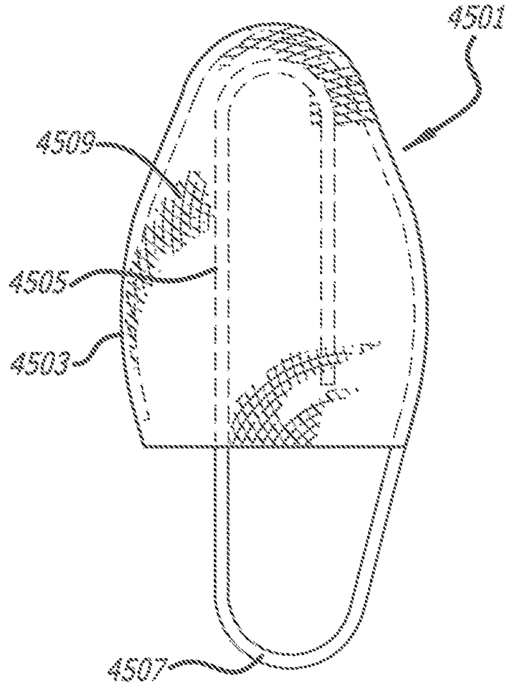

FIGS. 45 and 46 illustrate an implant or device configured as a compressive device or compressive wire form stent 4501 with a sheet on an influent portion to increase surface contact with a leaflet prolapse and/or flail. The device or wire form stent includes an influent portion 4503 and an effluent portion 4505 connected via a coaptation portion 4507. The influent portion 4503 includes a sheet or cover 4509 that increases the contact points of the influent portion 4503 with the influent face of a leaflet. The sheet or cover can be permeable (e.g., as a mesh, etc.), semipermeable, or impermeable.

Figure 47:
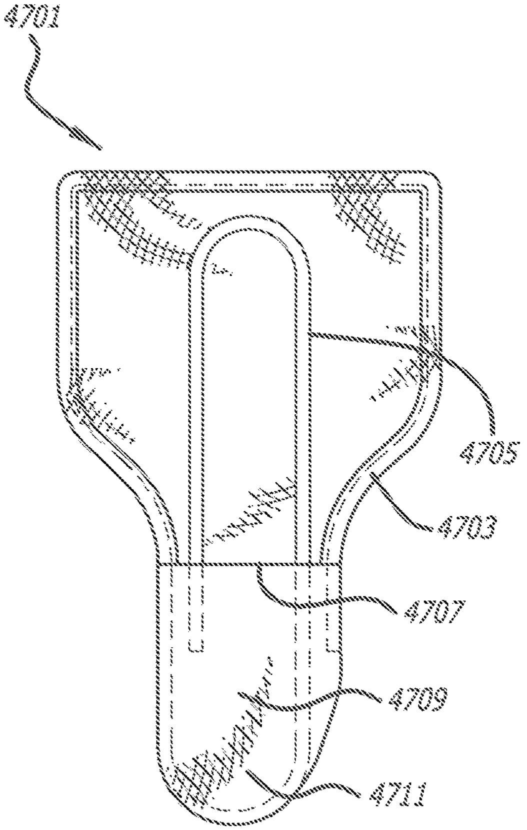
Figure 48:
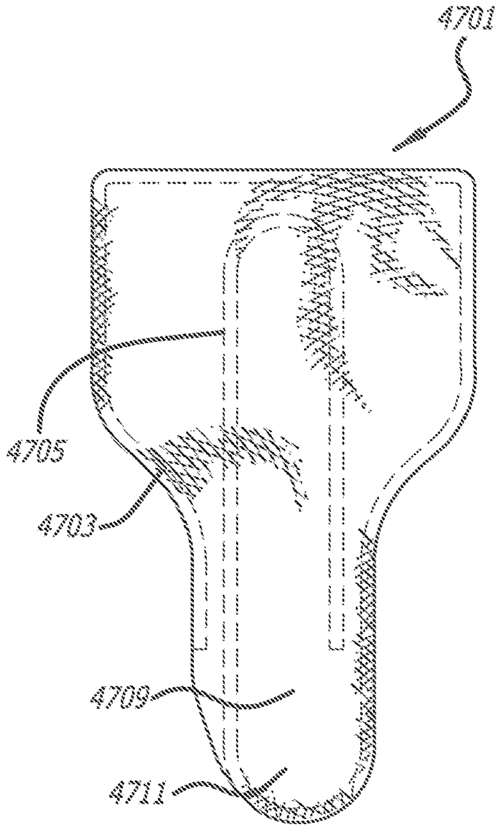

FIGS. 47 and 48 illustrate an implant or device configured as a compressive device or compressive wire form stent 4701 with a sheet or cover on an influent portion to surface contact with a leaflet prolapse and/or flail. The implant/device can also have an extended coaptation area help the leaflets coapt when the valve is closed. The device or wire form stent includes an influent portion 4703 and an effluent portion 4705 connected via a coaptation portion 4707. The influent portion 4703 and includes a sheet or cover 4709 that increases the contact points of the influent portion 4703 with the influent face of a leaflet. The coaptation portion 4707 also includes the sheet or cover 4709, but the coaptation portion 4707 with sheet or cover is extended 4711 such that it capable of extending beyond the leaflet edge when situated upon.

FIG. 49 illustrates an implant or device configured as a compressive device or compressive wire form stent 4901 with a sheet on an influent portion to surface contact with a leaflet prolapse and/or flail. This example utilizes the same basic wire form described and shown in FIG. 38, and thus includes additional curvature to increase wire contact with a leaflet prolapse and/or flail. The device or wire form stent includes an influent portion 4903 and an effluent portion 4905 connected via a coaptation portion 4907. The influent portion 4903 includes two loops 4909, 4911 as additional curvature that increases the contact points of the influent portion 4903 with the influent face of a leaflet. The influent portion 4903 also includes a sheet or cover 4913 that increases the contact points of the influent portion 4903 with the influent face of a leaflet. The sheet or cover can be permeable, semipermeable, or impermeable. An example comprising a permeable mesh sheet is depicted in FIG. 50.

FIG. 51 illustrates an implant or device configured as a compressive device or compressive wire form stent 5101 with a sheet on an influent portion to surface contact with a leaflet prolapse and/or flail. This example utilizes the same basic wire form and connector described and shown in FIG. 42, and thus includes a connector to connect with an anchor. The device or wire form stent includes an influent portion 5103 and an effluent portion 5105 connected via a coaptation portion 5107. A connector 5109 is extended from the influent portion 5103 and connects with an anchor (not shown) and is capable of traversing through heart or vasculature tissue. The influent portion 5103 also includes a sheet or cover 5111 that increases the contact points of the influent portion 5103 with the influent face of a leaflet. The sheet or cover can be permeable, semipermeable, or impermeable. An example with a permeable mesh sheet or cover is depicted in FIG. 52.

Figure 53:
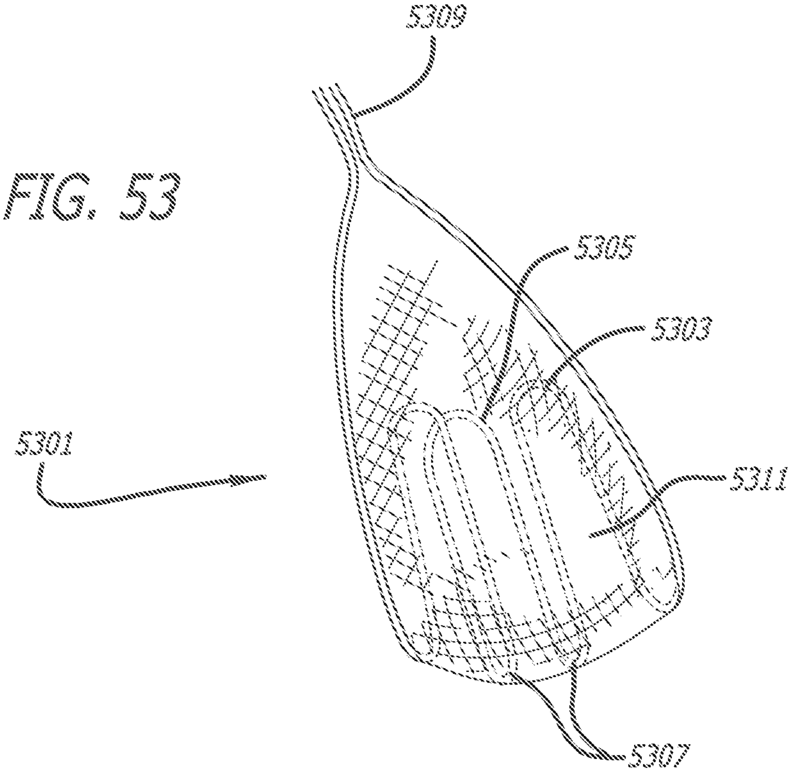

FIG. 53 illustrates an implant or device configured as a compressive device or compressive wire form stent 5301 with a sheet on an influent portion to surface contact with a leaflet prolapse and/or flail. This example utilizes the same basic wire form and connector described and shown in FIG. 44, and thus includes a connector and additional curvature to increase wire contact with a leaflet prolapse and/or flail. The wire form stent includes an influent portion 5303 and an effluent portion 5305 connected via coaptation portions 5307. A connector 5309 is extended from the influent portion 5303 and connects with an anchor (not shown) and is capable of traversing through heart or vasculature tissue. The influent portion 5303 includes a back-and-forth pattern as additional curvature that increases the contact points of the influent portion 5303 with the influent face of a leaflet. The influent portion 5303 also includes a sheet or cover 5311 that increases the contact points of the influent portion 5303 with the influent face of a leaflet. The sheet or cover can be permeable (e.g., a mesh, etc.), semipermeable, or impermeable.

Figure 54:
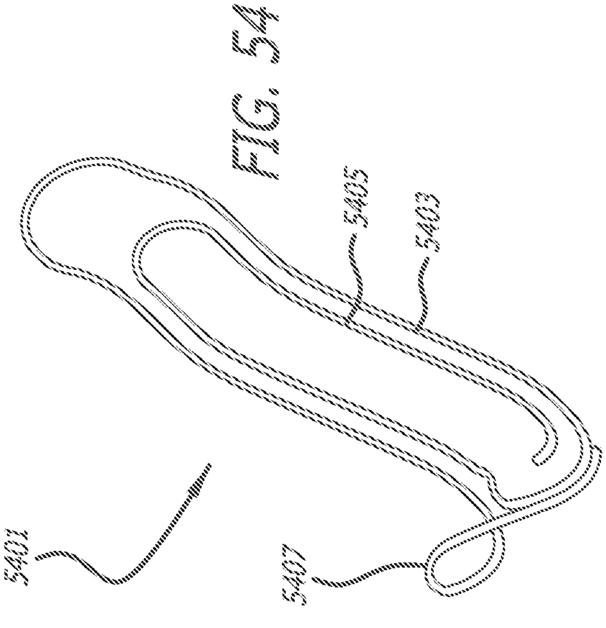
Figure 55:
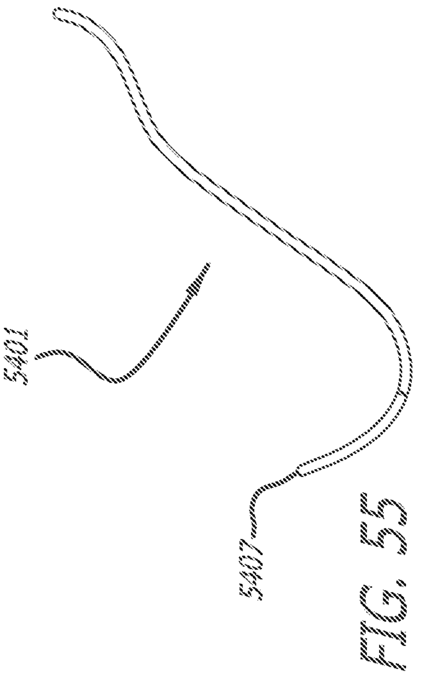

FIGS. 54 and 55 illustrate an implant or device configured as a compressive implant/device comprising a compressive wire form stent 5401 with an extended and contoured coaptation portion to help leaflet coaptation. The implant/device or wire form stent includes an influent portion 5403 and an effluent portion 5405 connected via a coaptation portion 5407. The coaptation portion 5407 is extended beyond the edge of a leaflet experiencing issues, e.g., flail, prolapse, rigidity, and/or abnormality. The coaptation portion 5407 is also contoured to be able to reach a leaflet opposite of the leaflet experiencing issues, e.g., flail, prolapse, rigidity, and/or abnormality. The contoured portion lifts and pulls the opposite leaflet towards the leaflet experiencing issues to help the leaflets close.

Figure 56:
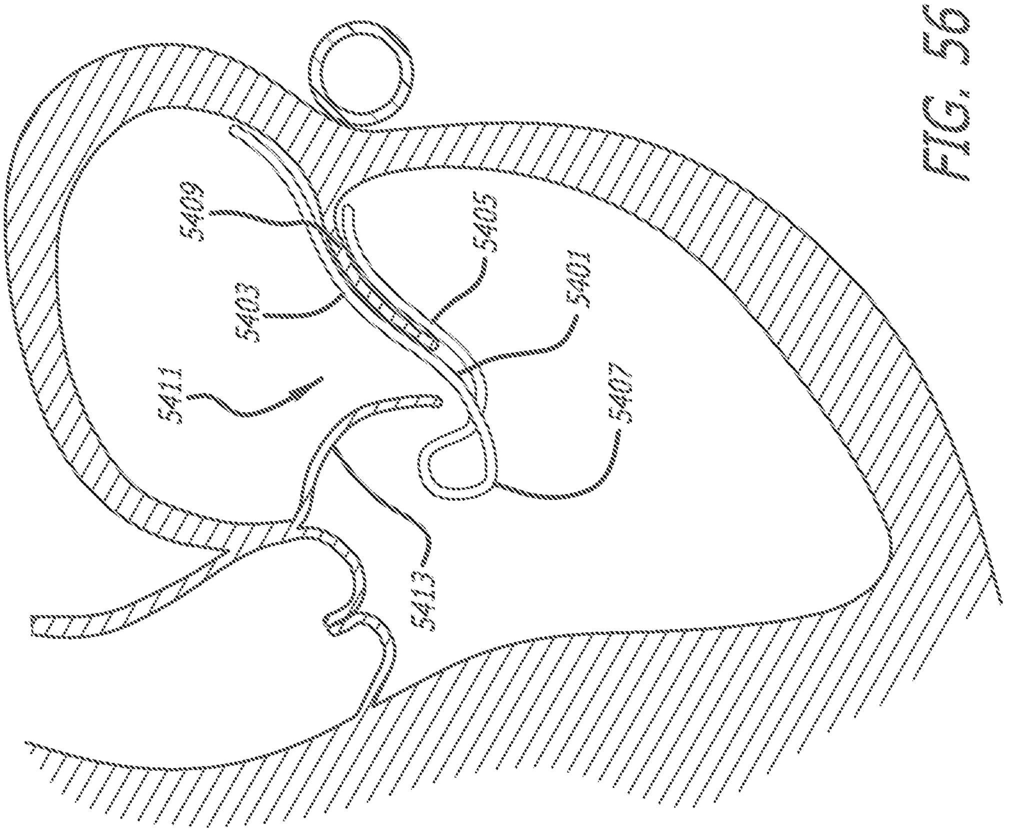

FIG. 56 shows the implant/device depicted in FIGS. 54 and 55 on a posterior leaflet 5409 of a mitral valve 5411. The coaptation portion 5407 extends beyond the posterior leaflet 5413 edge and into the left ventricle. The coaptation portion 5407 is also contoured such that, as valve closes, the distal edge of the coaptation portion 5407 contacts the effluent face of the anterior leaflet 5413 to assist bringing the anterior leaflet and posterior leaflet together and coapt.

Figure 58:
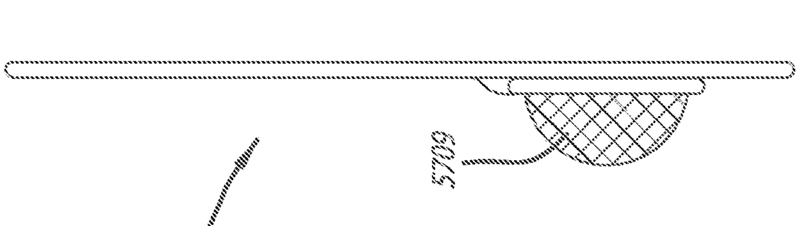
Figure 57:
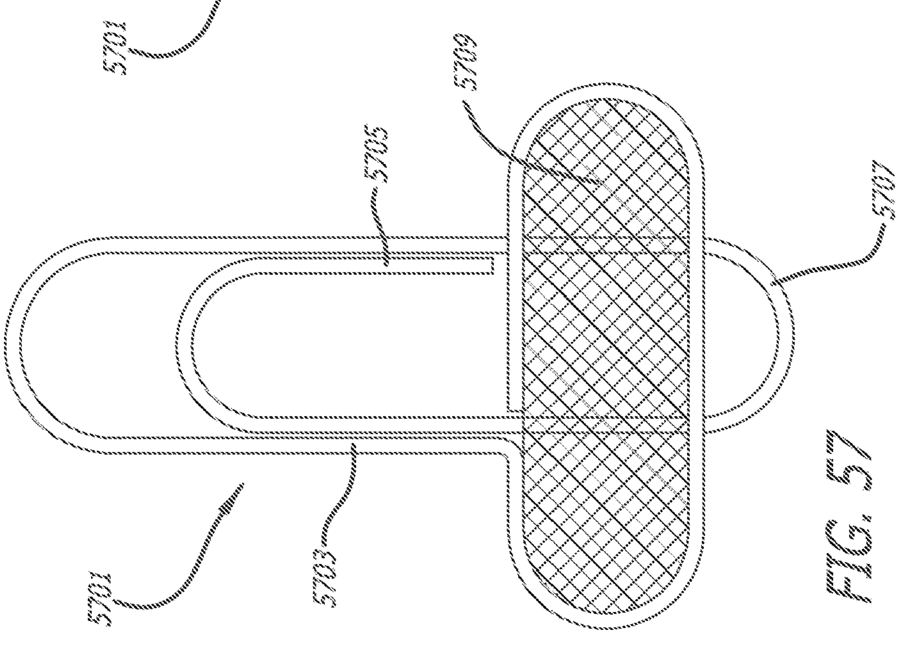

FIGS. 57 and 58 illustrates an implant or device configured as a compressive implant/device comprising a compressive wire form stent 5701 with an attached gap filler, coaptation element, or spacer. The implant/device or wire form stent includes an influent portion 5703 and an effluent portion 5705 connected via a coaptation portion 5707. The effluent portion 5705 includes a bulky gap filler/coaptation element/spacer 5709 situated near the coaptation portion 5707. The gap filler/coaptation element/spacer 5709 has a bulky conformation such that it fit within a valve aperture and fill in gaps when the valve is closed.

Figure 59:
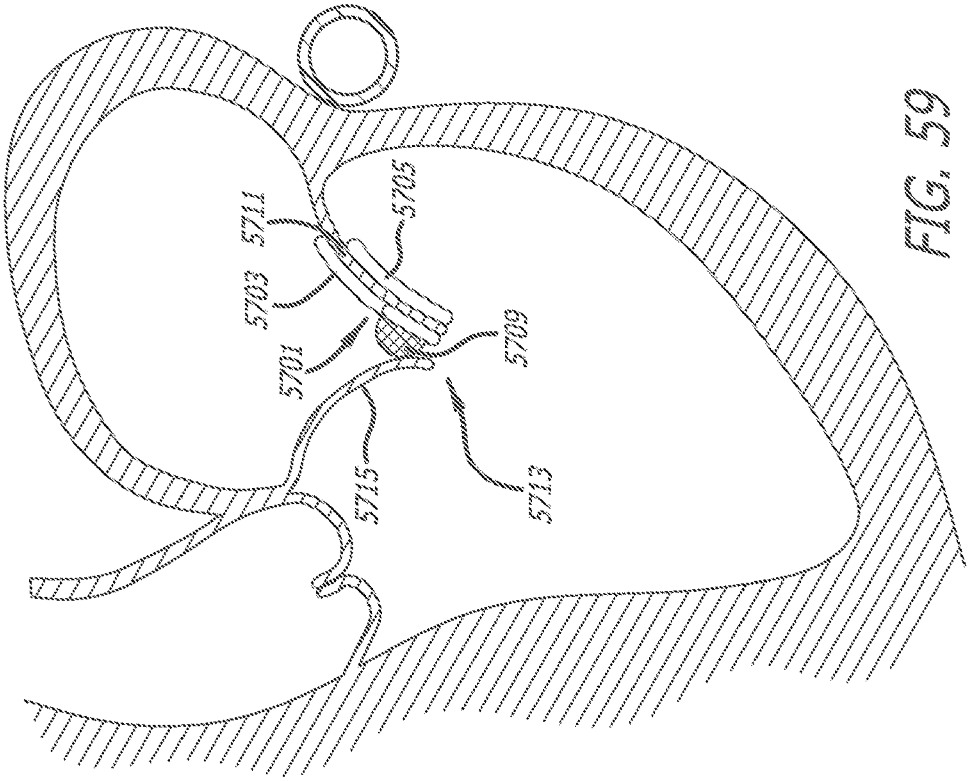

FIG. 59 shows the implant/device depicted in FIGS. 57 and 58 on a posterior leaflet 5711 of a mitral valve 5713. When the valve is closed, the gap filler/coaptation element/spacer 5709 situates between the posterior leaflet 5711 and the anterior leaflet 5715 to fill any gaps that may exist.

FIGS. 60A-60D are schematic views of example steps in delivering an implant/device to a native valve via a blood vessel of the heart, described here in the context of delivering an implant/device to a mitral valve via the coronary sinus for illustration (but similar steps can be used at other locations mutatis mutandis). For example, the steps can include accessing the blood vessel or coronary sinus, and traversing through a wall of the coronary sinus and left atrium. The initial steps of reaching the left chambers via the coronary sinus are similar to steps shown FIGS. 31A to 31F and described in accompanying text. To help understand the delivery process, several figures provide a coronal-plane view within the left chambers sectioning through the coaptation area of the mitral valve.

After a puncture catheter is removed from the left chambers (see FIG. 31F), a delivery catheter enters into the left chambers via a guide wire.

Figure 60A:
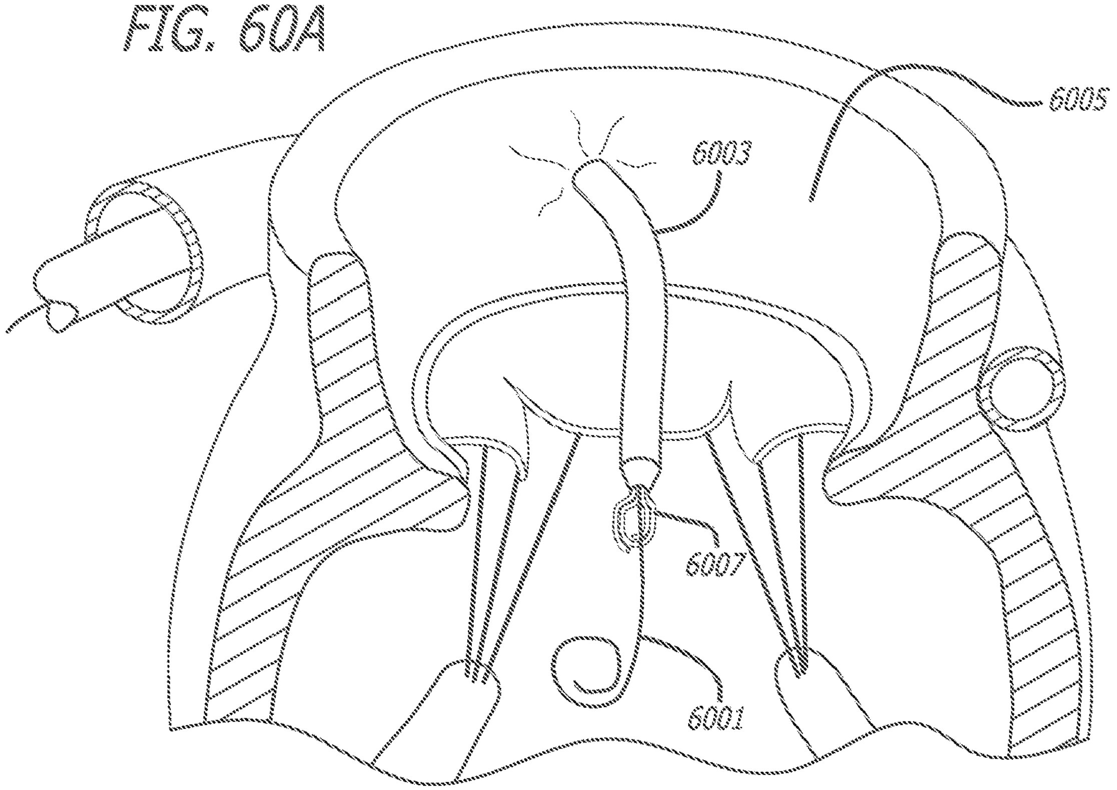
FIGS. 60A-60D are schematic illustrations of an example method to deliver a compressive device to a native valve via a transcatheter procedure.
Figure 60B:
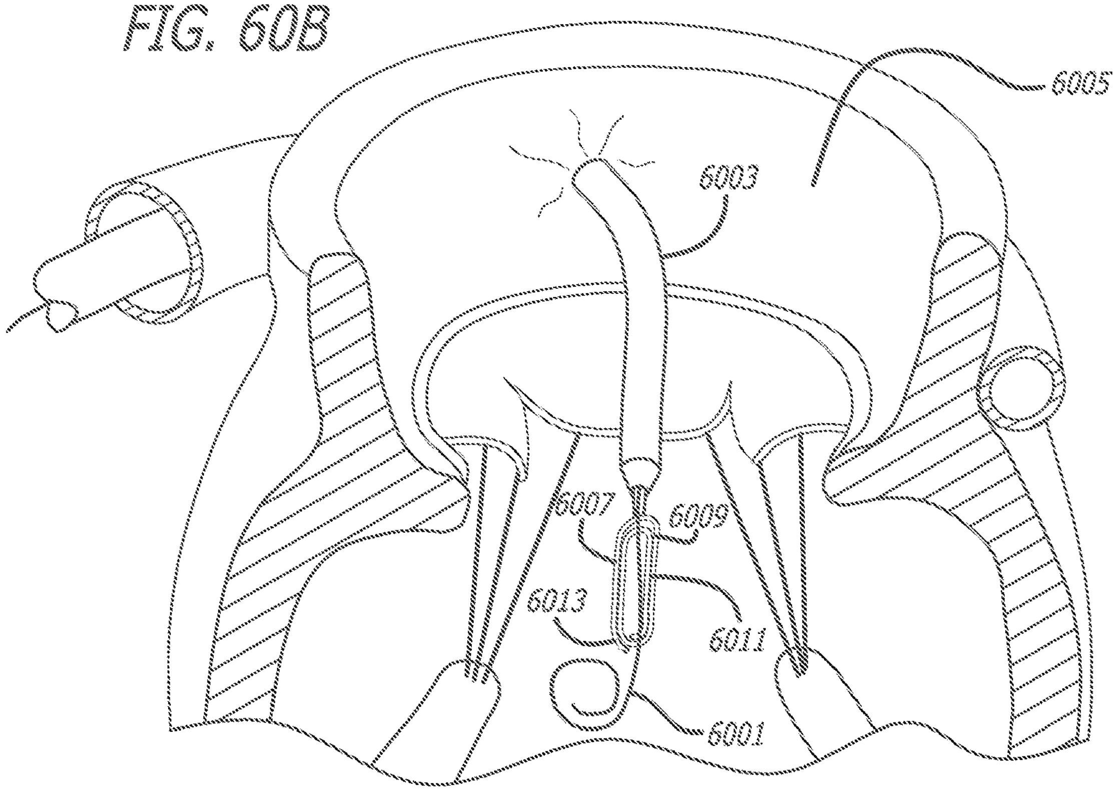

FIG. 60A shows a guide wire 6001 and a delivery catheter 6003 that has been advanced along the guidewire 6001 and through the tissue wall 6005 into the left chambers. A condensed compressive splint device 6007 is being released and expanded within the left ventricle such that compressive splint device 6007 is to be implanted onto a flail, prolapse, rigidity, and/or abnormality of the posterior leaflet.

Figure 60C:
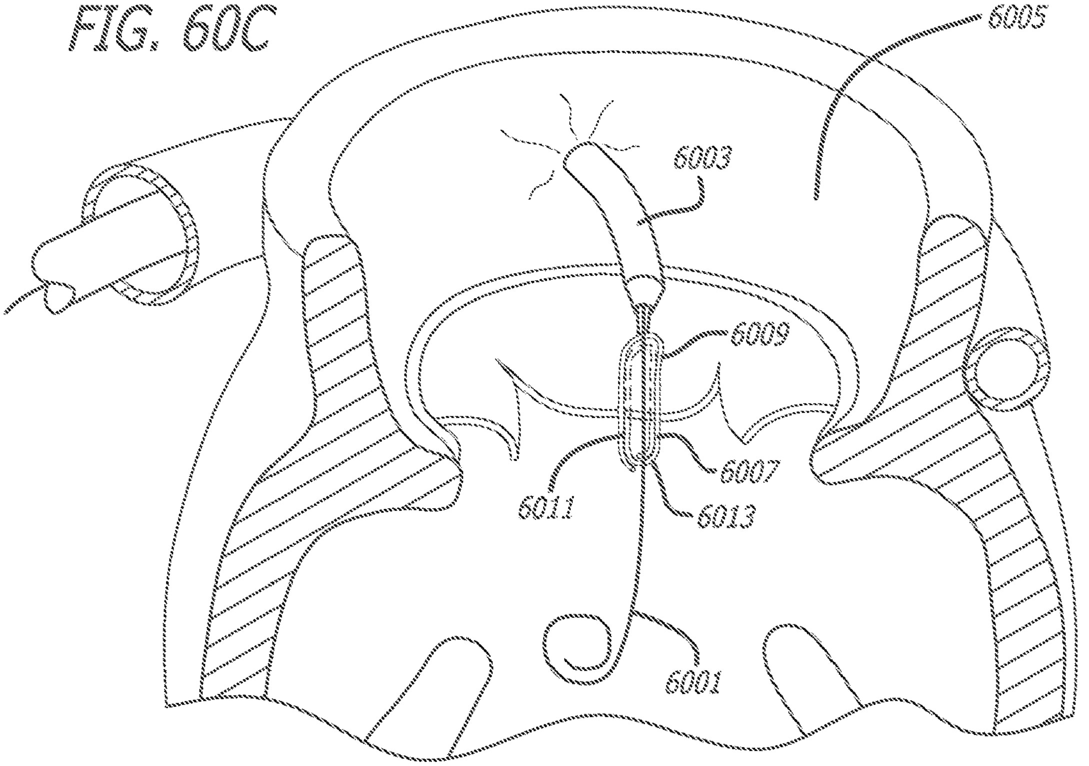

FIG. 65B then shows full advancement of the compressive splint device 6007 within left ventricle and the simultaneous retraction of the delivery catheter 6003. The delivery catheter includes an actuator to actuate the compressive splint device 6007 by opening up the device by distancing an influent portion 6009 of the device from an effluent portion 6011. FIG. 60C shows the delivery catheter 6003 retracting back toward the coronary sinus, while the actuator positions the influent portion 6009 on the influent face of the mitral valve leaflet and the effluent portion 6011 on the effluent face of the leaflet. A coaptation portion 6013 of the compressive splint device 6007 is pulled towards the mitral leaflet edge such that the compressive splint device 6007 is situated on a leaflet flail, prolapse, rigidity, and/or abnormality.

Figure 60D:
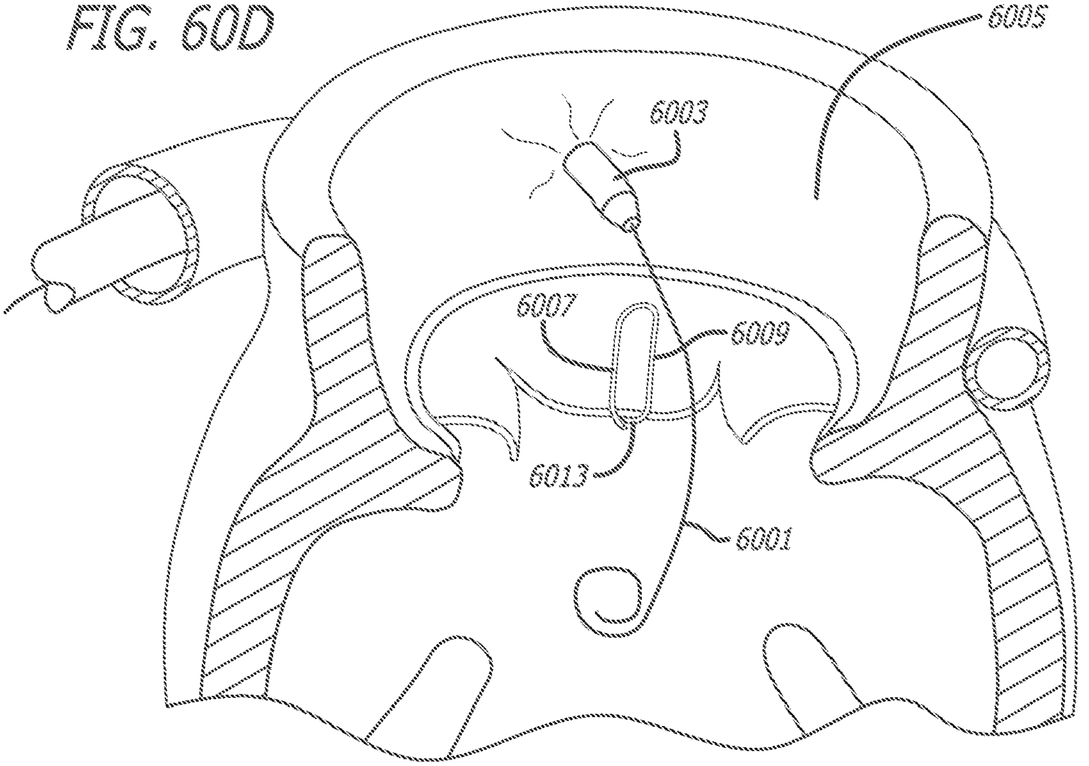

FIG. 60D shows further retraction of the delivery catheter 6003. Subsequently, the entire delivery catheter 6003 is removed along the guide wire 6001 from the body, which is then removed from the body. The delivery process results in the compressive splint device 6007 implanted onto the P2 segment of the mitral valve's posterior leaflet.

Many examples herein are directed towards valve implants or devices for mitigating heart valve leaflet flail, prolapse, rigidity, and/or other abnormalities that include a bar or elongate extension that can span between portions or commissures of a native valve. In some applications, a valve device is capable of situating within the effluent side of a valve, the bar or elongate extension holding onto its place on the leaflet while providing contact pressure onto a region of flail, prolapse, rigidity, and/or abnormality. The contact pressure provided by various bar or extension implants/devices helps flatten out and/or reshape the flail, prolapse, rigidity, and/or abnormality, which helps extend the coapting edge of a leaflet back towards the coaptation area when in a closed position. Proper coaptation that results in a fully closed valve prevents valve regurgitation.

In some applications, a bar/elongate extension is configured as an elongated arch with two distal ends, each end having an anchor or means to hook, latch, anchor, fasten, etc. within two leaflet commissures. In some applications, each of the distal ends of the bar/extension includes an indentation or hook, which can help secure the bar/extension within the site of implantation by latching or hooking onto the commissures. In some applications, the bar/extension is telescoped such that there is an inner bar and an outer bar, allowing the bar to be shortened and elongated between a variety of sizes or lengths. Accordingly, in some applications, the telescoping bar/extension can be shortened or elongated to extend over and provide contact pressure upon a leaflet issue, e.g., flail or prolapse.

In some applications, a bar/extension/arch includes an anchor to stabilize the bar/extension/arch at the site of implantation beyond the anchors or means to hook, latch, anchor, fasten, etc. within two leaflet commissures (though in some circumstances the anchors or means to hook, latch, anchor, fasten, etc. within two leaflet commissures can be sufficient to secure the implant/device within the native valve without an additional anchor). In some applications, a bar/extension/arch includes a portion that is in connection with the anchor. In some applications, an anchor connection point extends from the bar/extension/arch and towards a ventricle or atrium wall. In some applications, an anchor is situated near or in contact with the ventricle or atrium wall on the opposite side of the wall from the bar/extension/arch connection point. In some applications, a connector is utilized to connect the anchor with the anchor connection point, the connector traversing through the ventricle or atrium wall. Any appropriate connector can be utilized, such as (for example) a screw, rivet, suture, staple, wire, pin, shaft, sheet, mesh, etc.

In some applications, an anchor is situated within vasculature that is on the opposite side of a ventricle or atrium wall. For example, various bar or elongate extension examples mitigate leaflet issues (e.g., flail, prolapse, rigidity, and/or abnormality) of the mitral valve and thus are situated within the left atrium. In these various implementations, a bar/extension can be connected with an anchor situated within the coronary sinus utilizing a connector traversing through the atrial wall. Any appropriate anchor can be utilized. In some applications, an anchor is wire stent capable of expanding within vasculature. In some applications, an anchor is a pin (e.g., R-pin) or wire fastener capable of pinning an arched telescoping bar via a connector to the ventricle or atrium wall. In some applications, a pin or wire fastener is utilized on the opposite side of a ventricle or atrium wall and the connector traverses the wall. In some applications, a pin or wire fastener is utilized within vasculature that is on the opposite of a ventricle or atrium wall. In some applications, a wire fastener is capable of pinching a connector wire to hold the wire in place and create tension between the wire anchor or wire fastener and the telescoping bar. In some applications, an anchor is a screw, helix, or helical anchor that is anchored within the valve annulus or wall of an atrium or ventricle.

Various implementations of bars, elongate extensions, arches, or arched bars help promote coaptation of the leaflets when closed. In some applications, a gap filler, coaptation element, or spacer is incorporated to extend from the bar/extension/arch and into the valve aperture, which can help fill gaps within the valve aperture. In some applications, a bar/extension/arch includes a sheet extension with an impermeable sheet that hangs off the bar/extension/arch along the leaflet coaptation area and into the valve aperture, which can help form coaptation with the other leaflet(s). In some applications, the sheet includes wire form along the border to help the sheet maintain within the aperture of a valve when implanted.

Any appropriate material to produce a bar form, elongate extension, arch, or an arched bar form can be utilized. In some applications, the bar/extension/arch comprises one or more of the following: nitinol, cobalt-chrome (CoCr), stainless steel, titanium, polyglycolic acid (PGA), polylactic acid (PLA), poly-D-lactide (PDLA), polyurethane (PU), poly-4-hydroxybutyrate (P4HB), polycaprolactone (PCL), polyether ether ketone (PEEK), cyclic olefin copolymers (COCs), poly ethylene vinyl acetate (EVA), polytetrafluoroethylene (PTFE), perfluoroether (PFA), fluorinated ethylene propylene (FEP), additives thereof, and derivatives thereof.

Figure 61:
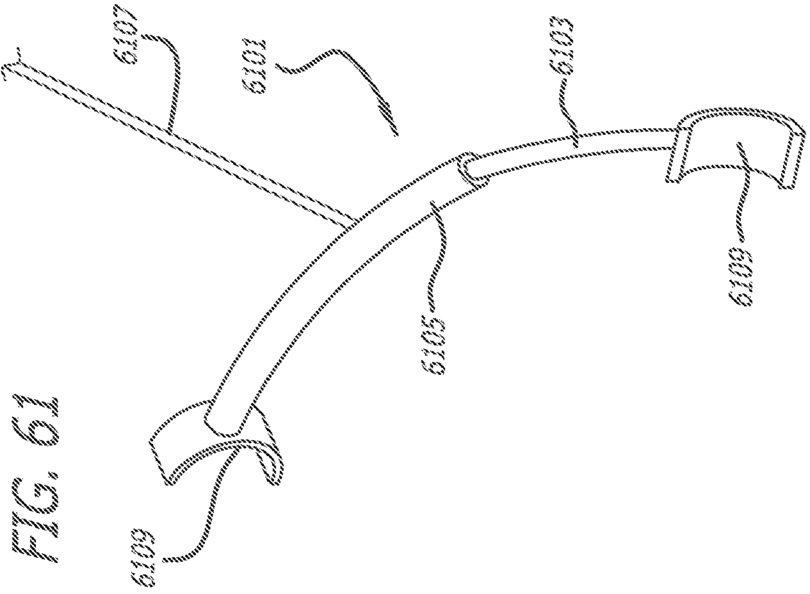

FIG. 61 illustrates an example telescoping bar/extension or telescoping arched bar 6101 capable of situating within a valve and providing contact pressure onto a leaflet flail, prolapse, rigidity, and/or other leaflet abnormality. The telescoping bar/extension or arched bar 6101 as an inner bar/extension 6103 and an outer bar/extension 6105. The inner bar/extension 6103 is capable of sliding within the outer bar/extension 6105 such that the length of the bar/extension and arc angle can be modulated. In some applications, the bar/extension or arched bar 6101 includes a connector 6107 to connect the bar/extension or arched bar 6101 to an anchor, to provide added stability to the bar/extension or arched bar. In some applications, the bar/extension or arched bar 6101 includes hooks 6109 that are capable of securing within a leaflet commissure or cleft.

Figure 62:
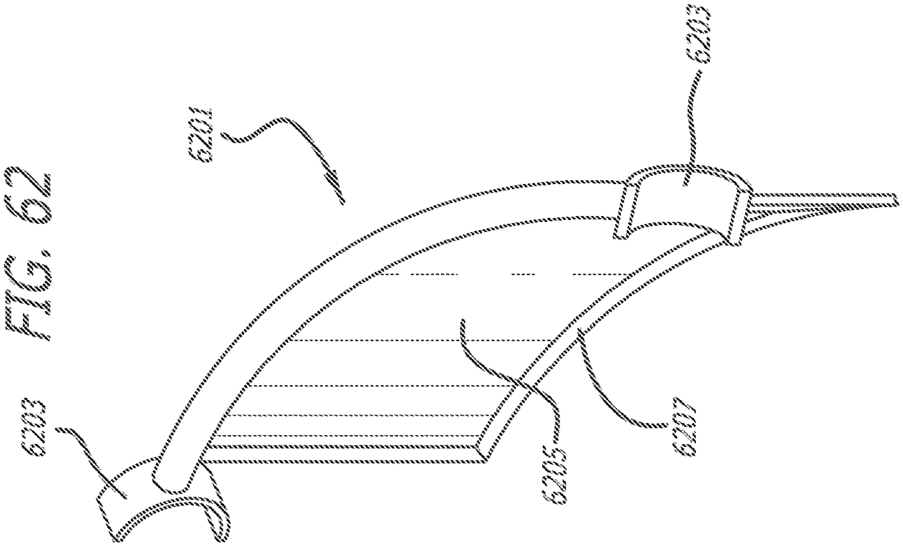

FIG. 62 illustrates an example a bar/extension device comprising an arch or arched bar 6201 with a sheet extension capable extending a leaflet edge such that it can better coapt. The bar/extension or arched bar 6201 is a single bar/extension that can be situated within the aperture of a valve. In some applications, the bar/extension or arched bar 6201 includes hooks 6203 that are capable of securing within a leaflet commissure or cleft. A sheet 6205 hangs down from the bar/extension or arched bar 6201 to reach and extend beyond a leaflet edge, thus extending the leaflet to provide more area for coaptation. In some applications, the sheet comprises a wire 6207 along its border, which can help hold the sheet within the coaptation area when implanted.

Figure 63:
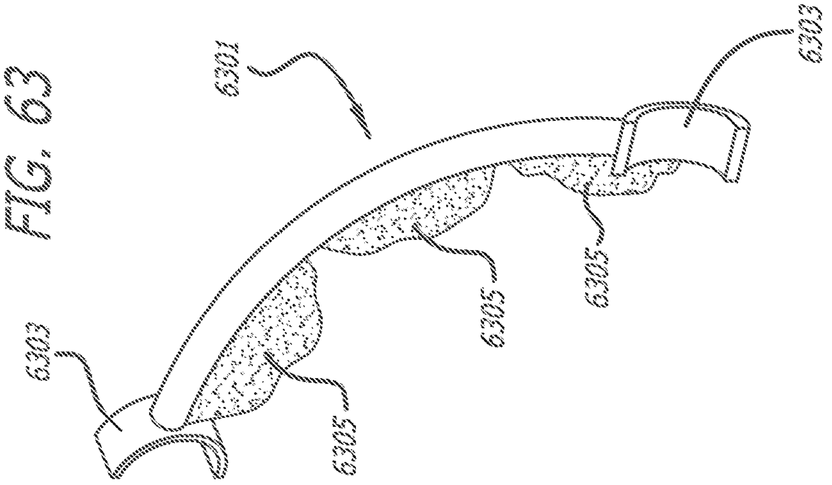
FIGS. 61-63 are schematic illustrations of example repair devices including a bar.

FIG. 63 illustrates an example bar/extension device or an arched bar 6301 with a gap filler, coaptation element, or spacer capable of filling a gap(s) within a valve coaptation area when the valve is closed. In some applications, the bar/extension or arched bar 6301 is a single bar/extension that can be situated within the aperture of a valve. In some applications, the bar/extension or arched bar 6301 includes hooks 6303 that are capable of securing within a leaflet commissure or cleft. Multiple gap fillers, coaptation elements, or spacers 6305 hang down from the bar/extension or arched bar 6301 to situate within the valve coaptation area helping the leaflets coapt by filing in any gaps when the leaflet is closed.

Some examples herein are directed towards implants or devices comprising netting (e.g., mesh, sheet, drape, etc.) for mitigating heart valve leaflet issues, such as flail, prolapse, rigidity, and/or other abnormalities. In some applications, a netting implant/device is capable of situating within the effluent side of a valve, the lateral edges situated within a crevice within the heart valve (e.g., cleft or commissure) while providing contact pressure onto and/or support to a region of flail, prolapse, rigidity, and/or abnormality. The contact pressure provided by various netting devices/implants helps flatten out and/or reshape the leaflet or the flail, prolapse, rigidity, and/or abnormality of the leaflet, which helps extend the coapting edge of a leaflet back towards the coaptation area when in a closed position. Proper coaptation that results in a fully closed valve prevents valve regurgitation.

In some applications, a netting implant/device includes (but is not limited to) one face configured to directly contact the face of a leaflet experiencing flail, prolapse, rigidity, and/or other issues. Typically, the influent face of a leaflet is the face that experiences flail, prolapse, rigidity, and/or other issues. In some applications, the contact face of the netting device is pliable and thus contours to the influent face of a leaflet, which can be a hyperbolic paraboloid-like contour. In some applications, the contact face of the netting device provides contact pressure on a leaflet flail, prolapse, rigidity, and/or abnormality. In some applications, the contact face of the netting implant/device has a width and a length such that it can cover the region of the leaflet experiencing flail, prolapse, rigidity, and/or abnormality. In some applications, the length of an implant/device extends just beyond the coaptation area of the leaflet.

In some applications, a netting implant/device includes an anchor to stabilize the device at the site of implantation. In some applications, an anchor is situated near or in contact with the valve annulus, leaflet area, or atrium/ventricle wall. In some applications, an anchor is a screw, helix, helical anchor, or other feature capable of screwing within or embedding within the valve annulus, leaflet, or atrium/ventricle wall. In some applications, a helical anchor is housed within a tubular compartment, the tubular compartment connected to or a part of the netting implant/device to be anchored.

In some applications, an anchored netting implant/device incorporates a tether for further stabilization at the site of implantation. In some applications, a tether extends from the coaptation portion of a netting implant/device to a pinning location on the effluent side of the valve, where the tether is pinned down. The pinning location can be any sturdy feature, such as (for example) ventricle wall, atrium wall, papillary muscle, and/or nearby vasculature.

The netting of a netting device can be impermeable, semipermeable, or permeable to fluids (e.g., blood or plasma). In some applications, the netting is a mesh. In some applications, a mesh is formed utilizing interleaving strings that overlap and crisscross. In some applications, a mesh is formed utilizing a mesh sheet. Any appropriate material can be utilized for a netting, for example, a netting can comprise one or more of the following: poly(lactic-co-glycolic) acid (PLGA), polyvinylchloride (PVC), polyethylene (PE), polypropylene (PP), polytetrafluoroethylene (PTFE), polyurethane (PU), polyethylene terephthalate (PET), polyethersulfone (PES), polyglycolic acid (PGA), polylactic acid (PLA), poly-D-lactide (PDLA), poly-4-hydroxybutyrate (P4HB), and polycaprolactone (PCL). Any appropriate means to attach a netting to an anchor(s) can be utilized, including (but not limited to) stitching, staples, and glue.

In some applications, a netting device includes a wire form outlining the netting or a portion of the netting. Any appropriate material to produce a wire form can be utilized, for example, the wire form can comprise one or more of the following: nitinol, cobalt-chrome (CoCr), stainless steel, titanium, polyglycolic acid (PGA), polylactic acid (PLA), poly-D-lactide (PDLA), polyurethane (PU), poly-4-hydroxybutyrate (P4HB), polycaprolactone (PCL), polyether ether ketone (PEEK), cyclic olefin copolymers (COCs), poly ethylene vinyl acetate (EVA), polytetrafluorethylene (PTFE), perfluoroether (PFA), fluorinated ethylene propylene (FEP), additives thereof, and derivatives thereof.

In some applications, a netting device is contractible, which may be useful to fit within a catheter device for less invasive catheter delivery methodologies. In some applications, nitinol is utilized for its self-expanding properties, which may be useful to implant the device in less invasive catheter delivery methodologies.

Some applications of netting devices are configured to be used on any leaflet experiencing flail or prolapse. Accordingly, in some applications, a netting device is capable of being utilized on a leaflet of a mitral, a tricuspid, an aortic, and/or a pulmonic valve. Likewise, various devices/implants can be utilized on any area of the leaflet experiencing flail or prolapse. In some applications, a netting device is capable of being utilized on any area between a leaflet's crevices (e.g., commissures and clefts).

To reach the site of implantation, any appropriate surgical technique may be utilized, including (but not limited to) a transcatheter delivery system, which can utilize a transfemoral, subclavian, transapical, transseptal, or transaortic approach. In some applications, a delivery catheter is utilized to incorporate a device, then delivered to the site of deployment via a guidewire and utilized to anchor the device at the site of implantation.

Some examples herein are directed to methods of delivering a netting device to the site of deployment. The various methods described or suggested anywhere herein (including in documents incorporated by reference herein) can be performed on a living animal (e.g., human, mammal, other animal, etc.) or on a non-living simulation, such as on a cadaver, cadaver heart, simulator (e.g., with the body parts, tissue, etc. being simulated), etc. Accordingly, methods of delivery include both methods of treatment (e.g., treatment of human subjects) and methods of training and/or practice (e.g., utilizing an anthropomorphic phantom that mimics human vasculature to perform method).

Figure 64:
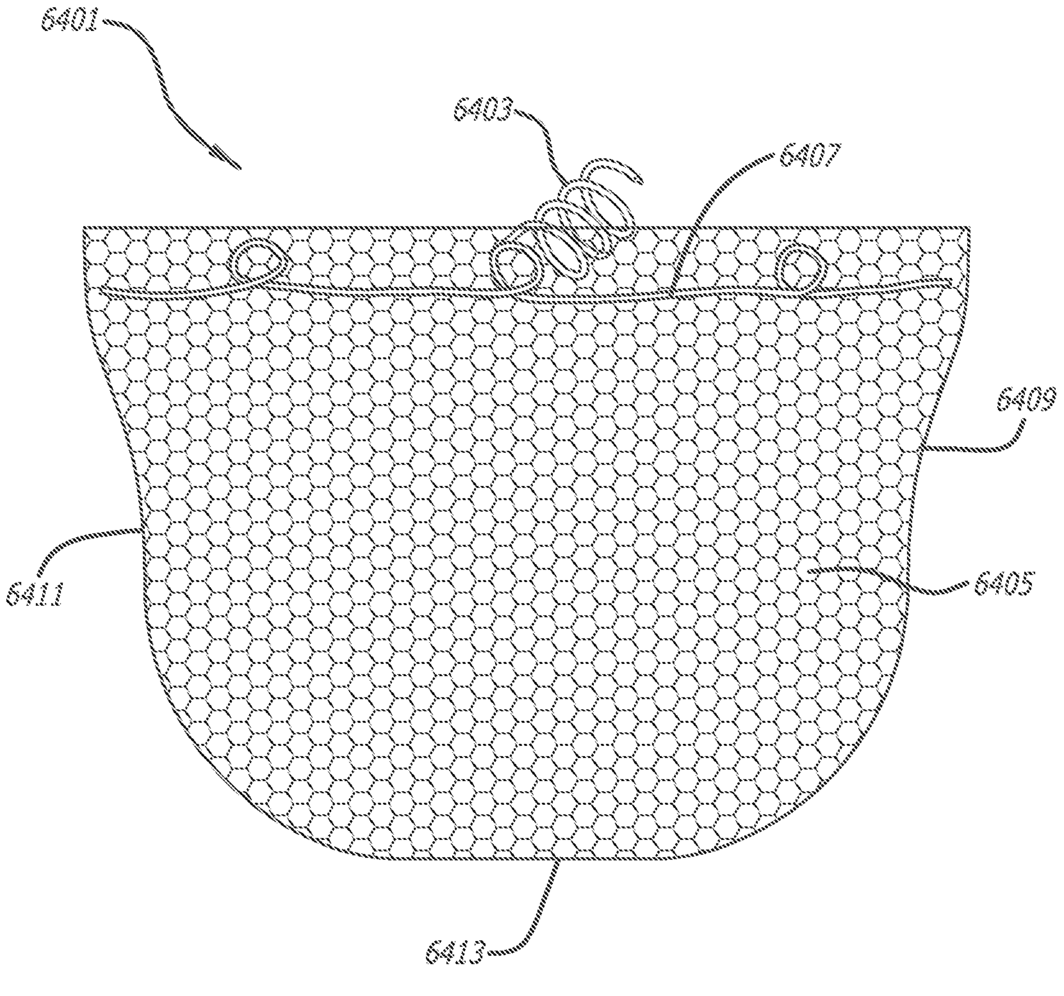
FIGS. 64-66 are schematic illustrations of example repair devices including netting or mesh.

FIG. 64 illustrates an example netting implant or netting device 6401 with a helical anchor 6403. The netting implant/device 6401 is shown with a mesh material 6405 that extends from anchoring portion 6407. The lateral edges 6409 and 6411 of the netting implant/device 6401 can be positioned into a crevice of the heart valve (e.g., commissure or cleft) and the mesh material 6405 can be positioned over an provide contact pressure upon a leaflet to address flail, prolapse, rigidity, and/or other issues. The lateral edges 6409 and 6411 can optionally incorporate a wire form. The coaptation portion 6413 can optionally include a tether or weight to further stabilize the netting the device at the site of implantation.

Figure 65:
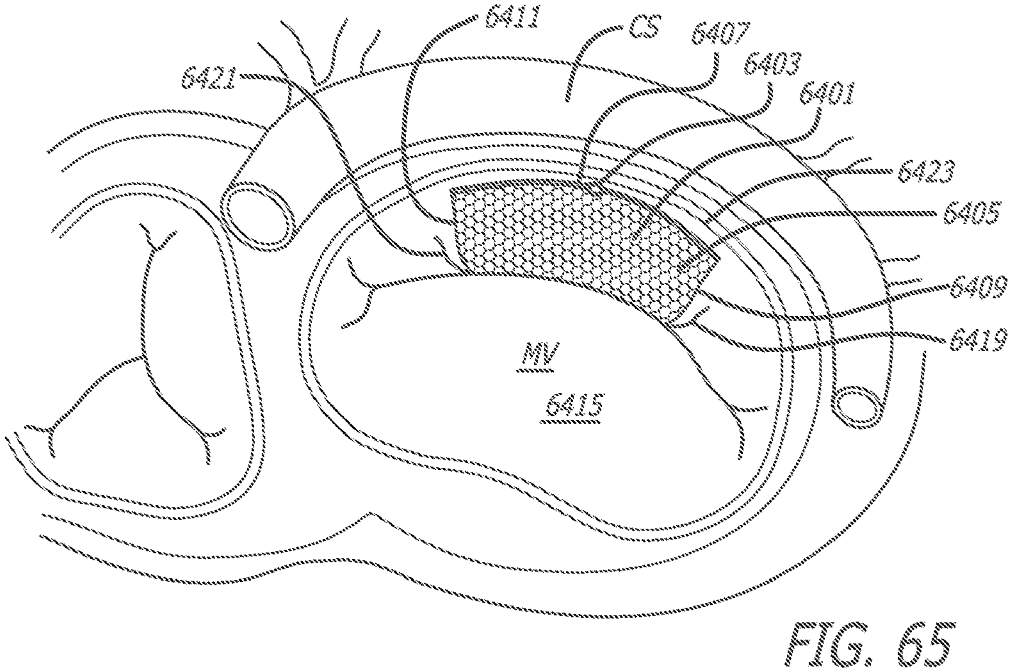
Figure 66:
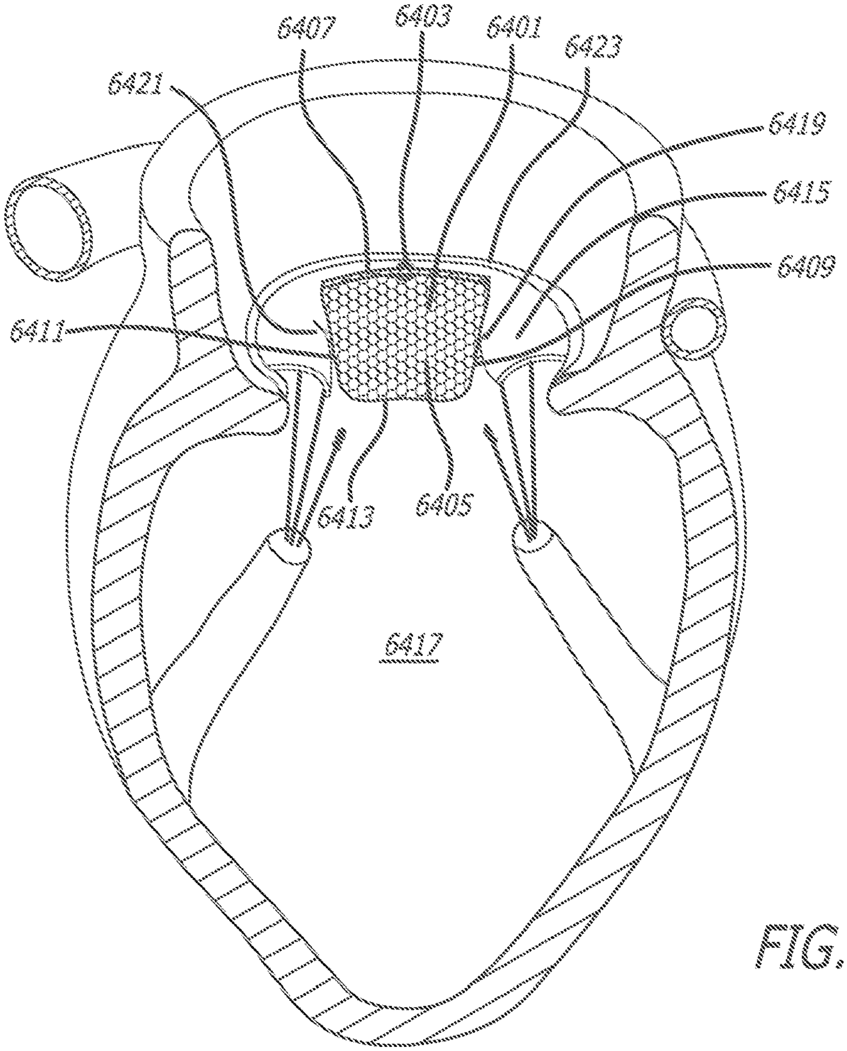

FIGS. 65 and 66 an example depicting the netting implant/device 6401 with a helical anchor 6403 at a site of implantation. As shown here, the netting implant/device is on the mitral valve 6415. The contact face of the netting implant/device 6401 is situated on the influent face of the posterior leaflet within the left atrium 6419 at the site of flail, prolapse, rigidity, and/or abnormality. The contact face can provide contact pressure onto and/or support to the leaflet, e.g., to address flail, prolapse, rigidity, and/or abnormality and to help flatten out and/or reshape the leaflet or a protrusion, bulge, flail, etc. of the leaflet and mitigate regurgitant blood flow. The implant/device 6401 includes a coaptation portion 6413 that extends beyond the edge (e.g., below the edge) of the posterior leaflet and into the left ventricle 6417.

The lateral edges 6409 and 6411 of the netting implant/device 6401 can be positioned into the clefts between P1 and P2 6419 and between P2 and P3 6421. Any of the anchors described herein can be used. In some applications, the anchor 6403 is a helical anchor configured to be anchored into the valve annulus 6423. The anchor 6403 stabilizes the netting device 6401 at the native valve 6415.

Reference is made to FIGS. 67A-B, 68A-G, and 69-75, which are schematic illustrations of a system 20 for use with a valve of a heart 4 of a subject, in accordance with some applications. System 20 is shown being used with a mitral valve 10 of the heart, the heart chamber upstream of the mitral valve being left atrium 6, and the heart chamber downstream of the mitral valve being left ventricle 8. However, system 20 can also be used, mutatis mutandis, with the other atrioventricular valve (the tricuspid valve) from which another atrium (the right atrium) is upstream, and another ventricle (the right ventricle) is downstream. System 20 can also be used with the aortic valve or the pulmonary valve, from which the heart chamber upstream is a ventricle (the left ventricle and the right ventricle, respectively).

System 20 comprises an implant 100, an anchor 30, a catheter 40, and a delivery tool 50. Implant 100 comprises an interface 110, and a flexible wing 120, coupled to the interface. Wing 120 can comprise a contact face or surface 122 and an opposing face or surface 123 opposite the contact face. For some applications, implant 100 can have features or elements similar to those described for implant 1101, implant 2101, 2301, and/or 2421 described hereinabove, mutatis mutandis.

Delivery tool 50 can comprise a shaft 60 and a driver 70. Shaft 60 is configured to engage interface 110, and via this engagement, to deploy and position implant 100, e.g., as described in more detail hereinbelow. This engagement can be achieved by shaft 60 having a shaft head 62 that comprises one or more couplings 64, such as latches or arms, which engage one or more couplings 114 (e.g., recesses, slots, notches, or receptacles) of interface 110.

Driver 70 is configured to engage anchor 30 (e.g., a head 32 thereof), and is configured to secure implant 100 to tissue of the heart by using the anchor to anchor interface 110 to the tissue. In some applications, driver 70 comprises a flexible shaft 74 and a drive head 72 at a distal end of the shaft, the drive head engaging anchor 30.

For some applications, and as shown, wing 120 comprises a frame (e.g., a wire frame) 124, and a sheet 126 spread over the frame. For some applications, wing 120 has a root 130 that is coupled to interface 110, and a tip 132 at an opposite end of the wing from the root. Tip 132 represents a free end of wing 120.

For some applications, frame 124 is attached to interface 110. For example, and as shown, at root 130 frame 124 may define a ring 128 that fits around interface 110. Wing 120 may define two lateral sides 134 (e.g., a first lateral side 134*a* and a second lateral side 134*b*) extending from the root to the tip.

For some applications, and as shown, frame 124 defines two loops 136 (e.g., a first loop 136*a* and a second loop 136*b*) extending from root 130 alongside each other, e.g., all the way to tip 132. It is to be noted that, as shown, loops 136 can be discrete loops, rather than cells of a cellular or lattice structure. For example, loops 136 can be unconnected to each other and/or to any other metallic component of implant 100 except for at root 130 (e.g., at ring 128 and/or interface 110). Furthermore, each of loops 136 can be configured to circumscribe a space 137 that is substantially absent of frame components. For some applications, and as shown, each of loops 136 is substantially teardrop-shaped.

For some applications in which frame 124 defines loops 136, frame 124 defines an elongate space 138 between the two loops. Space 138 can extend from root 130 toward tip 132, e.g., all the way to the tip (e.g., such that the frame 124 does not bridge the two loops at the tip). For some applications, and as shown, space runs 138 along a plane of reflectional symmetry of wing 120.

For applications in which frame 124 defines loops 136, sheet 126 can be configured to extend over and between the loops, e.g., across both loops and space 138.

For some applications, sheet 126 has a plurality of holes 140 therethrough. For some such applications, and as shown, holes 140 are polygonal and tessellated with each other. For example, and as shown, holes 140 can be hexagonal. As shown, some of holes 140 can be disposed over spaces 137. Alternatively or additionally, some of holes 140 can be disposed over space 138. For some applications, and as shown, the size and number of openings or holes 140 is such that the wing 120 (or its area/surface area) is, overall, more than 20 percent and/or less than 80 percent open, e.g., 20-80 percent open, such as 20-70 percent open (e.g., 30-70 percent open, such as 30-60 percent open or 40-70 percent open) or 30-80 percent open (e.g., 40-80 percent open).

Figure 67A:
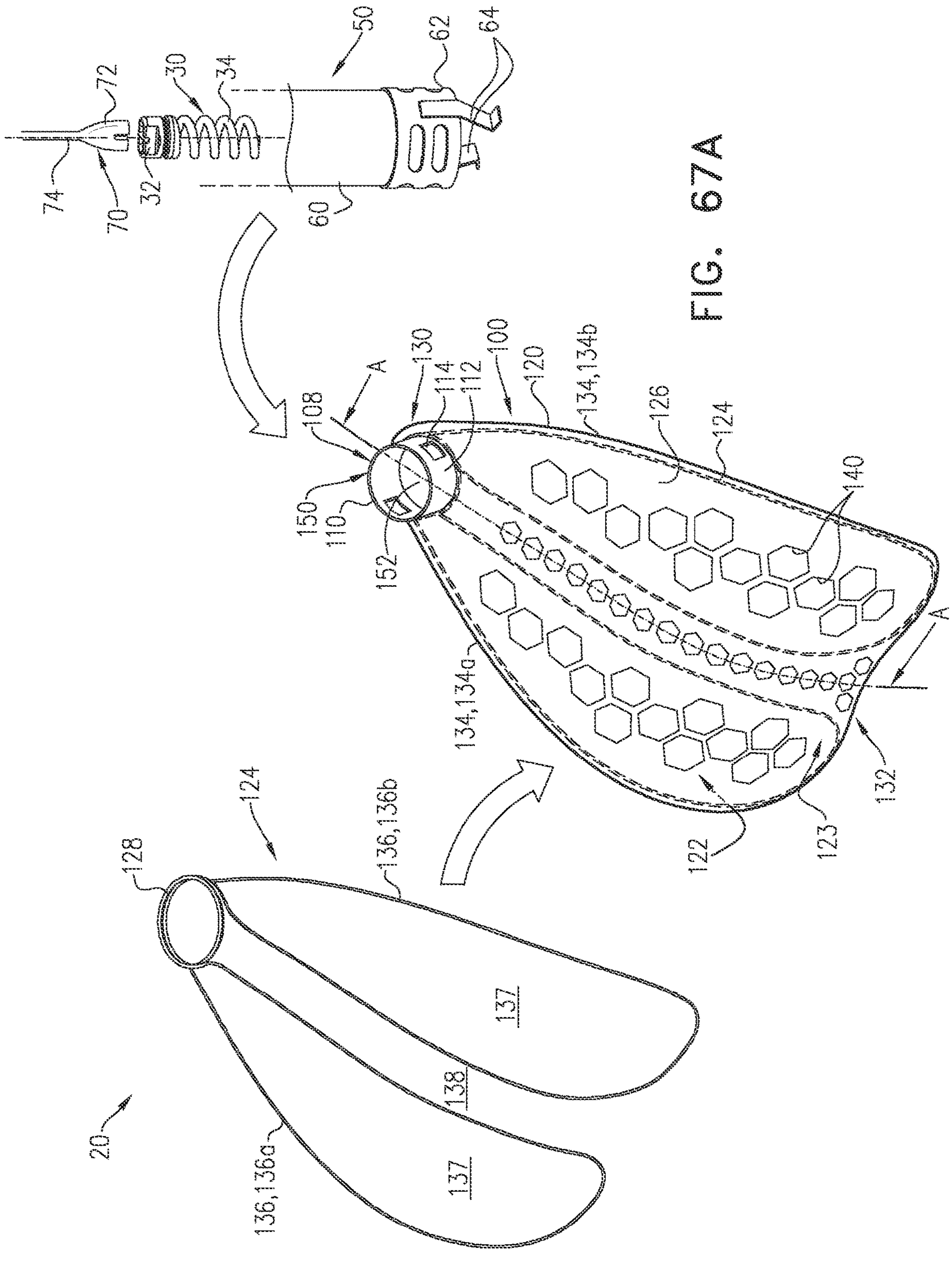
FIGS. 67A-B, 68A-G, 69-71, 72A-C, and 73-75 are schematic illustrations of a system for use with a valve of a heart of a subject, in accordance with some applications.
Figure 67B:
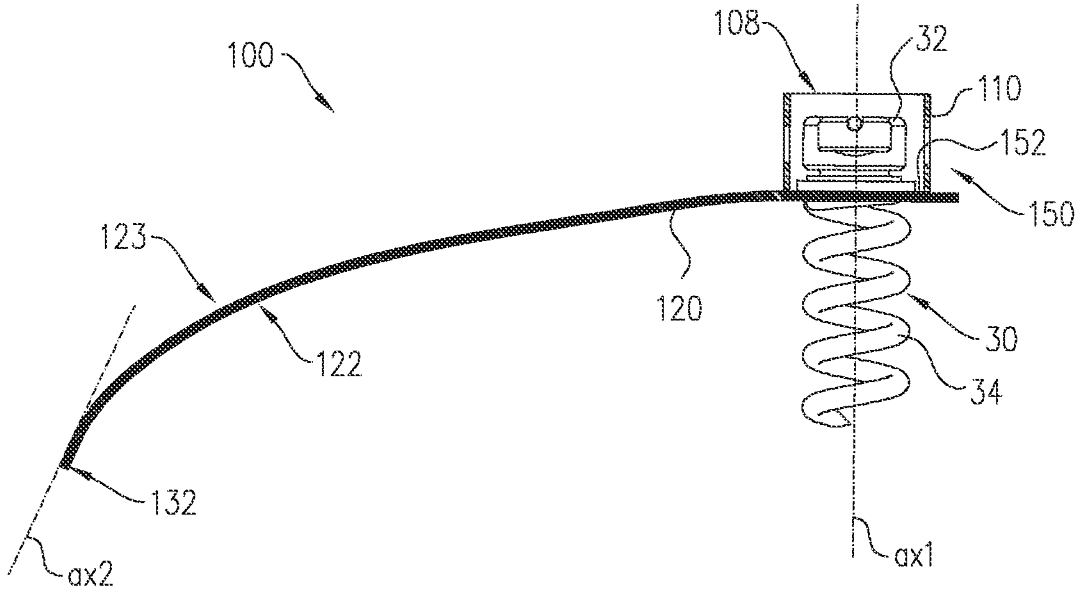

In some applications, wing 120 is curved, such that contact face 122 is concave. That is, a curvature of wing 120 is such that, in a cross-section of implant 100 through interface 110 and the wing, contact face 122 is concave. FIG. 67B is a schematic illustration of this cross-section, and in FIG. 67A the position of the cross-section is shown by the indicators A. However, FIG. 67B shows implant 100 with anchor 30 in place, e.g., as though the implant has been implanted. As shown, this cross-section can be in a plane of reflectional symmetry of the implant, e.g., in space 138, between loops 136. For some applications, and as shown, the curvature of wing 120 increases with distance from interface 110, e.g., such that the curvature is greatest at tip 132. For example, and as shown in FIG. 67B, at tip 132, following anchoring of implant 100 by anchor 30, a tangent ax2 of the curvature of wing 120 can be less than 60 degrees, (e.g., less than 45 degrees, such as less than 35 degrees) with respect to an anchor axis ax1 of anchor 30. This angle between tangent ax2 and axis ax1 can be at least in part dictated by geometry of interface 110 and/or an anchor receiver 150 at the interface (described hereinbelow), e.g., with respect to geometry of anchor 30.

For some applications, and as described in more detail hereinbelow, an angular disposition of wing 120 with respect to interface 110 and/or anchor receiver 150 is such that positioning the interface against tissue of an atrium of the heart (e.g., against an annulus of an atrioventricular valve of the heart, or against a wall of the atrium) disposes tip 132 within the ventricle that is downstream of the atrium and the atrioventricular valve.

Figure 68A:
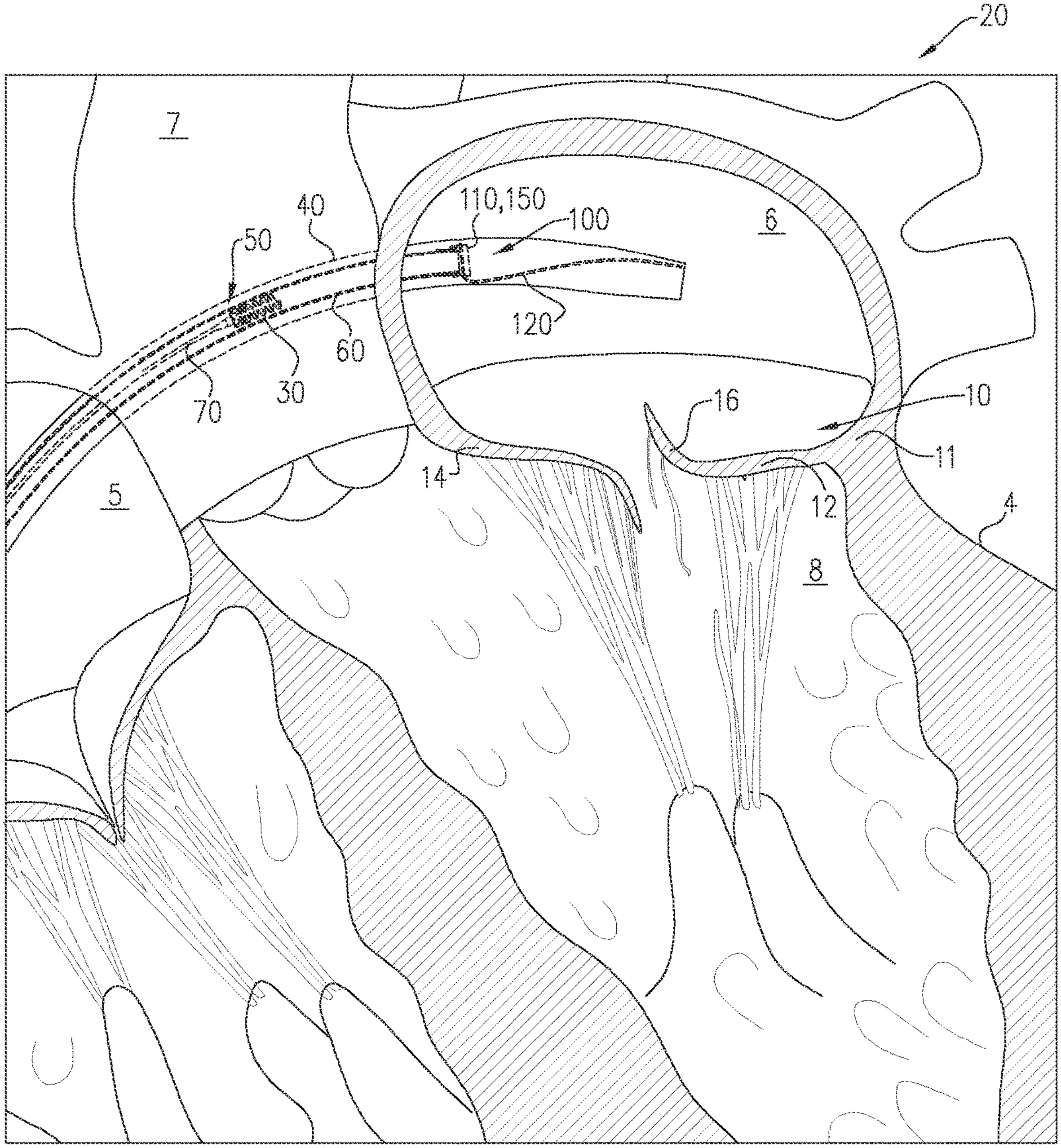

FIGS. 68A-G show at least some steps in the implantation of implant 100, in accordance with some applications. Within catheter 40, implant 100 is advanced to a heart chamber that is upstream of the heart valve that is to be treated (FIG. 68A). For example, catheter 40 can be advanced to the chamber prior to advancing implant 100 through the catheter, or the catheter can be advanced to the chamber with the implant already disposed therein. In the illustrated example, mitral valve 10 of heart 4 is being treated, and therefore implant 100 is advanced to left atrium 6 of the heart. Mitral valve 10 has a first leaflet (e.g., a posterior leaflet) 12 and an opposing leaflet (e.g., an anterior leaflet) 14. In the illustrated example, the posterior leaflet is the leaflet that is experiencing flail. The part of the posterior leaflet that is flailing is indicated by reference numeral 16. It is to be noted that, system 20 can similarly be used to treat flail in anterior leaflet 14, mutatis mutandis.

In the example shown, catheter 40 is advanced to the heart chamber transluminally. However, a transatrial approach is also within the scope of the disclosure. Similarly, although a transfemoral approach is shown, the scope of the disclosure includes advancement via the superior vena cava. It is to be noted that, although a transseptal approach is shown from right atrium 5 into left atrium 6, the interatrial septum is not shown, as it lies behind aorta 7. Part of catheter 40 is shown in phantom in order to illustrate that it is behind aorta 7.

As shown, the advancement of implant 100 within catheter 40 is performed while shaft 60 (e.g., head 62 thereof) is engaged with interface 110 of the implant. In some applications, implant 100 is advanced within catheter 40 while wing 120 is constrained (e.g., compressed, folded, and/or rolled) within the catheter.

Figure 68B:
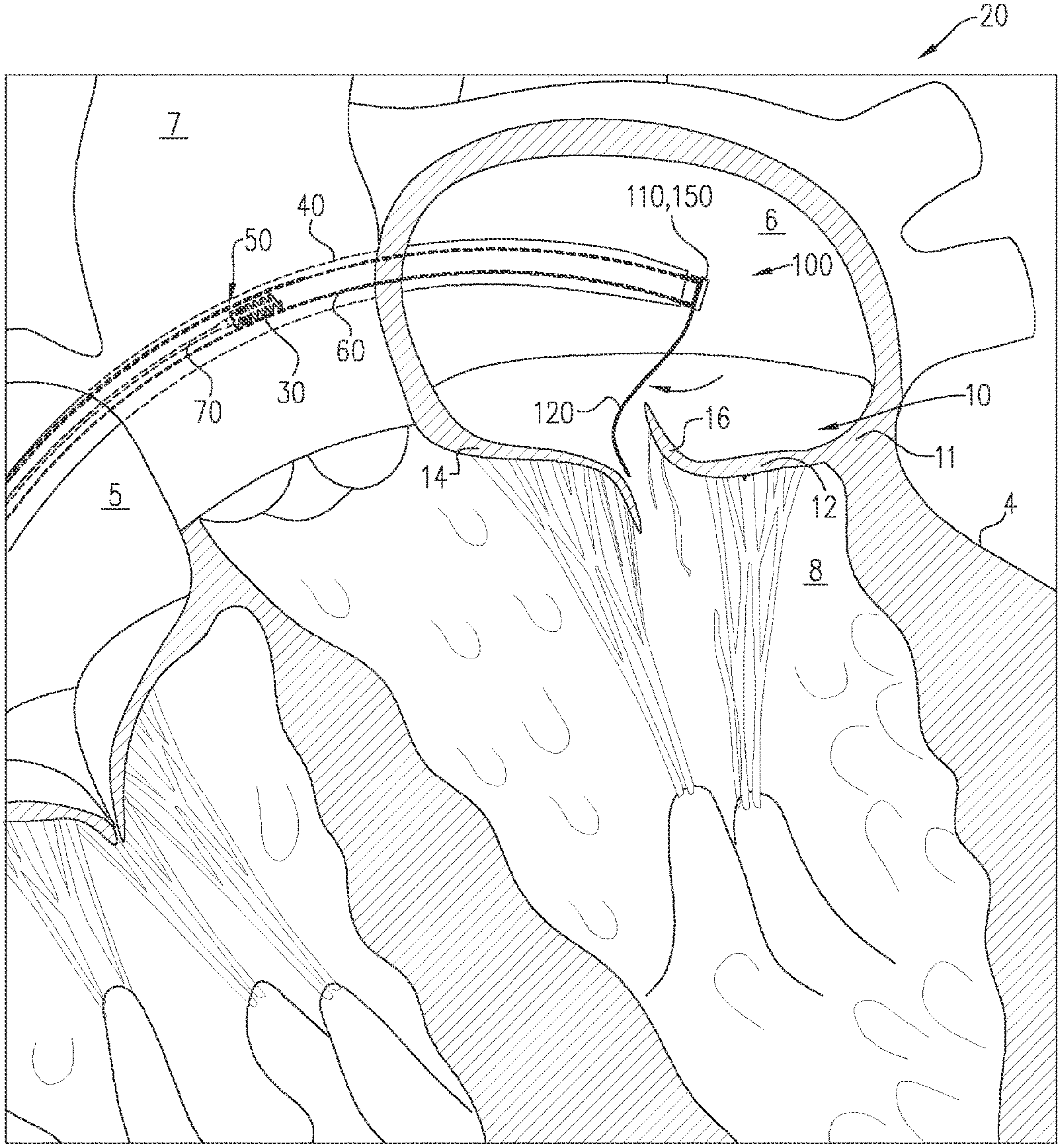
Figure 68C:
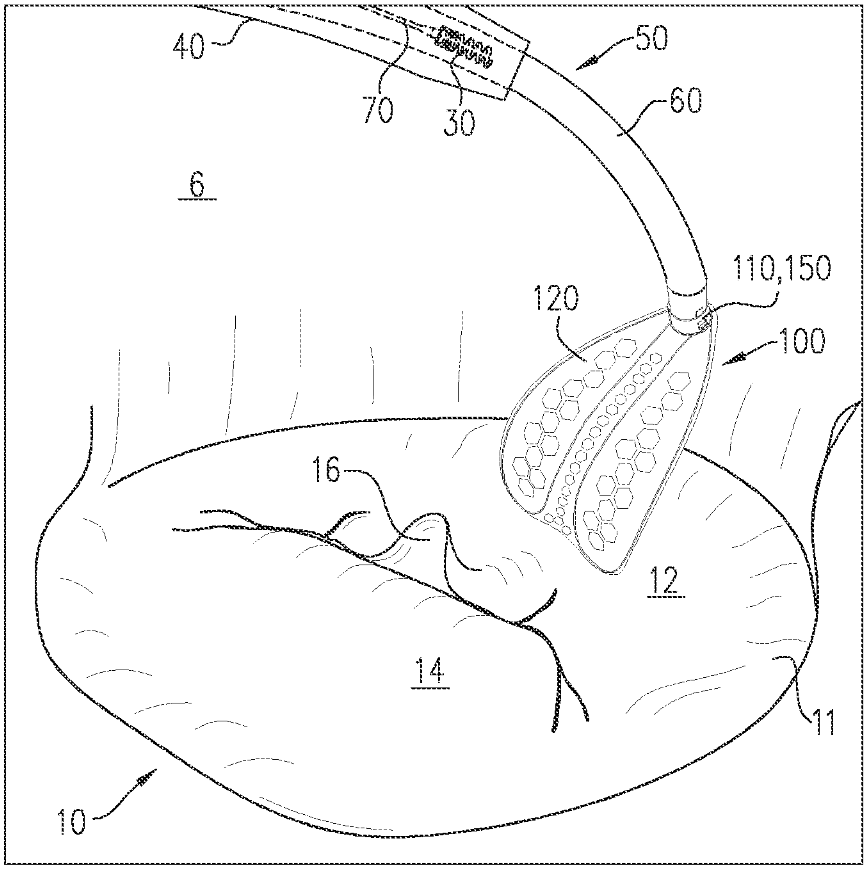

Using shaft 60, implant 100 is deployed out of catheter 40 such that, within atrium 6, wing 120 extends away from interface 110 (FIGS. 68B-C). For some applications, upon deployment wing 120 automatically expands toward the shape described with reference to FIGS. 67A-B, e.g., due to elasticity and/or shape memory of frame 124.

Figure 68D:
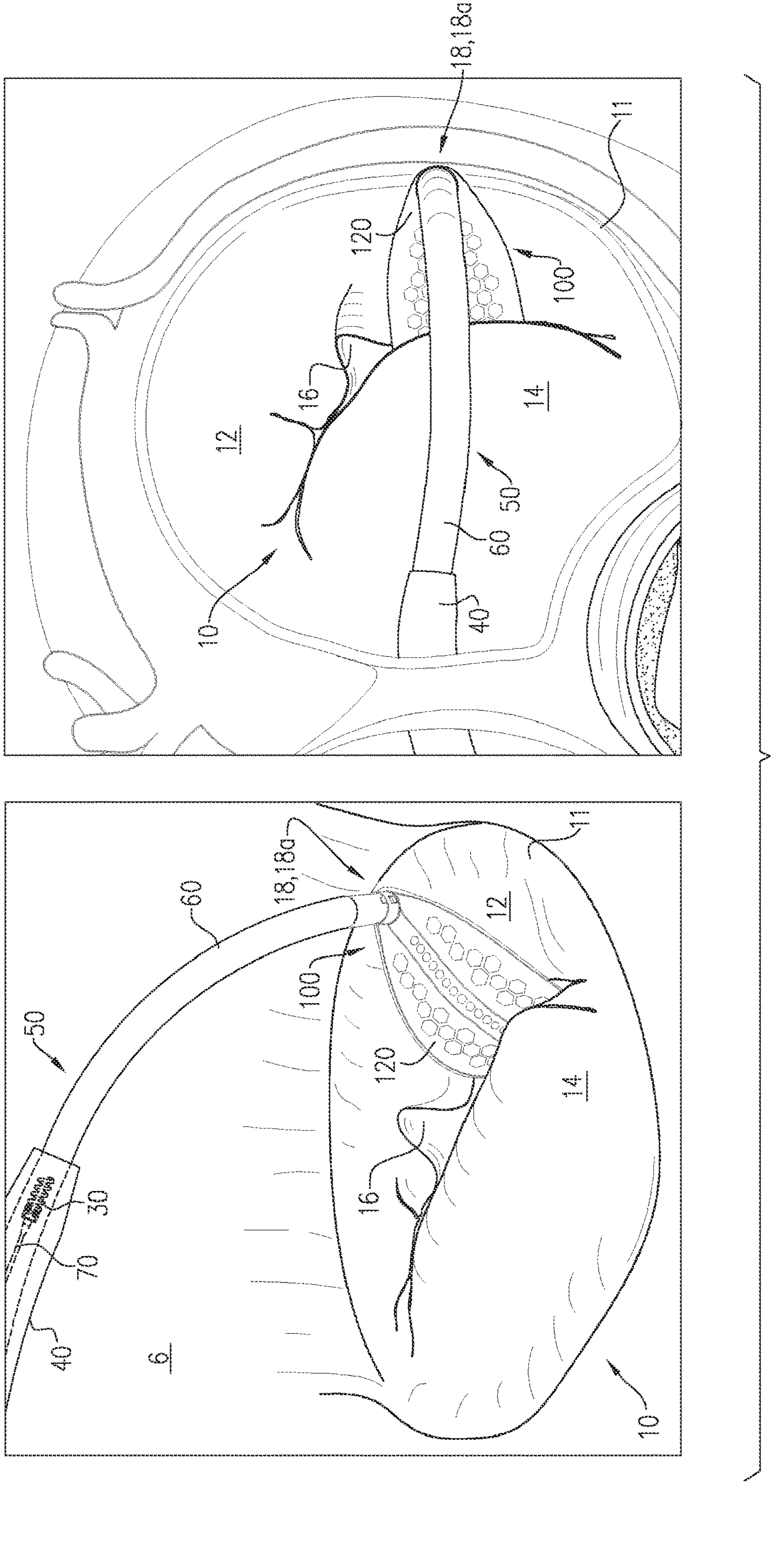

Subsequently, again using shaft 60, implant 100 is positioned in a position in which interface 110 is at a site 18 in the heart, wing 120 extends over first leaflet 12 toward opposing leaflet 14, and contact face 122 faces the first leaflet (FIG. 68D). For some applications, and as shown, wing 120 extends over first leaflet 12 such that tip 132 is disposed beyond (e.g., downstream) the lip of the first leaflet, e.g., within left ventricle 8, e.g., with opposing face 123 facing opposing leaflet 14. Typically, this is due at least in part to the geometry and dimensions of implant 100, and/or at least in part to site 18. Site 18 can be, but not necessarily, on the annulus of the valve being treated, e.g., at the root of the leaflet that is experiencing flail. Thus, in the example shown, wing 120 extends from interface 110 at site 18 on mitral annulus 11 at the root of posterior leaflet 12, over posterior leaflet 12 toward opposing leaflet 14, and curves downstream between leaflets 12 and 14, beyond the lip of leaflet 12, such that tip 132 is disposed within ventricle 8.

For some applications, and as shown, wing 120 (and optionally implant 100 as a whole) is entirely deployed (i.e., exposed) from catheter 40 prior to being positioned against the tissue.

The wing 120 can be configured to be at a variety of angles relative to the catheter shaft and/or relative to the native anatomy (e.g., the annulus and/or leaflet) during delivery to appropriately repair the function of the native leaflet as it is positioned for anchoring, for example, in some applications, the device is angled between 20-160 degrees, between 30-150 degrees, between 40-140 degrees, between 50-130 degrees, between 60-120 degrees, between 70-110 degrees, etc. relative to an axis of the tip of the catheter (and/or relative to a plane of the annulus) during delivery.

Figure 68E:
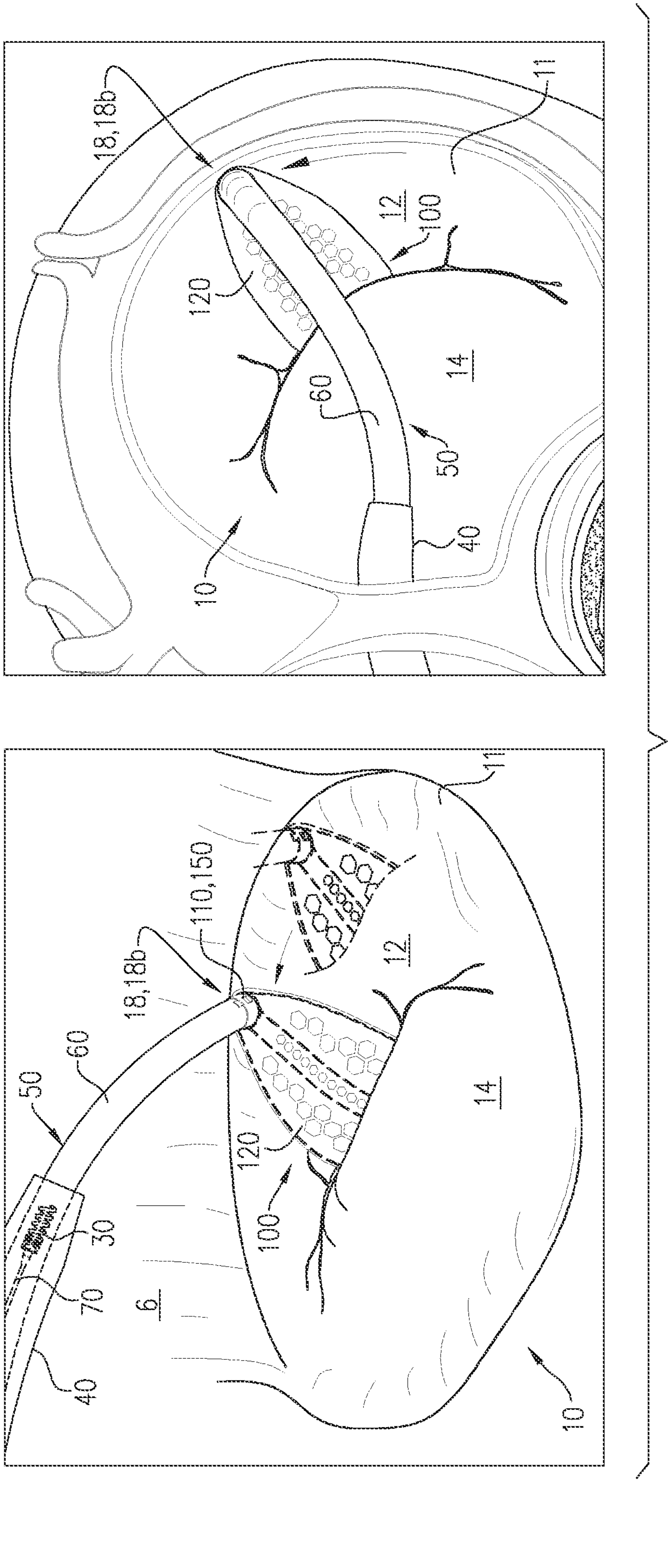

Optimality of a given position of implant 100 can be determined during the implantation procedure, e.g., prior to anchoring the implant to the tissue. For example, optimality can be determined using blood pressure sensing and/or imaging techniques such as fluoroscopy and echocardiography. For example, Doppler echocardiography can be used to determine a degree to which regurgitation through the valve remains or has been reduced. In order to illustrate an advantage of system 20, FIG. 68D shows implant 100 having been initially positioned suboptimally, e.g., with wing 120 positioned away from flail 16. That is, site 18 is an initial site 18*a* at which interface 110 has been positioned. At this point, implant 100 has not yet been anchored to tissue, and interface 110 can simply be moved to another site 18, e.g., a second site 18*b* (FIG. 68E). For example, interface 110 can be simply slid along annulus 11. Alternatively, the interface can be lifted away from the tissue at the first location, and then replacing it against the tissue at the second location. As shown, this repositioning can be performed without withdrawal (e.g., even partial withdrawal) of implant 100 into catheter 40. In the illustrated example, this second position of implant 100 is more suitable than the first (e.g., is optimal), e.g., wing 120 is disposed over flail 16, and valve regurgitation is minimized or eliminated.

Figure 68F:
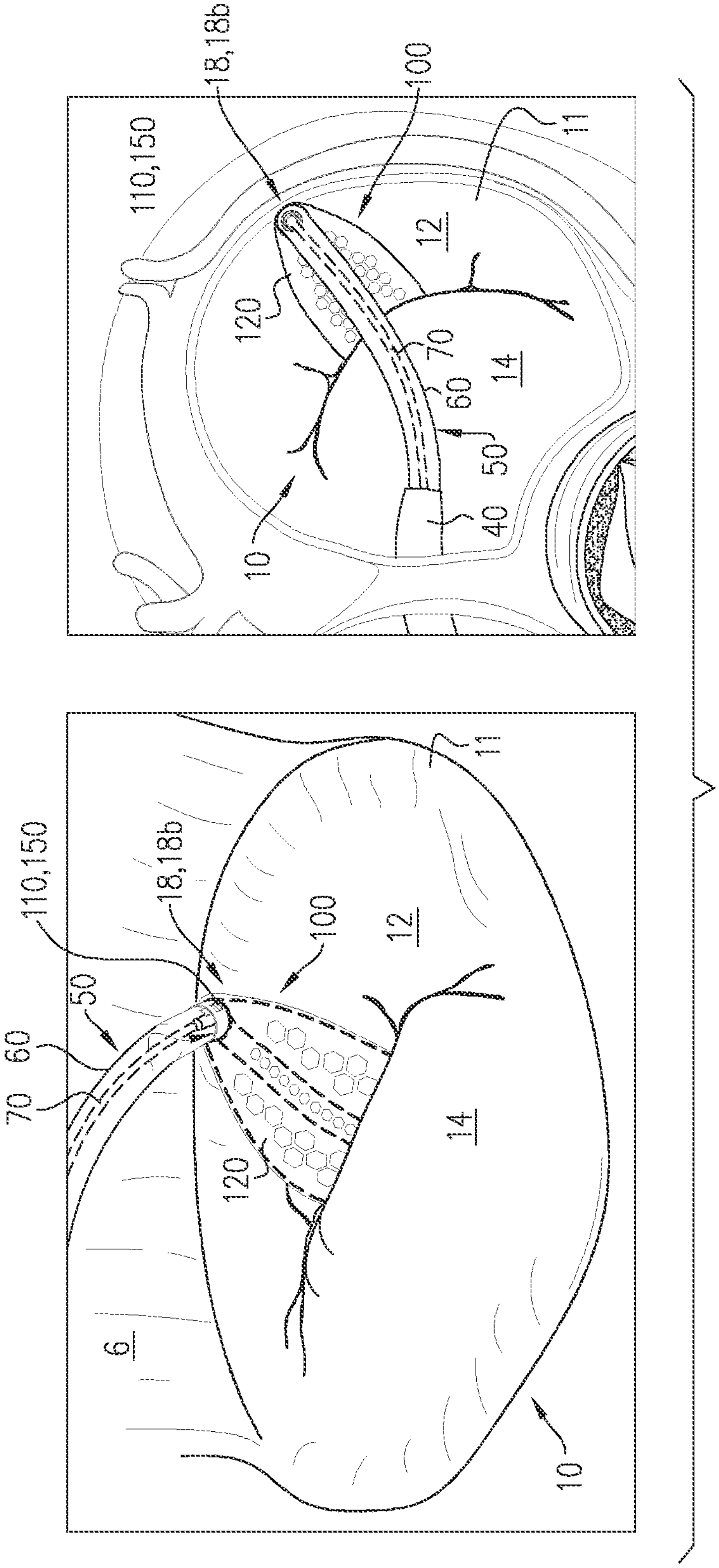

Upon determining that implant 100 is positioned suitably (e.g., optimally), the implant is secured in its position by anchoring interface 110 to tissue of the heart, e.g., at the current site 18 (FIG. 68F). This can be achieved by using driver 70 to advance anchor 30 distally while maintaining the position of implant 100. Subsequently, driver 70 (e.g., drive head 72 thereof) is disengaged from anchor 30, shaft 60 (e.g., shaft head 62 thereof) is disengaged from interface 110, and tool 50 is removed, leaving implant 100 in place.

It is to be noted that tip 132, which is a free end of wing 120, is typically not anchored to tissue during the implantation process. It is to be further noted that, at least for applications in which interface 110 is anchored to annulus 11, implant 100 is typically not anchored downstream of the leaflets of the valve being treated (e.g., within the ventricle downstream of the valve being treated), e.g., implant 100 does not comprise a downstream anchor (e.g., a ventricular anchor). For example, and as shown, at least for applications in which interface 110 is anchored to annulus 11, any anchoring of implant 100 to tissue of the heart is typically within the atrium upstream of the valve being treated.

For some applications, implant 100 can be repositioned even after anchoring, by driver 70 being used to de-anchor interface 110 from the tissue (e.g., by unscrewing anchor 30).

Figure 68G:
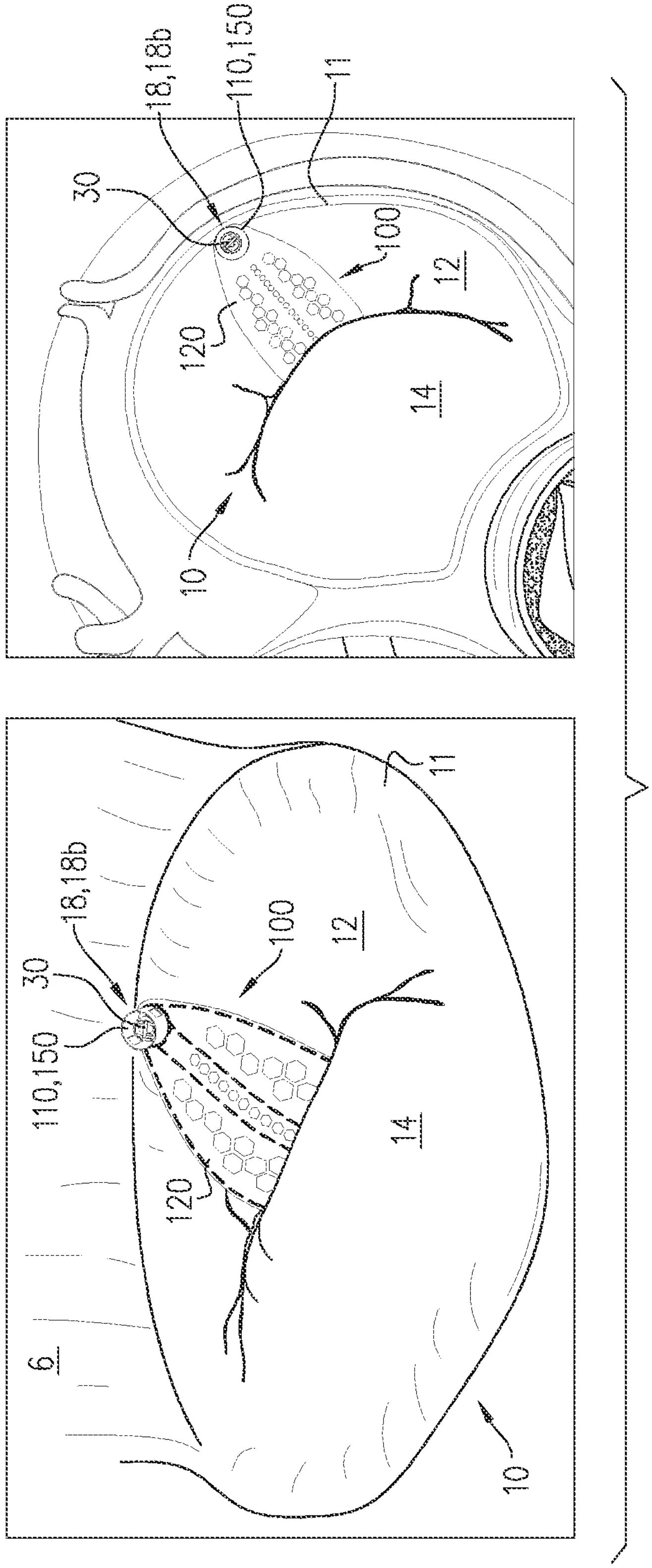

FIG. 68G shows implant 100 following its implantation, and subsequently to disengagement of tool 50 from the implant (e.g., disengagement of driver 70 from anchor 30, and disengagement of shaft 60 from interface 110), and withdrawal of the tool from the subject.

It is hypothesized that the simplicity of repositioning implant 100 is at least in part due to the simplicity and minimalistic nature of the implant itself, and/or due to the simplicity of its anchoring (e.g., via a single anchor). It is further hypothesized that, because shaft 60 holds implant 100 in each position in which the implant will potentially be secured (e.g., because the shaft holds interface 110 at (e.g., against) each site 18 to which the interface will potentially be anchored), and because the subsequent anchoring of the implant causes minimal (e.g., no) alteration in the implant's position, the determination of position optimality described hereinabove is, advantageously, particularly accurate and reliable for system 20. It is still further hypothesized that this advantage can be additionally facilitated by the complete deployment of wing 120 (e.g., of implant 100 as a whole) prior to placing the implant at each position.

Moreover, if it is decided to abort the implantation after implant 100 has been deployed in the atrium, it is possible to withdraw the implant into catheter 40 and out of the subject simply by retracting shaft 60 into the catheter. The shape and flexibility of wing 120 facilitate it being recompressed by its reentry into the catheter. If interface 110 has already been anchored before the decision to abort has been made, driver 70 can be used to de-anchor anchor 30 before retraction of shaft 60.

Further regarding the simplicity of implant 100, for some applications, implant 100 consists essentially of interface 110 and wing 120 (i.e., frame 124 and sheet 126).

For some applications, and as shown, driver 70 is disposed within shaft 60, and can advance anchor 30 through the shaft. For some such applications, and as shown, driver 70 and anchor 30 can be present within shaft 60 throughout the procedure. In some applications, driver 70 and anchor 30 can be introduced into shaft 60 after implant 100 has been introduced to the heart.

Anchor 30 can include a tissue-engaging element 34, and driver 70 can anchor interface 110 to the tissue by driving the tissue-engaging element into the tissue. Tissue-engaging element 34 can take one of various forms known in the art, such as helical, dart, staple, etc. In the example shown, tissue-engaging element 34 is a helical tissue-engaging element, which driver 70 screws into the tissue.

For some applications, implant 100 comprises an anchor receiver 150 at interface 110 (or interface 110 comprises an anchor receiver 150), such that the anchoring of the interface to the tissue is achieved by anchoring the receiver to the tissue. This itself can be achieved by using driver 70 to anchor anchor 30 to receiver 150, e.g., by driving the anchor through the receiver and into the tissue.

For some applications, and as shown, receiver 150 defines an aperture therethrough, and includes an obstruction 152 that protrudes medially into or across the aperture. For such applications, anchor 30 and driver 70 can be configured such that the driver can drive tissue-engaging element 34 beyond obstruction 152 until head 32 becomes obstructed by the obstruction.

For some applications, receiver 150 can be similar to and/or can be substituted with an anchor connection point described hereinabove, such as anchor connection point 2107, mutatis mutandis.

Figure 69:
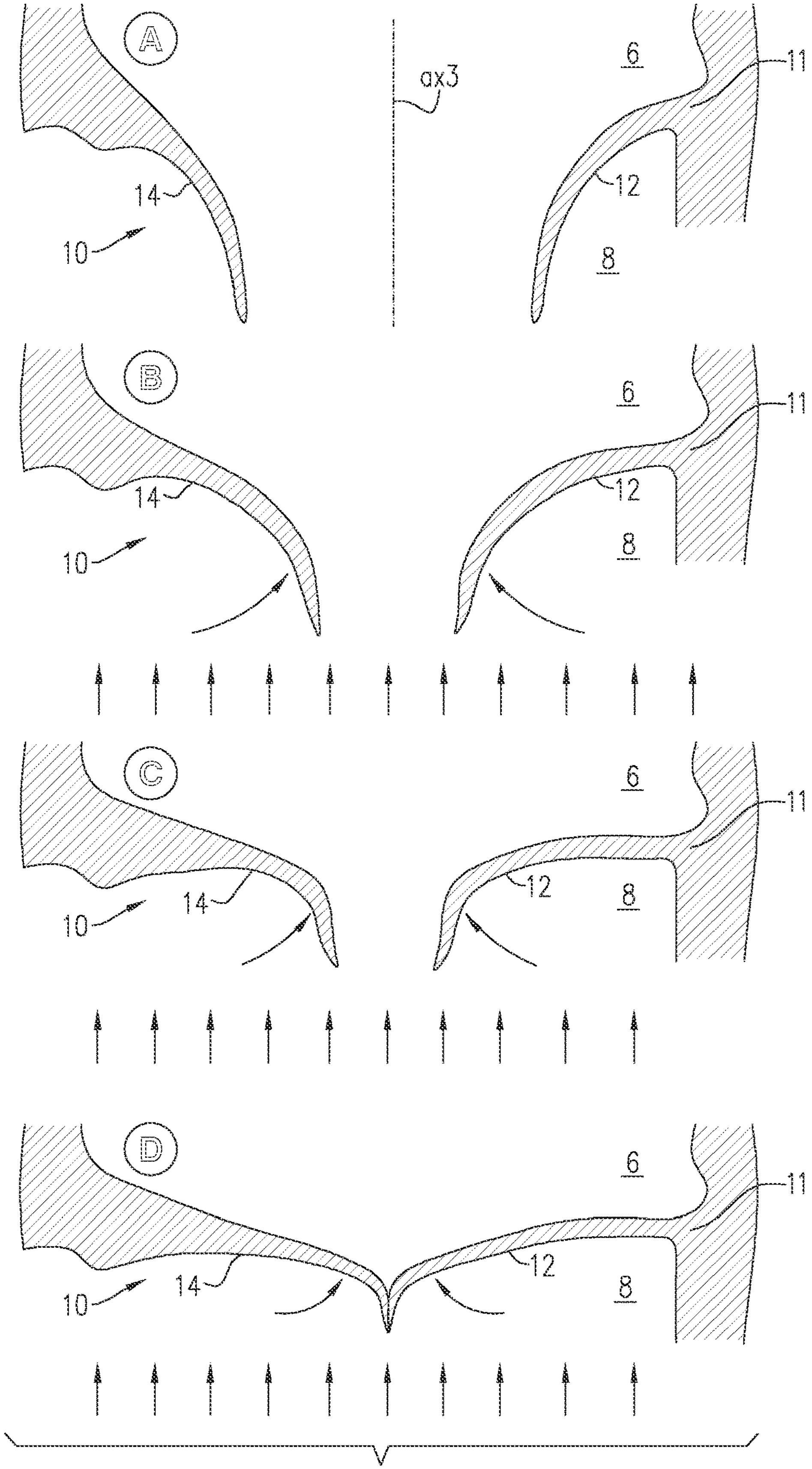
Figure 70:
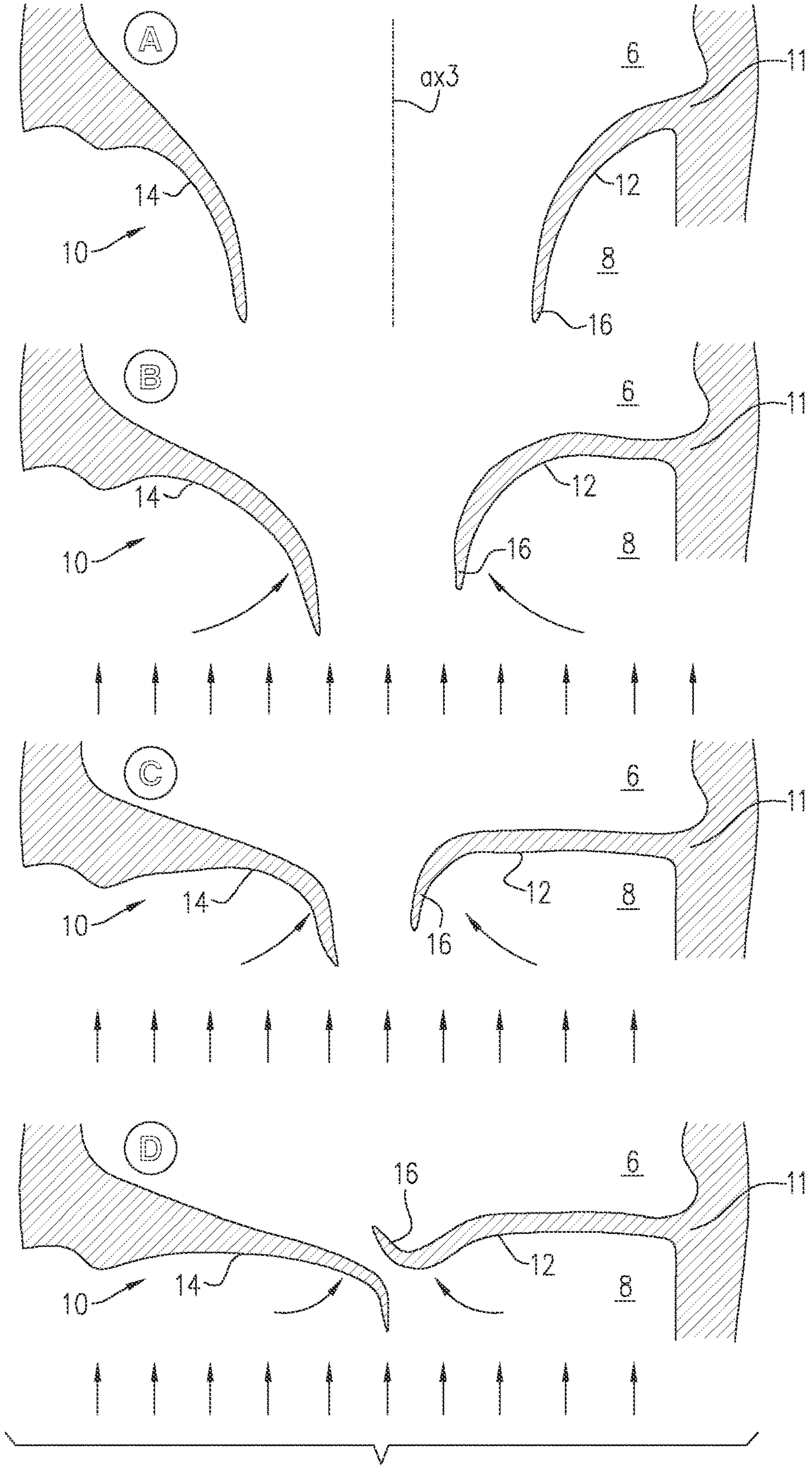
Figure 71:
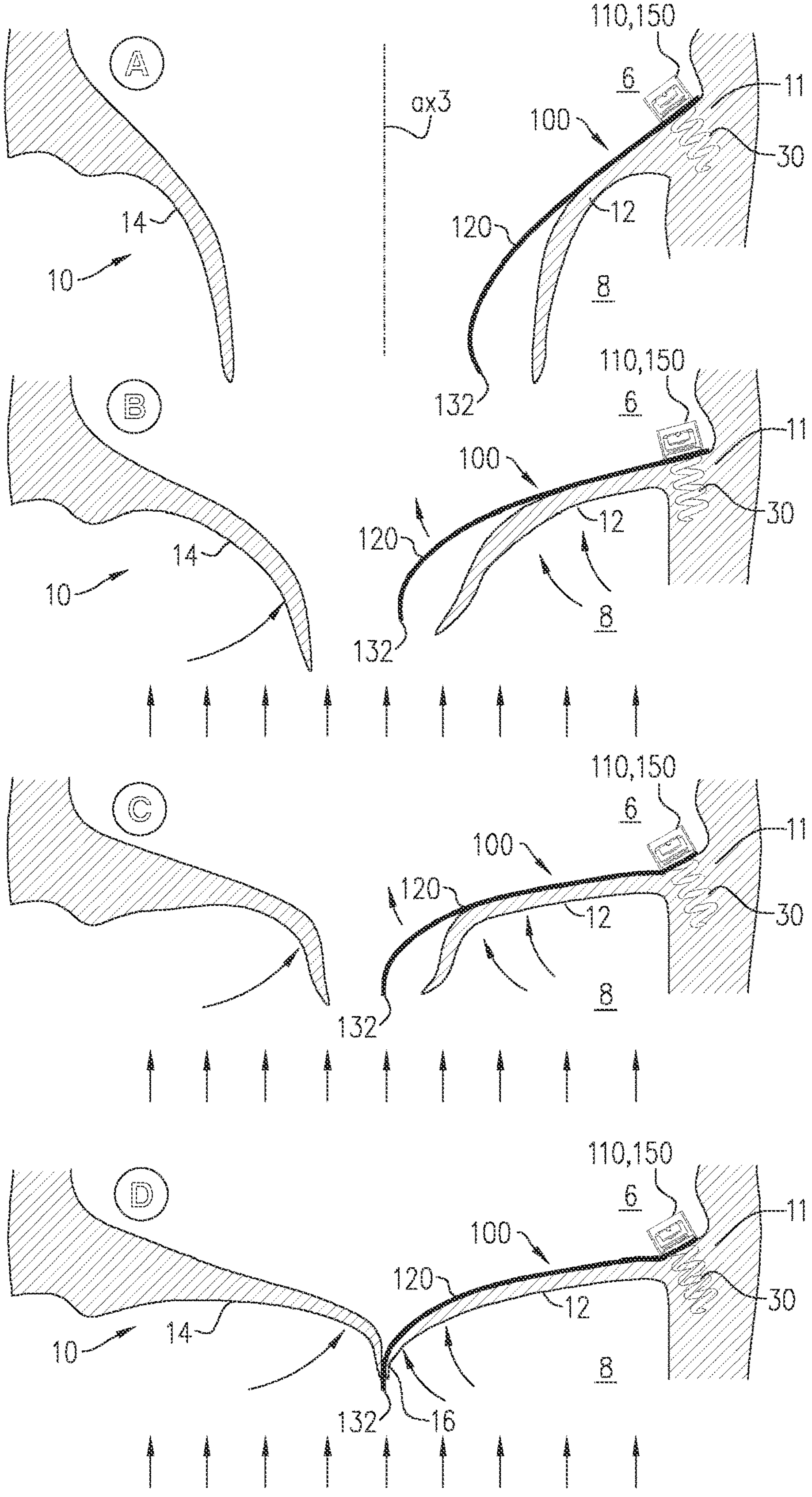

Reference is now made to FIGS. 69, 70, and 71, which are schematic illustrations of valve 10 during a transition from ventricular diastole to ventricular systole, in accordance with some applications. In frames B-D of each of these figures, a series of small arrows pointing upwards represent pressure from ventricle 8 contracting during ventricular systole. FIG. 69 shows valve 10 as a healthy valve 10, whereas FIGS. 70-71 show valve 10 as an injured valve 10 in which leaflet 12 is experiencing flail (e.g., as described for valve 10 hereinabove). FIG. 70 shows the injured valve 10 before implantation of implant 100, whereas FIG. 71 shows the valve after implantation of the implant, in accordance with some applications. In each of FIGS. 69-71, frames A-D represent sequential snapshots during the transition from ventricular diastole to ventricular systole. When viewed in reverse order frames D-A can be considered to represent sequential snapshots during the return transition from ventricular systole to ventricular diastole.

In healthy valve 10, leaflets 12 and 14 close synchronously during ventricular systole, thereby coapting and preventing retrograde flow into atrium 6. In injured valve 10, flail 16 occurs at a site on leaflet 12 (e.g., due to one or more damaged chordae tendineae), thereby allowing retrograde leakage into atrium 6. Previously-described treatments for flail are based on inhibiting movement of the leaflet in an atrial direction (e.g., along an atrioventricular axis ax3), such as by implanting a constraining device in the ventricle (e.g., a prosthetic chorda tendinea) or in the atrium (e.g., an obstructing frame), the constraining device opposing (e.g., directly opposing) the ventriculo-atrial movement of the flail, and thereby requiring substantial strength to oppose the force that ventricular pressure applies to the leaflet. It is hypothesized that implant 100 advantageously manipulates the force of the ventricular pressure, deflecting the otherwise ventriculo-atrial movement of leaflet 12 toward opposing leaflet 14, such that the part of leaflet 12 that would otherwise flail coapts with leaflet 14—albeit with wing 120 sandwiched therebetween.

It is hypothesized that this directed coaptation simulates physiological coaptation in a healthy valve, allowing the leaflets to cooperatively resist ventricular pressure. That is, due to the directed coaptation leaflet 14 provides leaflet 12 with support to resist flailing. It is further hypothesized that, due to this, implant 100 advantageously does not require the substantial strength that would be required to oppose the force applied by ventricular pressure. Instead, advantageously, implant 100 can be anchored by a single anchor (though multiple anchors can also be used), can be implanted using a simple and highly maneuverable delivery system, and wing 120 can be highly flexible. For some applications, implant 100 and/or its anchoring can in fact be insufficiently strong to directly resist (e.g., obstruct) leaflet 12 from flailing in response to the force from ventricular pressure—but is nonetheless able to reduce or eliminate the flail by (re)directing the leaflet toward the opposing leaflet.

Comparison of FIGS. 70 and 71 further illustrate an example of this hypothesized behavior, although this example should not be construed as limiting the scope of the disclosure. In FIG. 70, frames B-D show uninjured leaflet 14 swinging toward leaflet 12 in response to ventricular pressure. That is, although the ventricular pressure is broadly directed atrially (e.g., along axis ax3), and although leaflet 14 moves atrially in response to this pressure, it also swings/deflects toward leaflet 12. In a healthy valve, both leaflets behave in this manner, and thereby coapt (FIG. 69). In contrast, in FIG. 70, injured leaflet 12 (e.g., flailing part 16 thereof) has relatively less movement toward leaflet 14 and is thereby able to slip past the lip of leaflet 14 and flail into atrium 6. In FIG. 71, implant 100 (e.g., wing 120 thereof) redirects leaflet 12 toward leaflet 14, facilitating sealing of valve 10.

In many applications, portions of the native leaflet being treated (e.g., leaflet 12) still directly coapt against another native leaflet. In some cases, more than 20%, more than 30%, more than 40%, more than 50%, more than 60%, or more than 70% of the native leaflet being treated (or of a coaptation surface of the native leaflet) coapts directly against another native leaflet. Further, typically, at least during part of the cardiac cycle (e.g., ventricular diastole), the native leaflet being treated (in this case leaflet 12) separates from wing 120 (FIG. 71, frame A), and during another part of the cardiac cycle (e.g., ventricular systole), the leaflet becomes pushed against wing 120 by ventricular pressure. Thus, wing 120 does not serve as a prosthetic leaflet, but rather a guide and/or support for the native leaflet, aiding the native leaflet to assume an appropriate conformation for coaptation with the opposing leaflet. It is hypothesized that, at least for some applications, the shape of wing 120 and/or the position and orientation in which implant 100 is implanted is such that, during systole, the native leaflet becomes molded to or follows or conforms to the shape of wing 120 as contact between the native leaflet and the wing propagates toward the lip of the leaflet and tip 132 of the wing, e.g., as shown. Implant/device 100 (and any of the implants/devices herein) can be beneficially configured to extend beyond (and/or below) the edge of the native leaflet (e.g., when the valve is closed). It is hypothesized that this may beneficially help ensure the leaflet assumes the correct shape without requiring the end of the implant/device 100 to be anchored in the ventricle or clipped to the edge of the native leaflet.

It is hypothesized that holes 140 (or other opening(s)) facilitate the native leaflet becoming molded to or following or conforming to the shape of the wing by allowing blood to flow downstream through wing 120 during diastole (e.g., pushing leaflet 12 away from the wing), and allowing blood to escape from between the leaflet and the wing during the first moments of systole, thereby allowing the leaflet to promptly flatten against the wing and coapt with the opposing leaflet, thus facilitating a small regurgitant volume. A permeable portion and/or and open/uncovered portion similar to that described with respect to FIG. 21A may provide similar benefits, and it is possible to include or use covered portions and/or uncovered portions with this device that are similar to those show and described with respect to FIG. 21A. The hole(s), open portion(s), and/or permeable portion may also help facilitate implantation in a beating heart and allow easier positioning of the device, without the circulating blood catching the wing like a sail and causing too much movement of the wing or device. This may similarly help avoid undesired device/implant migration after implantation.

Typically, and as shown, wing 120 beats or moves during the cardiac cycle, e.g., facilitated by manner in which implant 100 is anchored, and/or by the flexibility of the wing (e.g., of frame 124). For example, as the leaflet being treated is pushed upstream by ventricular pressure, it pushes wing 120 upstream. The transition from frame A to frame B of FIG. 71 represents implant 100 as a whole pivoting about anchor 30 in response to leaflet 12 being pushed against wing 120, e.g., due to implant 100 being anchored only at interface 110. The transition from frame B to frame C of FIG. 71 represents wing 120 deflecting with respect to interface 110 and anchor 30 in response to further pushing of the wing by leaflet 12, e.g., due to the flexibility of the wing (e.g., of frame 124).

Figure 72C:
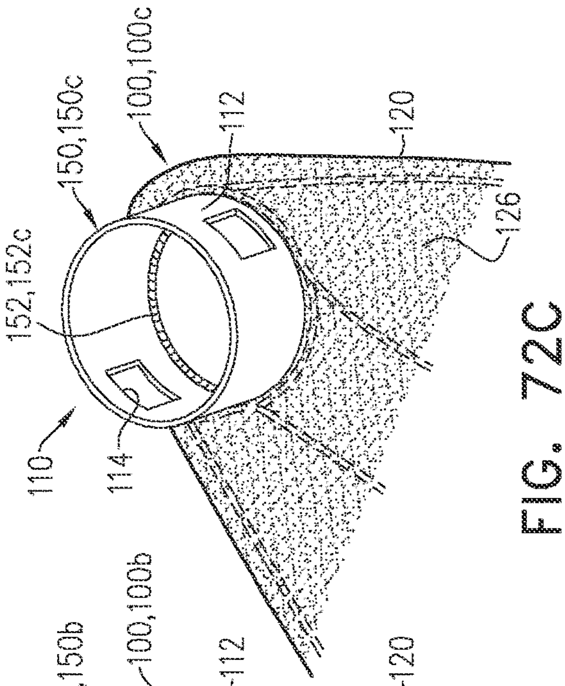
Figure 72B:
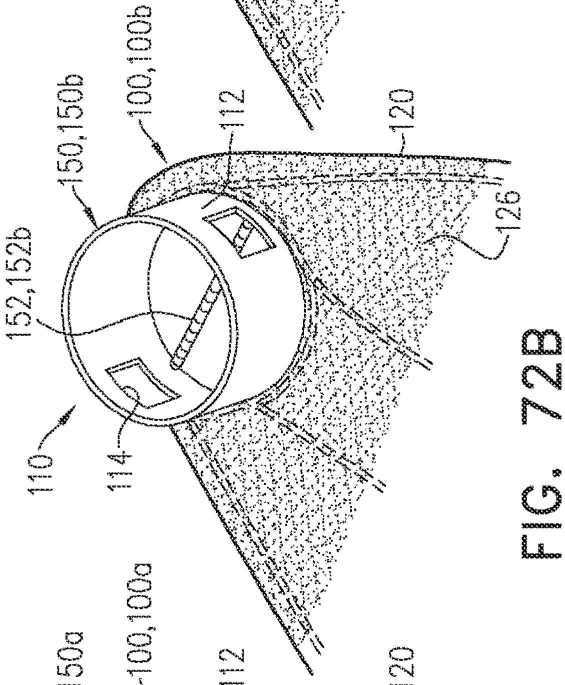
Figure 72A:
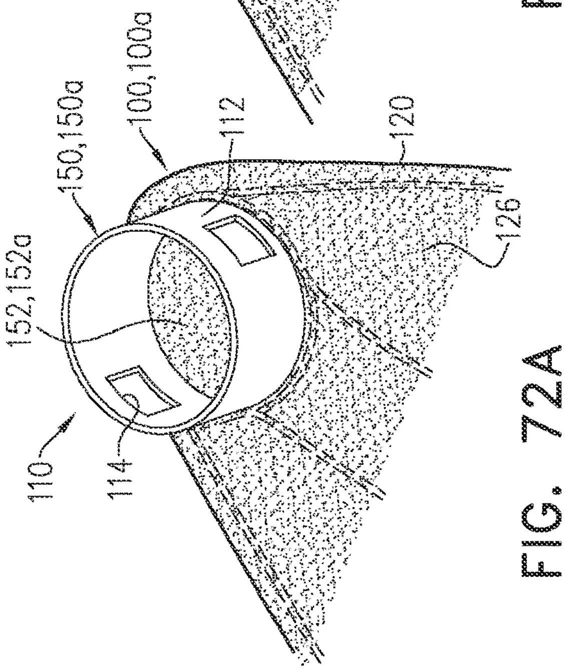

FIG. 72A schematically illustrates an implant 100*a*, FIG. 72B schematically illustrates an implant 100*b*, and FIG. 72C schematically illustrates an implant 100*c*. Implants 100*a*, 100*b*, and 100*c* are variants of implant 100. Implants 100*a*, 100*b*, and 100*c* can be identical to each other except that implant example 100*a* comprises a receiver 150*a* of anchor receiver 150 or interface 110, implant example 100*b* comprises a receiver 150*b* of anchor receiver 150 or interface 110, and implant example 100*c* comprises a receiver 150*c* of anchor receiver 150 or interface 110.

Receiver 150*a* comprises an example obstruction element 152*a* of obstruction 152. Obstruction element 152*a* is defined by part of sheet 126 extending over the aperture defined by the anchor receiver. During anchoring, tissue-engaging element 34 is driven through and beyond the sheet (e.g., piercing the sheet) until head 32 becomes obstructed by (e.g., abuts) the sheet, e.g., pressing/sandwiching the sheet toward/against the tissue. For some applications, receiver 150*a* has features in common with those described with reference to FIGS. 24C-D, mutatis mutandis. For example, the part of sheet 126 that defines obstruction element 152*a* may define a hinge that is similar to hinge 2427, described with reference to FIGS. 24C-D.

Receiver 150*b* comprises an example obstruction element 152*b* of obstruction 152. Obstruction element 152*b* comprises (or is defined by) a cross-bar that traverses the aperture defined by the anchor receiver. During anchoring, tissue-engaging element 34 is driven beyond the cross-bar until head 32 becomes obstructed by (e.g., abuts) the cross-bar, e.g., pressing/sandwiching the cross-bar toward/against the tissue. For some applications, receiver 150*b* has features in common with those described with reference to FIGS. 23B-C, mutatis mutandis. For example, the cross-bar that defines obstruction element 152*b* can correspond or be similar to the cross-bar that traverses aperture 2317. For some applications, the cross-bar that defines obstruction element 152*b* can correspond or be similar to fulcrum 1905, described with reference to FIG. 19A, mutatis mutandis.

Receiver 150*c* comprises an example obstruction element 152*c* of obstruction 152. Obstruction element 152*c* comprises (or is defined by) a collar. During anchoring, tissue-engaging element 34 is driven beyond the collar until head 32 becomes obstructed by (e.g., abuts) the collar, e.g., pressing/sandwiching the collar toward/against the tissue.

A variety of different types of obstruction elements are also possible, e.g., sheet(s), fabric(s), weave(s), panel(s), metal (e.g., metal sheet, metal fabric, metal structure configured to interface with anchor, etc.), one or more holes (e.g., hole(s) sized for allowing tissue penetration portion of anchor to pass, but not anchor head), cross-bar(s), collar(s), hub(s), polymer layer(s), mesh, nut(s), threaded portion(s) (e.g., with threads that interact with anchor to allow tissue penetration, but keep anchor attached to device), stop(s), etc.

For some applications, implant 100 comprises a lateral (e.g., tubular) wall 112 that defines at least part of interface 110, and in which couplings 114 may be defined. For example, implant 100 can comprise a housing 108 that comprises or defines interface 110 (e.g., wall 112 and couplings 114 thereof), and receiver 150 (e.g., obstruction 152 thereof). Housing 108 can be formed from a single piece of stock, integrating all of these elements. Housing 108 can have features in common with housing 2313, described hereinabove, mutatis mutandis.

For some applications, implant 100 comprises a counterforce support, such as support 1113 and/or support 2309, described hereinabove. For some such applications, during delivery the counterforce support is disposed proximally from interface 110 and/or receiver 150 while within catheter 40. For example, the counterforce support can be deployed from catheter 40 only after the optimal position of implant 100 has been identified and/or only after interface 110 has been anchored to the tissue (e.g., such that while wing 120 is being deployed out of the catheter, shaft 60 extends, within the catheter, proximally away from the interface and past the counterforce support). Alternatively, despite the counterforce support being disposed proximally from interface 110, it can be deployed from catheter 40 prior to placement of interface 110 against the tissue. For some applications, during delivery the counterforce support is disposed distally from interface 110 and/or receiver 150 (e.g., alongside wing 120) while within catheter 40, and can be deployed from the catheter simultaneously with the wing.

Once deployed, the counterforce support extends from interface 110 and away from wing 120, and following implantation of implant 100 typically lies against the wall of the chamber in which the implant has been implanted, e.g., similarly to as described with reference to FIGS. 11-12, mutatis mutandis.

Figure 73:
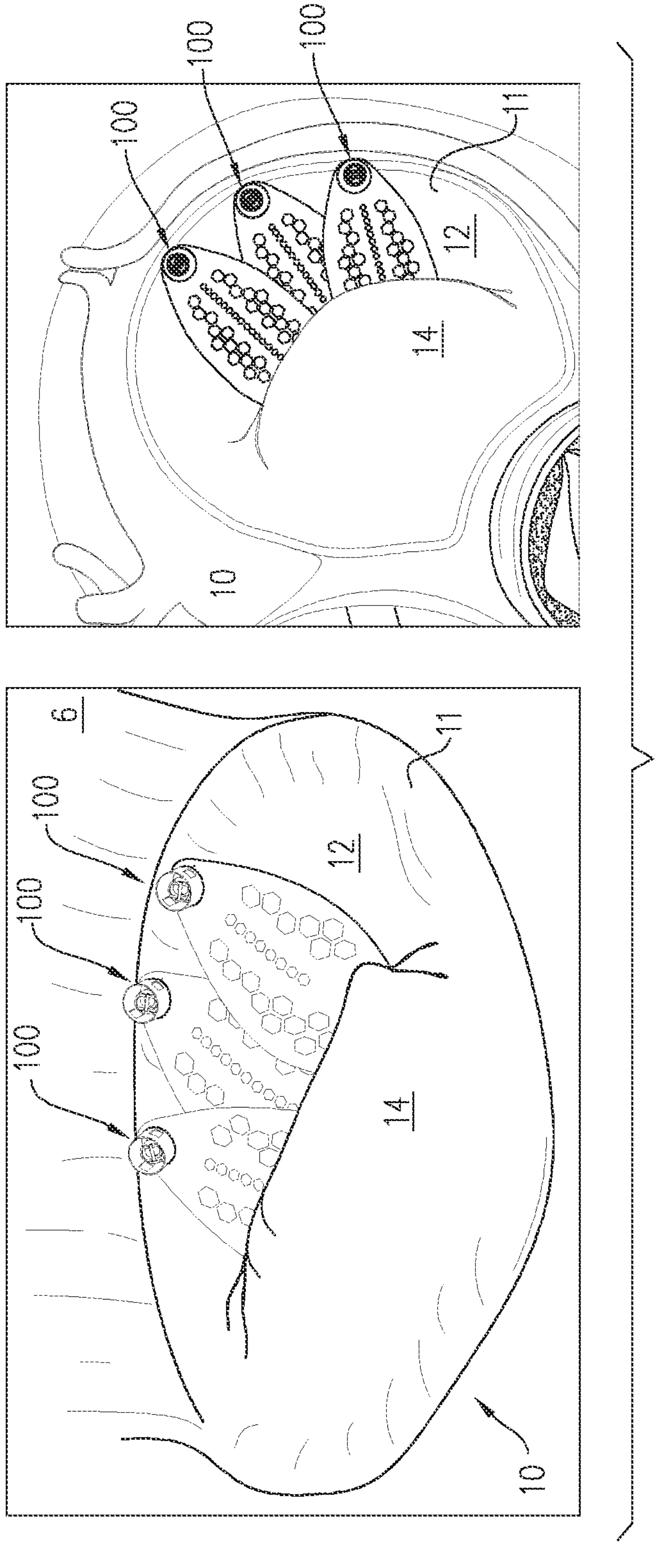

Reference is made to FIG. 73, which is a schematic illustration of multiple implants 100 having been implanted at a single heart valve, in accordance with some applications. Advantageously, and at least in part due to the simplicity of implant 100, the implant typically allows for the implantation of multiple implants 100 at the same valve. It is hypothesized that the simplicity of implant 100 and/or the flexibility of wing 120 allows such multiple implants to be implanted without preventing the underlying leaflet from coapting with the opposing leaflet—even with wings 120 of the implants overlapping, e.g., as shown.

Although all three implants 100 in FIG. 73 are shown over the same leaflet, it is to be understood that the scope of the disclosure includes implanting one or more implants 100 over one leaflet of the valve, and one or more implants 100 over another leaflet of the valve.

Furthermore, implant 100 is compatible with the implantation of other implants, either before or after the implantation of implant 100. For example, because implant 100 has a relatively small footprint on the valve annulus, an annuloplasty structure could also be implanted, if necessary. Similarly, because wing 120 is flexible, if it were to be subsequently determined that the subject requires a prosthetic valve to be implanted at the heart valve (e.g., due to further deterioration of the condition being treated), a transluminally-delivered prosthetic valve can be implanted without removing implant 100, e.g., by wing 120 being simply pushed/deflected laterally by the expansion of the prosthetic valve. It is hypothesized that the size and simple design of wing 120 would mean that the wing would not obscure the outflow of a prosthetic valve implanted without removing the implant.

Furthermore, it may be possible to implant implant 100 with wing 120 over one part of a leaflet, and to perform an edge-to-edge repair (e.g., by implanting a leaflet clip that holds edges of the leaflet together). This edge-to-edge repair can be done at another portion of the leaflet not covered by the implant, or in some applications, may be able to be performed over or through a portion of the implant 100.

Figure 74:
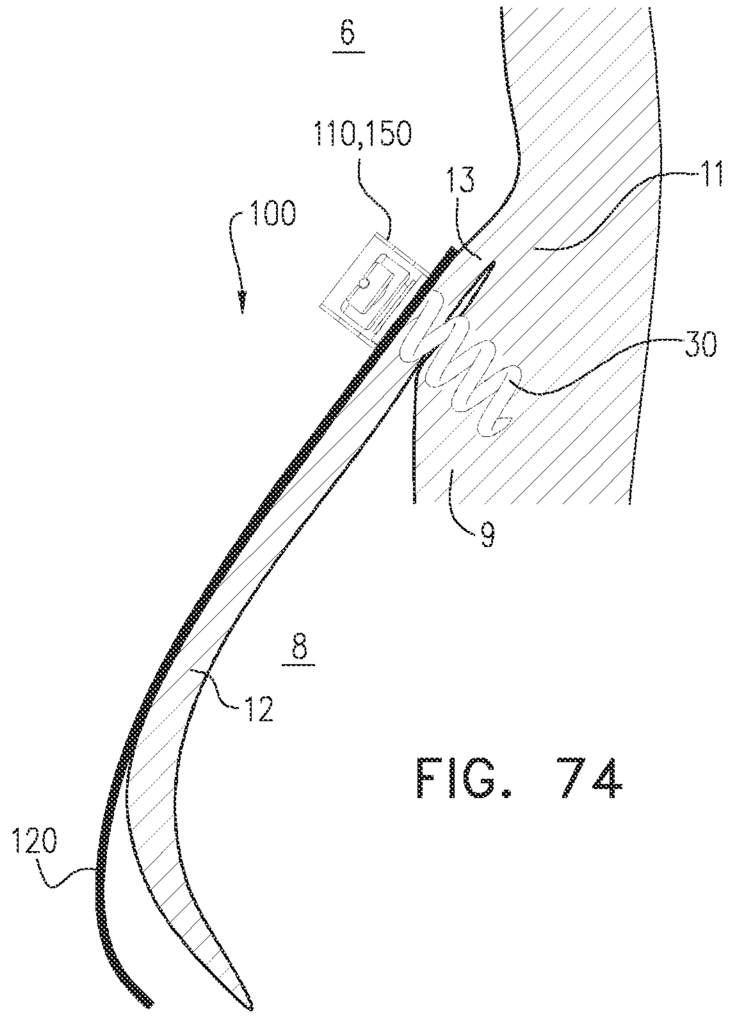
Figure 75:
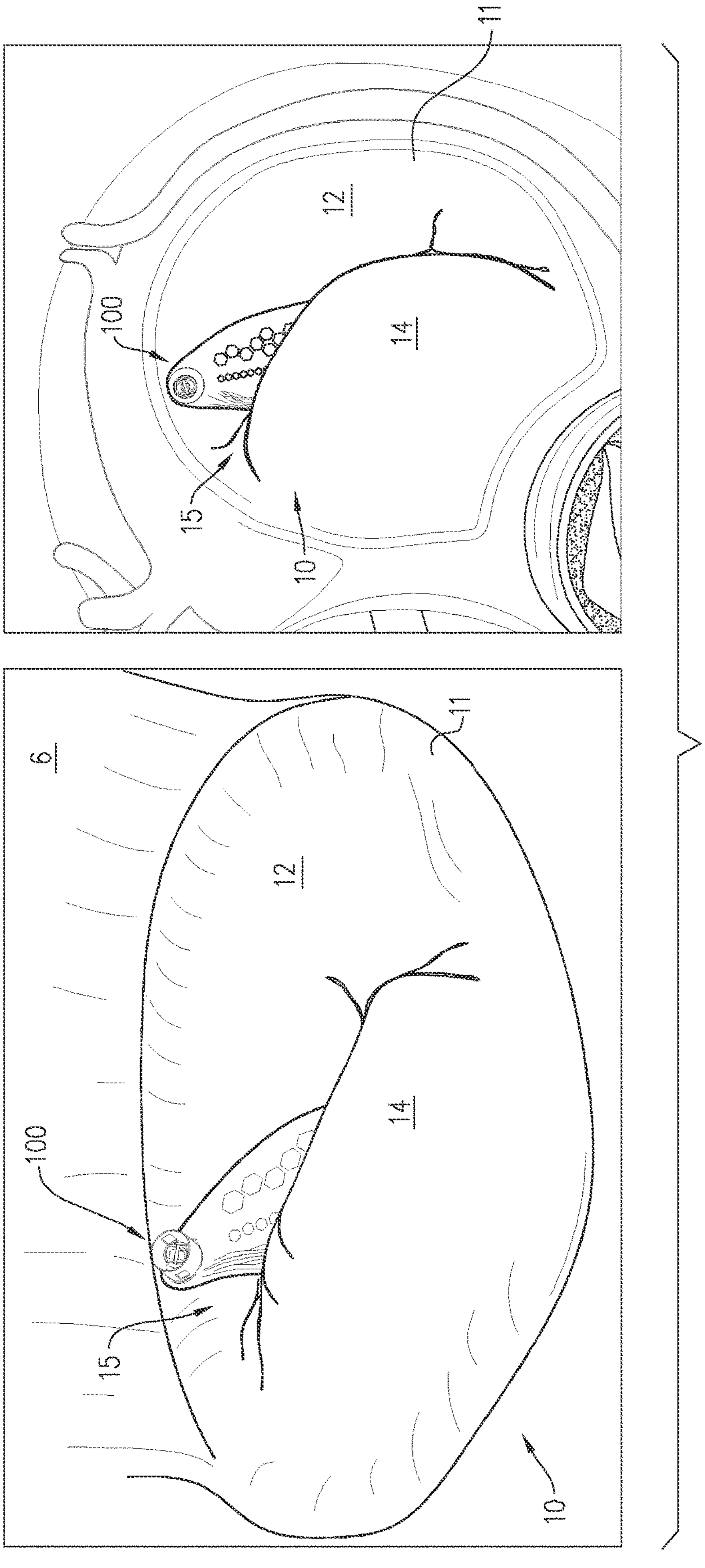

Reference is made to FIGS. 74-75, which are schematic illustrations of implant 100 having been implanted at a location different to that shown above, in accordance with some applications.

In FIGS. 68A-G and 71, interface 110 is anchored to annulus 11 which, vis-à-vis valve 10, is more lateral than the root 13 of the leaflet (in this case, leaflet 12). In contrast, in FIG. 74, interface 110 has been anchored medially from the root of the leaflet, with tissue-engaging element 34 of anchor 30 penetrating entirely through the leaflet and into the wall 9 of ventricle 8. This pins, to ventricular wall 9, the part of the leaflet that is closest to root 13, thereby in effect reducing the effective length of the leaflet. It is hypothesized that, in addition to the advantages of implant 100 described hereinabove, such an anchoring site may be particularly useful in cases of leaflet prolapse.

Typically, for applications in which this anchoring site is used, prior to anchoring interface 110 is pressed against the leaflet such that the leaflet becomes sandwiched between delivery tool 50 (e.g., shaft 60 thereof) and the wall of ventricle 8.

In FIGS. 68A-G and 71, implant 100 thereof is shown as being implanted medially on leaflet 12 (e.g., at the P2 scallop). In contrast, in FIG. 75, implant 100 has been implanted further laterally on the leaflet, e.g., close to or at a commissure 15 of valve 10. It is hypothesized that the flexibility of wing 120 allows it to conform to the anatomy while still improving coaptation. Moreover, it is further hypothesized that this flexibility and conformation may themselves make implant 100 particularly suitable for implantation at such sites, e.g., compared with a more rigid implant that may inhibit the first leaflet from moving toward, and from coapting with, the opposing leaflet. In the example shown, implant 100 has been implanted at a location and in an orientation in which wing 120 deflects asymmetrically, facilitating coaptation, at commissure 15, between the P3 scallop of leaflet 12 and the A3 scallop of leaflet 14. For such applications, the two-loop structure of wing 120 may facilitate such asymmetric deflection, e.g., allowing the wing to fold along a central longitudinal axis of the wing (on which the cross-section indicated by indicators A in FIG. 67A lies).

Figure 76:
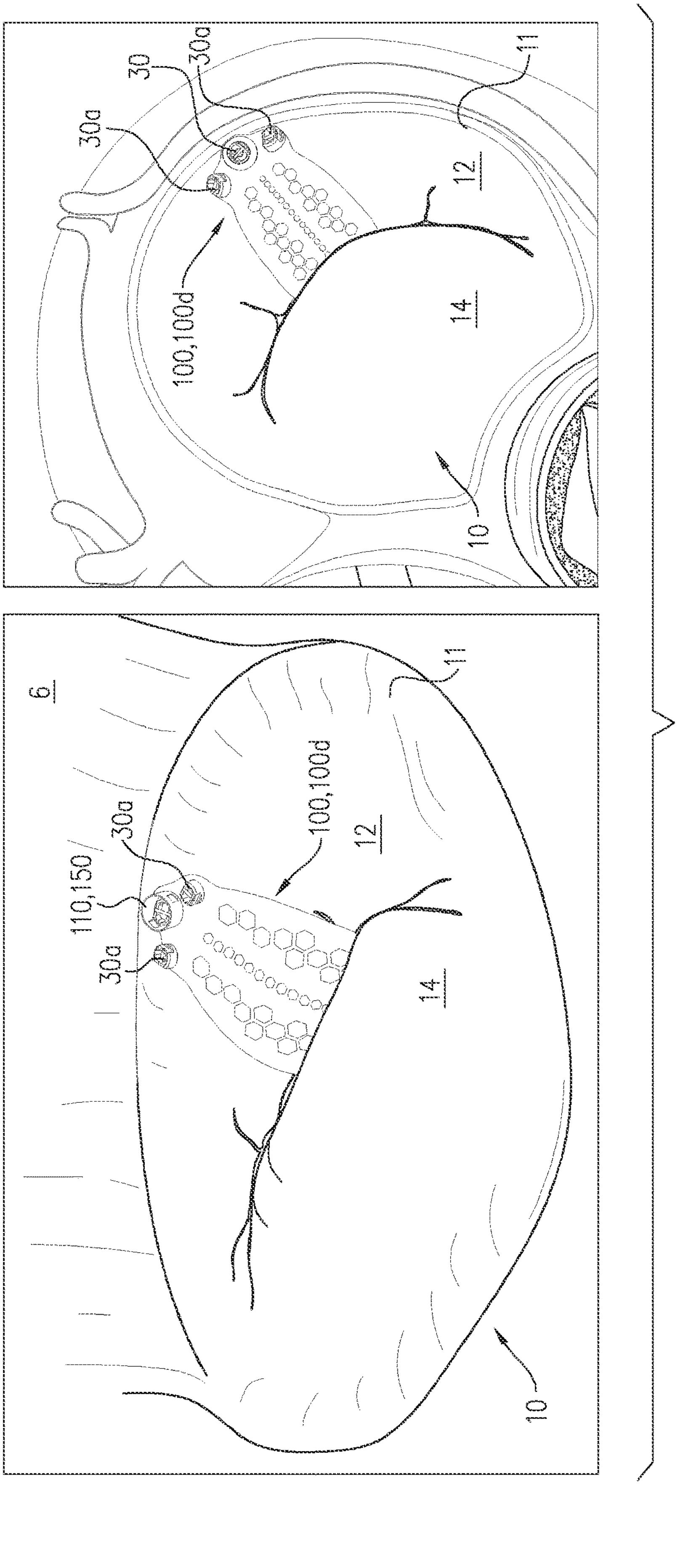
FIG. 76 is a schematic illustration of an implant, in accordance with some applications.

Reference is made to FIG. 76, which is a schematic illustration of an implant **100*d*, in accordance with some applications. Implant 100*d* is a variant of implant 100, and can be the same as or similar to implant 100 as described hereinabove, mutatis mutandis, except that implant 100*d* is anchored by multiple anchors. In some applications, Implant 100*d* can comprise multiple discrete anchor receivers 150**, or multiple anchors may be received by a single anchor receiver or interface.

In some applications, and as shown, implant **100*d* can have a single anchor receiver 150, which receives a single anchor 30, with additional anchors 30*a* being driven through sheet 126 in a vicinity of interface 110. For some applications, implant 100*d* comprises multiple interfaces 110, each of which can comprise an anchor receiver. For some applications, implant 100*d*** (e.g., an anchor interface thereof) is configured to receive multiple anchors at different angular dispositions, e.g., such that the multiple anchors cooperate to provide improved anchoring.

Having one anchoring point provides the benefit of easier and quicker implantation, making it very easy to position the device, confirm proper functioning (e.g., using fluoroscopy and/or echocardiography), and simply anchor in place. Having multiple anchors and anchor connection points may allow for greater stability and redundancy ensuring the implant is safely and permanently secured in place. Where multiple anchor connection points and anchors are used, a delivery device can be use that is configured to delivery multiple (e.g., 2, 3, 4, etc.) anchors simultaneously to help provide greater stability and redundancy while maintaining a quick an easy delivery.

Figure 77A:
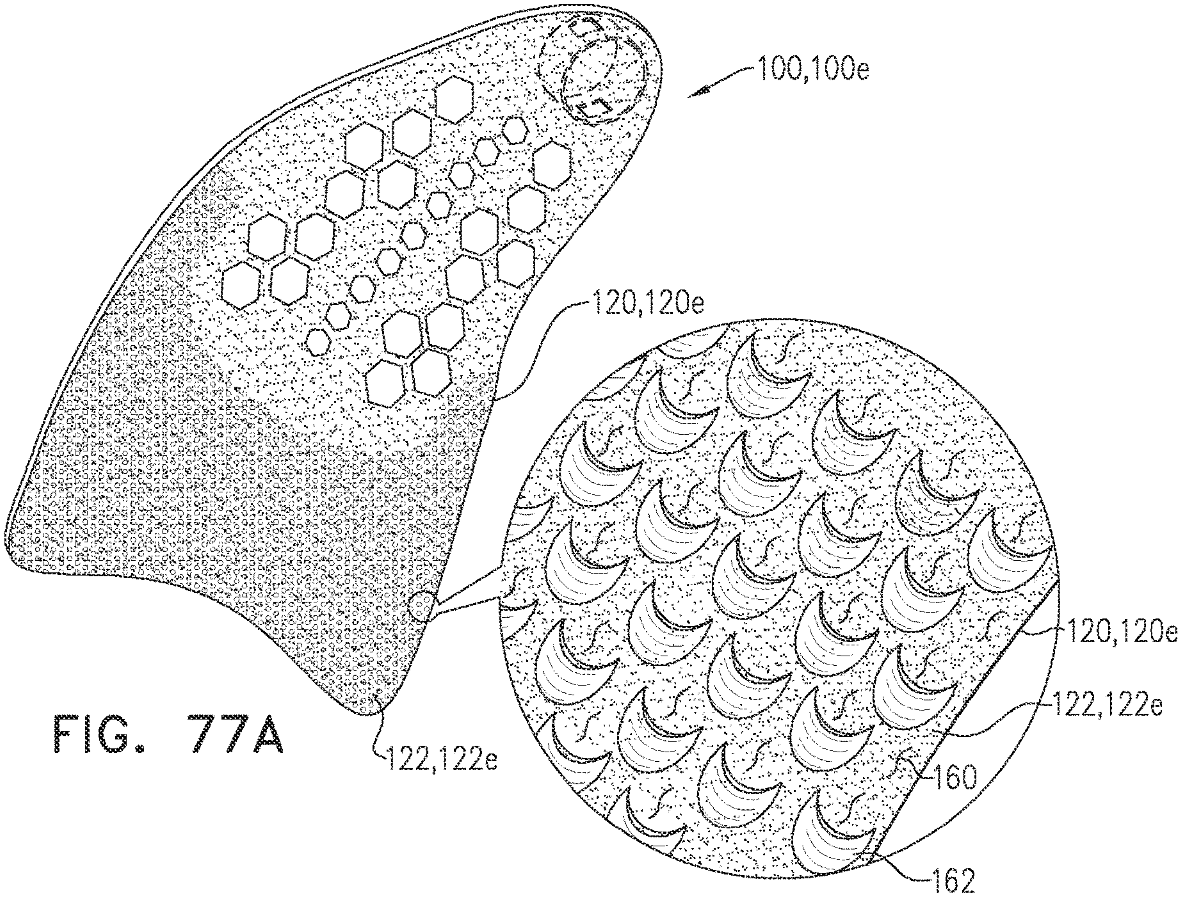
FIGS. 77A-B are schematic illustrations of an implant, in accordance with some applications.
Figure 77B:
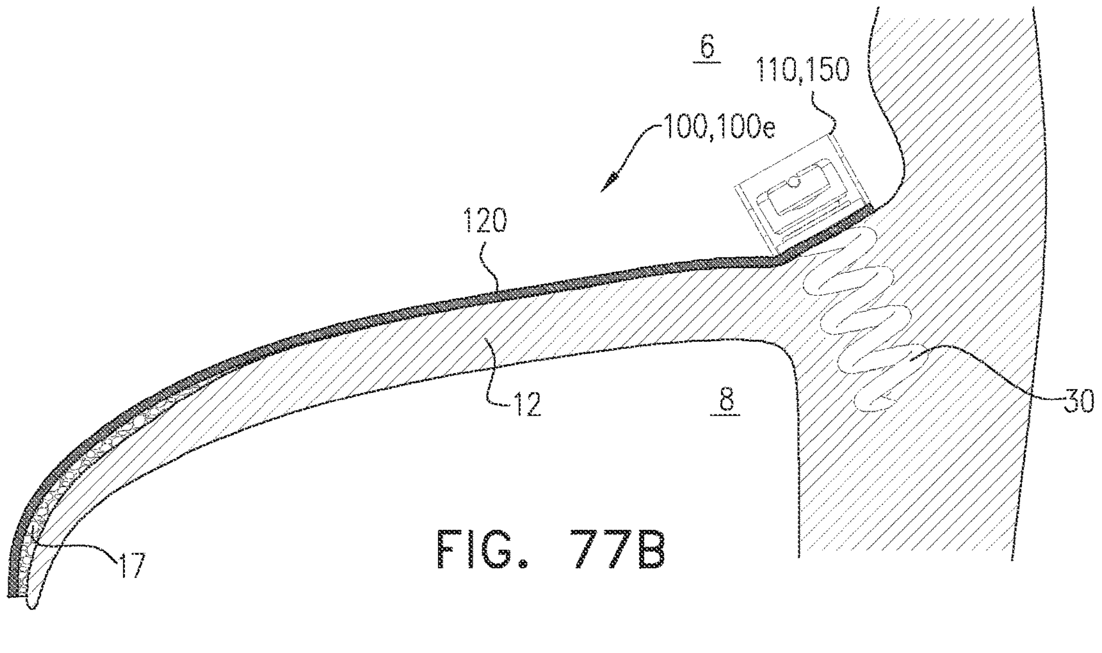

Reference is made to FIGS. 77A-B, which are schematic illustrations of an implant **100*e*, in accordance with some applications. Implant 100*e* is a variant of implant 100, and can be identical to implant 100 as described hereinabove, mutatis mutandis, except that it comprises a wing 120*e*, which is a variant of wing 120. Contact face 122*e* of wing 120*e* (corresponding to contact face 122 of wing 120) defines protrusions (e.g., cilia or bumps) 160 and/or recesses (e.g., dimples or pockets) 162 that are configured to capture blood cells and cell fragments, and/or to induce tissue growth and/or mild inflammation that locally thickens the underlying leaflet—this is represented by reference numeral 17**. It is hypothesized that this thickening further facilitates reduction of regurgitation, e.g., by increasing local rigidity and/or the reach of the underlying leaflet, thereby improving coaptation with the opposing leaflet.

As shown, the protrusions and/or recesses can be defined by sheet **126*e***, e.g., by the sheet being textured. For some applications, the protrusions and/or recesses can be defined by discrete elements that are attached to the sheet.

Figure 78A:
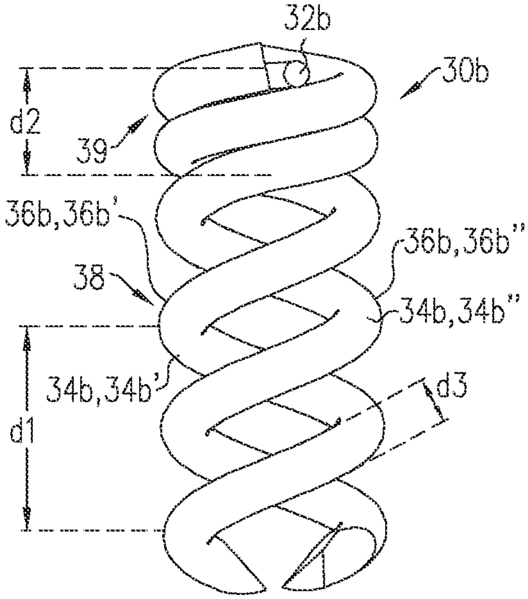
FIGS. 78A-B and 79 are schematic illustrations of anchors, in accordance with some applications.
Figure 78B:
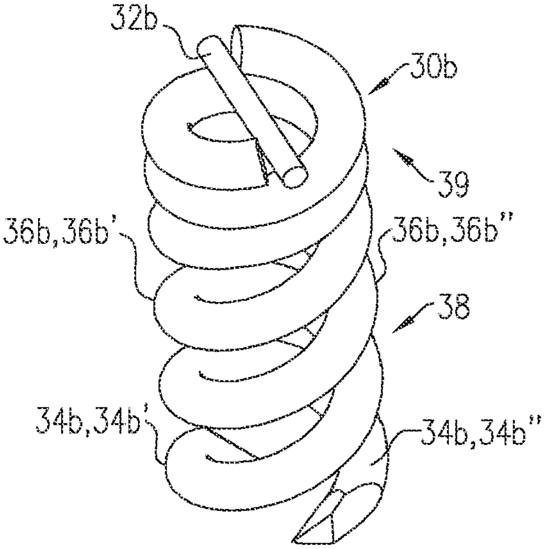
Figure 79:
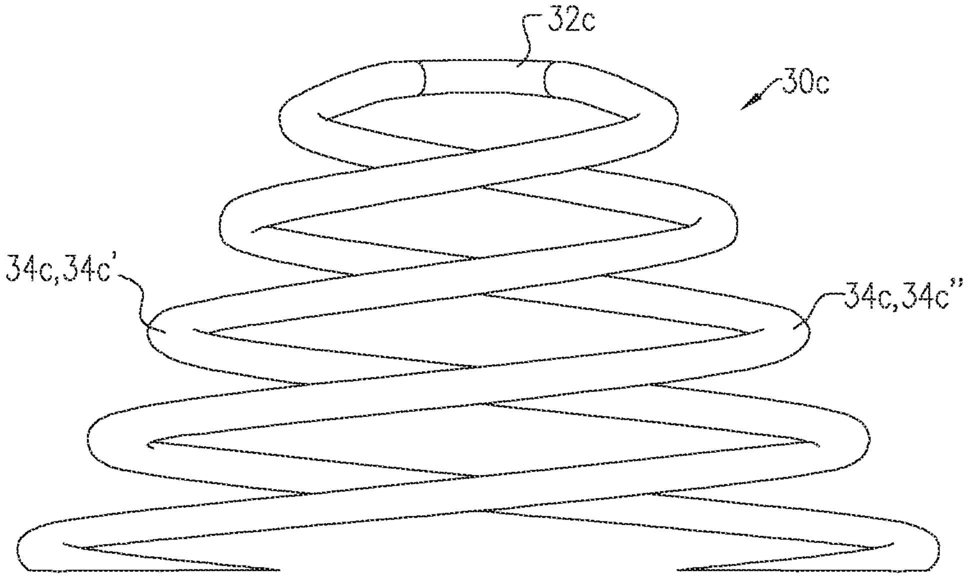

Reference is now made to FIGS. 78A-B and 79, which are schematic illustrations of an anchor 30*b* and an anchor 30*c*, in accordance with some applications. Anchors 30*b* and 30*c* can be used in place of any of the other anchors described hereinabove, mutatis mutandis. For some applications, anchors 30*b* and 30*c* can be considered variants of anchor 30. Moreover, features of anchors 30*b* and 30*c* can be combined with each other, and/or with features of other anchors described herein.

Whereas anchor 30 has a single helical tissue-engaging element 34, each of anchors 30*b* and 30*c* has two tissue-engaging elements, arranged as a double helix, each of the tissue-engaging elements having a sharpened distal tip. Anchor 30*b* comprises two tissue-engaging elements 34*b* (i.e., a first tissue-engaging element 34*b*' and a second tissue-engaging element 34*b*"), and anchor 30*c* comprises two tissue-engaging elements 34*c* (i.e., a first tissue-engaging element 34*c*' and a second tissue-engaging element 34*c*").

It is hypothesized that such use of two tissue-engaging elements may provide greater stability during initial penetration of the anchor into the tissue, and/or greater anchoring strength.

Although anchors 30*b* and 30*c* are shown with both tissue-engaging elements having the same length, for some applications one tissue-engaging element can be longer than the other, e.g., such that one penetrates the tissue first, providing stability as the other is penetrated into the tissue.

For some applications, and as shown, each of the tissue-engaging elements is defined by a respective wire. This is indicated for anchor 30*b* as wire 36*b*, with a first wire 36*b*' defining tissue-engaging element 34*b*', and a second wire 36*b*" defining tissue-engaging element 34*b*".

For some applications, anchor 30*b* or 30*c* can comprise a discrete component 32*b* that serves as an anchor head and/or the part of the anchor that is engaged by the anchor driver. Component 32*b* is shown in FIGS. 78A-B as a bar that traverses across a central longitudinal axis of the anchor, between wires 36*b*' and 36*b*". For some applications, anchor 30*b* or 30*c* can comprise a single wire that defines (i) both tissue-engaging elements, and (ii) an anchor head 32*c* and/or the part of the anchor that is engaged by the anchor driver. This is shown in FIG. 79. Other anchor head designs are also possible.

Anchor 30*b* has a tissue-engaging region 38 and a head region 39. For some applications, and as shown, (i) in tissue-engaging region 38, each wire 36*b* defines its respective tissue-engaging element, and has a tissue-engaging pitch d1 that is such that, within the double helix, turns of each wire are axially spaced apart from turns of the other wire, whereas (ii) in head region 39 each wire 36*b* has a head pitch d2 that is such that, within the double helix, turns of the first wire abut turns of the second wire.

For some applications, pitch d1 facilitates screwing of tissue-engaging region 38 into tissue, whereas pitch d2 configures head region 39 to resist being screwed into the tissue, e.g., such that head region 39 serves as an anchor head.

As shown for anchor 30*c*, tissue-engaging elements 34*c* can, individually and/or collectively, be shaped as a conic helix that widens toward the distal end of the anchor. For some applications, such tissue-engaging elements are delivered in a radially compressed state, and expand to become conical (or more conical) during deployment.

While the above description contains many specific embodiments of the invention, these should not be construed as limitations on the scope of the invention, but rather as an example of one embodiment thereof. Accordingly, the scope of the invention should be determined not by the embodiments illustrated, but by the appended claims and their equivalents. Features of one embodiment can be combined with the features of other embodiments herein. In particular, features of a given variant of implant 100 can be combined with features of another variation of implant 100, mutatis mutandis.

What is claimed is:

1. A system for use with a valve of a heart of a subject, the valve having a first leaflet and an opposing leaflet, the heart having a chamber upstream of the valve, and the system comprising:
- an implant, comprising:
  - an interface,
  - an anchor receiver at the interface, and
  - a flexible wing, coupled to the interface, and having a contact face and an opposing face opposite the contact face;
- an anchor, comprising a tissue-engaging element;
- a catheter, transluminally advanceable to the chamber, and configured to house the implant; and
- a delivery tool, comprising:
  - a shaft, housing the anchor, engaged with the interface, and configured via the engagement with the interface to, while the anchor remains within the shaft:
    - deploy the implant out of the catheter such that, within the chamber, the wing extends away from the interface, and
    - position the implant in a position in which the interface is at a site in the chamber, the wing extends over the first leaflet toward the opposing leaflet, and the contact face faces the first leaflet, and
  - a driver, engaged with the anchor within the shaft, and configured to secure the implant in the position by, while the implant remains in the position, anchoring the anchor receiver to the site by driving the tissue-engaging element distally through the anchor receiver and into tissue at the site.

2. The system according to claim 1, wherein the site is on an annulus of the valve, the delivery tool is configured to position the implant in the position in which the interface is at the site on the annulus, and the driver is configured to secure the implant in the position by, while the implant remains in the position, anchoring the anchor receiver to the site on the annulus by driving the tissue-engaging element distally through the anchor receiver and into tissue at the site on the annulus.

3. The system according to claim 1, wherein the shaft is configured, via the engagement with the interface, to deploy the wing entirely out of the catheter, and the driver is configured to secure the implant in the position subsequently to the shaft deploying the wing entirely out of the catheter.

4. The system according to claim 3, wherein the shaft is configured, via the engagement with the interface, to deploy the implant entirely out of the catheter, and the driver is configured to secure the implant in the position subsequently to the shaft deploying the implant entirely out of the catheter.

5. The system according to claim 1, wherein the shaft is configured to advance the implant through the catheter with the wing distal to the interface.

6. The system according to claim 1, wherein:
- the anchor comprises a head, the tissue-engaging element extending distally away from the head,
- the anchor receiver defines an obstruction, and the driver is configured to anchor the interface to the tissue by driving the anchor through the housing until the head becomes obstructed by the obstruction and presses the obstruction toward the tissue.

7. The system according to claim 6, wherein the anchor receiver defines an aperture, and the obstruction protrudes medially into the aperture in a manner that facilitates passage of the tissue-engaging element through the aperture but obstructs passage of the head through the aperture.

8. The system according to claim 1, wherein the interface defines a tubular wall, and the shaft is engaged with the interface via engagement with the tubular wall.

9. The system according to claim 1, wherein:

the position is a first position, the site is a first site, and via the engagement with the interface, the shaft is configured to, after placing the implant in the first position, reposition the implant into a second position in which the interface is at a second site in the heart, the wing extends over the first leaflet toward the opposing leaflet, and the contact face faces the first leaflet, the second position being different from the first position, and the second site being different from the first site.

10. The system according to claim 9, wherein the shaft is configured to reposition the implant into the second position while the implant remains entirely outside of the catheter.

11. The system according to claim 1, wherein the wing:

comprises a frame and a sheet spread over the frame, and has a root that is coupled to the interface, a free end at an opposite end of the wing from the root, and two lateral sides extending from the root to the free end.

12. The system according to claim 11, wherein the frame comprises at least one frame material selected from the group consisting of: of nitinol, cobalt-chrome, stainless steel, titanium, polyglycolic acid, polylactic acid, poly-D-lactide, polyurethane, poly-4-hydroxybutyrate, polycaprolactone, polyether ether ketone, a cyclic olefin copolymer, polyethylene vinyl acetate, polytetrafluorethylene, a perfluoroether, and fluorinated ethylene propylene.

13. The system according to claim 11, wherein the frame is self-expanding.

14. The system according to claim 11, wherein the frame is attached to the interface.

15. The system according to claim 11, wherein the sheet comprises at least one sheet material selected from the group consisting of: poly (lactic-co-glycolic) acid, polyvinylchloride, polyethylene, polypropylene, polytetrafluoroethylene, polyurethane, polyethylene terephthalate, polyethersulfone, polyglycolic acid, polylactic acid, poly-D-lactide, poly-4-hydroxybutyrate, and polycaprolactone.

16. The system according to claim 11, wherein:

the chamber is an upstream chamber, the heart has a downstream chamber downstream of the valve, and an angular disposition of the wing with respect to the interface is such that positioning, by the shaft, of the implant in the position disposes the free end within the downstream chamber.

17. The system according to claim 11, wherein the frame defines two loops extending alongside each other from the root toward the free end.

18. The system according to claim 17, wherein the two loops meet only at the interface.

19. The system according to claim 17, wherein each of the two loops is substantially teardrop-shaped.

20. The system according to claim 17, wherein the frame defines an elongate space between the two loops, extending from the root toward the free end, and the sheet is spread over the frame such that the sheet extends across the two loops and the elongate space.

21. The system according to claim 11, wherein the sheet defines holes therethrough.

22. The system according to claim 21, wherein the holes are polygonal.

23. The system according to claim 22, wherein the holes are hexagonal.

24. The system according to claim 1, wherein a curvature of the wing is such that, in a cross-section of the implant through the interface and the wing, the contact face is concave and the curvature of the wing increases with distance from the interface.

25. The system according to claim 1, wherein the implant further comprises a counterforce support, extending from the interface and away from the wing such that, in the position, the counterforce support lies against a wall of the chamber.

26. The system according to claim 1, wherein the anchor is a first anchor, and wherein the system further comprises a second anchor that is configured to implant to the tissue within the chamber.

* * * * *